United States Patent
Rogers et al.

(10) Patent No.: US 11,160,458 B2
(45) Date of Patent: Nov. 2, 2021

(54) EPIDERMAL DEVICES FOR ANALYSIS OF TEMPERATURE AND THERMAL TRANSPORT CHARACTERISTICS

(71) Applicant: The Board of Trustees of the University of Illinois, Urbana, IL (US)

(72) Inventors: John A. Rogers, Champaign, IL (US); Li Gao, Urbana, IL (US); Viktor Malyarchuk, Urbana, IL (US); Richard Chad Webb, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 539 days.

(21) Appl. No.: 15/501,379

(22) PCT Filed: Aug. 11, 2015

(86) PCT No.: PCT/US2015/044588
§ 371 (c)(1),
(2) Date: Feb. 2, 2017

(87) PCT Pub. No.: WO2016/025438
PCT Pub. Date: Feb. 18, 2016

(65) Prior Publication Data
US 2018/0014734 A1    Jan. 18, 2018

Related U.S. Application Data
(60) Provisional application No. 62/035,866, filed on Aug. 11, 2014.

(51) Int. Cl.
*A61B 5/01* (2006.01)
*A61B 5/00* (2006.01)
(Continued)

(52) U.S. Cl.
CPC .............. *A61B 5/015* (2013.01); *A61B 5/002* (2013.01); *A61B 5/0048* (2013.01);
(Continued)

(58) Field of Classification Search
CPC .. A61B 5/00; A61B 5/01; A61B 5/015; A61B 2562/164; A61B 2562/0271;
(Continued)

(56) References Cited

U.S. PATENT DOCUMENTS

| 3,822,115 A | 7/1974 | Morin et al. |
| 3,852,092 A | 12/1974 | Patterson et al. |

(Continued)

FOREIGN PATENT DOCUMENTS

| CN | 102448369 A | 5/2012 |
| CN | 102711600 A | 10/2012 |

(Continued)

OTHER PUBLICATIONS

Webb, R. C., Bonifas, A. P., Behnaz, A., Zhang, Y., Yu, K. J., Cheng, H., . . . Yeo, W. H. (2013). Ultrathin conformal devices for precise and continuous thermal characterization of human skin. Nature materials, 12(10), 938. (Year: 2013).*

(Continued)

*Primary Examiner* — Tse W Chen
*Assistant Examiner* — Avery M Foley
(74) *Attorney, Agent, or Firm* — Leydig, Voit & Mayer, Ltd.

(57) ABSTRACT

Provided are tissue-mounted devices and methods for monitoring a thermal transport property (e.g., thermal conductivity, thermal diffusivity, heat capacity) of tissue, such as skin. The devices conformally mount to the tissue and have one or more thermal actuators and a plurality of sensors. The actuator applies heat to the tissue and the sensors to detect a spatio temporal distribution of a physiological tissue (Continued)

parameter or physical property resulting from the heating. This spatio temporal information may be correlated with a rate, velocity and/or direction of blood flow, the presence of a vascular occlusion, circulation changes due to inflammation, hydration level and other physiological parameters.

22 Claims, 72 Drawing Sheets

(51) Int. Cl.
   A61B 5/318     (2021.01)
   A61B 5/369     (2021.01)
   A61B 5/389     (2021.01)
   A61B 5/02      (2006.01)
   A61B 5/0205    (2006.01)
   A61B 5/026     (2006.01)
   A61B 5/028     (2006.01)
   A61B 5/0537    (2021.01)

(52) U.S. Cl.
   CPC ........ *A61B 5/0205* (2013.01); *A61B 5/02007* (2013.01); *A61B 5/028* (2013.01); *A61B 5/0261* (2013.01); *A61B 5/318* (2021.01); *A61B 5/369* (2021.01); *A61B 5/389* (2021.01); *A61B 5/4875* (2013.01); *A61B 5/6832* (2013.01); *A61B 5/0537* (2013.01); *A61B 5/6802* (2013.01); *A61B 5/683* (2013.01); *A61B 5/6824* (2013.01); *A61B 2560/04* (2013.01); *A61B 2562/028* (2013.01); *A61B 2562/0271* (2013.01); *A61B 2562/0285* (2013.01); *A61B 2562/046* (2013.01); *A61B 2562/12* (2013.01); *A61B 2562/164* (2013.01)

(58) Field of Classification Search
   CPC ..... A61B 5/683; A61B 5/6824; A61B 5/6802; A61B 5/6832; A61B 5/028; A61B 5/0261; A61B 5/0205; A61B 5/02007; A61B 5/0048; A61B 5/389; A61B 5/318; A61B 5/365; A61B 5/1455; A61B 5/002; A61B 5/0022; A61B 5/0537; A61B 5/1451; A61B 5/14521; A61B 5/14532; A61B 5/14539; A61B 5/14546; A61B 5/1468; A61B 5/4875; A61B 2562/12; A61B 2564/046; A61B 2564/0285; A61B 2562/028; A61B 2562/0233; A61B 2560/04; A61B 2560/0214; A61B 2560/0223; A61B 2560/0242; A61B 10/0041

See application file for complete search history.

(56) References Cited

U.S. PATENT DOCUMENTS

| | | |
|---|---|---|
| 3,951,133 A | 4/1976 | Reese |
| 3,993,809 A | 11/1976 | Schranz et al. |
| 4,327,742 A | 5/1982 | Meyers et al. |
| 4,393,142 A | 7/1983 | Stephens |
| 4,433,637 A | 2/1984 | Buirley et al. |
| 5,032,506 A | 7/1991 | Palmer et al. |
| 5,053,339 A | 10/1991 | Patel |
| 5,096,671 A | 3/1992 | Kane et al. |
| 5,207,227 A | 5/1993 | Powers |
| 5,290,519 A | 3/1994 | Bar-Or et al. |
| 5,678,566 A | 10/1997 | Dribbon |
| 5,763,282 A | 6/1998 | Zhang |
| 6,743,982 B2 | 6/2004 | Biegelsen et al. |
| 7,195,733 B2 | 3/2007 | Rogers et al. |
| 7,383,072 B2 | 6/2008 | Edmonson et al. |
| 7,521,292 B2 | 4/2009 | Rogers et al. |
| 7,557,367 B2 | 7/2009 | Rogers et al. |
| 7,622,367 B1 | 11/2009 | Nuzzo et al. |
| 7,635,362 B2 | 12/2009 | Hwang et al. |
| 7,704,684 B2 | 4/2010 | Rogers et al. |
| 7,705,280 B2 | 4/2010 | Nuzzo et al. |
| 7,799,699 B2 | 9/2010 | Nuzzo et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,357,335 B1 | 1/2013 | Harvey et al. |
| 8,367,035 B2 | 2/2013 | Rogers et al. |
| 8,394,706 B2 | 3/2013 | Nuzzo et al. |
| 8,440,546 B2 | 5/2013 | Nuzzo et al. |
| 8,470,701 B2 | 6/2013 | Rogers et al. |
| 8,552,299 B2 | 10/2013 | Rogers et al. |
| 8,562,095 B2 | 10/2013 | Alleyene et al. |
| 8,664,699 B2 | 3/2014 | Nuzzo et al. |
| 8,666,471 B2 | 3/2014 | Rogers et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 8,865,489 B2 | 10/2014 | Rogers et al. |
| 8,895,406 B2 | 11/2014 | Rogers et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,057,994 B2 | 6/2015 | Rogers et al. |
| 9,061,494 B2 | 6/2015 | Rogers et al. |
| 9,105,555 B2 | 8/2015 | Rogers et al. |
| 9,105,782 B2 | 8/2015 | Rogers et al. |
| 9,117,940 B2 | 8/2015 | Rogers et al. |
| 9,278,522 B2 | 3/2016 | Rogers et al. |
| 9,324,733 B2 | 4/2016 | Rogers et al. |
| 9,349,900 B2 | 5/2016 | Rogers et al. |
| 9,442,285 B2 | 9/2016 | Rogers |
| 9,450,043 B2 | 9/2016 | Nuzzo et al. |
| 9,487,002 B2 | 11/2016 | Rogers et al. |
| 9,496,229 B2 | 11/2016 | Rogers et al. |
| 9,515,025 B2 | 12/2016 | Rogers et al. |
| 9,554,484 B2 | 1/2017 | Rogers et al. |
| 9,555,644 B2 | 1/2017 | Rogers et al. |
| 9,601,671 B2 | 3/2017 | Rogers et al. |
| 9,613,911 B2 | 4/2017 | Rogers et al. |
| 9,647,171 B2 | 5/2017 | Rogers et al. |
| 9,691,873 B2 | 6/2017 | Rogers et al. |
| 9,761,444 B2 | 9/2017 | Nuzzo et al. |
| 9,765,934 B2 | 9/2017 | Rogers et al. |
| 9,768,086 B2 | 9/2017 | Nuzzo et al. |
| 9,825,229 B2 | 11/2017 | Rogers et al. |
| 9,875,974 B2 | 1/2018 | Rogers et al. |
| 2002/0135772 A1 | 9/2002 | Bornhop et al. |
| 2002/0156411 A1 | 10/2002 | Stern et al. |
| 2005/0048571 A1 | 3/2005 | Danielson et al. |
| 2005/0238967 A1 | 10/2005 | Rogers et al. |
| 2006/0038182 A1 | 2/2006 | Rogers et al. |
| 2006/0117859 A1 | 6/2006 | Liu et al. |
| 2006/0286488 A1 | 12/2006 | Rogers et al. |
| 2006/0286785 A1 | 12/2006 | Rogers et al. |
| 2007/0032089 A1 | 2/2007 | Nuzzo et al. |
| 2007/0106172 A1* | 5/2007 | Abreu ................. A61B 5/6821 600/549 |
| 2007/0118045 A1* | 5/2007 | Naghavi ................. A61B 5/01 600/549 |
| 2008/0055581 A1 | 3/2008 | Rogers et al. |
| 2008/0108171 A1 | 5/2008 | Rogers et al. |
| 2008/0157235 A1 | 7/2008 | Rogers et al. |
| 2008/0212102 A1 | 9/2008 | Nuzzo et al. |
| 2008/0275319 A1 | 11/2008 | Van Gogh et al. |
| 2009/0199960 A1 | 8/2009 | Nuzzo et al. |
| 2009/0204100 A1* | 8/2009 | Van Pieterson ...... A61B 5/0008 604/503 |
| 2009/0294803 A1 | 12/2009 | Nuzzo et al. |
| 2010/0002402 A1 | 1/2010 | Rogers et al. |

(56) References Cited

U.S. PATENT DOCUMENTS

| | | |
|---|---|---|
| 2010/0052112 A1 | 3/2010 | Rogers et al. |
| 2010/0059863 A1 | 3/2010 | Rogers et al. |
| 2010/0072577 A1 | 3/2010 | Nuzzo et al. |
| 2010/0113894 A1 | 5/2010 | Padiy |
| 2010/0283069 A1 | 11/2010 | Rogers et al. |
| 2010/0289124 A1 | 11/2010 | Nuzzo et al. |
| 2010/0302040 A1 | 12/2010 | Davidowitz |
| 2010/0317132 A1 | 12/2010 | Rogers et al. |
| 2011/0147715 A1 | 6/2011 | Rogers et al. |
| 2011/0152643 A1 | 6/2011 | Xue et al. |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0245713 A1 | 10/2011 | Rensen et al. |
| 2011/0266561 A1 | 11/2011 | Rogers et al. |
| 2011/0277813 A1 | 11/2011 | Rogers et al. |
| 2011/0316120 A1 | 12/2011 | Rogers et al. |
| 2012/0024833 A1 | 2/2012 | Klewer et al. |
| 2012/0071783 A1 | 3/2012 | Klee et al. |
| 2012/0083099 A1 | 4/2012 | Nuzzo et al. |
| 2012/0105528 A1 | 5/2012 | Alleyne et al. |
| 2012/0157804 A1 | 6/2012 | Rogers et al. |
| 2012/0165759 A1 | 6/2012 | Rogers et al. |
| 2012/0190989 A1 | 7/2012 | Kaiser et al. |
| 2012/0238901 A1 | 9/2012 | Augustine |
| 2012/0261551 A1 | 10/2012 | Rogers |
| 2012/0296224 A1 | 11/2012 | Klee et al. |
| 2012/0320581 A1 | 12/2012 | Rogers et al. |
| 2012/0321785 A1 | 12/2012 | Rogers et al. |
| 2012/0327608 A1 | 12/2012 | Rogers et al. |
| 2013/0036928 A1 | 2/2013 | Rogers et al. |
| 2013/0041235 A1* | 2/2013 | Rogers ............... A61B 5/6867 600/306 |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0150685 A1 | 6/2013 | Toth |
| 2013/0218046 A1 | 8/2013 | Bowman et al. |
| 2013/0245546 A1 | 9/2013 | Hayn |
| 2013/0320503 A1 | 12/2013 | Nuzzo et al. |
| 2013/0333094 A1 | 12/2013 | Rogers et al. |
| 2014/0025000 A1 | 1/2014 | Currie et al. |
| 2014/0092158 A1 | 4/2014 | Alleyne et al. |
| 2014/0140020 A1 | 5/2014 | Rogers et al. |
| 2014/0163390 A1 | 6/2014 | Rogers et al. |
| 2014/0191236 A1 | 7/2014 | Nuzzo et al. |
| 2014/0216524 A1 | 8/2014 | Rogers et al. |
| 2014/0220422 A1 | 8/2014 | Rogers et al. |
| 2014/0305900 A1 | 10/2014 | Rogers et al. |
| 2014/0323968 A1 | 10/2014 | Rogers et al. |
| 2014/0361409 A1 | 12/2014 | Rogers et al. |
| 2014/0373898 A1 | 12/2014 | Rogers et al. |
| 2014/0374872 A1 | 12/2014 | Rogers et al. |
| 2015/0001462 A1 | 1/2015 | Rogers et al. |
| 2015/0080695 A1 | 3/2015 | Rogers et al. |
| 2015/0132873 A1 | 5/2015 | Rogers et al. |
| 2015/0141767 A1 | 5/2015 | Rogers et al. |
| 2015/0181700 A1 | 6/2015 | Rogers et al. |
| 2015/0207012 A1 | 7/2015 | Rogers et al. |
| 2015/0237711 A1 | 8/2015 | Rogers et al. |
| 2015/0290938 A1 | 10/2015 | Rogers et al. |
| 2015/0373831 A1 | 12/2015 | Rogers et al. |
| 2015/0380355 A1 | 12/2015 | Rogers et al. |
| 2016/0005700 A1 | 1/2016 | Rogers et al. |
| 2016/0027737 A1 | 1/2016 | Rogers et al. |
| 2016/0050750 A1 | 2/2016 | Rogers et al. |
| 2016/0066789 A1 | 3/2016 | Rogers et al. |
| 2016/0072027 A1 | 3/2016 | Rogers et al. |
| 2016/0133843 A1 | 5/2016 | Rogers et al. |
| 2016/0136877 A1 | 5/2016 | Rogers et al. |
| 2016/0284544 A1 | 9/2016 | Nuzzo et al. |
| 2016/0293794 A1 | 10/2016 | Nuzzo et al. |
| 2016/0381789 A1 | 12/2016 | Rogers et al. |
| 2017/0020402 A1 | 1/2017 | Rogers et al. |
| 2017/0128015 A1 | 5/2017 | Rogers et al. |
| 2017/0164482 A1 | 6/2017 | Rogers et al. |
| 2017/0179085 A1 | 6/2017 | Rogers et al. |
| 2017/0179100 A1 | 6/2017 | Rogers et al. |
| 2017/0179356 A1 | 6/2017 | Rogers et al. |
| 2017/0181704 A1 | 6/2017 | Rogers et al. |
| 2017/0200679 A1 | 7/2017 | Rogers et al. |
| 2017/0200707 A1 | 7/2017 | Rogers et al. |
| 2017/0210117 A1 | 7/2017 | Rogers et al. |
| 2017/0224257 A1 | 8/2017 | Rogers et al. |
| 2017/0231571 A1 | 8/2017 | Rogers et al. |
| 2017/0291817 A1 | 10/2017 | Rogers et al. |
| 2017/0309733 A1 | 10/2017 | Nuzzo et al. |
| 2017/0347891 A1 | 12/2017 | Rogers et al. |
| 2017/0365557 A1 | 12/2017 | Rogers et al. |
| 2018/0064377 A1 | 3/2018 | Rogers et al. |

FOREIGN PATENT DOCUMENTS

| | | |
|---|---|---|
| DE | 1087752 B | 8/1960 |
| JP | 2009521972 A | 6/2009 |
| JP | 2013514146 A | 4/2013 |
| WO | WO 1996/004876 | 2/1996 |
| WO | WO 2001/083027 | 11/2001 |
| WO | WO 2005/057467 | 6/2005 |
| WO | WO 2007/074422 A2 | 7/2007 |
| WO | WO 2009/144615 A1 | 12/2009 |
| WO | WO 2010/045247 | 4/2010 |
| WO | WO 2010/136984 A1 | 12/2010 |
| WO | WO 2011/084450 A1 | 7/2011 |
| WO | WO 2011/086481 A1 | 7/2011 |
| WO | WO 2013/149181 A1 | 10/2013 |
| WO | WO 2013/152087 | 10/2013 |
| WO | WO 2016/196673 | 12/2016 |
| WO | WO 2016/196675 | 12/2016 |
| WO | WO 2017/004531 | 1/2017 |
| WO | WO 2017/004576 | 1/2017 |

OTHER PUBLICATIONS

Ashauer, M., Glosch, H., Hedrich, F., Hey, N., Sandmaier, H., & Lang, W. (1999). Thermal flow sensor for liquids and gases based on combinations of two principles. Sensors and Actuators A: Physical, 73(1-2), 7-13. (Year: 1999).*

Aberg et al. (2004) "Skin cancer identification using multifrequency electrical impedance-a potential screening tool," IEEE Transactions on Biomedical Engineering. 51(12):2097-2102.

Agache et al. (1980) Mechanical properties and Young's modulus of human skin in vivo. Arch. Dermatol. Res. 269:221-232.

Ahn et al. (2012) "Stretchable electronics: materials, architectures and integrations," J. Phys. D: Appl. Phys. 45:103001.

Aitken et al. (1996) "Textile applications of thermochromic systems," Rev. Prog. Coloration. 26:1-8.

Akhtar et al. (2010) "Sensitivity of digital thermal monitoring parameters to reactive hyperemia," J. Biomech. Eng. 132:051005.

Alanen et al. (2004) "Measurement of hydration in the stratum corneum with the MoistureMeter and comparison with the Corneometer," Skin Research and Technology. 10(1):32-37.

Alba (Jul. 11, 2014) "Startup Builds Sensors that Will Analyze Sweat to Track Your Health," WIRED. Accessible on the Internet at URL: https://www.wired.com/2014/11/sweat-sensors. [Last Accessed Feb. 27, 2015] 2 pgs.

Allen (2007) "Photoplethysmography and its application in clinical physiological measurement," Physiol. Meas. 28:R1-R39.

Allen et al. (2002) "Microvascular blood flow and skin temperature changes in the fingers following a deep nspiratory gasp," Physiol. Meas. 23:365-373.

Anderson et al. (2005) "Liquid-crystal thermography: Illumination spectral effects. Part 1—Experiments," J. Heat. Trans. 127:581-587.

Armstrong (2007) "Assessing hydration status: the elusive gold standard," Journal of the American College of Nutrition. 26(Suppl 5): 575S-584S.

Armstrong et al. (1997) "Bioimpedance spectroscopy technique: intra-, extracellular, and total body water," Med. Sci. Sports Exerc. 29:1657-1663.

(56) References Cited

OTHER PUBLICATIONS

Arnaud et al. (1994) "A micro thermal diffusion sensor for non-invasive skin characterization," Sensors and Actuators: A. Physical. 41:240-243.
Arora et al. (2008) "Effectiveness of a noninvasive digital infrared thermal imaging system in the detection of breast cancer," Am. J. Surg. 196:523-526.
Arora et al. (2008) "Micro-scale devices for transdermal drug delivery," International Journal of Pharmaceutics. 364(2):227-236.
Arumugam et al. (1994) "Effect of strain-rate on the fracture-behavior of skin," Journal of Biosciences. 19:307-313.
Asada et al. (2003) "Hutchinson, Mobile monitoring with wearable photoplethysmographic biosensors," IEEE engineering in medicine and biology magazine: The quarterly magazine of the Engineering in Medicine & Biology Society. 22:28-40.
Badugu et al. (2003) "A Glucose Sensing Contact Lens: A Non-Invasive Technique for Continuous Physiological Glucose Monitoring," J. Fluoresc. 13:371-374.
Badugu et al. (2003) "Non-invasive continuous monitoring of physiological glucose using a monosaccharide-sensing contact lens," Anal. Chem. 76:610-618.
Bakan et al. (1984) "Liquid-crystal microcapsule medical device used for thermographic examination of the human female breast," Appl. Biochem. Biotechnol. 10:289-299.
Bandodkar et al. (2012) "Tattoo-based potentiometric ion-selective sensors for epidermal pH monitoring," Analyst. 138:123-128.
Bandodkar et al. (Apr. 15, 2014) "Epidermal tattoo potentiometric sodium sensors with wireless signal transduction for continuous non-invasive sweat monitoring," Biosensors and Bioelectronics. 54:603-609.
Bandodkar et al. (Dec. 12, 2014) "Tattoo-Based Noninvasive Glucose Monitoring: A Proof-of-Concept Study," Analytical Chemistry. 87(1):394-398.
Bandodkar et al. (Jul. 18, 2013) "Solid-state Forensic Finger sensor for integrated sampling and detection of gunshot residue and explosives: towards 'Lab-on-a-finger'," Analyst. 138:5288-5295.
Bandodkar et al. (Jul. 2014) "Non-invasive wearable electrochemical sensors: a review," Trends in Biotech. 32(7):363-371.
Barone et al. (1992) "Blood-flow measurements of injured peripheral nerves by laser Doppler flowmetry," J. Reconstr. Microsurg. 8(4):319-323.
Batt et al. (1986) "Hydration of the stratum corneum," International Journal of Cosmetic Science. 8(6):253-264.
Benelam et al. (2010) "Hydration and Health: A Review," Nutr. Bull. 35:3-25.
Bernjak et al. (2008) "Low-frequency blood flow oscillations in congestive heart failure and after beta1-blockade treatment," Microvasc. Res. 76:224-232.
Bhadra et al. (2011) "Wireless Passive Sensor for Remote pH Monitoring," J. Nanotechnol. Eng. Med. 2:011011.
Biagi et al. (2012) "Simultaneous determination of lactate and pyruvate in human sweat using reversed-phase high-performance liquid chromatography: a noninvasive approach," Biomedical Chromatography. 26(11):1408-1415.
Birklein et al. (2008) "Neuropeptides, neurogenic inflammation and complex regional pain syndrome (CRPS)," Neurosci. Lett. 437(3):199-202.
Boas et al. (2010) "Laser speckle contrast imaging in biomedical optics," J. Biomed. Opt. 15(1):011109.
Bohling et al. (Jun. 12, 2013) "Comparison of the stratum corneum thickness measured in vivo with confocal Raman spectroscopy and confocal reflectance microscopy," Skin Res. Technol. 20(1):50-57.
Bonato (2010) "Wearable sensors and systems. From enabling technology to clinical applications," IEEE Eng. Med. Biol. Mag. 29:25-36.
Brenner et al. (1995) "A quantitative test for copper using bicinchoninic acid," Anal. Biochem. 226(1):80-84.
Brull et al. (1990) "Comparison of crystalline skin temperature to esophageal temperatures during anesthesia," Anesthesiology. 73(3A):A472.

Caduff et al. (2009) "Non-invasive glucose monitoring in patients with Type 1 diabetes: a Multisensor system combining sensors for dielectric and optical characterisation of skin," Biosens. Bioelectron. 24:2778-84.
Cameron et al. (1991) "Liquid-crystal thermography as a screening-test for deep-vein thrombosis in patients with cerebral infarction," Eur. J. Clin. Invest. 21:548-550.
Cametti et al. (2011) "Dielectric Relaxation Spectroscopy of Lysozyme Aqueous Solutions: Analysis of the δ-Dispersion and the Contribution of the Hydration Water," J. Phys. Chem. B. 115:7144-7153.
Carmichael et al. (2008) "Activation of the 5-HT1B/D receptor reduces hindlimb neurogenic inflammation caused by sensory nerve stimulation and capsaicin," Pain. 134(1-2):97-105.
Celermajer et al. (1992) "Non-invasive detection of endothelial dysfunction in children and adults at risk of atherosclerosis," Lancet. 340:1111-1115.
Chan et al. (2012) "Smart wearable systems: current status and future challenges," Artif. Intell. Med. 56:137-156.
Cheng et al. (Sep. 6, 2013) "Analysis of a concentric coplanar capacitor for epidermal hydration sensing," Sensors and Actuators A: Physical. 203:149-153.
Ching et al. (2008) "Simultaneous Transdermal Extraction of Glucose and Lactate From Human Subjects by Reverse Iontophoresis," Int. J. Nanomedicine. 3(2):211-223.
Chowdhury et al. (2012) "Application of thermochromic colorants on textiles: temperature dependence of colorimetric properties," Color. Technol. 129:232-237.
Chowdhury et al. (Jan. 2014) "Photochromic and thermochromic colorants in textile applications," J. Eng. Fiber. Fabr. 9:107-123.
clinicaltrials.gov "Genetics and Pain Severity in Sickle Cell Disease," National Institutes of Health. Accessible on the Internet at URL: https://clinicaltrials.gov/ct2/show/NCT01441141. [Last Accessed Sep. 5, 2017].
Cohen (1977) "Measurement of thermal-properties of human-skin—review," J. Invest Dermatol. 69:333-338.
Coyle et al. (2010) "Biotex-Biosensing Textiles for Personalized Healthcare Management," IEEE Trans. Inf. Technol. Biomed. 14(2):364-370.
Coyle et al. (2010) "On-Body Chemical Sensors for Monitoring Sweat," In; Lecture Notes in Electrical Engineering: Wearable and Autonomous Biomedical Devices and Systems for Smart Environment. Eds.: Lay-Ekuakille et al. vol. 75. Springer. pp. 177-193.
Crandall et al. (2005) "Palmar skin blood flow and temperature responses throughout endoscopic sympathectomy," Anesth. Anal. 100:277-283.
Curto et al. (2012) "Real-Time Sweat pH Monitoring Based on a Wearable Chemical Barcode Micro-fluidic Platform Incorporating Ionic Liquids," Sensors and Actuators B. 171-172:327-1334.
Davison et al. (1972) "Detection of breast-cancer by liquid-crystal thermography—preliminary report," Cancer 29:1123-1132.
De La Hera et al. (1988) "Co-expression of Mac-1 and p150,95 on CD5+ B cells Structural and functional characterization in a human chronic lymphocytic leukemia," Eur. J. Immunol. 18(7):1131-4.
Deshmukh (2012) "Enhancing clinical measures of postural stability with wearable sensors," Presented at Engineering in Medicine and Biology Society (EMBC), 2012 Annual International Conference of the IEEE, Aug. 28, 2012-Sep. 1, 2012.
Deshpande (2007) "Thermal analysis of vascular reactivity," MS thesis, Texas A&M University.
Dolphin et al. (1973) "Low-temperature chiral nematic liquid-crystals derived from beta-methylbutylaniline," J. Chem. Phys. 58:413-419.
Drack et al. (Oct. 20, 2014) "An imperceptible plastic electronic wrap," Adv. Mater. 27:34-40.
Draijer et al. (2009) "Review of laser speckle contrast techniques for visualizing tissue perfusion," Lasers in Medical Science. 24:639-651.
Ducharme et al. (1991) "In vivo thermal conductivity of the human forearm tissues," Journal of Applied Physiology. 70:2682-2690.
Dunn et al. (2001) "Dynamic imaging of cerebral blood flow using laser speckle," Journal of Cerebral Blood Flow and Metabolism. 21:195-201.

(56) References Cited

OTHER PUBLICATIONS

Egawa et al. (2007) "In vivo estimation of stratum corneum thickness from water concentration profiles obtained with Raman spectroscopy," Acta Derm. Venereol. 87(1):4-8.
El-Brawany et al. (2009) "Measurement of thermal and ultrasonic properties of some biological tissues," Journal of Medical Engineering and Technology. 33:249-256.
Farina et al. (1994) "Illuminant invariant calibration of thermochromic liquid-crystals," Exp. Therm. Fluid. Sci. 9:1-12.
Fiala et al. (1999) "computer model of human thermoregulation for a wide range of environmental conditions: The passive system," J. App. Physiol. 87:1957-1972.
Flammer et al. (2012) "The assessment of endothelial function: from research into clinical practice," Circulation. 126:753-767.
Fonseca et al. (2002) "Wireless micromachined ceramic pressure sensor for high-temperature application," J. Microelectromech. Syst. 11:337-343.
Fujikawa et al. (2009) "Measurement of hemodynamics during postural changes using a new wearable cephalic laser blood flowmeter," Circ. J. 73:1950-1955.
Gao et al. (Sep. 19, 2014) "Epidermal photonic devices for quantitative imaging of temperature and thermal transport characteristics of the skin," Nat. Commun. 5:4938.
Gorbach et al. (2012) "Infrared imaging of nitric oxide-mediated blood flow in human sickle cell disease," Microvasc. Res. 84:262-269.
Guidotti et al. (2008) "The interpretation of trace element analysis in body fluids," Indian J. Med. Res. 128:524-532.
Guinovart et al. (Sep. 26, 2013) "A potentiometric tattoo sensor for monitoring ammonium in sweat," Analyst. 138:7031-7038.
Gustafsson (1991) "Transient plane source techniques for thermal conductivity and thermal diffusivity measurements of solid materials," Review of Scientific Instruments. 62:797-804.
Hamraoui et al. (2002) "Analytical Approach for the Lucas-Washburn Equation," J. Colloid Interf. Sci. 250:415-421.
Harpster et al. (2002) "A passive wireless integrated humidity sensor," Sens. Actuators A. 95:100-107.
Hassan et al. (2001) "Observation of skin thermal inertia distribution during reactive hyperaemia using a single-hood measurement system," Physiol. Meas. 22:187-200.
Heikenfeld (Oct. 22, 2014) "Sweat Sensors Will Change How Wearables Track Your Health," IEEE Spectrum. Accessible on the Internet at URL: http://spectrum.ieee.org/biomedical/diagnostics/sweat-sensors-will-change-how-wearables-track-your-health. [Last Accessed Feb. 27, 2015] 4 pgs.
Higurashi et al. (2003) "An integrated laser blood flowmeter," Journal of Lightwave Technology. 21:591-595.
Holowatz et al. (2008) "The human cutaneous circulation as a model of generalized microvascular function," J. App. Physiol. 105:370-372.
Hu et al. (2006) "Human body fluid proteome analysis," Proteomics. 6(23):6326-53.
Huang et al. (2007) "Predictive value of reactive hyperemia for cardiovascular events in patients with peripheral arterial disease undergoing vascular surgery," Arterioscl. Throm. Vasc. 27:2113-2119.
Huang et al. (Apr. 6, 2014) "Stretchable, Wireless Sensors and Functional Substrates for Epidermal Characterization of Sweat," Small. 10(15):3083-3090.
Huang et al. (May 31, 2013) "Epidermal impedance sensing sheets for precision hydration assessment and spatial mapping," IEEE Trans. Biomed. Eng. 60(10):2848-57.
Ikeda et al. (1997) "Influence of thermoregulatory vasomotion and ambient temperature variation on the accuracy of core-temperature estimates by cutaneous liquid crystal thermometers," Anesthesiology. 86:603-612.
Ikeda et al. (1998) "Local radiant heating increases subcutaneous oxygen tension," Am. J. Surg. 175:33-37.
Intaglietta (1972) "On-line measurement of microvascular dimensions by television microscopy," J. Appl. Physiol. 32:546-551.
Ireland et al. (1987) "The response-time of a surface thermometer employing encapsulated thermochromic liquid-crystals," J. Phys. E. Sci. Instrum. 20:1195-1199.
Ishibashi et al. (2006) "Short duration of reactive hyperemia in the forearm of subjects with multiple cardiovascular risk factors," Circ. J. 70:115-123.
Jang et al. (Sep. 3, 2014) "Rugged and breathable forms of stretchable electronics with adherent composite substrates for transcutaneous monitoring," Nat. Commun. 5:4779.
Jansky et al. (2003) "Skin temperature changes in humans induced by local peripheral cooling," J. Therm. Biol. 28:429-437.
Jia et al. (Jul. 5, 2013) "Electrochemical tattoo biosensors for real-time noninvasive lactate monitoring in human perspiration," Anal. Chem. 85(14):6553-60.
Jin et al. (2012) "A feasible method for measuring the blood flow velocity in superficial artery based on the laser induced dynamic thermography," Infrared Physics and Technology. 55:462-468.
Kakade et al. (2009) "Accurate heat transfer measurements using thermochromic liquid crystal. Part 1: Calibration and characteristics of crystals," Int. J. Heat. Fluid Fl. 30:939-949.
Kaltenbrunner et al. (Jul. 25, 2013) "An ultra-lightweight design for imperceptible plastic electronics," Nature. 499:458-463.
Kathirgamanathan et al. (2009) "Delineation of distal ulnar nerve anatomy using ultrasound in volunteers to identify an optimum approach for neural blockade," Eur. J. Anaesth. 26:43-46.
Kehoe et al. (Aug. 9, 2013) "Introducing Colorimetric Analysis with Camera Phones and Digital Cameras: An Activity for High School or General Chemistry," J. Chem. Educ. 90:1191-1195.
Kennedy et al. (2009) "A Comparative Review of Thermography as a Breast Cancer Screening Technique," Integr. Cancer Ther. 8:9-16.
Kerr (2004) "Review of the effectiveness of infrared thermal imaging (thermography) for population screening and diagnostic testing of breast cancer," NZHTA Tech Brief Series. vol. 3. No. 3. pp. 1-49.
Khodagholy et al. (2012) "Organic electrochemical transistor incorporating an ionogel as a solid state electrolyte for lactate sensing," J. Mater. Chem. 22:4440-4443.
Kim et al. (2011) "Epidermal Electronics," Science. 333:838-843.
Kim et al. (2012) "Flexible and stretchable electronics for biointegrated devices," Annu. Rev. Biomed. Eng. 14:113-128.
Kim et al. (Nov. 3, 2014) "Epidermal Electronics with Advanced Capabilities in Near-Field Communication," Small. 11(8):906-912.
Klosowicz et al. (2001) "Liquid-crystal thermography and thermovision in medical applications," Proc. SPIE 4535, Optical Sensing for Public Safety, Health, and Security. 4535:24-29.
Kodzwa et al. (2007) "Angular effects on thermochromic liquid crystal thermography," Exp. Fluids. 43:929-937.
Kohler et al. (1998) "Diagnostic value of duplex ultrasound and liquid crystal contact thermography in preclinical detection of deep vein thrombosis after proximal femur fractures," Arch. Orthop. Trauma Surg. 117:39-42.
Kramer et al. (2009) "Increased pain and neurogenic inflammation in mice deficient of neutral endopeptidase," Neurobiol. Dis. 35(2):177-83.
Kvandal et al. (2006) "Low-frequency oscillations of the laser Doppler perfusion signal in human skin," Microvascular Research. 72:120-127.
Lacour et al. (2004) "Design and performance of thin metal film interconnects for skin-like electronic circuits," IEEE Electr. Device. Lett. 25:179-181.
Larranaga et al. (2012) "Heat Stress," In; Patty's Toxicology. 98:37-78.
Less et al. (1991) "Microvascular architecture in a mammary carcinoma: branching patterns and vessel dimensions," Cancer Research. 51:265-273.
Li et al. (2004) "Stretchability of thin metal films on elastomer substrates," Appl. Phys. Lett. 85:3435-3437.
Liao et al. (2012) "A 3-muhboxW CMOS Glucose Sensor for Wireless Contact-Lens Tear Glucose Monitoring," IEEE J. Solid State Circuits. 47:335-344.
Lindner (2004) "Microbubbles in medical imaging: Current applications and future directions," Nature Reviews Drug Discovery. 3:527-532.

(56) References Cited

OTHER PUBLICATIONS

Lossius et al. (1993) "Fluctuations in blood-flow to acral skin in humans—connection with heart-rate and blood-pressure variability," J. Physiol. 460:641-655.
Lu et al. (2012) "A thermal analysis of the operation of microscale, inorganic light-emitting diodes," Proceedings of the Royal Society A. 468:3215-3223.
Lu et al. (2012) "Highly Sensitive Skin-Mountable Strain Gauges Based Entirely on Elastomers," Adv. Funct. Mater. 22:4044-4050.
Lymberis (2010) "Advenced Wearable Sensors and Systems Enabling Personal Applications," In; Lecture Notes in Electrical Engineering: Wearable and Autonomous Biomedical Devices and Systems for Smart Environment. Eds.: Lay-Ekuakille et al. vol. 75. Springer. pp. 237-257.
Mangos et al. (1967) "Sodium Transport: Inhibitory Factor in Sweat of Patients with Cystic Fibrosis," Science. 158:135-136.
Mannsfeld et al. (2010) "Highly sensitive flexible pressure sensors with microstructured rubber dielectric layers," Nat. Mater. 9:859-864.
Marceau et al. (1983) "Pharmacology of kinins: their relevance to tissue injury and inflammation," Gen. Pharmacol. 14(2):209-29.
Martinez et al. (2007) "Patterned Paper as a Platform for Inexpensive, Low-Volume, Portable Bioassays," Angewandte Chemie International Edition. 46(8):1318-1320.
Martinez et al. (2008) "Simple Telemedicine for Developing Regions: Camera Phones and Paper-Based Microfluidic Devices for Real-Time, Off-Site Diagnosis," Analytical Chemistry. 80(10):3699-3707.
Martinez et al. (2010) "Diagnostics for the Developing World: Microfluidic Paper-Based Analytical Devices," Analytical Chemistry. 82(1):3-10.
Martinsen et al. (1999) "Measuring depth depends on frequency in electrical skin impedance measurements," Skin Research and Technology. 5(3):179-181.
Matzeu et al. (May 2015) "Advances in wearable chemical sensor design for monitoring biological fluids," Sensors and Actuators B. 211:403-418.
Mayrovitz et al. (2002) "Inspiration-induced vascular responses in finger dorsum skin," Microvasc. Res. 63:227-232.
McCartney et al. (2007) "Ultrasound Examination of Peripheral Nerves in the Forearm," Reg. Anesth. Pain Med. 32:434-439.
McDonald et al. (2002) "Poly(dimethylsiloxane) as a Material for Fabricating Microfluidic Devices," Accounts of Chemical Research. 35(7):491-499.
Mishra et al. (2005) "The Relevance of Sweat Testing for the Diagnosis of Cystic Fibrosis in the Genomic Era," Clin. Biochem. Rev. 26(4):135-153.
Moyer et al. (2012) "Correlation Between Sweat Glucose and Blood Glucose in Subjects with Diabetes," Diabetes Technology & Therapeutics. 14(5):398-402.
Mukerjee et al. (2004) "Microneedle Array for Transdermal Biological Fluid Extraction and In Situ Analysis," Sensors and Actuators A: Physical. 114(2-3):267-275.
Newman et al. (1984) "Liquid-crystal thermography in the evaluation of chronic back pain—a comparative-study," Pain. 20:293-305.
Nilsson et al. (1980) "Evaluation of a laser Doppler flowmeter for measurement of tissue blood flow," IEEE Transactions on Biomedical Engineering. 27:597-604.
Nitzan et al. (1986) "Theoretical-Analysis of the Transient Thermal Clearance Method for Regional Blood-Flow Measurement," Medical & Biological Engineering & Computing. 24:597-601.
Nitzan et al. (1988) "Simultaneous measurement of skin blood flow by the transient thermal-clearance method and laser Doppler flowmetry," Medical & Biological Engineering & Computing. 26:407-410.
Nopper et al. (2010) "Wireless Readout of Passive LC Sensors," IEEE Trans. Instrum. Meas. 59:2450-57.
Nordin (1990) "Sympathetic discharges in the human supraorbital nerve and their relation to sudo- and vasomotor responses," J. Physiol. 423:241-255.
Oberg (1990) "Laser-Doppler flowmetry," Critical Reviews in Biomedical Engineering. 18(2):125-163.
Oncescu et al. (Jun. 19, 2013) "Smartphone based health accessory for colorimetric detection of biomarkers in sweat and saliva," Lab Chip 13:3232-3238.
Paranjape et al. (2003) A PDMS dermal patch for non-intrusive transdermal glucose sensing. Sens. Actuat. A. 104:195-204.
Park et al. (2008) "The effect of heat on skin permeability," Int. J. Pharm. 359(1-2):94-103.
Pelrine et al. (2000) "High-field deformation of elastomeric dielectrics for actuators," Mater. Sci. Eng. C. 11:89-100.
Petrie et al. (1988) "How reproducible is bilateral forearm plethysmography?" British Journal of Clinical Pharmacology. 45:131-139.
Petrofsky (2012) "Resting blood flow in the skin: does it exist, and what is the influence of temperature, aging, and diabetes?" Journal of Diabetes Science and Technology. 6:674-685.
Pochaczevsky (1983) "The value of liquid-crystal thermography in the diagnosis of spinal root compression syndromes," Orthop. Clin. N. Am. 14:271-288.
Pochaczevsky et al. (1979) "Vacuum contoured, liquid-crystal, dynamic breast thermoangiography as an aid to mammography in the detection of breast-cancer," Clin. Radiol. 30:405-411.
Pochaczevsky et al. (1982) "Liquid crystal contact thermography of deep venous thrombosis," Am. J. Roentgenol. 138:717-723.
Pochaczevsky et al. (1982) "Liquid-crystal thermography of the spine and extremities—its value in the diagnosis of spinal root syndromes," J. Neurosurg. 56:386-395.
Polliack et al. (1997) "Sweat analysis following pressure ischaemia in a group of debilitated subjects," J. Rehabil. Res. Dev. 34(3):303-308.
Powers et al. (2009) :Rapid Measurement of Total Body Water to Facilitate Clinical Decision Making in Hospitalized Elderly Patients, J. Gerontol. A. Biol. Sci. Med. Sci. 64(6):664-9.
Prausnitz et al. (2008) "Transdermal drug delivery," Nature Biotechnology. 26(11):1261-1268.
Raamat et al. (2002) "Simultaneous recording of fingertip skin blood flow changes by multiprobe laser Doppler flowmetry and frequency-corrected thermal clearance," Microvascular Research. 64:214-219.
Rao et al. (2010) "Calibrations and the measurement uncertainty of wide-band liquid crystal thermography," Meas. Sci. Technol. 21(1):015105. pp. 1-8.
Ritz (2001) "Bioelectrical impedance analysis estimation of water compartments in elderly diseased patients: the source study," J. Gerontol. 56:M344-M348.
Robertson et al. (2010) "Variation in epidermal morphology in human skin at different body sites as measured by reflectance confocal microscopy," Acta Derm. Venereol. 90(4):368-73.
Roda et al. (Dec. 21, 2014) "A 3D-printed device for a smartphone-based chemilumin-escence biosensor for lactate in oral fluid and sweat," Analyst. 139:6494-6501.
Rogers et al. (2010) "Materials and mechanics for stretchable electronics," Science. 327:1603-1607.
Rose et al. (Nov. 11, 2014) "Adhesive RFID Sensor Patch for Monitoring of Sweat Electrolytes," IEEE Trans. Biomed. Eng. 62(6):1457-65.
Rosenbaum (2001) "Thermal properties and characterization of methane hydrates," M.S. thesis, University of Pittsburgh.
Sabatino et al. (2000) "A high-accuracy calibration technique for thermochromic liquid crystal temperature measurements," Exp. Fluids. 28:497-505.
Sage (2011) "Thermochromic liquid crystals," Liquid Crystals. 38:1551-1561.
Salvo et al. (2010) "A Wearable Sensor for Measuring Sweat Rate," IEEE Sens. J. 10:1557-1558.
Sandby-Moller et al. (2003) "Epidermal thickness at different body sites: Relationship to age, gender, pigmentation, blood content, skin type and smoking habits," Acta. Derm. Venereol. 83:410-413.
Sangkatumvong et al. (2011) "Peripheral vasoconstriction and abnormal parasympathetic response to sighs and transient hypoxia in sickle cell disease," Am. J. Respir. Crit. Care Med. 184:474-481.

(56) References Cited

OTHER PUBLICATIONS

Schrope et al. (1993) "Second harmonic ultrasonic blood perfusion measurement," Ultrasound in Medicine and Biology. 19:567-579.
Schwartz et al. (May 14, 2013) "Flexible polymer transistors with high pressure sensitivity for application in electronic skin and health monitoring," Nat. Commun. 4:1859. pp. 1-8.
Sekitani et al. (2008) "A rubberlike stretchable active matrix using elastic conductors," Science 321:1468-1472.
Sekitani et al. (2009) "Organic nonvolatile memory transistors for flexible sensor arrays," Science. 326:1516-1519.
Shen et al. (2006) "A genomewide scan for quantitative trait loci underlying areal bone size variation in 451 Caucasian families," J. Med. Genet. 43:873-880.
Shih et al. (2002) "Effect of effective tissue conductivity on thermal dose distributions of living tissue with directional blood flow during thermal therapy," International Communications in Heat and Mass Transfer. 29:115-126.
Shima et al. (1996) "An anatomical study on the forearm vascular system," J. Cranio. Maxill. Surg. 24:293-299.
Shpilfoygel et al. (2000) "X-ray videodensitometric methods for blood flow and velocity measurement: a critical review of literature," Medical Physics. 27:2008-2023.
Sieg et al. (2003) "Subcutaneous fat layer in different donor regions used for harvesting microvascular soft tissue flaps in slender and adipose patients," International Journal of Oral and Maxillofacial Surgery. 32:544-547.
Sikirzhytski et al. (2010) "Discriminant Analysis of Raman Spectra for Body Fluid Identification for Forensic Purposes," Sensors. 10(4):2869-2884.
Someya et al. (2005) "Conformable, flexible, large-area networks of pressure and thermal sensors with organic transistor active matrixes," Proc. Natl. Acad. Sci. USA. 102:12321-12325.
Son et al. (Mar. 30, 2014) "Multifunctional wearable devices for diagnosis and therapy of movement disorders," Nat. Nanotechnol. 9:397-404.
Sondheimer (1952) "The Mean Free Path of Electrons in Metals," Adv. Phys. 1:1-42.
Song et al. (1988) "A combined macro and microvascular model for whole limb heat transfer," J. Biomech. Eng. 110:259-268.
Stasiek et al. (2002) "Thermochromic liquid crystals applied for heat transfer research," Proceedings of the SPIE, vol. 4759:374-383.
Strommer et al. (2007) "Ultra-low Power Sensors with Near Field Communication for Mobile Applications," In; Wireless Sensor and Actor Networks. vol. 248. Springer. pp. 131-142.
Sun et al. (2009) "Inorganic islands on a highly stretchable polyimide substrate," J. Mater. Res. 24:3338-3342.
Sutera et al. (1993) "The History of Poiseuille's Law," Annu. Rev. Fluid Mech. 25:1-20.
Suzuki (1998) "Nickel and gold in skin lesions of pierced earlobes with contact dermatitis. A study using scanning electron microscopy and x-ray microanalysis," Arch. Dermatol. Res. 290:523-527.
Tee et al. (2012) "An electrically and mechanically self-healing composite with pressure- and flexion-sensitive properties for electronic skin applications," Nat. Nanotechnol. 7:825-832.
Ten Berge et al. (2011) "Perforating Veins: An Anatomical Approach to Arteriovenous Fistula Performance in the Forearm," European Journal of Vascular and Endovascular Surgery. 42:103-106.
Thalayasingam et al. (1989) "Thermal Clearance Blood-Flow Sensor Sensitivity, Linearity and Flow Depth Discrimination," Medical & Biological Engineering & Computing. 27:394-398.
Thomas et al. (1989) "Liquid-crystal thermography and c-reactive protein in the detection of deep venous thrombosis," Bri. Med. J. 299:951-952.
Thoresen et al. (1980) "Skin blood-flow in humans as a function of environmental-temperature measured by ultrasound," Acta Physiol. Scand. 109:333-341.
Togawa et al. (1994) "Non-contact imaging of thermal properties of the skin," Physiological Measurement. 15:291-298.

Van De Staak et al. (1968) "Measurements of Thermal Conductivity of Skin as an Indication of Skin Blood Flow," J. Invest. Dermatol. 51:149-154.
Varkey et al. (2011) "Human motion recognition using a wireless sensor-based wearable system," Pers. Ubiquit. Comput. 16(7):897-910.
Virkler et al. (2009) "Analysis of body fluids for forensic purposes: From laboratory testing to non-destructive rapid confirmatory identification at a crime scene," Forensci. Sci. Int. 188(1-3):1-17.
Wang et al. (2012) "Mechanics of Epidermal Electronics," Journal of Applied Mechanics. 79:031022.
Wang et al. (Jul. 21, 2013) "User-interactive electronic-skin for instantaneous pressure visualization," Nat. Mater. 12:899-904.
Wardell et al. (1993) "Laser Doppler perfusion imaging by dynamic light scattering," IEEE Transactions on Biomedical Engineering. 40:309-316.
Washburn (1921) "The Dynamics of Capillary Flow," Phys. Rev. 17(3):273.
Webb et al. (Feb. 6, 2015) "Thermal transport characteristics of human skin measured in vivo using ultrathin conformal arrays of thermal sensors and actuators," PLoS One. 10:e0118131. pp. 1-17.
Webb et al. (Oct. 30, 2015) "Epidermal devices for noninvasive, precise, and continuous mapping of macrovascular and microvascular blood flow," Sci Adv. 1(9):e1500701. pp. 1-13.
Webb et al. (Sep. 15, 2013) "Ultrathin conformal devices for precise and continuous thermal characterization of human skin," Nat. Mater. 12:938-944.
Weber et al. (2001) "Facilitated neurogenic inflammation in complex regional pain syndrome," Pain. 91(3):251-7.
Werner et al. (1992) "Measurement of the thermal diffusivity of human epidermis by studying thermal wave propagation," Physics in Medicine and Biology. 37:21-35.
Wilkinson et al. (2001) "Venous occlusion plethysmography in cardiovascular research: methodology and clinical applications," British Journal of Clinical Pharmacology. 52:631-646.
Windmiller et al. (Sep. 7, 2012) "Wearable Electrochemical Sensors and Biosensors: A Review," Electroanalysis. 25(1):29-46.
Wright et al. (2006) "Non-invasive methods and stimuli for evaluating the skin's microcirculation," Journal of Pharmacological and Toxicological Methods. 54:1-25.
Xiao et al. (1997) "Optothermal measurement of stratum corneum thickness and hydration-depth profile," In; The Proc. SPIE 2970, Lasers in Surgery: Advanced Characterization, Therapeutics, and Systems VII., 12 pgs.
Xiao et al. (2010) "Opto-thermal in-vivo skin hydration measurements—a comparison study of different measurement techniques," J. Phys. Conf. Ser. 214:012026. pp. 1-4.
Xiao et al. (2010) "Thermal diffusivity effect in opto-thermal skin measurements," J. Phys. Conf. Ser. 214:012027. pp. 1-4.
Xu et al. (Apr. 4, 2014) "Soft Microfluidic Assemblies of Sensors, Circuits, and Radios for the Skin," Science. 344:70-74.
Yamamoto et al. (1976) "Electrical properties of the epidermal stratum corneum," Medical and Biological Engineering. 14(2):151-158.
Yeo et al. (Feb. 26, 2013) "Multifunctional Epidermal Electronics Printed Directly Onto the Skin," Advanced Materials. 25:2773-2778.
Yu et al. (2012) "An Interstitial Fluid Transdermal Extraction System for Continuous Glucose Monitoring," J. Microelectromech. Syst. 21(4):917-925.
Zakharov et al. (2009) "A wearable diffuse reflectance sensor for continuous monitoring of cutaneous blood content," Physics in Medicine and Biology. 54:5301-5320.
Zamir et al. (2012) "Intrinsic microvasculature of the sciatic nerve in the rat," J. Peripher. Nerv. Syst. 17(4):377-84.
Zeng et al. (Jun. 18, 2014) "Fiber-Based Wearable Electronics: A Review of Materials, Fabrication, Devices, and Applications," Adv. Mater. 26:5310-5336.
International Search Report with Written Opinion corresponding to International Patent Application No. PCT/US2015/044573, dated Nov. 19, 2015, 8 pgs.

(56) References Cited

OTHER PUBLICATIONS

International Search Report with Written Opinion corresponding to International Patent Application No. PCT/US2015/044588, dated Jan. 7, 2016, 9 pgs.
International Search Report with Written Opinion corresponding to International Patent Application No. PCT/US2015/044638, dated Apr. 21, 2016, 23 pgs.
International Search Report with Written Opinion corresponding to International Patent Application No. PCT/US2015/053452, dated Mar. 10, 2016, 10 pgs.
U.S. Appl. No. 11/001,689, filed Dec. 1, 2004, 2006/0286488, Dec. 21, 2006, U.S. Pat. No. 7,704,684, Apr. 27, 2010.
U.S. Appl. No. 11/115,954, filed Apr. 27, 2005, 2005/0238967, Oct. 27, 2005, U.S. Pat. No. 7,195,733, Mar. 27, 2007.
U.S. Appl. No. 11/145,574, filed Jun. 2, 2005, 2009/0294803, Dec. 3, 2009, U.S. Pat. No. 7,622,367, Nov. 24, 2009.
U.S. Appl. No. 11/145,542, filed Jun. 2, 2005, 2006/0038182, Feb. 23, 2006, U.S. Pat. No. 7,557,367, Jul. 7, 2009.
U.S. Appl. No. 11/421,654, filed Jun. 1, 2006, 2007/0032089, Feb. 8, 2007, U.S. Pat. No. 7,799,699, Sep. 21, 2010.
U.S. Appl. No. 11/423,287, filed Jun. 9, 2006, 2006/0286785, Dec. 21, 2006, U.S. Pat. No. 7,521,292, Apr. 21, 2009.
U.S. Appl. No. 11/423,192, filed Jun. 9, 2006, 2009/0199960, Aug. 13, 2009, U.S. Pat. No. 7,943,491, May 17, 2011.
U.S. Appl. No. 11/465,317, filed Aug. 17, 2006.
U.S. Appl. No. 11/675,659, filed Feb. 16, 2007, 2008/0055581, Mar. 6, 2008.
U.S. Appl. No. 11/782,799, filed Jul. 25, 2007, 2008/0212102, Sep. 4, 2008, U.S. Pat. No. 7,705,280, Apr. 27, 2010.
U.S. Appl. No. 11/851,182, filed Sep. 6, 2007, 2008/0157235, Jul. 3, 2008, U.S. Pat. No. 8,217,381, Jul. 10, 2012.
U.S. Appl. No. 11/858,788, filed Sep. 20, 2007, 2008/0108171, May 8, 2008, U.S. Pat. No. 7,932,123, Apr. 26, 2011.
U.S. Appl. No. 11/981,380, filed Oct. 31, 2007, 2010/0283069, Nov. 11, 2010, U.S. Pat. No. 7,972,875, Jul. 5, 2011.
U.S. Appl. No. 12/372,605, filed Feb. 17, 2009.
U.S. Appl. No. 12/398,811, filed Mar. 5, 2009, 2010/0002402, Jan. 7, 2010, U.S. Pat. No. 8,552,299, Oct. 8, 2013.
U.S. Appl. No. 12/405,475, filed Mar. 17, 2009, 2010/0059863, Mar. 11, 2010, U.S. Pat. No. 8,198,621, Jun. 12, 2012.
U.S. Appl. No. 12/418,071, filed Apr. 3, 2009, 2010/0052112, Mar. 4, 2010, U.S. Pat. No. 8,470,701, Jun. 25, 2013.
U.S. Appl. No. 12/564,566, filed Sep. 22, 2009, 2010/0072577, Mar. 25, 2010, U.S. Pat. No. 7,982,296, Jul. 19, 2011.
U.S. Appl. No. 12/669,287, filed Jan. 15, 2010, 2011/0187798, Aug. 4, 2011, U.S. Pat. No. 9,061,494, Jun. 23, 2015.
U.S. Appl. No. 12/778,588, filed May 12, 2010, 2010/0317132, Dec. 16, 2010, U.S. Pat. No. 8,865,489, Oct. 21, 2014.
U.S. Appl. No. 12/844,492, filed Jul. 27, 2010, 2010/0289124, Nov. 18, 2010, U.S. Pat. No. 8,039,847, Oct. 18, 2011.
U.S. Appl. No. 12/892,001, filed Sep. 28, 2010, 2011/0230747, Sep. 22, 2011, U.S. Pat. No. 8,666,471, Mar. 4, 2014.
U.S. Appl. No. 12/916,934, filed Nov. 1, 2010, 2012/0105528, May 3, 2012, U.S. Pat. No. 8,562,095, Oct. 22, 2013.
U.S. Appl. No. 12/947,120, filed Nov. 16, 2010, 2011/0170225, Jul. 14, 2011, U.S. Pat. No. 9,057,994, Jun. 16, 2015.
U.S. Appl. No. 12/996,924, filed Dec. 8, 2010, 2011/0147715, Jun. 23, 2011, U.S. Pat. No. 8,946,683, Feb. 3, 2015.
U.S. Appl. No. 12/968,637, filed Dec. 15, 2010, 2012/0157804, Jun. 21, 2012.
U.S. Appl. No. 13/046,191, filed Mar. 11, 2011, 2012/0165759, Jun. 28, 2012.
U.S. Appl. No. 13/071,027, filed Mar. 24, 2011, 2011/0171813, Jul. 14, 2011, U.S. Pat. No. 8,895,406, Nov. 25, 2014.
U.S. Appl. No. 13/095,502, filed Apr. 27, 2011.
U.S. Appl. No. 13/100,774, filed May 4, 2011, 2011/0266561, Nov. 3, 2011, U.S. Pat. No. 8,722,458, May 13, 2014.
U.S. Appl. No. 13/113,504, filed May 23, 2011, 2011/0220890, Sep. 15, 2011, U.S. Pat. No. 8,440,546, May 14, 2013.
U.S. Appl. No. 13/120,486, filed Aug. 4, 2011, 2011/0277813, Nov. 17, 2011, U.S. Pat. No. 8,679,888, Mar. 25, 2014.
U.S. Appl. No. 13/228,041, filed Sep. 8, 2011, 2011/0316120, Dec. 29, 2011.
U.S. Appl. No. 13/270,954, filed Oct. 11, 2011, 2012/0083099, Apr. 5, 2012, U.S. Pat. No. 8,394,706, Mar. 12, 2013.
U.S. Appl. No. 13/349,336, filed Jan. 12, 2012, 2012/0261551, Oct. 18, 2012, U.S. Pat. No. 9,442,285, Sep. 13, 2016.
U.S. Appl. No. 13/441,618, filed Apr. 6, 2012, 2013/0100618, Apr. 25, 2013, U.S. Pat. No. 8,754,396, Jun. 17, 2014.
U.S. Appl. No. 13/441,598, filed Apr. 6, 2012, 2012/0327608, Dec. 27, 2012, U.S. Pat. No. 8,729,524, May 20, 2014.
U.S. Appl. No. 13/472,165, filed May 15, 2012, 2012/0320581, Dec. 20, 2012, U.S. Pat. No. 9,765,934, Sep. 19, 2017.
U.S. Appl. No. 13/486,726, filed Jun. 1, 2012, 2013/0072775, Mar. 21, 2013, U.S. Pat. No. 8,934,965, Jan. 13, 2015.
U.S. Appl. No. 13/492,636, filed Jun. 8, 2012, 2013/0041235, Feb. 14, 2013.
U.S. Appl. No. 13/549,291, filed Jul. 13, 2012, 2013/0036928, Feb. 14, 2013, U.S. Pat. No. 9,555,644, Jan. 31, 2017.
U.S. Appl. No. 13/596,343, filed Aug. 28, 2012, 2012/0321785, Dec. 20, 2012, U.S. Pat. No. 8,367,035, Feb. 5, 2013.
U.S. Appl. No. 13/624,096, filed Sep. 21, 2012, 2013/0140649, Jun. 6, 2013, U.S. Pat. No. 9,691,873, Jun. 27, 2017.
U.S. Appl. No. 13/801,868, filed Mar. 13, 2013, 2013/0320503, Dec. 5, 2013, U.S. Pat. No. 8,664,699, Mar. 4, 2014.
U.S. Appl. No. 13/835,284, filed Mar. 15, 2013, 2014/0220422, Aug. 7, 2014.
U.S. Appl. No. 13/853,770, filed Mar. 29, 2013, 2013/0333094, Dec. 19, 2013, U.S. Pat. No. 9,554,484, Jan. 24, 2017.
U.S. Appl. No. 13/974,963, filed Aug. 23, 2013, 2014/0140020, May 22, 2014, U.S. Pat. No. 8,905,772, Dec. 9, 2014.
U.S. Appl. No. 14/033,765, filed Sep. 23, 2013, 2014/0092158, Apr. 3, 2014, U.S. Pat. No. 9,278,522, Mar. 8, 2016.
U.S. Appl. No. 14/140,299, filed Dec. 24, 2013, 2014/0163390, Jun. 12, 2014.
U.S. Appl. No. 14/155,010, filed Jan. 14, 2014, 2014/0191236, Jul. 10, 2014, U.S. Pat. No. 9,450,043, Sep. 20, 2016.
U.S. Appl. No. 14/173,525, filed Feb. 5, 2014, 2014/0216524, Aug. 7, 2014, U.S. Pat. No. 9,105,782, Aug. 11, 2015.
U.S. Appl. No. 14/209,481, filed Mar. 13, 2014, 2014/0373898, Dec. 25, 2014, U.S. Pat. No. 9,117,940, Aug. 25, 2015.
U.S. Appl. No. 14/220,910, filed Mar. 20, 2014, 2014/0374872, Dec. 25, 2014, U.S. Pat. No. 9,324,733, Apr. 26, 2016.
U.S. Appl. No. 14/220,923, filed Mar. 20, 2014, 2015/0001462, Jan. 1, 2015, U.S. Pat. No. 9,105,555, Aug. 11, 2015.
U.S. Appl. No. 14/246,962, filed Apr. 7, 2014, 2014/0361409, Dec. 11, 2014, U.S. Pat. No. 9,349,900, May 24, 2016.
U.S. Appl. No. 14/251,259, filed Apr. 11, 2014, 2014/0323968, Oct. 30, 2014.
U.S. Appl. No. 14/250,671, filed Apr. 11, 2014, 2014/0305900, Oct. 16, 2014, U.S. Pat. No. 9,496,229, Nov. 15, 2016.
U.S. Appl. No. 14/479,100, filed Sep. 5, 2014, 2015/0132873, May 14, 2015, U.S. Pat. No. 9,647,171, May 9, 2017.
U.S. Appl. No. 14/504,736, filed Oct. 2, 2014, 2015/0141767, May 21, 2015.
U.S. Appl. No. 14/521,319, filed Oct. 22, 2014, 2015/0181700, Jun. 25, 2015.
U.S. Appl. No. 14/532,687, filed Nov. 4, 2014, 2015/0080695, Mar. 19, 2015.
U.S. Appl. No. 14/599,290, filed Jan. 16, 2015, 2015/0207012, Jul. 23, 2015.
U.S. Appl. No. 14/686,304, filed Apr. 14, 2015, 2015/0290938, Oct. 15, 2015, U.S. Pat. No. 9,487,002, Nov. 8, 2016.
U.S. Appl. No. 14/706,733, filed May 7, 2015, 2015/0237711, Aug. 20, 2015.
U.S. Appl. No. 14/789,645, filed Jul. 1, 2015, 2016/0027737, Jan. 28, 2016, U.S. Pat. No. 9,515,025, Dec. 6, 2016.
U.S. Appl. No. 14/800,363, filed Jul. 15, 2015, 2016/0072027, Mar. 10, 2016, U.S. Pat. No. 9,601,671, Mar. 21, 2017.
U.S. Appl. No. 14/818,109, filed Aug. 4, 2015, 2016/0050750, Feb. 18, 2016.

(56) References Cited

OTHER PUBLICATIONS

U.S. Appl. No. 14/766,333, filed Aug. 6, 2015, 2015/0380355, Dec. 31, 2015, U.S. Pat. No. 9,613,911, Apr. 4, 2017.
U.S. Appl. No. 14/766,926, filed Aug. 10, 2015, 2016/0066789, Mar. 10, 2016.
U.S. Appl. No. 14/772,354, filed Sep. 2, 2015, 2016/0005700, Jan. 7, 2016, U.S. Pat. No. 9,875,974, Jan. 23, 2018.
U.S. Appl. No. 14/772,312, filed Sep. 2, 2015, 2016/0133843, May 12, 2016, U.S. Pat. No. 9,825,229, Nov. 21, 2017.
U.S. Appl. No. 14/944,039, filed Nov. 17, 2015, 2016/0136877, May 19, 2016.
U.S. Appl. No. 14/766,301, filed Dec. 24, 2015, 2015/0373831, Dec. 24, 2015.
U.S. Appl. No. 15/084,091, filed Mar. 29, 2016, 2016/0284544, Sep. 29, 2016, U.S. Pat. No. 9,761,444, Sep. 12, 2017.
U.S. Appl. No. 15/084,211, filed Mar. 29, 2016, 2016/0293794, Oct. 6, 2016, U.S. Pat. No. 9,768,086, Sep. 19, 2017.
U.S. Appl. No. 15/084,112, filed Mar. 29, 2016, 2016/0381789, Dec. 29, 2016.
U.S. Appl. No. 15/146,629, filed May 4, 2016, 2017/0020402, Jan. 26, 2017.
U.S. Appl. No. 15/339,338, filed Oct. 31, 2016, 2017/0200679, Jul. 13, 2017.
U.S. Appl. No. 15/349,525, Nov. 11, 2016, 2017/0128015, May 11, 2017.
U.S. Appl. No. 15/351,234, filed Nov. 14, 2016, 2017/0164482, Jun. 8, 2017.
U.S. Appl. No. 15/354,951, filed Nov. 17, 2016, 2017/0291817, Oct. 12, 2017.
U.S. Appl. No. 15/374,926, filed Dec. 9, 2016, 2017/0210117, Jul. 27, 2017.
U.S. Appl. No. 15/375,514, filed Dec. 12, 2016, 2017/0181704, Dec. 12, 2016.
U.S. Appl. No. 15/402,684, filed Jan. 10, 2017, 2017/0179100, Jun. 22, 2017.
U.S. Appl. No. 15/402,718, filed Jan. 10, 2017, 2017/0179085, Jan. 10, 2017.
U.S. Appl. No. 15/402,723, filed Jan. 10, 2017, 2017/0179356, Jun. 22, 2017.
U.S. Appl. No. 15/501,364, filed Feb. 2, 2017, 2017/0224257, Aug. 10, 2017.
U.S. Appl. No. 15/501,373, filed Feb. 2, 2017, 2017/0231571, Aug. 17, 2017.
U.S. Appl. No. 15/470,780, filed Mar. 27, 2017, 2017/0200707, Jul. 13, 2017.
U.S. Appl. No. 15/515,494, filed Mar. 29, 2017, 2017/0347891, Dec. 7, 2017.
U.S. Appl. No. 15/477,865, filed Apr. 3, 2017, 2017/0365557, Dec. 21, 2017.
U.S. Appl. No. 15/625,087, filed Jun. 16, 2017, 2018/0064377, Mar. 8, 2018.
U.S. Appl. No. 15/632,004, filed Jun. 23, 2017.
U.S. Appl. No. 15/640,206, filed Jun. 30, 2017, 2017/0309733, Oct. 26, 2017.
U.S. Appl. No. 15/578,602, filed Nov. 30, 2017.
U.S. Appl. No. 15/578,617, filed Nov. 30, 2017.
U.S. Appl. No. 15/741,081, filed Dec. 29, 2017.
U.S. Appl. No. 15/738,043, filed Dec. 19, 2017.
U.S. Appl. No. 15/861,257, filed Jan. 3, 2018.
U.S. Appl. No. 15/865,033, filed Jan. 8, 2018.
PCT/US16/35331, Jun. 1, 2016, WO 2016/196673, Dec. 8, 2016.
PCT/US16/35336, Jun. 1, 2016, WO 2016/196675, Dec. 8, 2016.
PCT/US16/40717, Jul. 1, 2016, WO 2017/004531, Jan. 5, 2017.
PCT/US16/40814, Jul. 1, 2016, WO 2017/004576, Jan. 5, 2017.
European Office Communication, corresponding to European Patent Application No. 15831510.1, dated Jan. 28, 2019, 10 pages.
Su et al. (2011) "A polymer stacking process with 3D electrical routings for flexible temperature sensor array and its heterogeneous integration," In; The 16th International Solid-State Sensors, Actuators and Microsystems Conference (Transducers), 2011. pp. 1396-1399.
Supplementary European Search Report corresponding to European Patent Application No. 15831510.1, dated Mar. 8, 2018.
First Office Action, CN Application No. 201580055213.7, dated Jun. 24, 2019, English translation, 9 pages.
Notice of Reasons for Rejection, JP Application No. P2017-507720, dated May 14, 2019, English translation, 7 pages.

\* cited by examiner

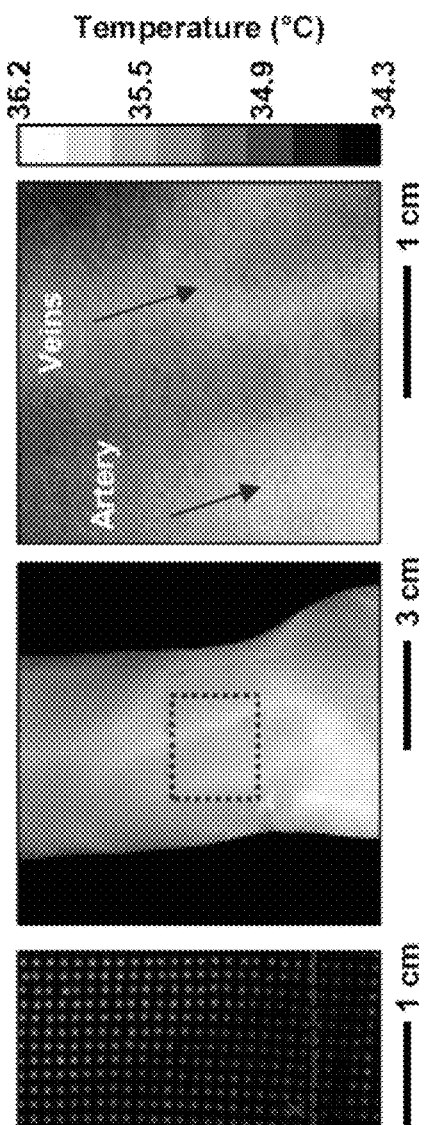
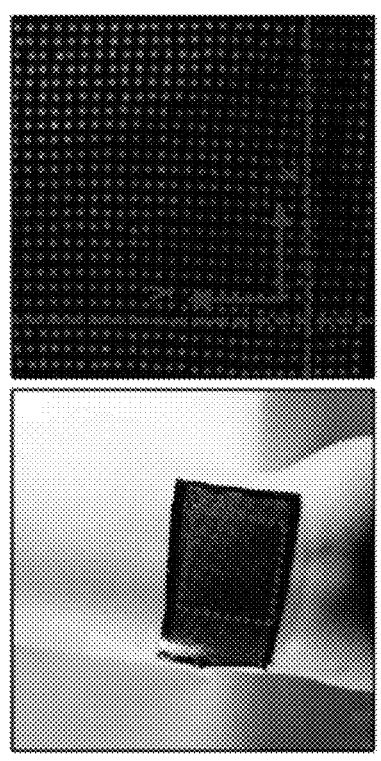
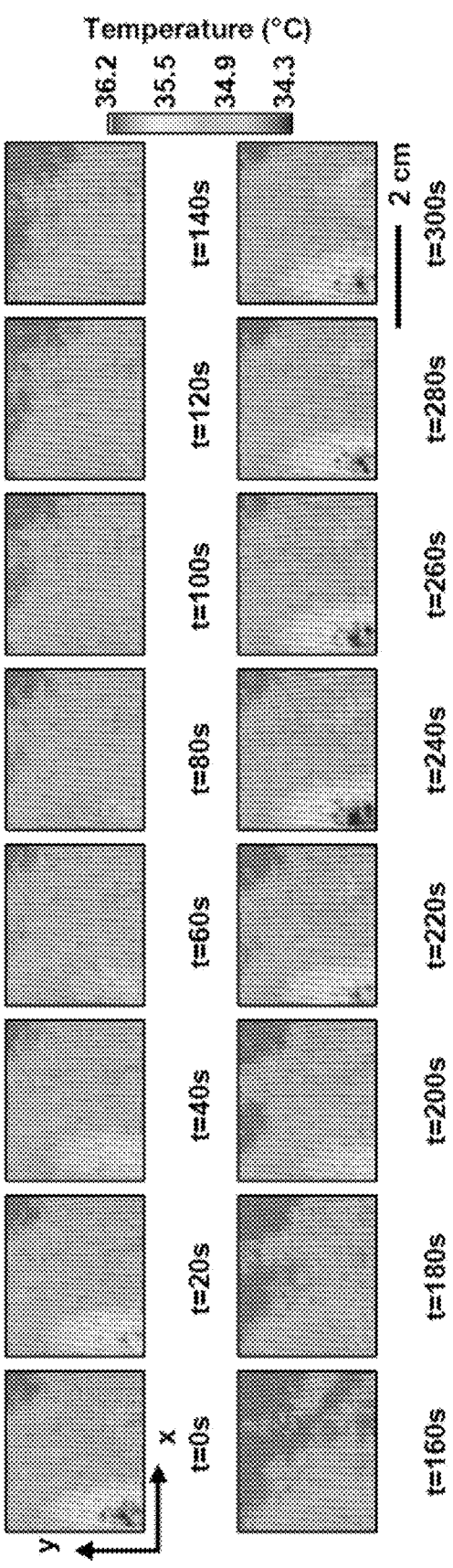
FIG. 33A
FIG. 33B
FIG. 33C

EPIDERMAL DEVICES FOR ANALYSIS OF TEMPERATURE AND THERMAL TRANSPORT CHARACTERISTICS

CROSS-REFERENCE TO RELATED APPLICATIONS

This application is a U.S. National Stage Application under 35 U.S.C. § 371 of International Application No. PCT/US2015/044588, filed Aug. 11, 2015, which claims the benefit of and priority to U.S. Provisional Patent Application No. 62/035,866, filed Aug. 11, 2014, each of which is hereby incorporated by reference in its entirety to the extent not inconsistent herewith.

STATEMENT REGARDING FEDERALLY SPONSORED RESEARCH OR DEVELOPMENT

This invention was made with government support under DGE-1144245 awarded by the National Science Foundation and 1 ZIA HL006012 04 awarded by the National Institutes of Health. The government has certain rights in the invention.

BACKGROUND

Wearable electronics are a class of systems with potential to broadly impact a range of technologies, industries and consumer products. Advances in wearable systems are driven, in part, by development of new materials and device architectures providing for new functionalities implemented using device form factors compatible with the body. Wearable consumer products are available, for example, that exploit small and portable electronic and/or photonic systems provided in body mounted form factors, such as systems building off of conventional body worn devices such as eye glasses, wrist bands, foot ware, etc. New device platforms are also under development to extend the range of wearable technology applications including smart textiles and stretchable/flexible electronic systems incorporating advanced electronic and photonic functionality in spatially complaint form factors compatible with low power operation, wireless communication and novel integration schemes for interfacing with the body. (See, e.g., Kim et al., Annu. Rev. Biomed. Eng. 2012.14; 113-128; Windmiller, et al., Electroanalysis; 2013, 25, 1, 29-46; Zeng et al., Adv. Mater., 2014, 26, 5310-5336; Ahn et al., J Phys. D: Appl. Phys., 2012, 45, 103001.)

Tissue mounted systems represents one class of wearable systems supporting diverse applications in healthcare, sensing, motion recognition and communication. Recent advances in epidermal electronics, for example, provide a class of skin-mounted electronic systems provided in physical formats enabling mechanically robust and physically intimate contact with the skin. Certain classes of epidermal electronic systems have been developed, for example, combining high performance stretchable and/or ultrathin functional materials with soft elastic substrates implemented in device geometries useful for establishing and maintaining conformal contact with the soft, curvilinear and time varying surface of the skin. (See, e.g., US Publication No. 2013/0041235; W. H. Yeo, Y. S. Kim, J. Lee, A. Ameen, L. Shi, M. Li, S. Wang, R. Ma, S. H. Jin, Z. Kang, Y. Huang and J. A. Rogers, "Multifunctional Epidermal Electronics Printed Directly Onto the Skin," Advanced Materials 25, 2773-2778 (2013).) Critical to adoption of the emerging class of epidermal electronic systems is the continued development of devices supporting a wide range of applications for this technology including for personal healthcare assessment and clinical medicine.

It will be appreciated from the foregoing that tissue mounted systems are needed to support the rapidly emerging applications in wearable electronics. New epidermal systems are needed, for example, providing new sensing, readout and analysis modalities to support diverse technology applications in physiological and environmental sensing.

SUMMARY OF THE INVENTION

The invention provides systems and methods for tissue-mounted electronic and photonics systems. Devices of some embodiments implement thermal sensing and actuation in flexible and stretchable device architectures compatible with achieving long term, mechanically robust conformal integration with a range of tissue classes, including in vivo biometric sensing for internal and external tissues. Tissue-mounted electronic and photonic systems of some embodiments combine thermal actuation with colorimetric and/or electronic thermal sensing provided in array formats on soft, elastomeric substrates to achieve spatially and/or temporally resolved sensing of thermal transport properties of tissue, while minimizing adverse physical effects to the tissue. Tissue-mounted electronic and photonic systems of some embodiments enable robust thermal transport sensing that may provide information relating to a range of physiological and/or physical properties of tissue including hydration state and/or vasculature information (e.g. blood flow rate and direction). Tissue-mounted electronic and photonic systems of some embodiments have a low effective modulus and small thickness providing mechanical properties compatible with a range of deployment modes such as direct adhesion on the surface of a tissue and deployment using adhesives or intermediate bonding structures.

Photonic structures useful in the present systems and methods include structures incorporating optical indicators, such as colorimetric or fluorometric indicators, having optical properties that are useful for characterizing tissue parameters or environmental parameters. In an embodiment, for example, at least a portion of the pixels comprise a colorimetric indicator, fluorometric indicator or both, including devices including pixels corresponding to different colorimetric and/or fluorometric indicators. The invention is compatible with a range of photonic structures incorporating indicators including embedded and/or encapsulated structures. In an embodiment, for example, the photonic structures are micro-encapsulated structures and/or nano-encapsulated structures, for example, having an indicator that is encapsulated by one or more encapsulation structures, such as laminating, embedding or encapsulation layers. In an embodiment, the micro-encapsulated structures and/or nano-encapsulated structures are in physical, thermal, optical or electrical contact with the tissue of a material(s) derived from the tissue, such as a biofluid.

In an embodiment, for example, at least a portion of the pixels comprise a colorimetric indicator that is a liquid crystal, an ionochromic dye, a pH indicator, a chelating agent, a fluorophore or a photosensitive dye. In an embodiment, for example, at least a portion of the pixels comprise a colorimetric indicator capable of generating a photonic response for characterizing a temperature, exposure to electromagnetic radiation or a chemical composition of a tissue or material derived from tissue. In an embodiment, for example, at least a portion of the pixels comprise a colorimetric indicator comprising a thermochromic liquid crystal that undergoes a measurable change in the wavelength of light that is absorbed, transmitted or scattered upon a change of the tissue parameter. In an embodiment, for example, at least a portion of the pixels comprise a colorimetric indicator comprising a chiral nematic liquid crystal that undergoes a measurable change in the wavelength of light that is absorbed, transmitted or scattered upon a change in temperature of the tissue.

In an embodiment, for example, at least a portion of the pixels comprise a colorimetric indicator comprising an ionochromic dye that under goes a measurable change in the wavelength of light that is absorbed, transmitted or scattered in response to a composition or property of the tissue or a material derived from the tissue such as a biological fluid. In an embodiment, for example, the composition or property of the biological fluid corresponds to a change in pH, concentration of free copper ion, or concentration of iron ion. In an embodiment, for example, at least a portion of the pixels comprise a colorimetric indicator that undergoes a measurable change in color in response to exposure to ultraviolet radiation. In an embodiment, for example, the photonic structures include colorimetric or fluorometric indicators that change optical properties upon contact with a biomarker in the tissue or in a material derived from the tissue such as a biological fluid In an embodiment, for example, the pixelated array further comprises one or more calibration pixels, such as dots having a fixed color.

In an embodiment, for example, the device further comprises one or more optical components supported by the stretchable or flexible substrate, and optionally provided in optical communication with the photonic structures. In an embodiment, for example, the optical components are one or more of a light collecting optical component, a light concentrating optical component, a light diffusing optical component, a light dispersing optical component and a light filtering optical component. In an embodiment, for example, the optical components are one or more of a lens, a lens array, a reflector, an array of reflectors, a waveguide, an array of waveguides, an optical coating, an array of optical coatings, an optical filter, an array of optical filters, a fiber optic element and an array of fiber optic elements.

The device level mechanical, thermal, electronic and optical properties of the present photonic devices is important for supporting a range of technology applications. In an embodiment, for example, the device has a modulus within a factor of 1,000, and optionally a factor of 10, of a modulus of the tissue at the interface with the device. In an embodiment, for example, the device has an average modulus less than or equal to 100 MPa, optionally for some embodiments less than or equal to 500 kPa, optionally for some embodiments less than or equal to 200 kPa and optionally for some embodiments less than or equal to 100 kPa. In an embodiment, for example, the device has an average modulus selected over the range of 0.5 kPa to 100 MPa, optionally for some embodiments selected over the range of 0.5 kPa to 500 kPa, optionally for some embodiments selected over the range of 1 kPa to 200 kPa.

Matching the physical dimensions and properties of the devices to that of the tissue is a useful design strategy in some embodiments to achieve robust conformal contact. In an embodiment, for example, the device has an average modulus equal to or less than 100 times, optionally equal to or less than 10 times, the average modulus of the tissue at the interface. In an embodiment, for example, the device has an average thickness less than or equal to 3000 microns, optionally for some embodiments less than or equal to 1,000 microns. In an embodiment, for example, the device has an average thickness selected over the range of 1 to 1,000 microns. In an embodiment, for example, the device has a net bending stiffness less than or equal to 1 mN m, optionally for some embodiments less than or equal to 1 nN m, optionally for some embodiments less than or equal to 0.1 nN m and optionally for some embodiments less than or equal to 0.05 nN m. In an embodiment, for example, the device has a net bending stiffness selected over the range of 0.01 nN m to 1 N m, optionally for some applications selected over the range of 0.01 to 1 nN m, and optionally for some embodiments selected over the range of 0.1 to 1 nN m. In an embodiment, for example, the device has an areal mass density less than or equal to 100 mg cm$^{-2}$, optionally for some applications less than or equal to 10 mg cm$^{-2}$. In an embodiment, for example, the device has an areal mass density selected over the range of 0.1 mg cm$^{-2}$ to 100 mg cm$^{-2}$, optionally for some applications elected over the range of 0.5 mg cm$^{-2}$ to 10 mg cm$^{-2}$. In an embodiment, the device is characterized by a stretchability greater than or equal to 5% and optionally for some applications 50% and optionally for some applications 100%, for example, by being able to undergo stretching to this extent without mechanical failure. In an embodiment, the device is characterized by a stretchability selected from the range of 5% to 200% and optionally for some applications 20% to 200%, for example, by being able to undergo stretching to this extent without mechanical failure.

In an embodiment, for example, at least a portion of the pixels comprise a colorimetric indicator comprising an ionochromic dye that under goes a measurable change in the wavelength of light that is absorbed, transmitted or scattered upon a change in the composition of the tissue or a material derived from the tissue such as a biological fluid. In an embodiment, for example, the change in the composition of the biological fluid corresponds to a change in pH, concentration of free copper ion, or concentration of iron ion. In an embodiment, for example, at least a portion of the pixels comprise a colorimetric indicator that undergoes a measurable change in color in response to exposure to ultraviolet radiation. In an embodiment, for example, the photonic structures include colorimetric or fluorometric indicators that change optical properties upon contact with a biomarker in the tissue or in a material derived from the tissue such as a biological fluid.

In one aspect, the invention provides a device for interfacing with a tissue in a biological environment, the device comprising: (i) a flexible or stretchable substrate; and (ii) one or more thermal actuators and a plurality of thermal sensors supported by the flexible or stretchable substrate, the one or more thermal actuators and the plurality of thermal sensors for characterizing a thermal transport property of the tissue; wherein the flexible or stretchable substrate, the one or more thermal actuators and the plurality of thermal sensors provide a net bending stiffness (and/or Young's modulus) such that the device is capable of establishing conformal contact with a surface of the tissue. In an embodiment, for example, the device is for thermally sensing and actuating the tissue so as to characterize physical, chemical and/or physiological properties of the tissue. In an embodiment, the device is for spatial and/or temporally characterizing tissue parameters, for example, in connection with characterization of physiological, chemical and or environment properties of the tissue at, or below, the surface of the tissue and/or corresponding to materials derived from the tissue, e.g., biofluids such as blood. In an embodiment, for example, the device is for the device is for thermal sensing and actuating tissue in an in vivo biological environment. In an embodiment, the device is a tissue-mounted device, for example, a device that is conformally interfaced with a surface of, and in physical contact with, a tissue surface.

In an embodiment, for example, the one or more thermal actuators and the plurality of thermal sensors spatially characterize the thermal transport property of the tissue, for example, as a function of position on the surface of the tissue or in connection with one or more physiological features (e.g., vasculature features). In an embodiment, for example, the one or more thermal actuators and the plurality of thermal sensors temporally characterize the thermal transport property of the tissue, such as thermal transport as a function of time. In an embodiment, for example, the thermal sensors are for characterizing a spatio temporal distribution of temperature resulting from heating provided by the one or more thermal actuators, for example, and in connection with physiological function, overall health of the tissue, and/diagnostic evaluation of the tissue.

The present methods are useful for characterization of a range of thermal, physiological and physical properties of a tissue. In an embodiment, for example, the thermal transport property is thermal conductivity, thermal diffusivity, heat capacity or a combination of these. In an embodiment, for example, the thermal transport property correlates with a tissue property selected from the group consisting of hydration state, inflammation state, occlusion state and any combination of these. In an embodiment, for example, the thermal transport property correlates with a physiological parameter selected from the group consisting of macrovascular blood flow direction, macrovascular blood flow rate, microvascular blood flow direction, microvascular blood flow rate, presence of an occlusion, macrovascular perfusion, microvascular perfusion, circulation changes due to inflammation, and any combination of these.

Device of certain embodiments the invention have a combination of physical and chemical properties and device geometries designed to minimize impact on the tissue while enabling a mechanically robust conformal tissue interface. In an embodiment, for example, the device does not substantially impact the natural temperature of the tissue upon establishing conformal contact. In an embodiment, for example, the device has an average thickness less than or equal to 1,000 microns, optionally for some embodiments less than 100 microns. In an embodiment, for example, the device has a thermal mass per area less than or equal to 50 mJ cm$^{-2}$ K$^{-1}$ and for some applications less than or equal to 10 mJ cm$^{-2}$ K$^{-1}$. In an embodiment, for example, the device has a gas permeability greater than or equal to 20 g h$^{-1}$m$^{-2}$, and for some applications greater than or equal to 5 g h$^{-1}$m$^{-2}$. In an embodiment, for example, the device has an area density less than or equal to 10 mg cm$^{-2}$.

Actuators and sensors having a range of physical and chemical properties are useful in the present devices and methods. In an embodiment, for example, the thermal actuators and thermal sensors comprise stretchable or flexible structures. In an embodiment, for example, the thermal actuators and thermal sensors comprise thin film structures. In an embodiment, for example, the thermal actuators and thermal sensors comprise filamentary metal structures. In an embodiment, for example, the thermal sensors provide a spatial resolution greater than or equal to 10 μm. In an embodiment, for example, the thermal sensors provide a temporal resolution greater than or equal to 1 μs.

In an embodiment, for example, the thermal actuators and thermal sensors are flexible or stretchable structures, for example, exhibiting stretchability without failure of greater than or equal to 20%, and greater than or equal 50% for some embodiments and greater than or equal 100% for some embodiments. In an embodiment, for example, the thermal actuators and thermal sensors are microstructures (e.g., having physical dimensions selected from the range of 1 micron to 1,000 microns) and/or nanostructures (e.g., having physical dimensions selected from the range of 1 nm to 1,000 nm). In an embodiment, for example, the thermal actuators and thermal sensors are characterized by an average modulus less than or equal to 500 kPa or have an average modulus selected over the range of 0.5 kPa to 500 kPa. In an embodiment, for example, the thermal actuators and thermal sensors are characterized by average lateral dimensions selected from the range of 10 μm to 1,000 μm and/or average thickness selected from the range of 1 μm to 100 μm. In an embodiment, for example, the thermal actuators and thermal sensors are capable of mechanical deformation in response to a stimulus, such as a change in temperature, input of energy, physical stress, etc. In an embodiment, for example, at least a portion of the one or more thermal actuators and thermal sensors are in thermal communication with the tissue. In an embodiment, for example, at least a portion of the thermal actuators and thermal sensors are in physical contact, fluid communication, optical communication, and/or electrical communication with the surface of the tissue.

The devices of the invention may be used in a variety of modalities to provide accurate tissue characterization. In an embodiment, for example, at least one of the thermal sensors is a temperature sensor for measuring background temperature to compensate for drift. In an embodiment, for example, the thermal actuators provide a power input to the tissue selected over the range of 0.1 mW mm$^{-2}$ to 50 mW mm$^{-2}$. In an embodiment, for example, the thermal actuators provide a constant heating of the tissue. In an embodiment, for example, the thermal actuators provide a pulsed heating of the tissue. In an embodiment, for example, the thermal sensors are symmetrically arranged with respect to the one or more thermal actuators. In an embodiment, for example, two of the thermal sensors form matched pairs on opposite sides of the thermal actuator for obtaining comparative data as an indication of an anisotropic thermal transport property. In an embodiment, for example, the anisotropic thermal transport property indicates a direction of blood flow Useful thermal actuators and thermal sensors for some embodiments of the present systems and methods are spatially distributed in an array, such as an array with individual thermal actuators and thermal sensors individually in physical, optical or thermal contact with specific regions of the tissue surface. Thermal actuators and thermal sensors provided in an array form factor is useful in certain systems and methods to provide characterization or spatial information corresponding to the tissue or tissue environment, such as a spatial distribution of tissue parameters with respect to a tissue surface. In an embodiment, for example, the array of thermal actuators and thermal sensors is a pixelated array; wherein each thermal actuator and thermal sensor provides an individual pixel independently corresponding to an individual position the array. In an embodiment, for example, individual pixels or the array have average lateral dimensions selected from the range of 10 μm to 1 cm, optionally for some embodiments selected from the range of 100 μm to 500 μm and further optionally for some embodiments selected from the range of 200 μm to 500 μm. In an embodiment, for example, the individual pixel of the actuator has an area 9× greater than an area of the individual pixel of the sensor, optionally for some embodiments an area 20× greater. In an embodiment, for example, the individual pixels have average thickness selected from the range of 1 µm to 1,000 µm, optionally for some embodiments selected from the range of 10 µm to 500 µm and further optionally for some embodiments selected from the range of 20 µm to 100 µm. In an embodiment, for example, the individual pixels are spaced from adjacent pixels in the array other by a distance selected from the range of 10 µm to 1,000 µm, optionally for some embodiments a distance selected from the range of 100 µm to 1,000 µm and further optionally for some embodiments a distance selected from the range of 250 µm to 500 µm. In an embodiment, for example, the pixelated array comprises 10 to 1,000,000 pixels, optionally for some embodiments 10 to 100,000 pixels. In an embodiment, for example, the pixelated array has an footprint selected from the range of 10 mm$^2$ to 2,000 cm$^2$, or 300 mm$^2$ to 2,000 cm$^2$.

Thermal sensors and actuators of the invention may be provided in a range of geometries supporting diverse sensing applications. In an embodiment, for example, the thermal sensors are arranged as one or more concentric rings having one of the thermal actuators at a center of the one or more concentric rings. In an embodiment, for example, at least a portion of the pixels comprise micro-encapsulated structures or nano-encapsulated structures. Thermal sensors useful in the present systems and methods include structures incorporating optical indicators, such as colorimetric or fluorometric indicators, capable of undergoing a change in an optical property resulting from a change in one or more tissue parameter, such as temperature. In an embodiment, for example, at least a portion of the pixels comprise a colorimetric indicator comprising a thermochromic liquid crystal that under goes a measurable change in the wavelength of light that is absorbed, transmitted or scattered upon a change of temperature. In an embodiment, for example, at least a portion of the pixels comprise a colorimetric indicator comprising chiral nematic liquid crystal that under goes a measurable change in the wavelength of light that is absorbed, transmitted or scattered upon a change in temperature of the tissue. In an embodiment, for example, the pixelated array further comprises one or more calibration pixels, such as dots having a fixed color.

A range of substrates are useful in embodiments of the present devices and methods. In some embodiment, the substrate is a functional substrate. Use of low modulus and thin substrates are beneficial in some embodiments for achieving a conformal contact with tissue surface having complex morphologies without delamination and achieving a conformal contact without movement of the device relative to the contact surface of the tissue, for example, during movement of tissue. Use of selectively colored or optically opaque substrates are useful for providing contrast sufficient for effective optical readout, for example, via imaging using a mobile electronic device. Use of porous substrates and substrates having fluidic structures (e.g., active or passive fluidic channels) are beneficial for embodiments capable of characterizing properties of fluids from the tissue.

In an embodiment, for example, the substrate is optically opaque. In an embodiment, for example, the flexible or stretchable substrate incorporates one or more fluidic structures for collecting or transporting fluid from the tissue. In an embodiment, for example, the flexible or stretchable substrate comprises an elastomer. In an embodiment, for example, the flexible or stretchable substrate is a low modulus rubber material or a low modulus silicone material. In an embodiment, for example, the flexible or stretchable substrate is a bioinert or biocompatible material. In an embodiment, for example, the flexible or stretchable substrate comprises a gas-permeable elastomeric sheet. In an embodiment, for example, the flexible or stretchable substrate has an average modulus less than or equal to 100 MPa, or less than or equal to 1 MPa, or less than or equal to 500 kPa. In an embodiment, for example, the flexible or stretchable substrate has an average modulus selected over the range of 0.5 kPa to 100 MPa or 0.5 kPa to 500 kPa. In an embodiment, for example, the flexible or stretchable substrate has an average thickness less than or equal to 3 mm, or less than or equal to 1 mm, or less than or equal to 1,000 microns. In an embodiment, for example, the flexible or stretchable substrate has an average thickness selected over the range of 1 to 3000 microns, or 1 to 1,000 microns.

Devices of the invention may further comprise a range of additional device components. In an embodiment, for example, the device further comprises one or more additional device components supported by the flexible or stretchable substrate, the device components selected from the group consisting of an electrode, strain gauge, optical source, temperature sensor, wireless power coil, solar cell, wireless communication component, photodiode, microfluidic component, inductive coil, high frequency inductor, high frequency capacitor, high frequency oscillator, high frequency antennae, multiplex circuits, electrocardiography sensors, electromyography sensors, electroencephalography sensors, electrophysiological sensors, thermistors, transistors, diodes, resistors, capacitive sensors, and light emitting diodes. In an embodiment, for example, the device further comprises one or more wireless communication antenna structures or near-field communication coil supported by the flexible or stretchable substrate. In an embodiment, for example, the device further comprises one or more single crystalline semiconductor structures supported by the flexible or stretchable substrate.

In an embodiment, for example, the one or more actuators and/or the plurality of sensors are connected by an electronic circuit. In an embodiment, for example, the electronic circuit is flexible or stretchable. In an embodiment, for example, the flexible or stretchable electronic circuit comprises one or more electronic devices or device components having a curved, serpentine, bent, wavy or buckled geometry. In an embodiment, for example, the electronic circuit comprises a plurality of electrodes selected from the group consisting of meander electrodes, interdigitated electrodes, circular electrodes and annular electrodes. In an embodiment, for example, the flexible or stretchable substrate and the electronic circuit provide a net bending stiffness of the device less than or equal to 0.1 mN m, less than or equal to 20 nN m, optionally less than or equal to 5 nNm.

In some embodiment, the thermal actuators and thermal sensors are in physical contact with the substrate. Devices of the invention include multilayer devices, for example, including one or more additional layer such as encapsulating layers at least partially encapsulating the thermal actuators and thermal sensors, and/or intermediate layers provided between the one or more thermal actuators and thermal sensors and the substrate.

The device level mechanical, thermal, electronic and optical properties of the present devices is important for supporting a range of tissue-mounted technology applications. In an embodiment, for example, the device has a modulus within a factor of 1,000, 100, 10 or 2 of a modulus of the tissue at the interface with the device. In an embodiment, for example, the device has an average modulus less than or equal to 100 MPa, optionally for some embodiments less than or equal to 500 kPa, optionally for some embodiments less than or equal to 200 kPa and optionally for some embodiments less than or equal to 100 kPa. In an embodiment, for example, the device has an average modulus selected over the range of 0.5 kPa to 100 MPa, optionally for some embodiments selected over the range of 0.5 kPa to 500 kPa, and optionally for some embodiments selected over the range of 1 kPa to 200 kPa. In an embodiment, for example, the device has an average modulus equal to or less than 100 times the average modulus of the tissue at the interface and optionally for some embodiments equal to or less than 10 times the average modulus of the tissue at the interface. In an embodiment, for example, the device has an average thickness less than or equal to 3000 microns, or less than or equal to 1,000 microns. In an embodiment, for example, the device has an average thickness selected over the range of 1 to 3000 microns and for some embodiments selected over the range of 1 to 1,000 microns. In an embodiment, for example, the device has a net bending stiffness less than or equal to 1 mN m, optionally for some embodiments less than or equal to 0.1 mN m and optionally for some embodiments less than or equal to 20 nN m. In an embodiment, for example, the device has a net bending stiffness selected over the range of 0.1 nN m to 1 mN m, and optionally for some embodiments selected over the range of 0.1 nN m to 0.5 mN m, and optionally for some embodiments selected over the range of 0.1 nN m to 20 nN m. In an embodiment, for example, the device has an areal mass density less than or equal to 100 mg cm$^{-2}$, or less than or equal to 10 mg cm$^{-2}$. In an embodiment, for example, the device has an areal mass density selected over the range of 0.1 mg cm$^{-2}$ to 100 mg cm$^{-2}$. In an embodiment, for example, the device exhibits a stretchability without failure of greater than 5%. In an embodiment, for example, the device exhibits a stretchability without failure selected over the range of 5% to 200%.

The devices of the invention are compatible with a range of tissue types including in vivo tissues, internal tissues and external tissues. In some embodiments, the tissue is skin, heart tissue, brain tissue, muscle tissue, nervous system tissue, vascular tissue, epithelial tissue, retina tissue, ear drum, tumor tissue, or digestive system structures. In some embodiments, for example, the device establishes conformal contact with the tissue when the device is placed in physical contact with the tissue, and wherein the conformal contact with the tissue in the biological environment is maintained as the tissue moves or when the device moves. In an embodiment where the tissue is skin, the device establishes conformal contact with an outer surface of the epidermis. The tissue may be of a subject that is undergoing treatment or diagnosis.

In an embodiment, the device further comprises a barrier layer at least partially encapsulating at least a portion of the thermal actuator and the thermal sensors. In an embodiment, for example, the barrier layer comprises a material selected from the group consisting of: a polymer, an inorganic polymer, an organic polymer, an elastomer, a biopolymer, a ceramic, and any combination of these. In an embodiment, for example, the barrier layer comprises polyvinylpyrrolidone, pyroxylin, nitrocellulose, poly(methylacrylate-isobutene-monoisopropylmaleate), pyroxylin, an acrylate polymer, a siloxane polymer, a cyanoacrylate, an octylcyanoacrylate, an acrylate copolymer, 2-octyl cyanoacrylate, ethyl cyanoacrylate, n-Butyl cyanoacrylate, an acrylate terpolymer, polyethylene, polydimethylsiloxane, or any combination thereof. In an embodiment, for example, the barrier layer comprises an elastomer. In an embodiment, for example, the barrier layer comprises PDMS, polyimide, SU-8, parylene, parylene C, silicon carbide (SiC), or Si$_3$N$_4$. In an embodiment, for example, the barrier layer is a biocompatible material or a bioinert material.

In an aspect, the invention provides a method of sensing a tissue of a biological environment, the method comprising: (i) providing a device comprising: (1) a flexible or stretchable substrate; and (2) one or more thermal actuators and a plurality of thermal sensors supported by the flexible or stretchable substrate, the one or more thermal actuators and the plurality of thermal sensors for characterizing a thermal transport property of the tissue; wherein the flexible or stretchable substrate, the one or more thermal actuators and the plurality of thermal sensors provide a net bending stiffness such that the device is capable of establishing conformal contact with a surface of the tissue; (ii) contacting the device to a receiving surface of the tissue, wherein contact results in the conformal contact with the surface of the tissue; (iii) thermally actuating the tissue with the one or more thermal actuators; and (iv) measuring one more temperatures of the tissue with at least a portion the thermal sensors.

In an embodiment, for example, the step of thermally actuating the tissue comprises heating the surface of the tissue. In an embodiment, for example, the step of heating comprises heating a selected area of the surface of the tissue. In an embodiment, for example, the step of heating comprises electronically, optically or mechanically providing energy to the tissue. In an embodiment, for example, the step of measuring one more temperatures of the tissue comprises making one or more voltage measurements, current measurements, electromagnetic radiation intensity or power measurements, temperature measurements, pressure measurements, tissue acceleration measurements, or tissue movement measurements of the tissue. In an embodiment, for example, the method further comprises measuring a temperature distribution of the surface of the tissue. In an embodiment, for example, the method further comprises spatio temporally mapping the surface of the tissue.

In an embodiment, for example, the method further comprises the step of determining a thermal transport property of the tissue using the one or more measured temperatures of the tissue. In an embodiment, for example, the thermal transport property is thermal conductivity, thermal diffusivity or heat capacity. In an embodiment, for example, the method further comprises determining one or more tissue parameters using the thermal transport property. In an embodiment, for example, the one or more tissue parameters is a physiological tissue parameter or a physical property of the tissue. In an embodiment, for example, the one or more tissue parameters is selected from the group consisting of hydration state, inflammation state, occlusion state and any combination of these. In an embodiment, for example, the one or more tissue parameters is selected from the group consisting of macrovascular blood flow direction, macrovascular blood flow rate, microvascular blood flow direction, microvascular blood flow rate, presence of an occlusion, macrovascular perfusion, microvascular perfusion, circulation changes due to inflammation and any combination of these.

In an embodiment, a method for characterizing vasculature of tissue comprises: providing a device comprising a flexible or stretchable substrate; and one or more thermal actuators and a plurality of thermal sensors supported by the flexible or stretchable substrate, the one or more thermal actuators and the plurality of thermal sensors for characterizing a thermal transport property of the tissue; wherein the flexible or stretchable substrate, the one or more thermal actuators and the plurality of thermal sensors provide a net bending stiffness such that the device is capable of establishing conformal contact with a surface of the tissue;

contacting the device to a receiving surface of the tissue, wherein contact results in the conformal contact with the surface of the tissue; sequentially measuring a steady-state temperature at the location of each thermal sensor; thermally actuating the tissue with the one or more thermal actuators while simultaneously recording a non-equilibrium temperature of the thermal actuator and the plurality of thermal sensors; and identifying pairs of symmetrically disposed thermal sensors on opposing sides of the thermal actuator.

In an embodiment, a method for characterizing vasculature of tissue further comprises comparing a normalized change in the non-equilibrium temperatures of the pairs of symmetrically disposed thermal sensors versus time to model results to determine vessel depth.

In an embodiment, a method for characterizing vasculature of tissue further comprises normalizing the steady-state temperature difference between the pairs of symmetrically disposed thermal sensors by the non-equilibrium temperature at the actuator to determine blood flow velocity.

In an embodiment, the step of thermally actuating comprises applying pulsed power. For example, the pulsed power may have a frequency between 0.05 and 0.1 Hz with a 33% duty cycle.

In an embodiment, a method for characterizing vasculature of tissue comprises: providing a device comprising a flexible or stretchable substrate; and one or more thermal actuators and a plurality of thermal sensors supported by the flexible or stretchable substrate, the one or more thermal actuators and the plurality of thermal sensors for characterizing a thermal transport property of the tissue; wherein the flexible or stretchable substrate, the one or more thermal actuators and the plurality of thermal sensors provide a net bending stiffness such that the device is capable of establishing conformal contact with a surface of the tissue; contacting the device to a receiving surface of the tissue, wherein contact results in the conformal contact with the surface of the tissue; sequentially supplying a current to each thermal sensor and measuring a voltage from each thermal sensor; and calculating resistance change over time to determine thermal conductivity and thermal diffusivity of each thermal sensor.

In an embodiment, a method for determining a hydration level of tissue comprises: providing a device comprising a flexible or stretchable substrate; and one or more thermal actuators and a plurality of thermal sensors supported by the flexible or stretchable substrate, the one or more thermal actuators and the plurality of thermal sensors for characterizing a thermal transport property of the tissue; wherein the flexible or stretchable substrate, the one or more thermal actuators and the plurality of thermal sensors provide a net bending stiffness such that the device is capable of establishing conformal contact with a surface of the tissue; contacting the device to a receiving surface of the tissue, wherein contact results in the conformal contact with the surface of the tissue; sequentially supplying a current to each thermal sensor and measuring a voltage from each thermal sensor; calculating resistance change over time to determine thermal conductivity; and comparing the thermal conductivity with a corresponding hydration level of the tissue.

ND. Induced errors occur in both the continuous and pulsed actuation modes, however the relative induced error in the pulsed actuation mode is ~20% that of the continuous mode.

Figure 27:
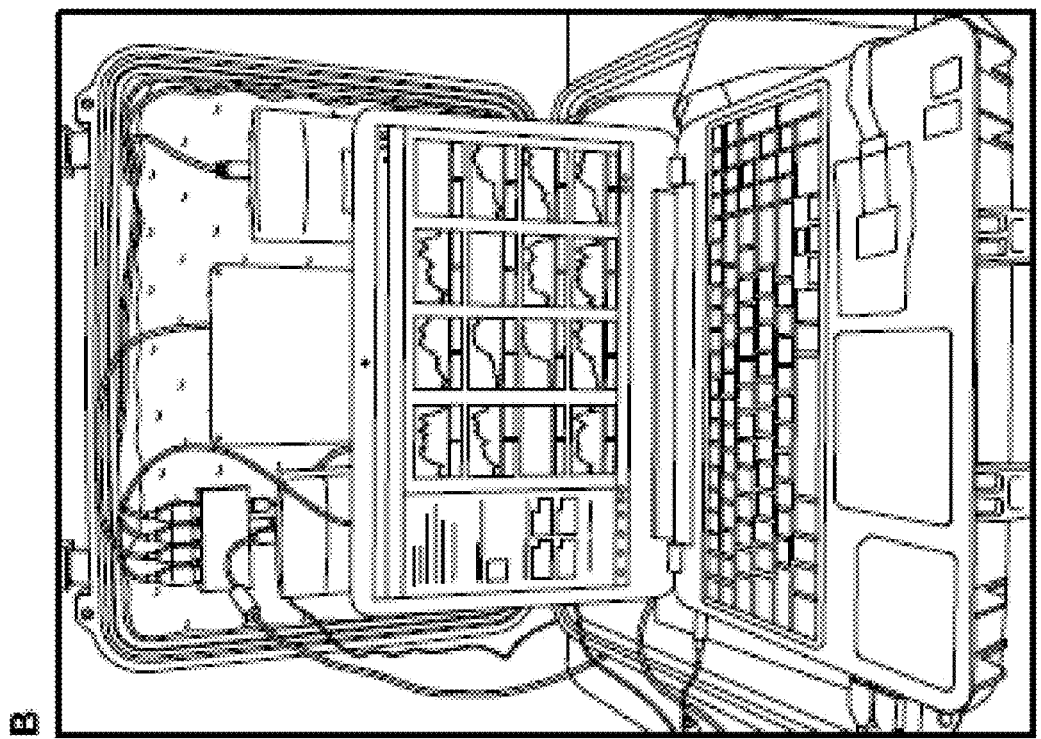
Figure 27:
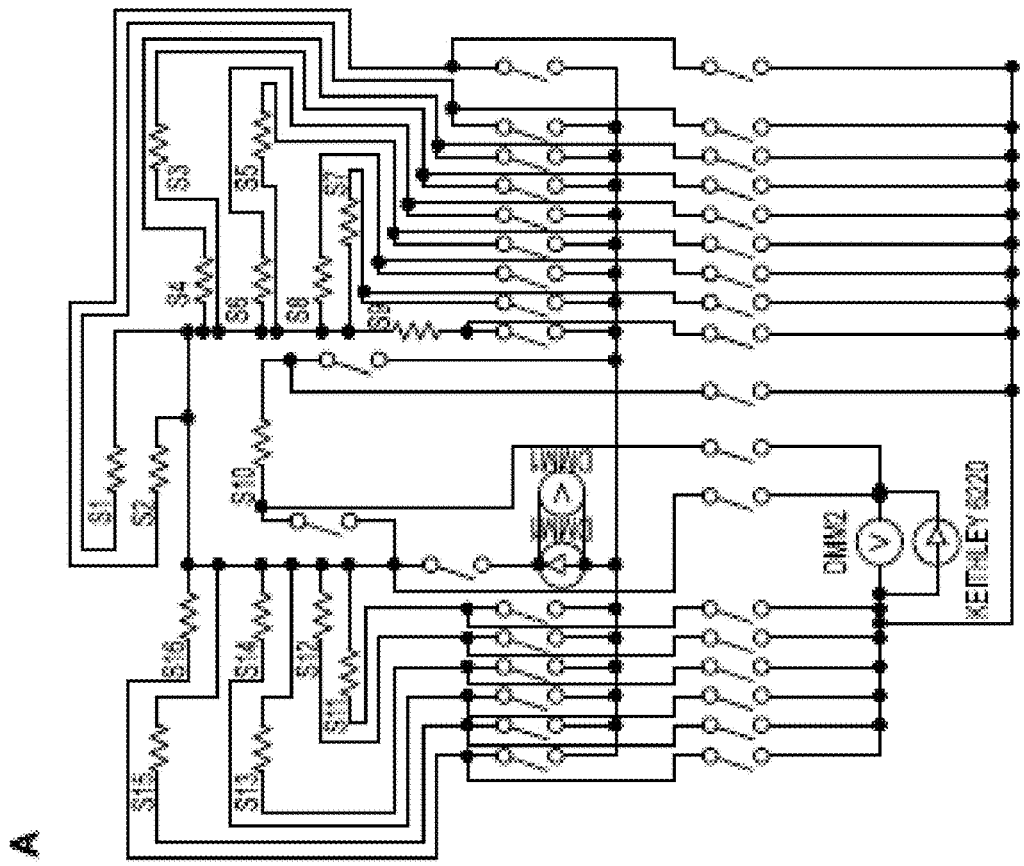

FIG. 27: Epidermal device (A) wiring diagram and (B) hardware setup. A detailed description of the system appears in the Materials and Methods section.

Figure 28:
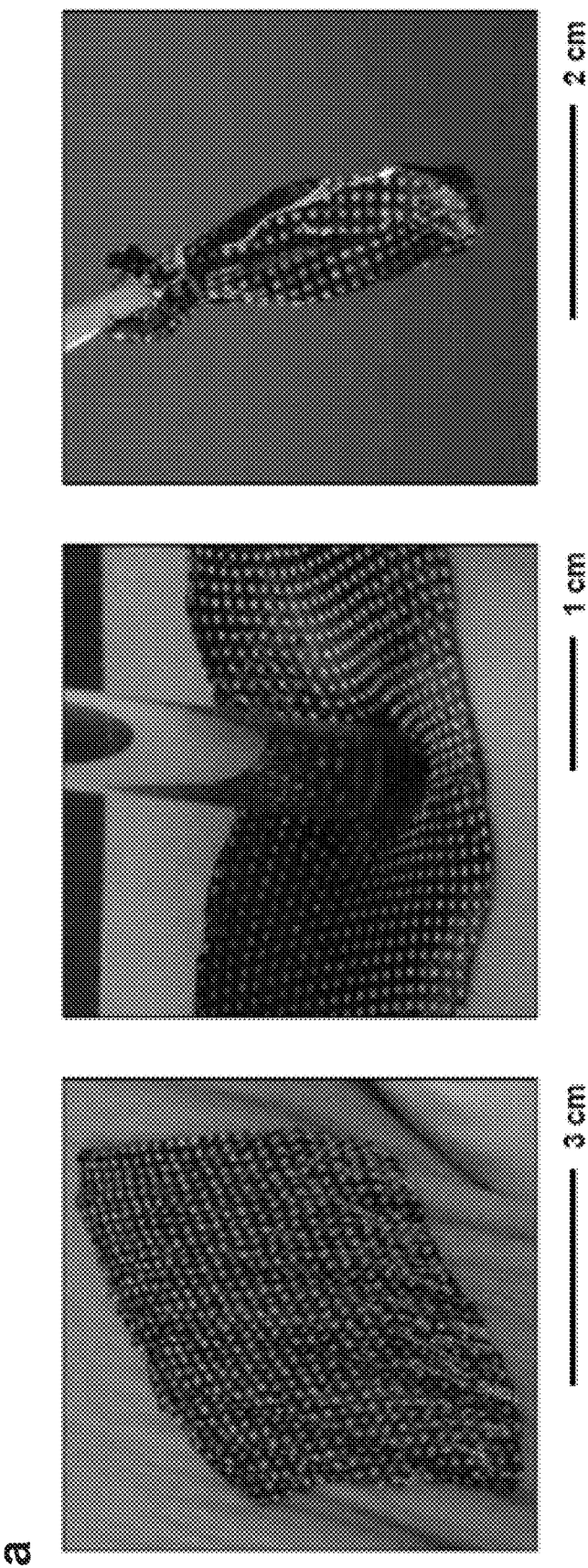
Figure 28:
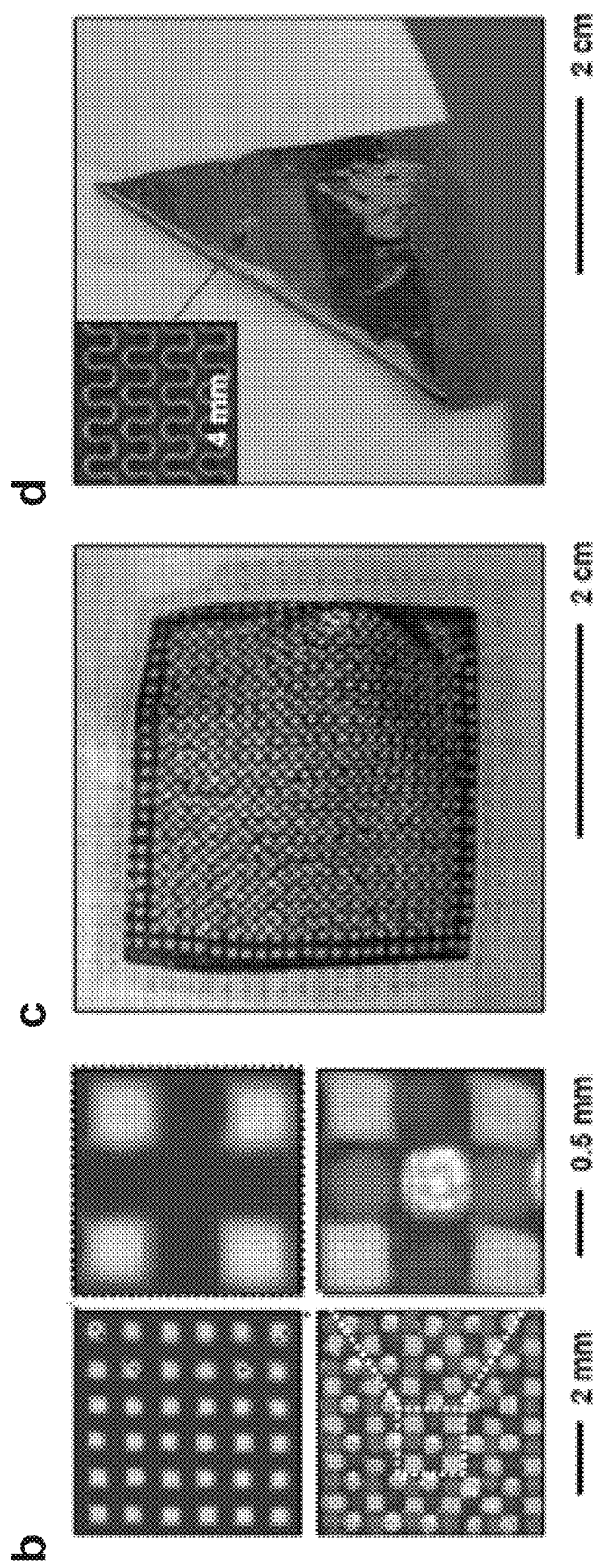
Figure 28:
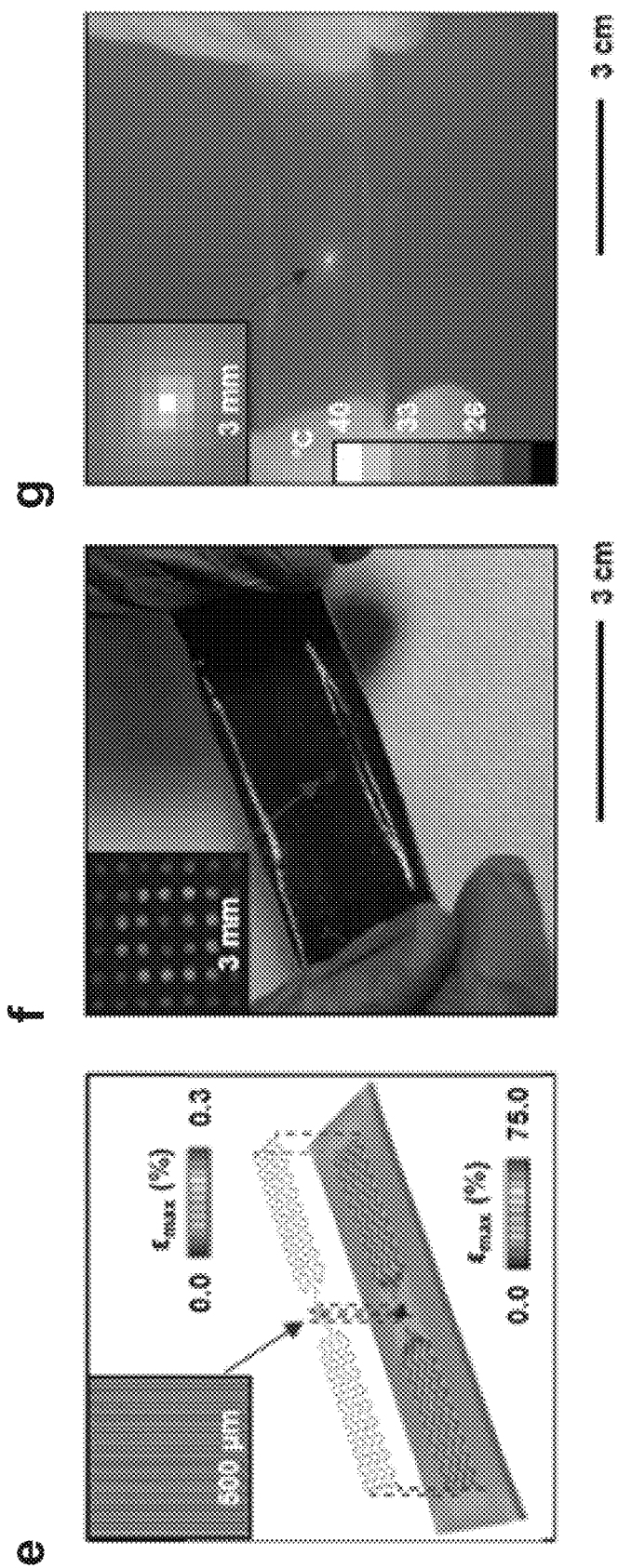

FIG. 28: Pictures, micrographs and design features of an 'epidermal' thermochromic liquid crystal (e-TLC) thermal imaging device. a, Picture of devices deformed by pinching the skin in a twisting motion (left), poking with a warm glass rod while on skin (middle) and collapsing under its own weight while free-standing (right). b, Magnified view of a device operating in the blue region of the spectrum, without (top) and with (bottom) integrated patterns of dots that have fixed colors for calibration. c, Picture of an e-TLC device with calibration system, operating the curved surface of the skin. d, Picture of a device that includes a radio frequency antenna and Joule heating element on its back surface, folded over and resting on palm, with an enlarged view of the serpentine antenna structure (inset). e, Schematic illustration of finite element modeling results for an e-TLC device with wireless heater under tensile strain, with magnified view of the Joule heating element (inset). f, Image of an active, wireless e-TLC device collected while exposed to RF power in air, with magnified view of the color changes induced by the heater (inset). g, Infrared image of the same device under similar conditions, with magnified view in the region of the heater (inset).

Figure 29:
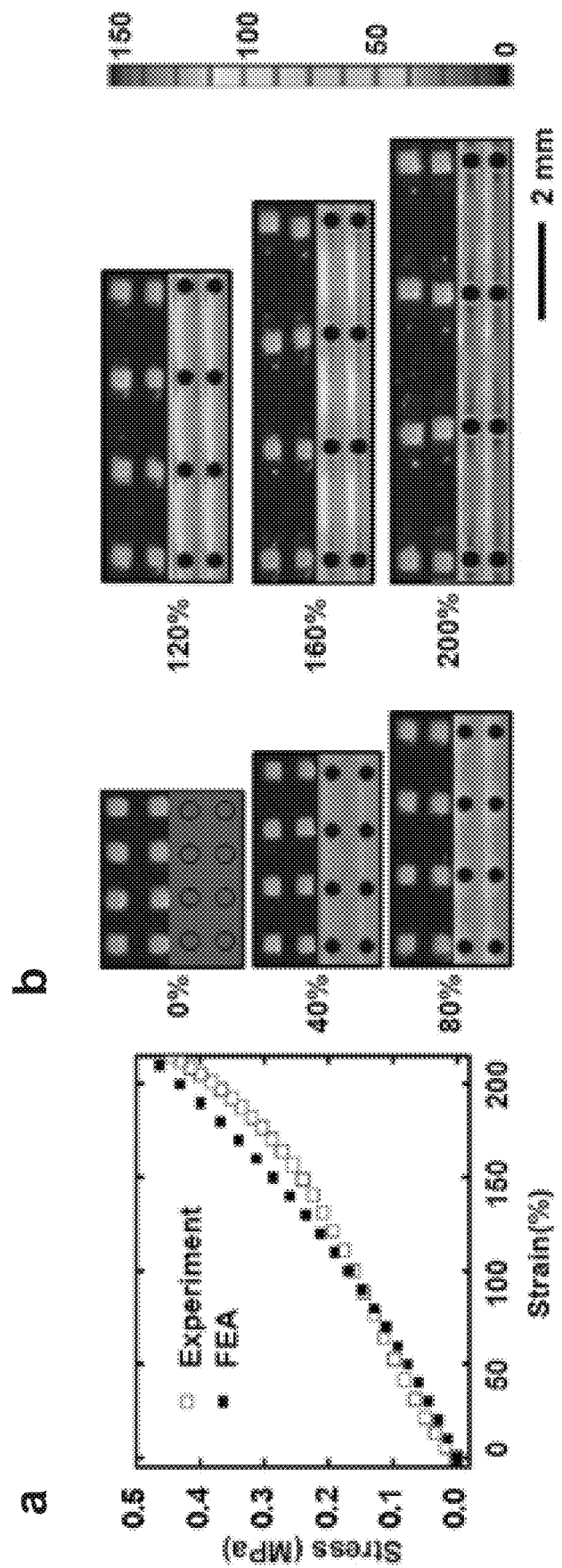

FIG. 29: Experimental and computational studies of the mechanical properties of e-TLC devices. a, Measurements and theoretical calculations of stress-strain responses of a device. b, Comparison between images and three dimensional finite element modeling of a representative region of e-TLC device under different levels of tensile strain.

Figure 30:
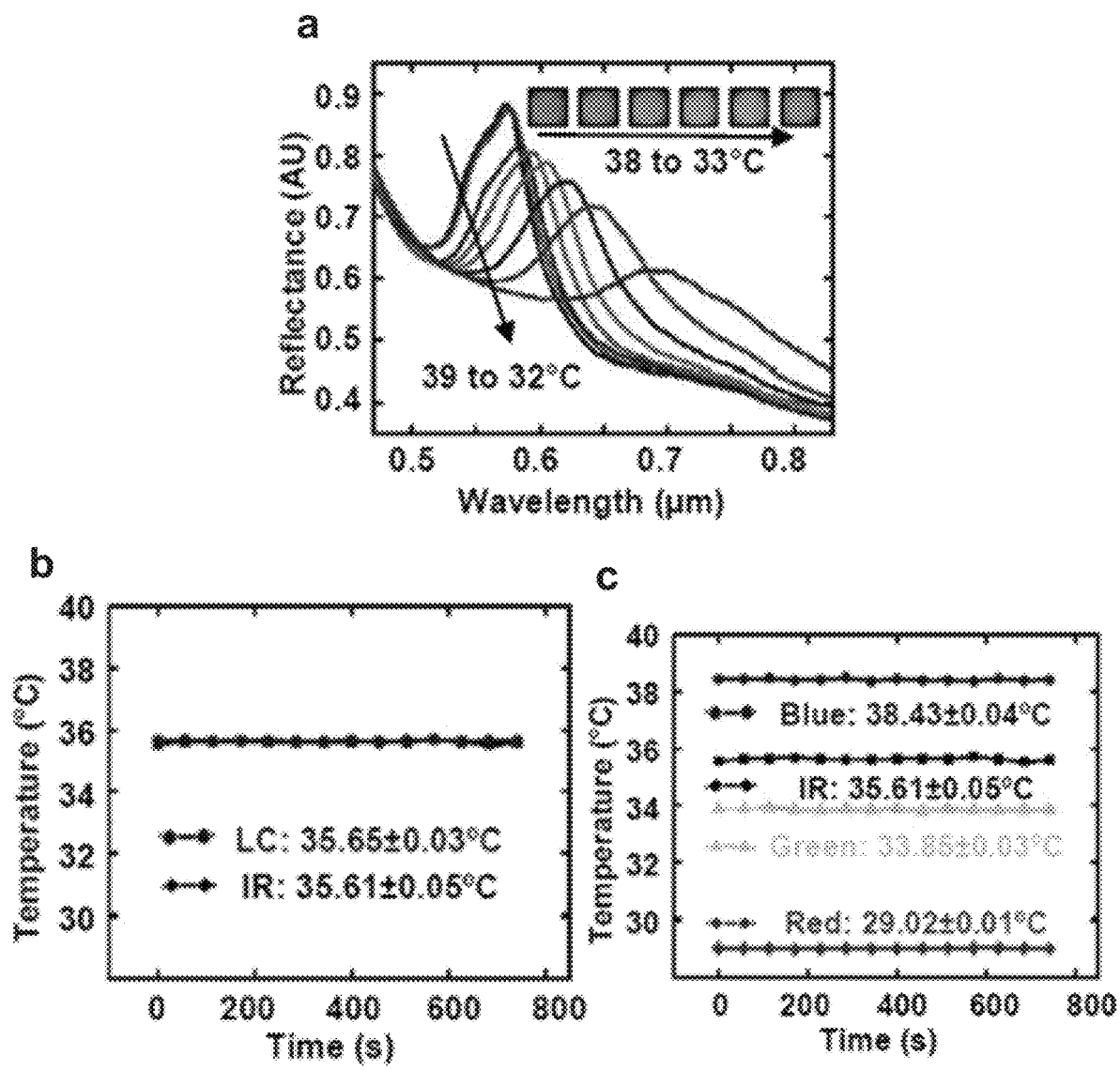
Figure 30:
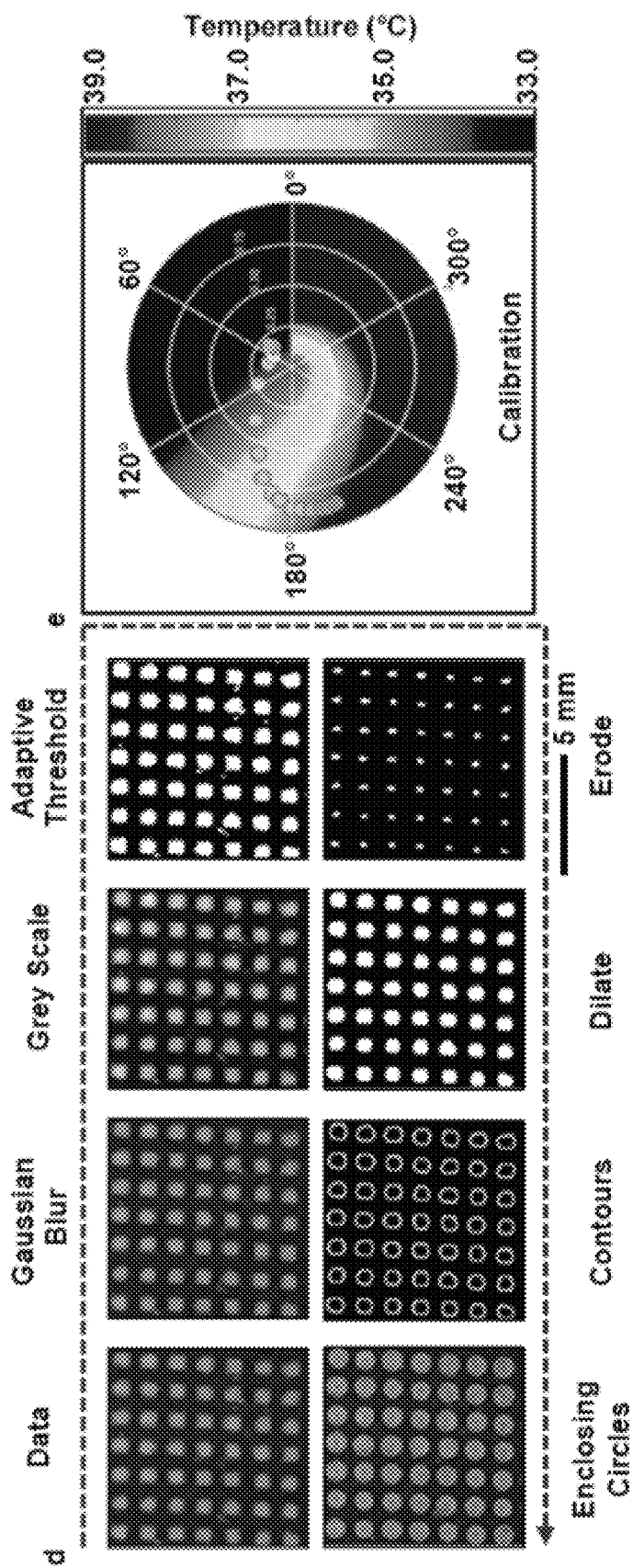
Figure 30:
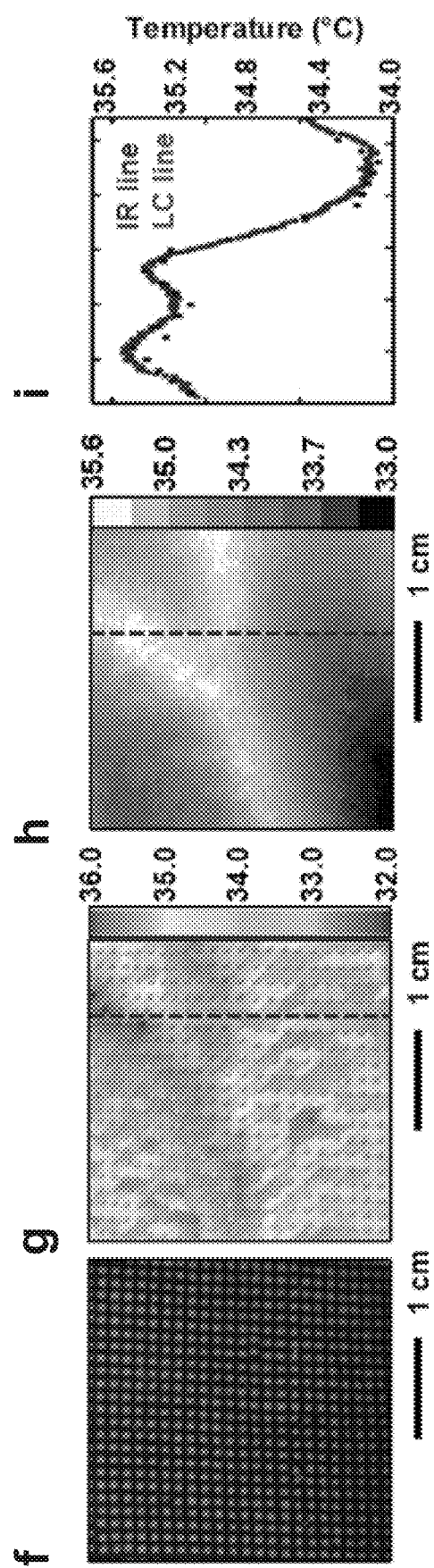

FIG. 30: Calibration and use of e-TLC devices for precision thermal imaging on the skin. a, Reflectance measured at a single pixel from 32° C. to 39° C. and corresponding images for 33° C. to 38° C. (inset). b, Temporal variations in temperature extracted from digital color analysis of an e-TLC held, nominally, at a constant temperature. c, Temporal variations in apparent temperature determined from color analysis of calibration pixels in an e-TLC device. Frames b and c also show results obtained with an infrared camera. d, Illustration of the steps for processing digital images of e-TLC devices, demonstrated on a representative 7×7 array of pixels. e, Color-temperature calibration determined using hue analysis. f, Images of a e-TLC device that consists of an 26×26 array of pixels, conformally mounted on the wrist. g, 3D rendering of the temperature distribution extracted from the color information obtained by hue value analysis of digital images of the device. h, 2D rendering of temperature captured by an infrared camera at the same time and at the same location as in g. i, Line-cut temperature profiles extracted from the data of g and h.

Figure 31:
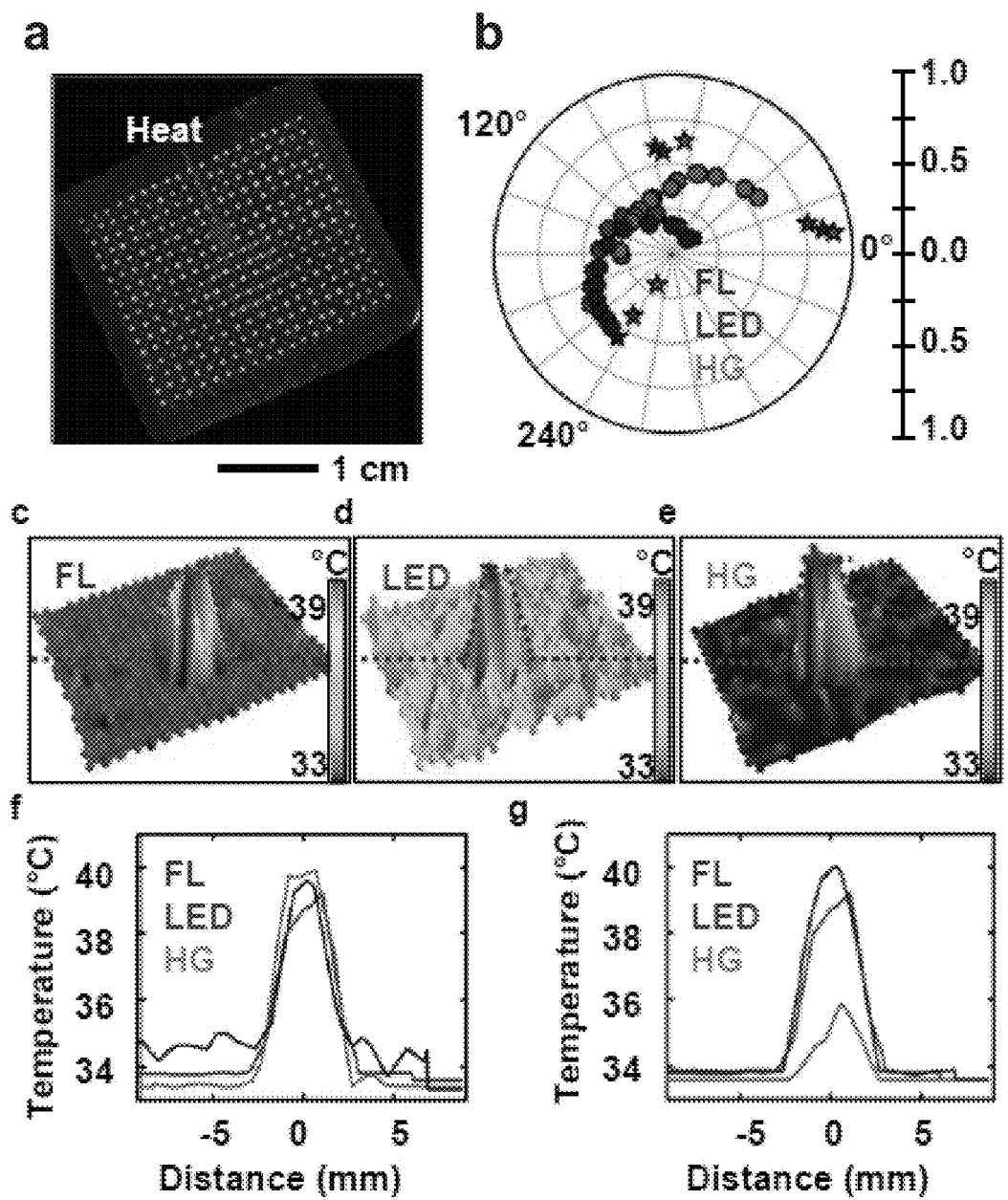

FIG. 31: Temperature analysis with an e-TLC device that incorporates an array of color calibration pixels co-located with sensing pixels, evaluated under different illumination conditions. a, Image of a device immediately after local heating at the center of the array. b, Hue and saturation values extracted for the calibration (stars) and sensing pixels (dots; red—illumination with a fluorescent light; blue—illumination with a light emitting diode; green—illumination with a halogen lamp). 3D rendering of color-corrected temperatures determined with c, white fluorescent light (FL), d, white light-emitting diode (LED), e, halogen light (HG). f, Line graphs of results collected along the dashed lines shown in c-e. g, Results similar to those in f, but without color correction.

Figure 32:
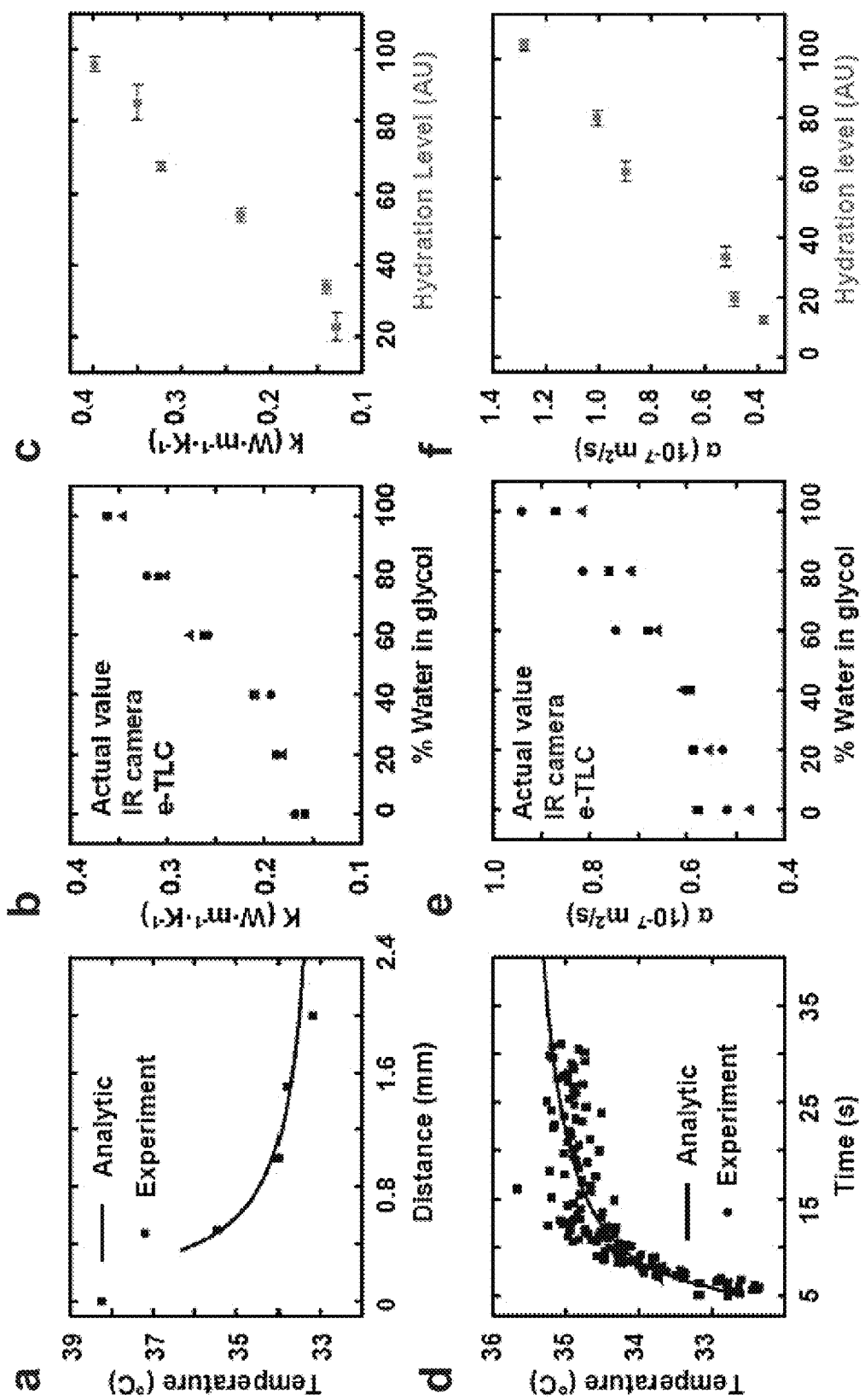

FIG. 32: Determination of thermal conductivity and thermal diffusivity of the skin using active e-TLC devices. a, Example of temperatures (symbols) as a function of distance from the position of local heating in an active e-TLC device and corresponding best fit modeling results (analytic; line), for determining the thermal conductivity. b, Thermal conductivity of water/ethylene glycol solutions evaluated using an active e-TLC device, with comparison to values obtained from the literature and from analysis of temperatures determined with an infrared camera. The error bars represent average standard deviations of measurements obtained with e-TLC. c, Thermal conductivities measured with an active e-TLC device on the skin at different levels of hydration, separately measured with a commercial moisture meter. The error bars represent average standard deviations of measurements obtained with the moisture meter. d, Example of temperatures (symbols) as a function of time for a location near a wireless heater in an active e-TLC device, and corresponding best fit modeling results (analytic; line) for determining the thermal diffusivity. e, Thermal diffusivity of water/ethylene glycol solutions evaluated using an active e-TLC device, with comparison to values obtained from the literature and from analysis of temperatures determined with an infrared camera. The error bars represent average standard deviations of measurements obtained with e-TLC. f, Thermal diffusivities measured with an active, wireless e-TLC device on the skin at different levels of hydration, separately measured with a commercial moisture meter. The error bars represent average standard deviations of measurements obtained with the moisture meter.

Figure 33E:
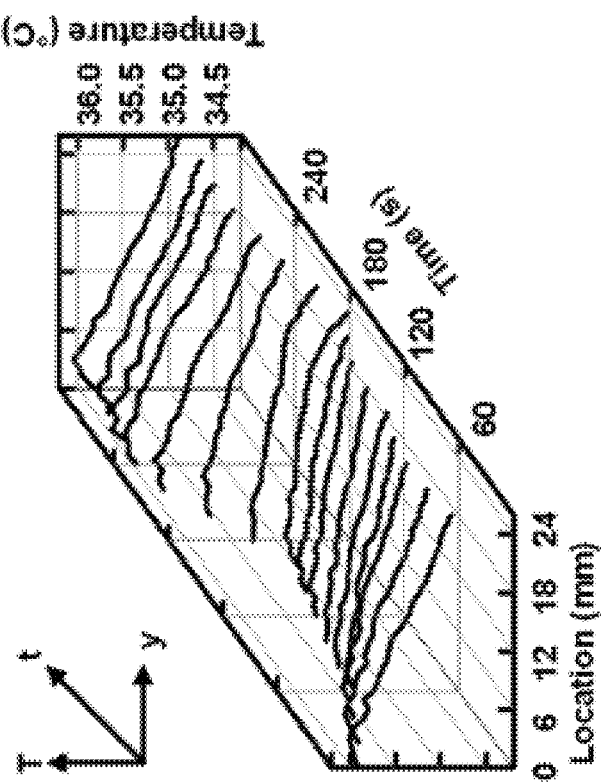
Figure 33D:
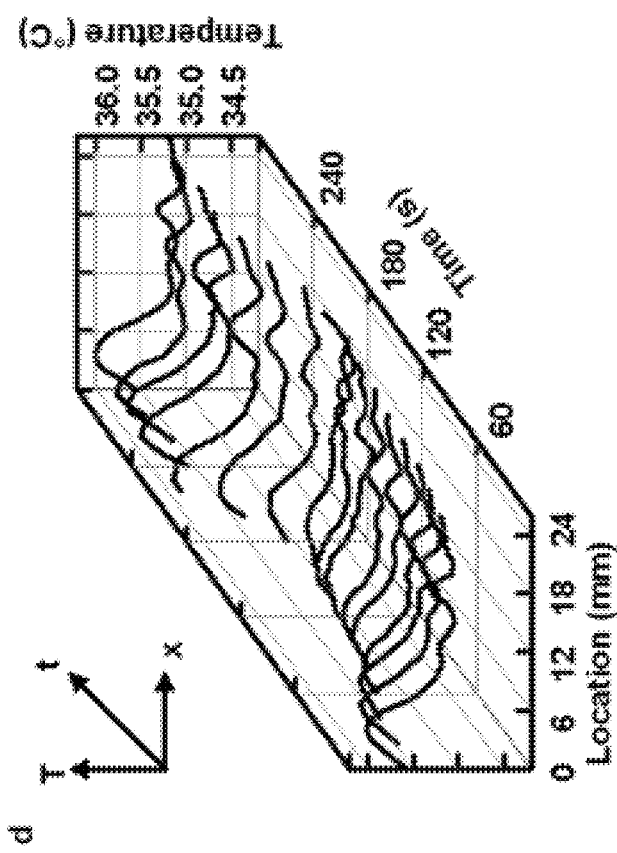
Figure 33G:
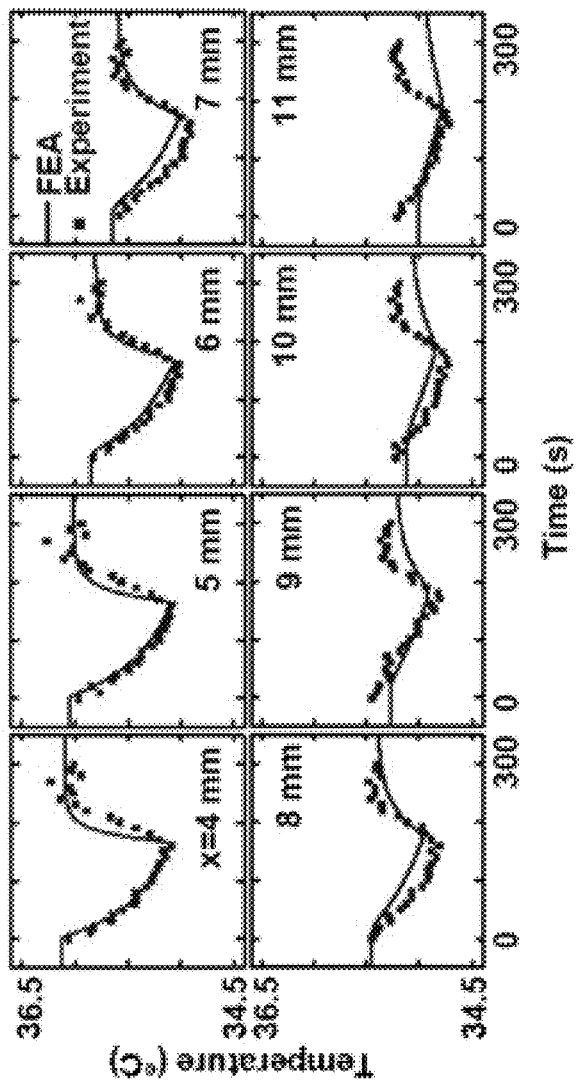
Figure 33F:
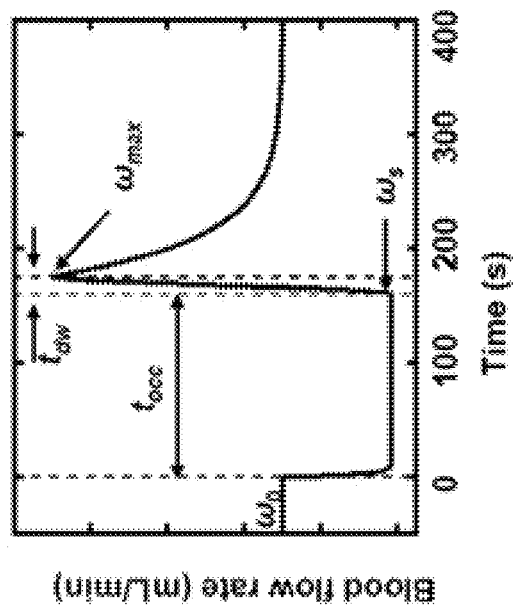

FIGS. 33A-33F: Application of an e-TLC thermal imaging device in a reactive hyperaemia test. FIG. 33A, Optical images of an e-TLC device on the wrist during an occlusion test after blood is released (left) with magnified view (right). FIG. 33B, Infrared image of the device (left) with magnified view (right). FIG. 33C, 3D rendering of spatial distributions of temperature determined with the e-TLC device at different times during and after occlusion (occlusion starts at t=0 s and ends at t=160 s). FIG. 33D, Line graphs of temperatures along the horizontal dashed red line in the right frame of a, at various times. FIG. 33E, Line graphs of temperatures along the vertical dashed red line in the right frame of a, at various times. FIG. 33F, Rate of blood flow through the ulnar artery determined by comparison of thermal models to experimental results. The key parameters include: the occlusion time (tocc)=160 s; time-to-peak-flow (tdw)=15 s; the baseline flow rate ($\omega 0$)=30 mL/min; the occluded flow rate ($\omega s$)=1.5 mL/min; and the peak flow rate ($\omega max$)=90 mL/min. g, Measured temperature rise at the surface of the skin above the ulnar artery during the occlusion along with results from finite element analyses (FEA) using the blood flow rate in frame FIG. 33F. The eight sub-frames correspond to the temperature histories of different points at the horizontal dashed red line in the right frame of FIG. 33A. FIG. 33G provides plots of temperature versus time.

Figure 34:
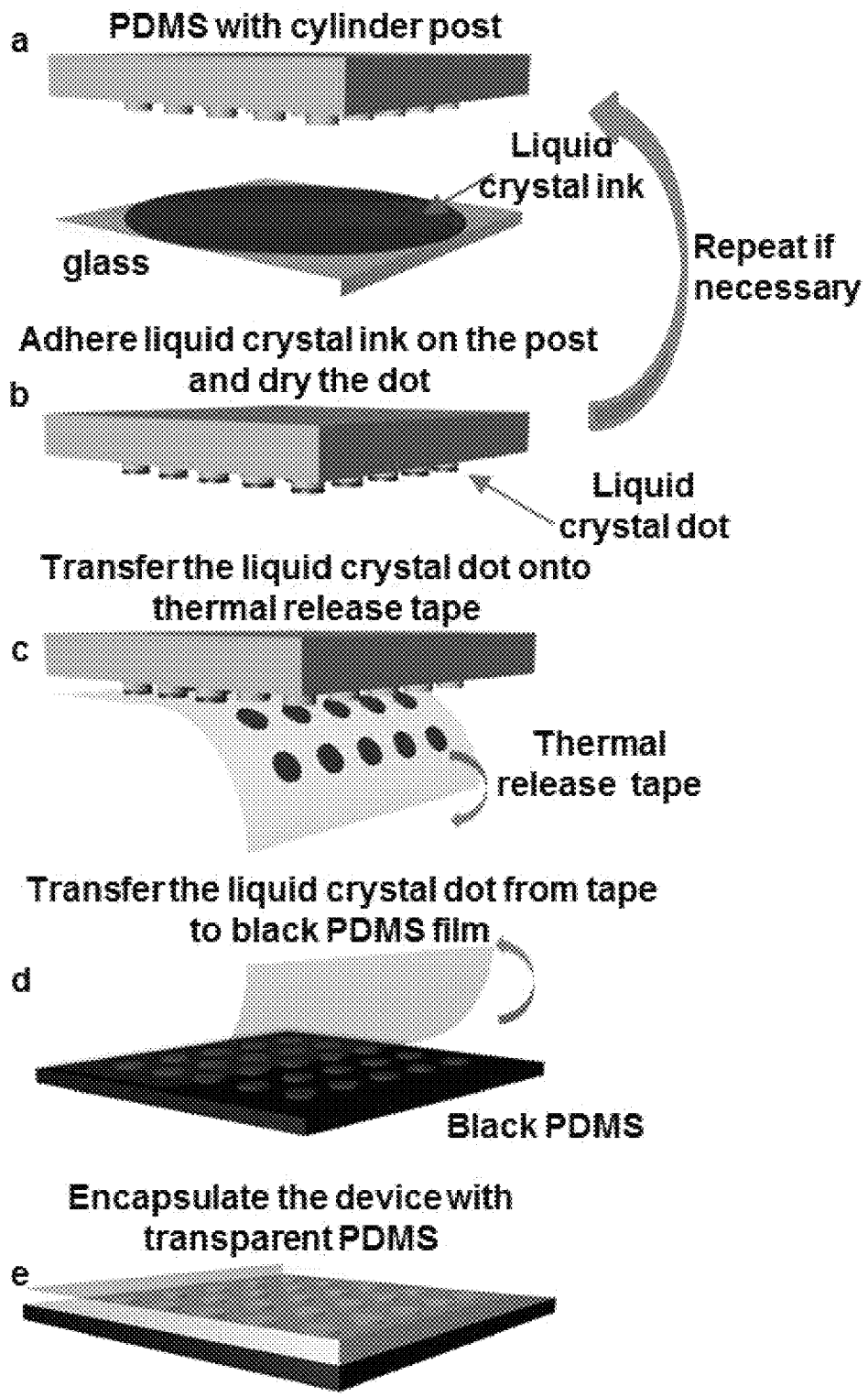

FIG. 34: Process for fabricating e-TLC devices. (a) A PDMS stamp with an array of posts embossed on its surface is 'inked' by bringing it into contact with a uniform layer of TLC aqueous slurry spin cast on a glass slide while still in wet state. The thickness of the ink was ~100 μm to ensure that the ink contacts on the top surfaces of the posts. (b) The inked TLC material on the PDMS stamp was allowed to dry in air for 15 minutes. The thickness of the dried film is ~15 μm. Additional 'inking' processes are repeated to achieve a final thickness of 25-30 µm. A typical TLC pixel is thickest in the center due to the hydrophobic nature of the PDMS surface and the large contact angle formed during the inking process. (c) Transfer printing allows delivery of the TLC to a piece of thermal release tape. (d) Transfer to the black PDMS substrate is enabled by heat activated release from the tape. (e) The device is encapsulated with a transparent layer of PDMS by spin casting.

Figure 35:
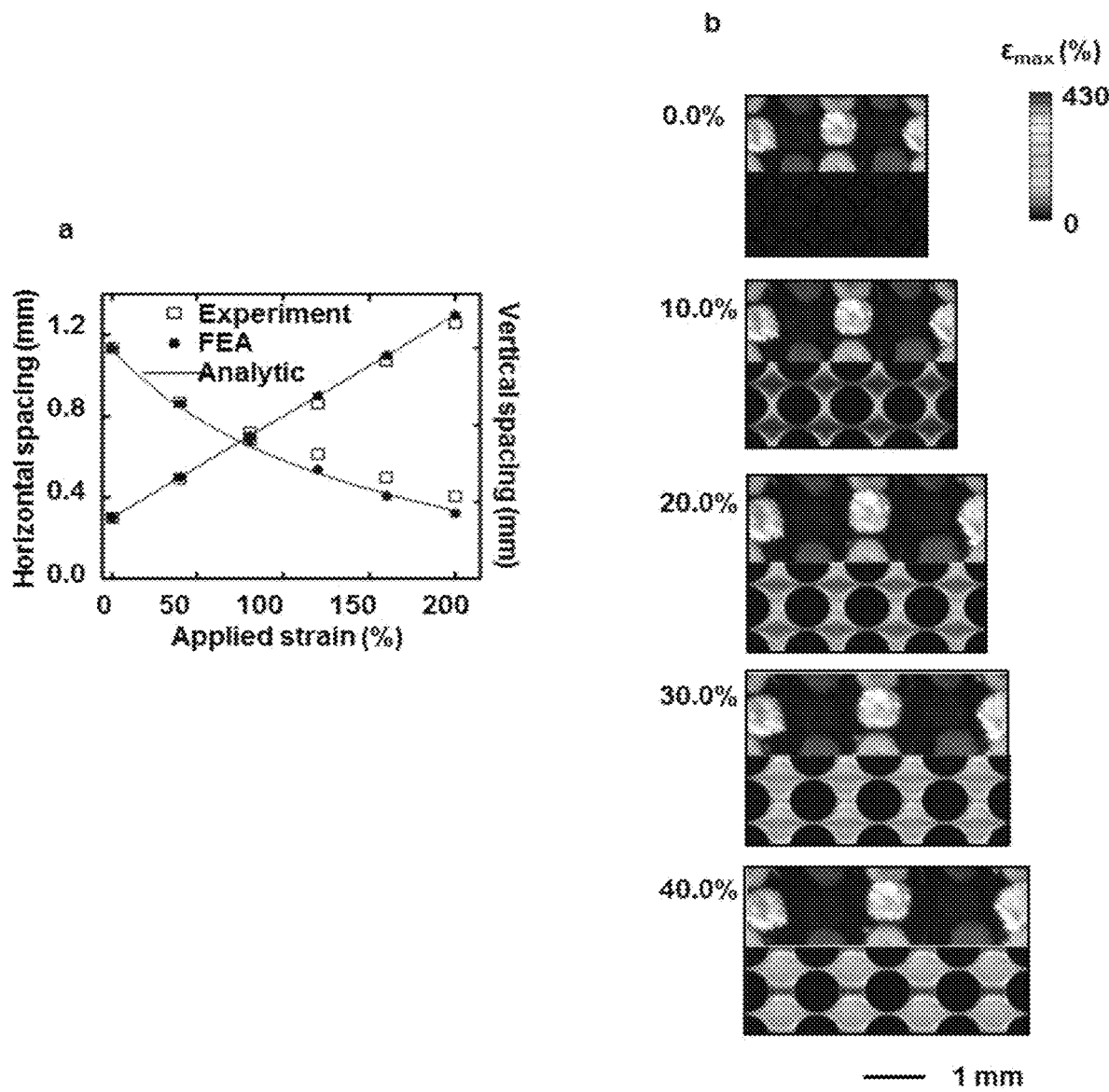

FIG. 35: Mechanical response of an e-TLC device to uniaxial strain. (a) Experimental, analytical and finite element modeling results for the change in horizontal and vertical spacings between adjacent pixels under different levels of tensile strain. (b) Comparison between images and three dimensional finite element modeling of a representative region of an e-TLC device that incorporates color calibration pixels under different levels of tensile strain.

Figure 36:
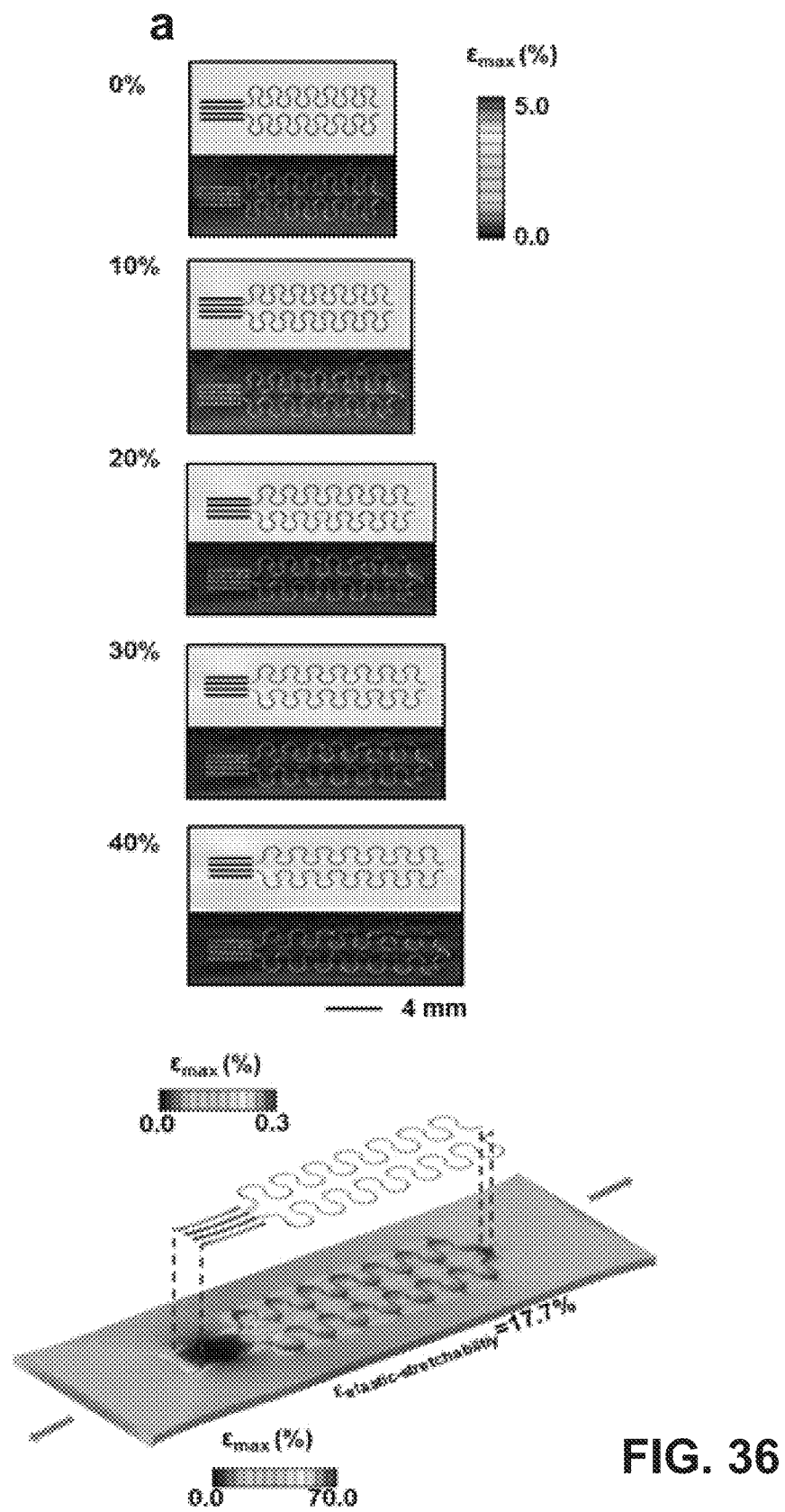
Figure 36:
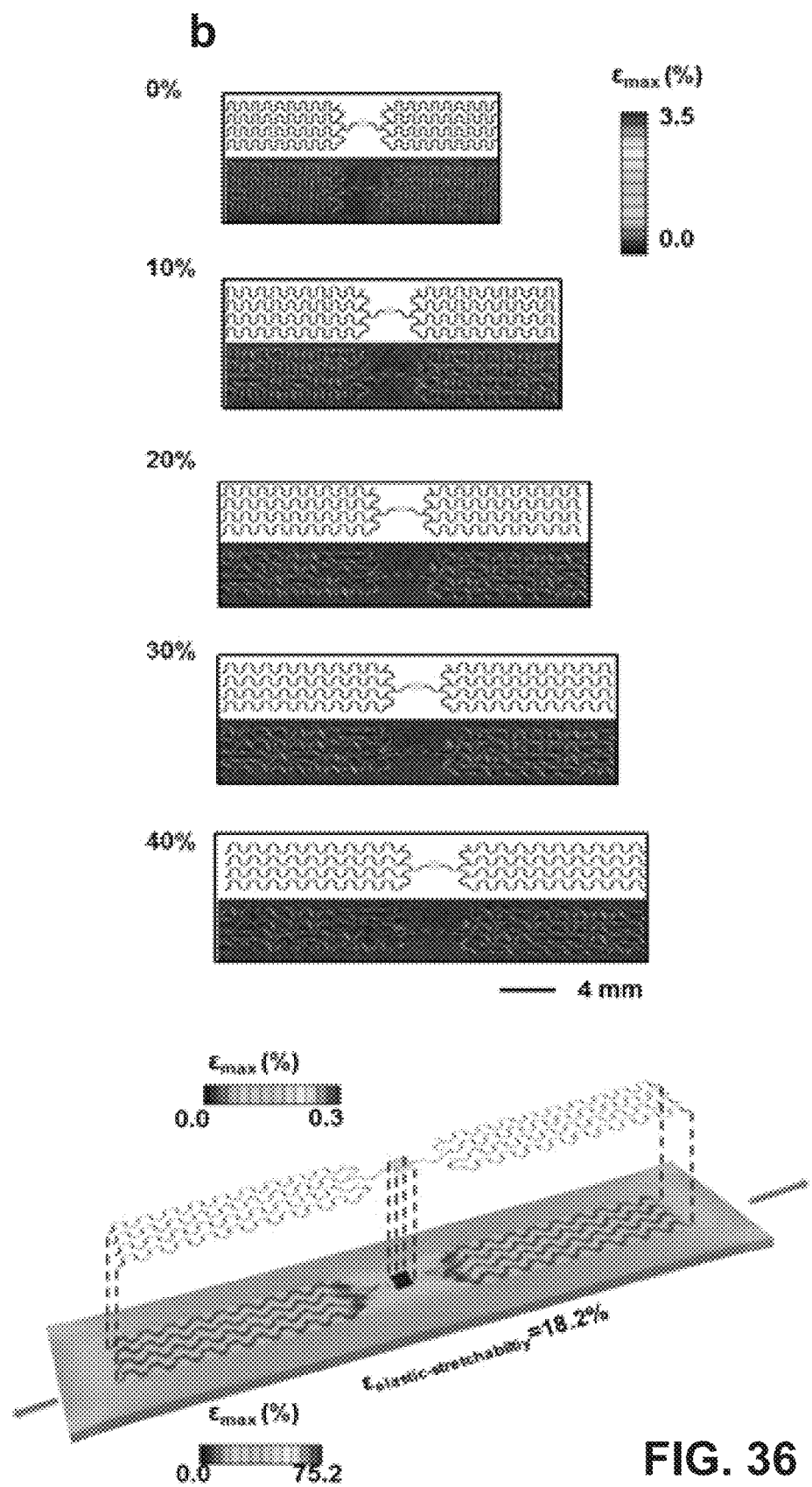

FIG. 36: Experimental and computational studies of the mechanical properties of Joule heater element. (a) Comparison between experimental images and three dimensional finite element modeling of a wired Joule heating element under different levels of tensile strain, and strain distribution computed for the case of stretching to 50%. (b) Comparison between experimental images and three dimensional finite element modeling of a wireless Joule heater under different levels of tensile strain, and strain distribution computed for the case of stretching to 50%.

Figure 37:
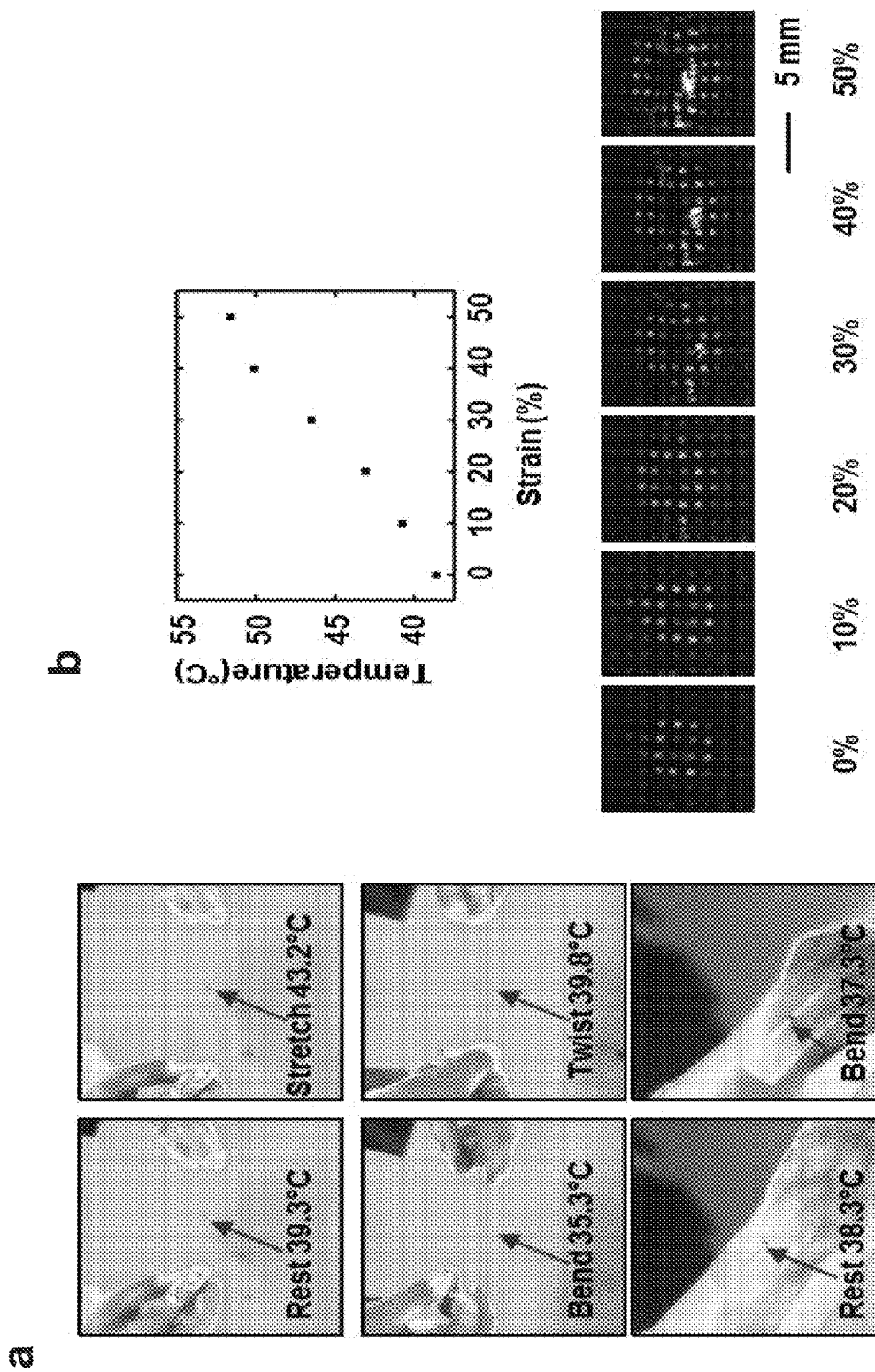

FIG. 37: Experimental studies of the effect of strain on the efficiency of wireless Joule heating. (a) Infrared temperature measurements for a wireless Joule heater under exposure to RF energy while mechanically deformed in different ways, both in air and on skin. (b) Measurements at different levels of tensile strain with corresponding images.

Figure 38:
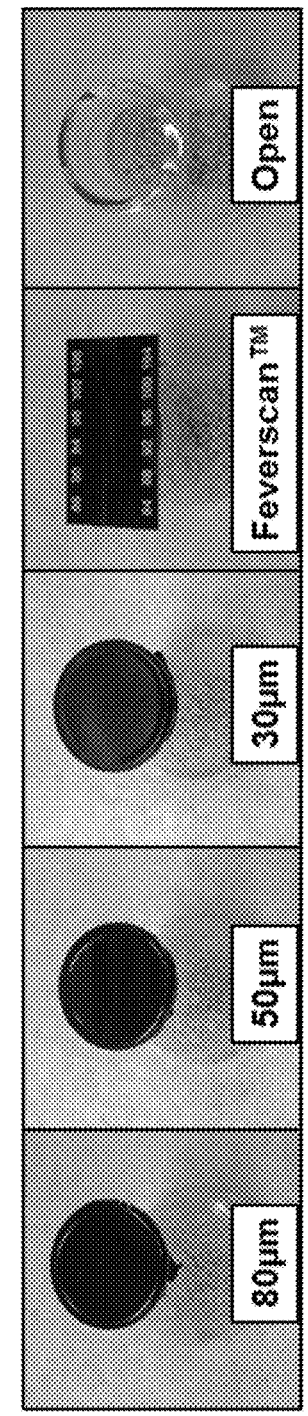
Figure 38:
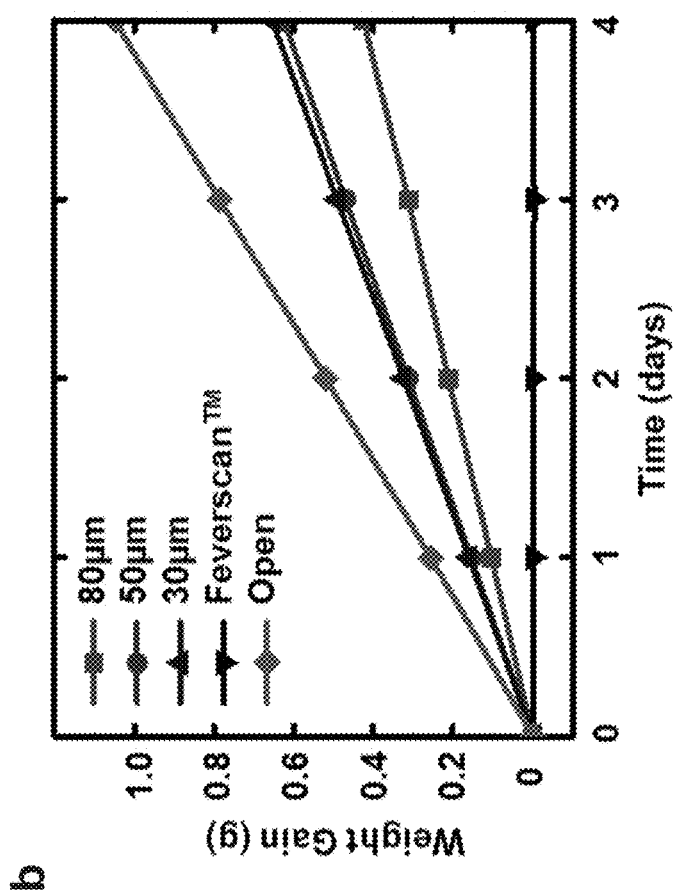

FIG. 38: Water permeability test. (a) Images of the experimental set-ups for measurement of water permeation according to ASTM E96-95 guidelines, and (b) Results of the change in weight as a function of time associated with water uptake by the desiccant, for e-TLC devices with different thicknesses and for a commercial TLC strip.

Figure 39:
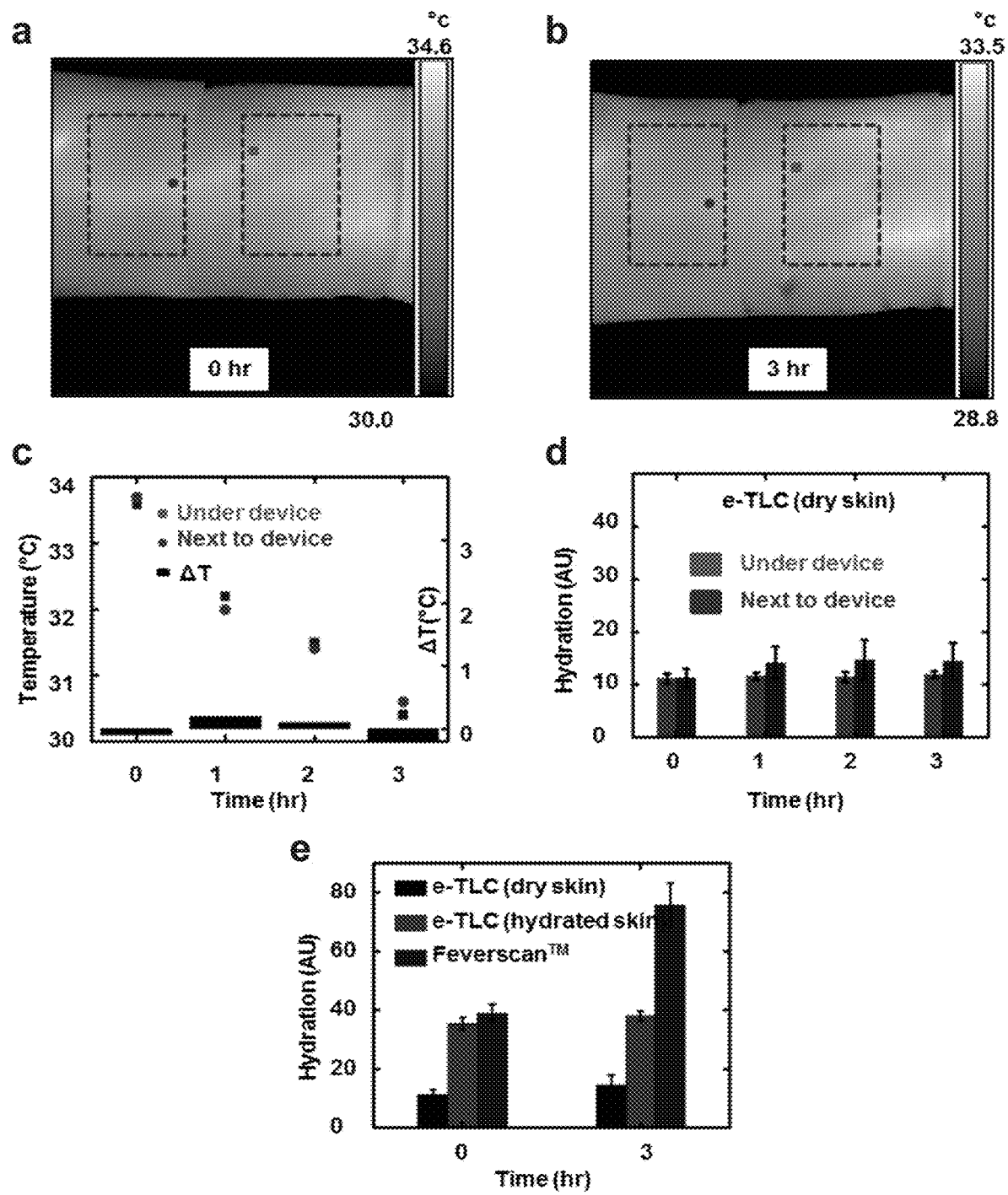

FIG. 39: Effect of e-TLC operation on temperature and hydration of the skin. (a) Infrared image captured immediately after mounting an e-TLC device on the wrist. (b) Infrared image captured 3 hours after mounting. For both (a) and (b), the data indicate that the average temperatures at the regions of the device are the same as those adjacent to the device. (c) Temperature difference between a point near the device and a point underneath the device shows no obvious increase during the three hour operation. (d) Measurement of hydration using a Delfin meter in a region of dry skin (baseline reading ~10) after 3 hours of contact with an 80 µm thick e-TLC indicates an increase of ~25%. (e) The same device, under identical conditions, on well hydrated skin (baseline reading ~35) leads to much smaller percentage increases (7.5%). For an otherwise identical set of testing conditions, the Feverscan™ strip led to a ~100% increase in the hydration.

Figure 40:
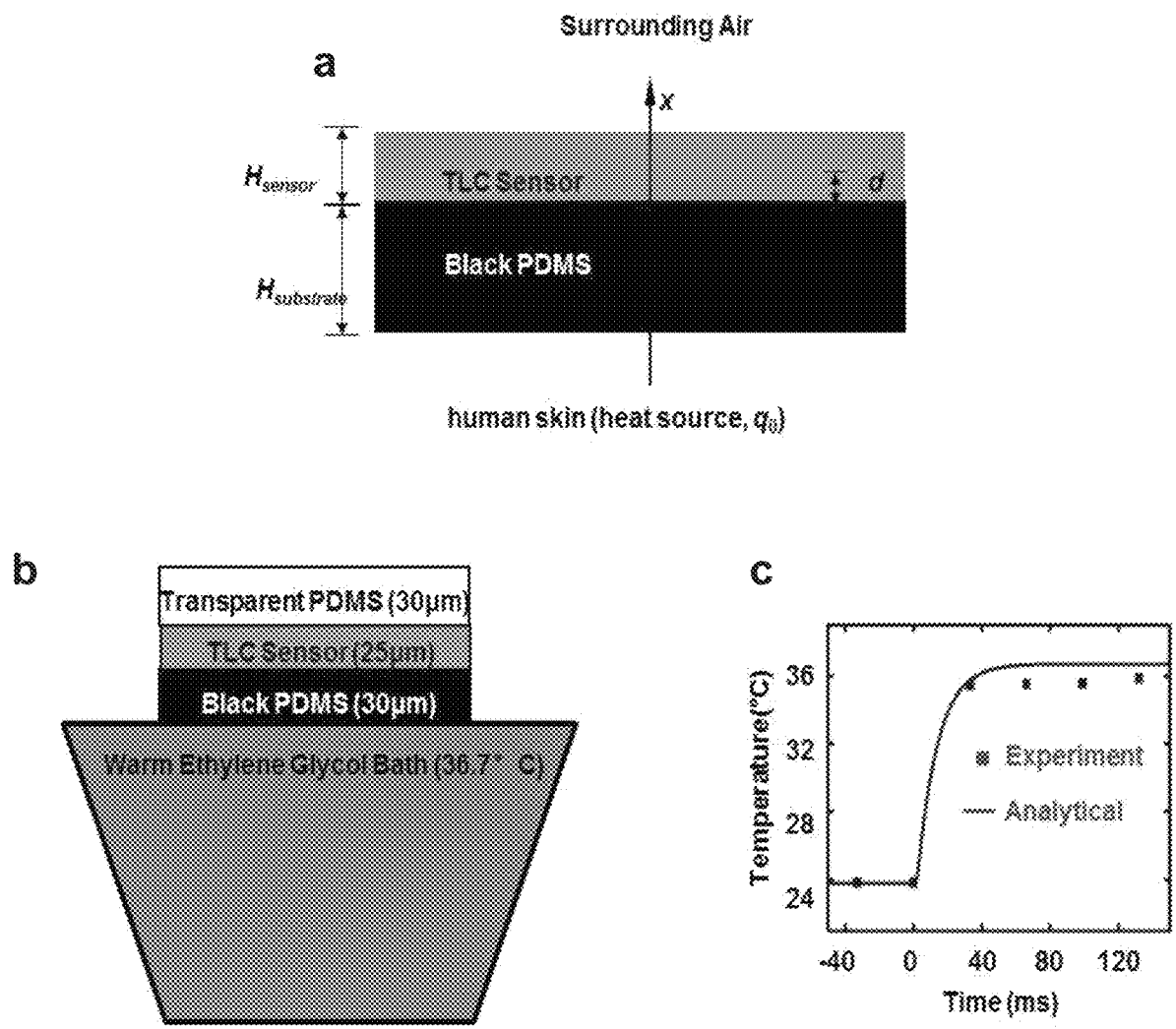

FIG. 40: Sensor response time. (a) Layers used in analytical modeling to determine sensor response time on skin. (b) Experimental setup for measuring sensor response time. A warm ethylene glycol bath, which has similar thermal properties to skin, is in contact with the e-TLC device from the back surface. (c) Experimental sensor response time captured by high speed camera, and corresponding analytic predictions based on a one-dimensional heat conduction model. In experiment, the time required for the sensor to reach 90% of the total temperature change is achieved in one frame which is approximate 33 ms for the case of 30 µm black PDMS and 25 µm liquid crystal.

Figure 41:
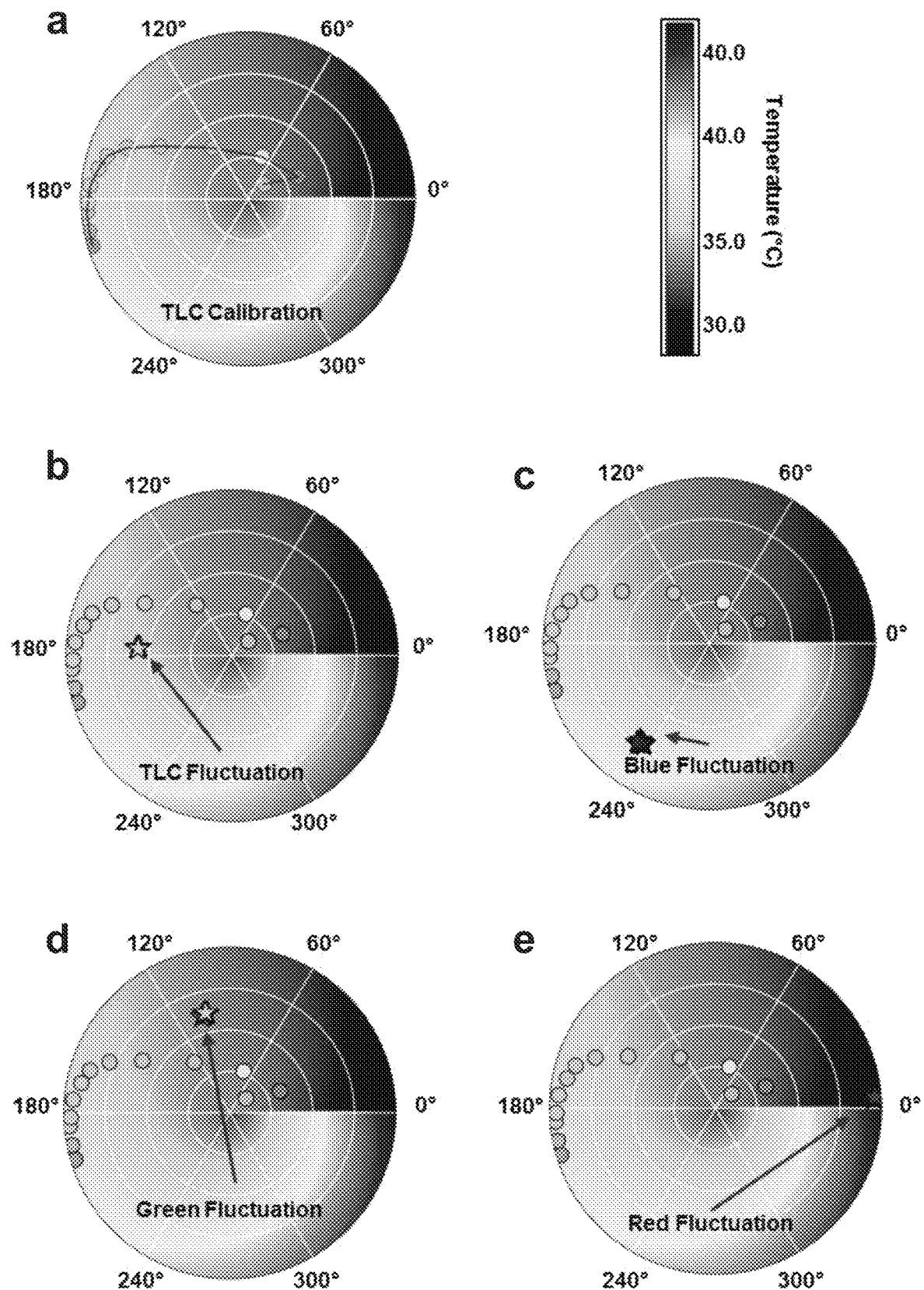

FIG. 41: Noise and uncertainty examined using temperature insensitive acrylic colors. (a) TLC color-temperature calibration plotted in the hue/saturation space. Symbols are located at positions corresponding to the hue/saturation values of the TLC during calibration runs, as indicated with their hue values. Temperatures are calculated with a two dimensional linear fit and are represented by a color gradient. (b) Temporal fluctuation in the color of the TLC, when held at a nominally fixed temperature. (c) Temporal fluctuation of the blue calibration color at fixed temperature. (d) Temporal fluctuation of the green calibration color at fixed temperature. (e) Temporal fluctuation of the red calibration color at fixed temperature.

Figure 42:
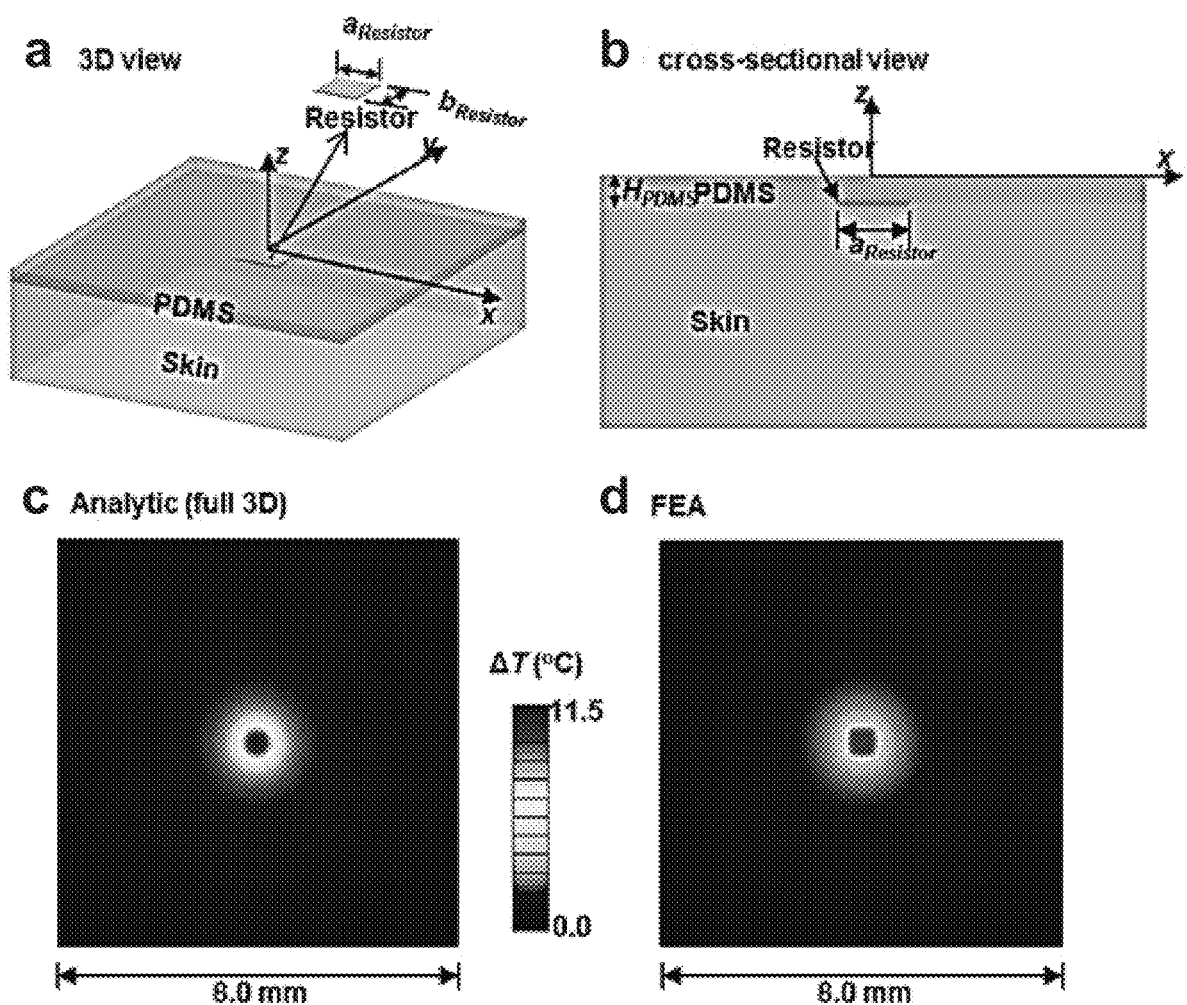
Figure 42:
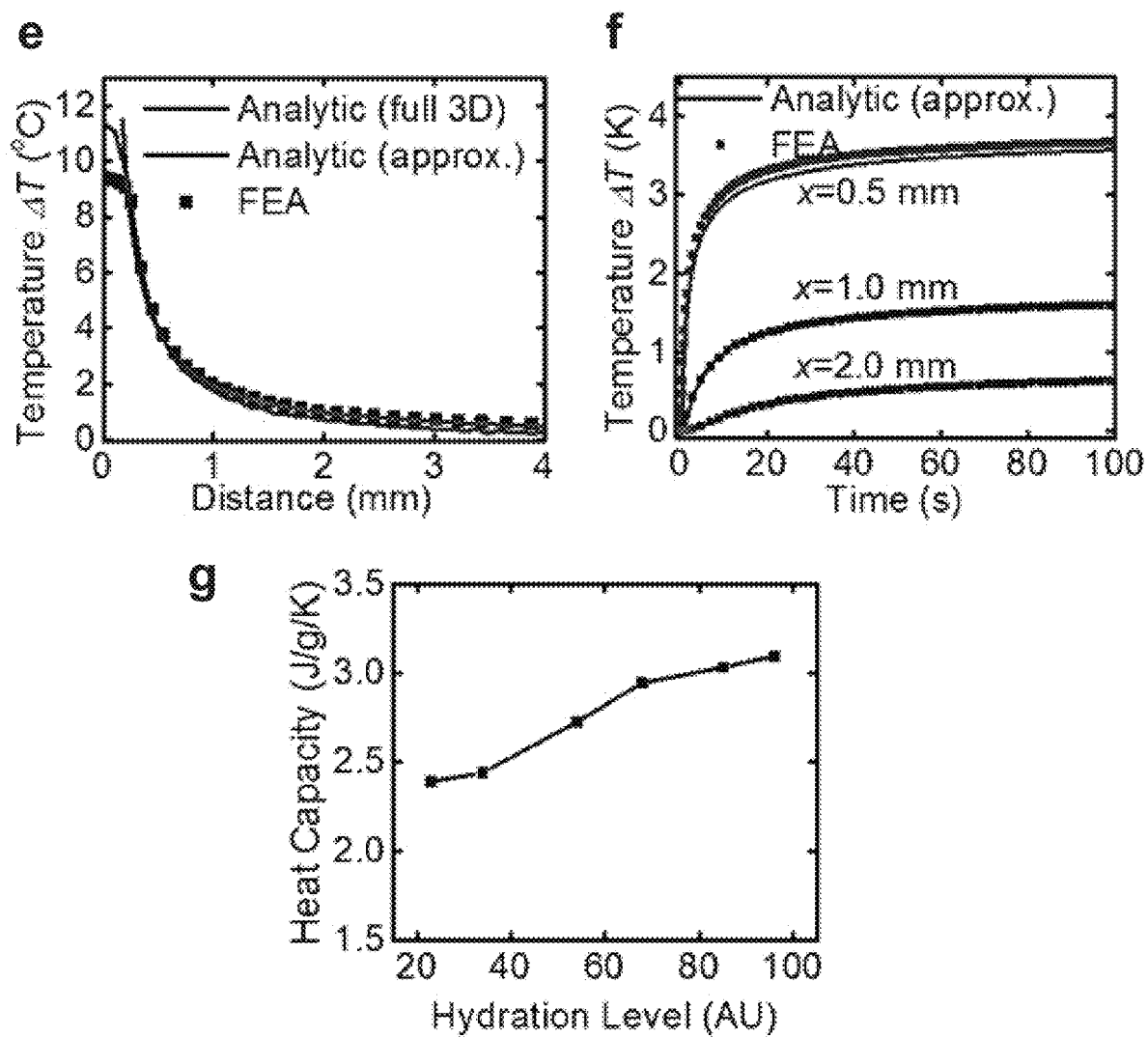

FIG. 42: Finite element models that allow determination thermal conductivity and diffusivity from data collected using active e-TLC devices. (a) A 3D view of a model with a Joule heater embedded between an e-TLC device and the skin. (b) A cross-sectional view of a model with a Joule heater embedded between an e-TLC device and the skin. (c) Analytical model of the spatial decay in temperature at steady state during operation of the Joule heater. (d) Corresponding finite element modeling results. (e) Analytical and finite element model of the spatial temperature decay with a wired Joule heater operation along one dimension. (f) Analytical and finite element model of the temporal temperature rise with a wireless Joule heater operation for locations away from the heater. (g) Skin heat capacity inferred from the skin thermal conductivity and diffusivity values in FIG. 32.

Figure 43:
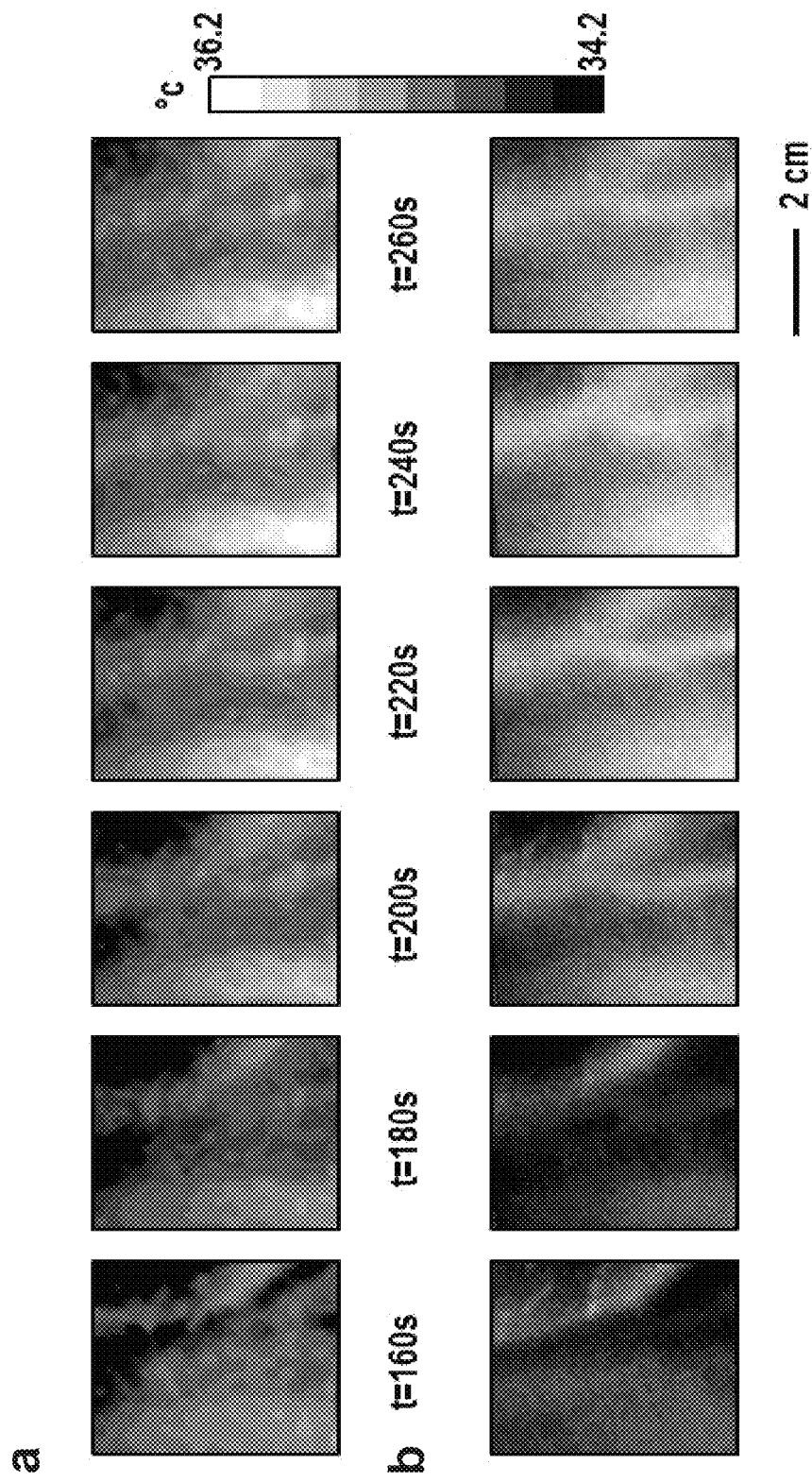

FIG. 43: Comparison of an e-TLC thermal imaging device and infrared camera measurement in a reactive hyperaemia test. (a) Spatial distributions of temperature determined with the e-TLC device at representative times from t=160 s to t=260 s at an interval of 20 s. (b) Spatial distributions of temperature determined with the infrared camera at representative times from t=160 s to t=260 s at an interval of 20 s.

Figure 44:
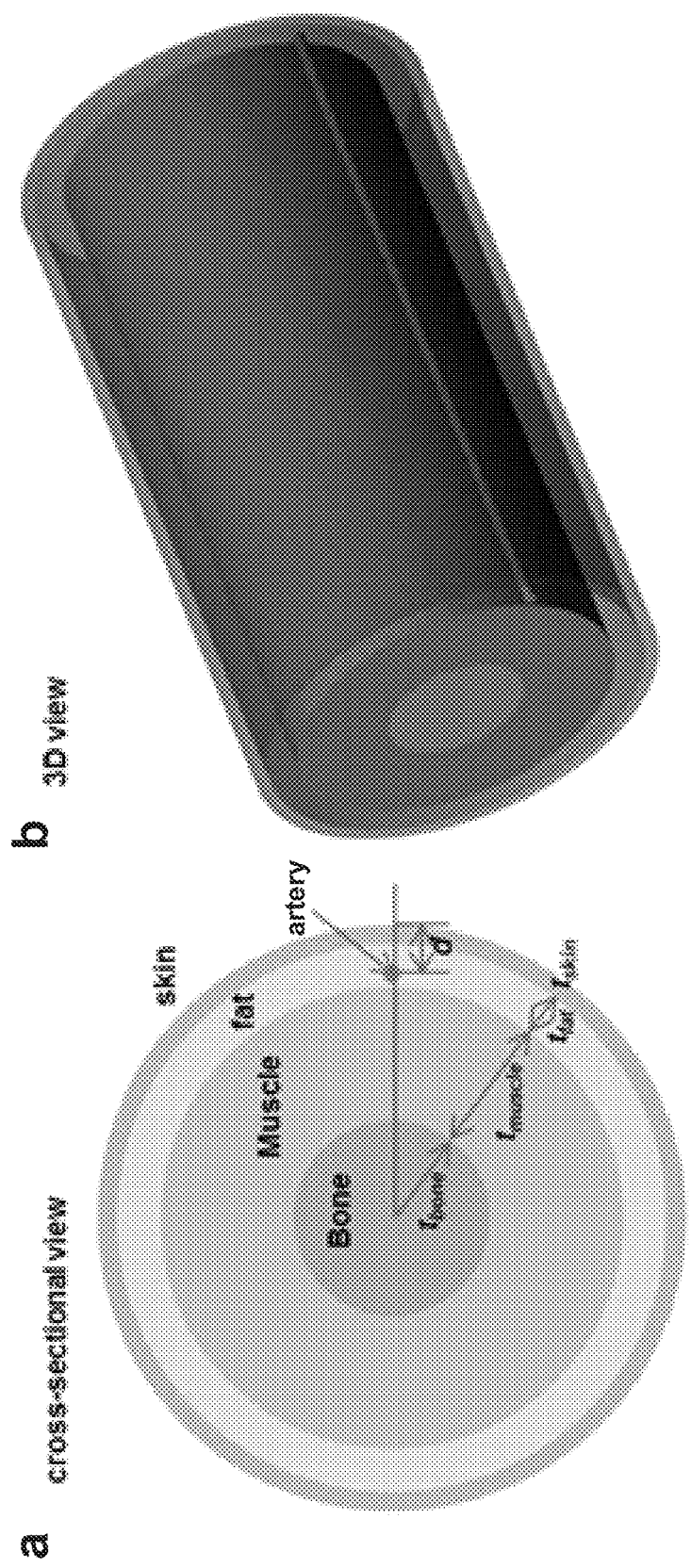
Figure 44:
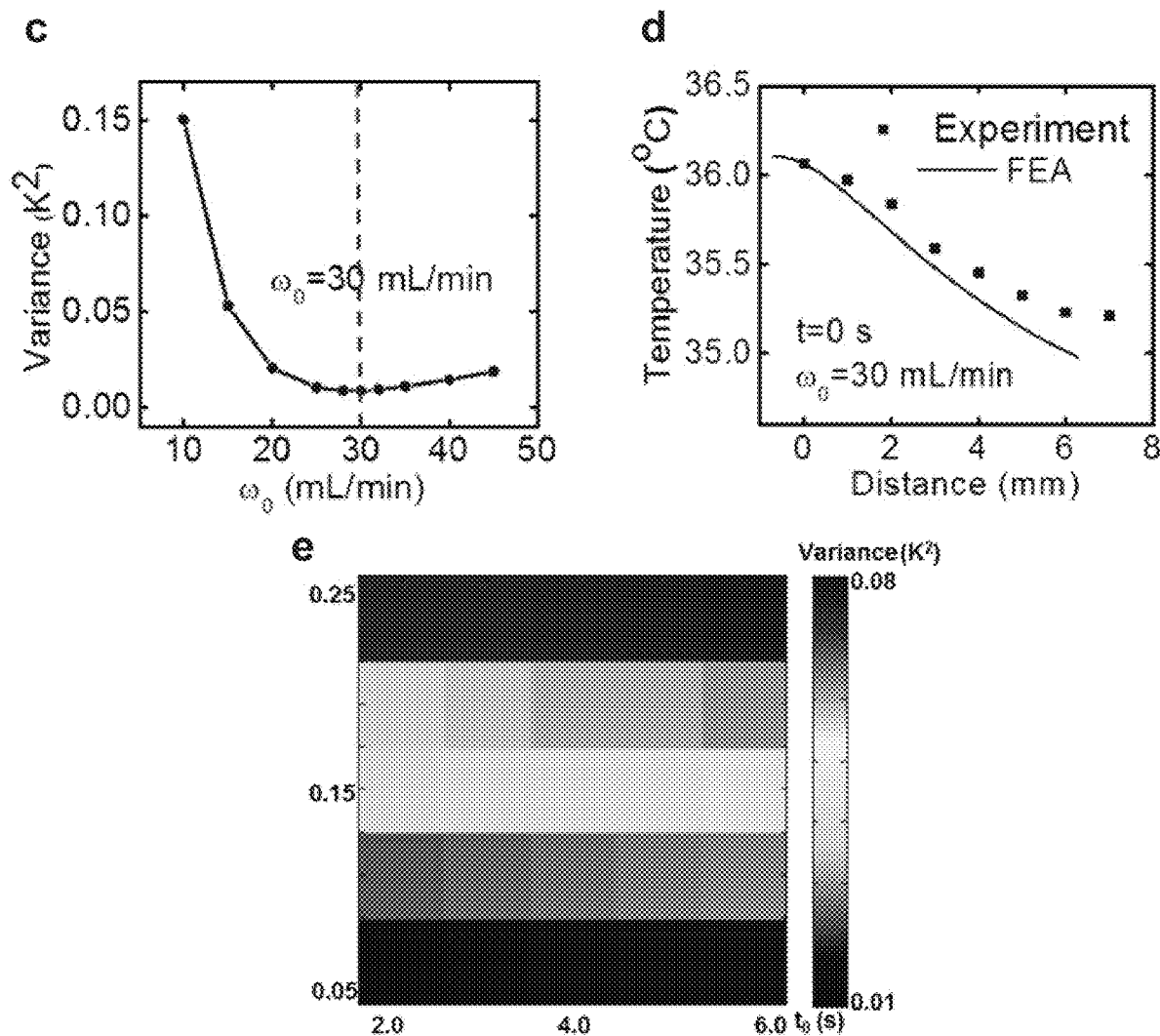

FIG. 44: Schematic illustration of the thermal conduction model that determines the blood flow rate during occlusion. (a) Cross-sectional view and (b) three-dimensional view of the wrist model; (c) Temperature variance of FEA and experiment versus the baseline flow rate; (d) Experimental results of the steady-state temperature as a function of the distance from the artery, as compared to the FEA calculations using the baseline flow rate of 30 mL/min; (e) Distribution of temperature variance in the space of parameters, $\alpha$ and $\tau_0$, during stage II of occlusion.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Functional substrate" refers to a substrate component for a device having at least one function or purpose other than providing mechanical support for a component(s) disposed on or within the substrate. In an embodiment, a functional substrate has at least one skin-related function or purpose. In an embodiment, a functional substrate has a mechanical functionality, for example, providing physical and mechanical properties for establishing conformal contact at the interface with a tissue, such as skin. In an embodiment, a functional substrate has a thermal functionality, for example, providing a thermal loading or mass small enough so as to avoid interference with measurement and/or characterization of a physiological parameter, such as the composition and amount of a biological fluid. In an embodiment, a functional substrate of the present devices and method is biocompatible and/or bioinert. In an embodiment, a functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another.

In some embodiments, a functional substrate that is mechanically matched to a tissue, such as skin, provides a conformable interface, for example, useful for establishing conformal contact with the surface of the tissue. Devices and methods of certain embodiments incorporate mechanically functional substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched functional substrate is characterized by one or more mechanical properties and/or physical properties that are within a specified factor of the same parameter for an epidermal layer of the skin, such as a factor of 10 or a factor of 2. In an embodiment, for example, a functional substrate has a Young's Modulus or thickness that is within a factor of 20, or optionally for some applications within a factor of 10, or optionally for some applications within a factor of 2, of a tissue, such as an epidermal layer of the skin, at the interface with a device of the present invention. In an embodiment, a mechanically matched functional substrate may have a mass or modulus that is equal to or lower than that of skin.

In some embodiments, a functional substrate that is thermally matched to skin has a thermal mass small enough that deployment of the device does not result in a thermal load on the tissue, such as skin, or small enough so as not to impact measurement and/or characterization of a physiological parameter, such as a characteristic of a biological fluid (e.g. composition, rate of release, etc.). In some embodiments, for example, a functional substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a functional substrate that is thermally matched to skin has a thermal mass low enough that is does not significantly disrupt water loss from the skin, such as avoiding a change in water loss by a factor of 1.2 or greater. Therefore, the device does not substantially induce sweating or significantly disrupt transdermal water loss from the skin.

In an embodiment, the functional substrate may be at least partially hydrophilic and/or at least partially hydrophobic.

In an embodiment, the functional substrate may have a modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 µm, or less than or equal to 50 µm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

A "component" is used broadly to refer to an individual part of a device.

"Sensing" refers to detecting the presence, absence, amount, magnitude or intensity of a physical and/or chemical property. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more other structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly (methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. Devices of certain aspects are capable of establishing conformal contact with internal and external tissue. Devices of certain aspects are capable of establishing conformal contact with tissue surfaces characterized by a range of surface morphologies including planar, curved, contoured, macro-featured and micro-featured surfaces and any combination of these. Devices of certain aspects are capable of establishing conformal contact with tissue surfaces corresponding to tissue undergoing movement.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1,000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Tissue parameter" refers to a property of a tissue including a physical property, physiological property, electronic property, optical property and/or chemical composition. Tissue parameter may refer to a surface property, a subsurface property or a property of a material derived from the tissue, such as a biological fluid. Tissue parameter may refer to a parameter corresponding to an in vivo tissue such as temperature; hydration state; chemical composition of the tissue; chemical composition of a fluid from the tissue; pH of a fluid from the tissue; the presence of absence of a biomarker; intensity of electromagnetic radiation exposed to the tissue; wavelength of electromagnetic radiation exposed to the tissue; and amount of an environmental contaminant exposed to the tissue. Devices of some embodiments are capable of generating a response that corresponds to one or more tissue parameters.

"Environmental parameter" refers to a property of an environment of a device, such as a device in conformal contact with a tissue. Environment parameter may refer to a physical property, electronic property, optical property and/or chemical composition, such as an intensity of electromagnetic radiation exposed to the device; wavelengths of electromagnetic radiation exposed to the device; a chemical composition of an environmental component exposed to the device; chemical composition of an environmental component exposed to the device; amount of an environmental contaminant exposed to the device; and/or chemical composition of an environmental contaminant exposed to the device. Devices of some embodiments are capable of generating a response that corresponds to one or more environmental parameters.

"Thermal transport property" refers to a rate of change of a temperature-related tissue property, such as a heat-related tissue property, over time and/or distance (velocity). In some embodiments, the heat-related tissue property may be temperature, conductivity or humidity. The heat-related tissue property may be used to determine a thermal transport property of the tissue, where the "thermal transport property" relates to heat flow or distribution at or near the tissue surface. In some embodiments, thermal transport properties include temperature distribution across a tissue surface, thermal conductivity, thermal diffusivity and heat capacity. Thermal transport properties, as evaluated in the present methods and systems, may be correlated with a physical or physiological property of the tissue. In some embodiments, a thermal transport property may correlate with a temperature of tissue. In some embodiments, a thermal transport property may correlate with a vasculature property, such as blood flow and/or direction.

The invention can be further understood by the following non-limiting examples.

Example 1

Epidermal Devices for Non-Invasive, Precise and Continuous Monitoring of Macrovascular and Microvascular Blood Flow Continuous monitoring of variations in blood flow is vital in assessments of the status of micro and macrovascular beds for a wide range of clinical and research scenarios. Although a variety of techniques exist, most require complete immobilization of the subject, thereby limiting their utility to hospital or clinical settings. Those techniques that can be rendered in wearable formats suffer from limited accuracy, motion artifacts and other shortcomings that follow from an inability to achieve intimate, non-invasive mechanical linkage of sensors with the surface of the skin. Here we introduce an ultrathin, soft, skin-conforming sensor technology that offers advanced capabilities in continuous and precise blood flow mapping. Systematic work establishes a set of experimental procedures and theoretical models for quantitative measurements and guidelines in design and operation. Experimental studies on human subjects, including validation with measurements performed using state-of-the-art clinical techniques, demonstrate sensitive and accurate assessment of both macro and microvascular flow under a range of differing physiological conditions. Refined operational modes eliminate long-term drifts and reduce power consumption, providing steps towards use of this technology for continuous monitoring, during daily activities.

Measurements of blood flow serve as important, often critical, indicators of vascular health [1]. Vascular endothelial dysfunction can result from aging, atherosclerosis [2], diabetes and other conditions that may also involve inflammation [3]. Considerable interest exists, therefore, in tools with capabilities for reliable, non-invasive monitoring of blood flow across various parts of the body under different conditions [4]. Existing techniques can be categorized according to the underlying measurement physics: mechanical (plethysmography), optical (photoplethysmography, laser Doppler flowmetry (LDF) and laser speckle contrast imaging (LSCI)), acoustic (ultrasound) and thermal (various forms of thermal clearance). Plethysmography relies on the measurement of bulk changes in limb dimensions caused by changes in blood volume, but only provides an estimate of flow to the entire limb. Measurements typically involve strain gauges wrapped around the limb to quantify dimensional changes [5, 6], or, in the case of photoplethysmography, optical illumination to identify changes in optical absorption, both of which follow from changes in blood volume [7]. Ultrasound techniques rely on acoustic Doppler shifts [8, 9]. Similar Doppler shifts in optical signals form the basis for laser LDF measurements [10-12]. Related optical phenomena, where blood flow induces spatiotemporal variations in reflected speckle patterns associated with a coherent light source, form the basis of modern LSCI techniques [13-15].

Acoustic and optical methods are especially useful due to their robustness as to spatio-temporal mapping. Extreme sensitivity to motion, however, demands immobilization of the subject during the measurement, thereby limiting use to controlled, clinical or laboratory settings. Paste-on, single point sensors have some potential to reduce the effects of movement, but likely not to levels that would allow use during normal body motions. Wearable optical measurement systems are becoming available [16-19], but present hardware involves rigid, bulky device components that are affixed to the skin in ways that can lead to irritation and discomfort after prolonged application, as well as generate pressure in the microcirculatory bed leading to erroneous readings.

Techniques based on thermal transport offer reduced sensitivity to motion. Existing non-invasive approaches exploit metal heating and sensing plates applied to the skin. Here, blood flow in the tissue [20, 21] influences the time and/or spatial dependence of the thermal response, as a means to determine spatial variations in effective thermal conductivity [22, 23] and, therefore, regional perfusion. Limitations of previous techniques follow from the use of bulky thermal components and pressure-induced coupling to the skin, resulting in an inability to (1) perform spatial mapping, (2) track subtle or rapid temporal changes, and (3) assess natural, unaltered patterns of blood flow. The use of laser heating and infrared mapping of thermal distributions in subsurface vessels [24] avoids these disadvantages, but re-introduces high sensitivity to motion.

Here we present strategies for exploiting electronic devices that adopt physical and topographic characteristics of the epidermis to allow precision thermal measurements of blood flow in ways that offer considerable advantages over existing methods. When combined with thermal analysis techniques, these platforms provide routes for quantitative monitoring of both the speed and direction of near surface blood flow, up to 1.5 mm in depth, without the aforementioned limitations and constraints associated with contact, movement and pressure, with potential for continuous use during daily activities. These capabilities follow from ultra-thin, flexible, stretchable mechanics of the device components, in which precision thermal detectors conform intimately to the surface of the skin through the action of van der Waals forces alone, without any externally applied pressure. The combination of intimate skin contact and extremely low mass (0.2-5 mg cm$^{-2}$, for 0-40 μm silicone support thickness) eliminates relative movement between the skin surface and detectors even during rapid motions of the body. The low thermal mass (0.2-5.7 mJ cm$^{-2}$ K$^{-1}$) and high gas permeability (2 g h$^{-1}$ m$^{-2}$ for solid silicone support, with options for porous/perforated versions for higher permeability [25] of these systems minimizes perturbation to the natural temperature of skin. Measurements involving human subject volunteers, with quantitative comparisons to state-of-the-art commercial optical blood flow measurement systems, demonstrate the ability to map directional blood flow in large subsurface vessels—i.e., veins, under varied physiological conditions. Quantitative analytical and finite element models provide a systematic framework for converting measured data to blood flow rates. Additional measurements demonstrate capacities for monitoring changes in flow through near surface microvasculature—i.e., arteriolar and capillary bed, induced by deep breathing and slap-mediated hyperemia associated with dermatographic urticaria. An advanced, pulsed operation mode offers potential long-term monitoring via elimination of key sources of drift in the measurement and reduction of the power consumption.

Results and Discussion

Device Design and Operational Principles

Figure 1:
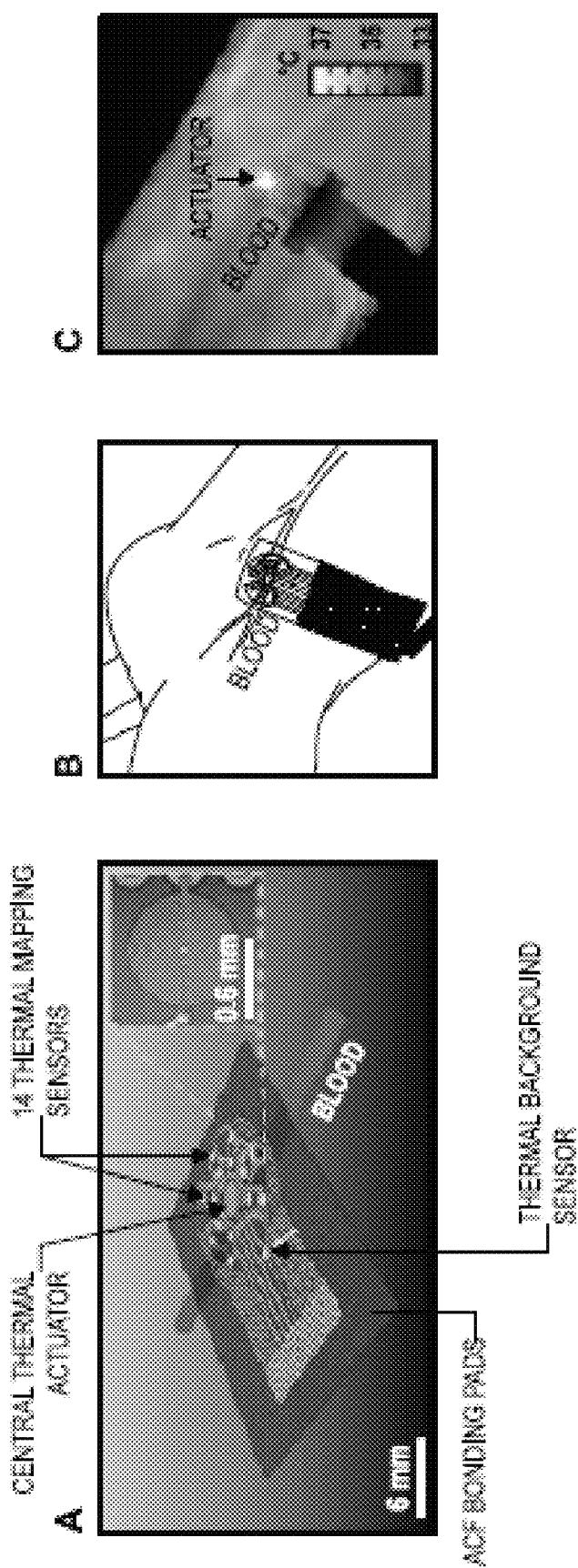
FIG. 1: Device design and thermal response to flow. a) Schematic illustration of the device layout, including a blood vessel near the skin surface. A large (3 mm diameter) central thermal actuator provides power input into the vessel (typically 25 mW or 3.5 mW/mm$^2$), at temperatures below the threshold for sensation (<8° C. rise above base skin temperature). Fourteen surrounding sensors allow measurement of the resulting thermal distribution (inset: magnified view of one sensor). An additional sensor serves to detect changes in the background temperature to compensate for drift. An array of bonding pads enable attachment of a thin (100 µm) flexible cable interface to external data acquisition electronics. b) Photograph of a device on the skin. c) An infrared image of a device on the skin over a vein, during application of power to the actuator. d) Raw data from a device applied to an area above a large vessel. The layout of the graphs corresponds approximately to the spatial distribution of the sensors (black) and actuator (red). The thermal distribution is strongly anisotropic, with bias in the direction of flow. Heating begins at t=60 s and ends at t=360 s. e) Spatial map of the temperature at t=300 s. The colormap uses spatially interpolated data. Black arrows indicate the relative magnitudes of the temperature rise measured by the inner ring of sensors. f) Same spatial map as that shown in e), with the signal of the heater removed to enhance the contrast of the data measured by the surrounding sensors. g) Results of measured thermal flow, calculated from the temperature distribution around the actuator. The vector arrow map shows the calculated convection-driven thermal flow fields. The colormap represents the magnitude of the flow field. h) Similar map as shown in g), where the colormaps represent the magnitude of flow in the x-direction (X-comp) and i) y-direction (Y-comp).
Figure 1:
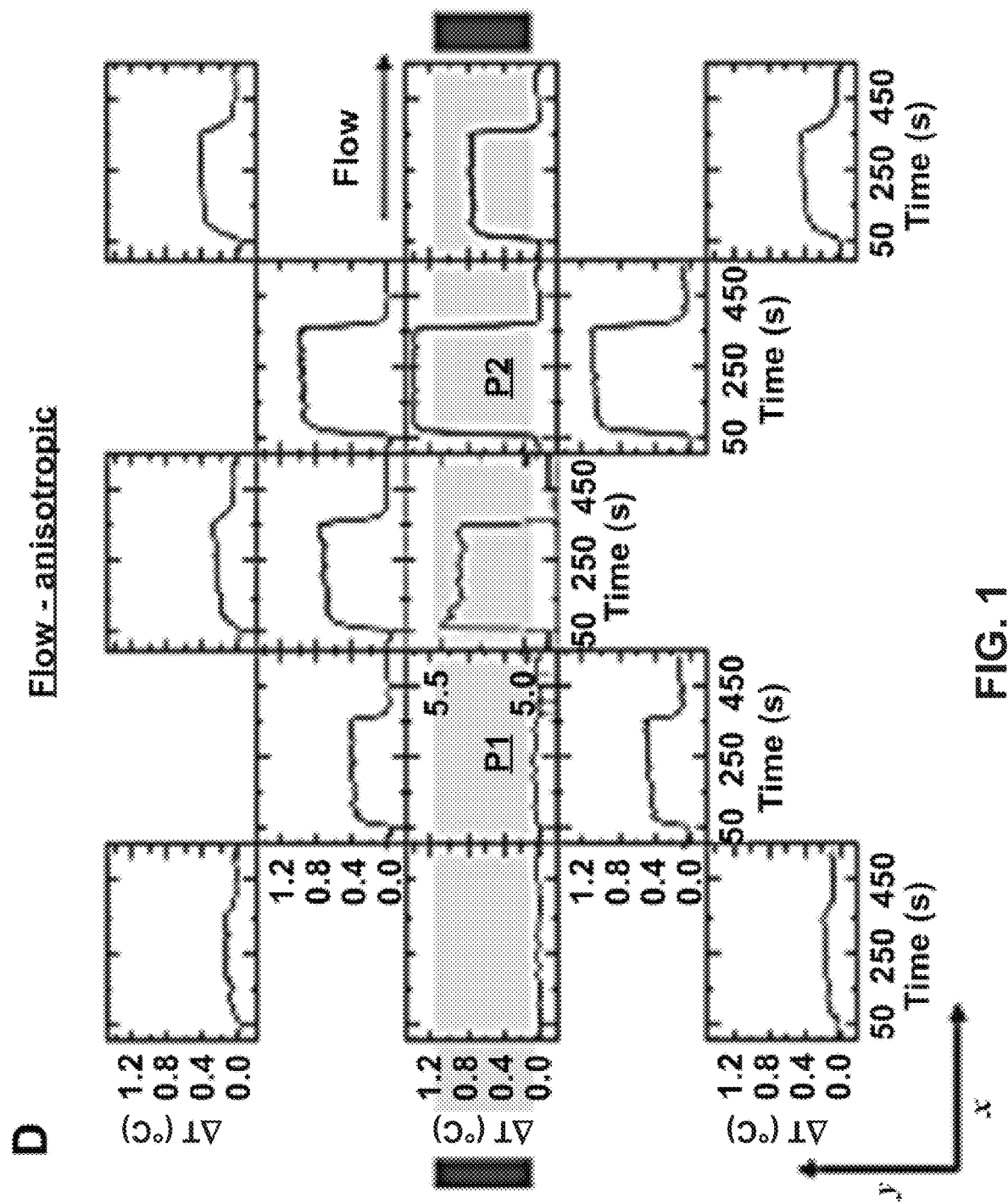
Figure 1:
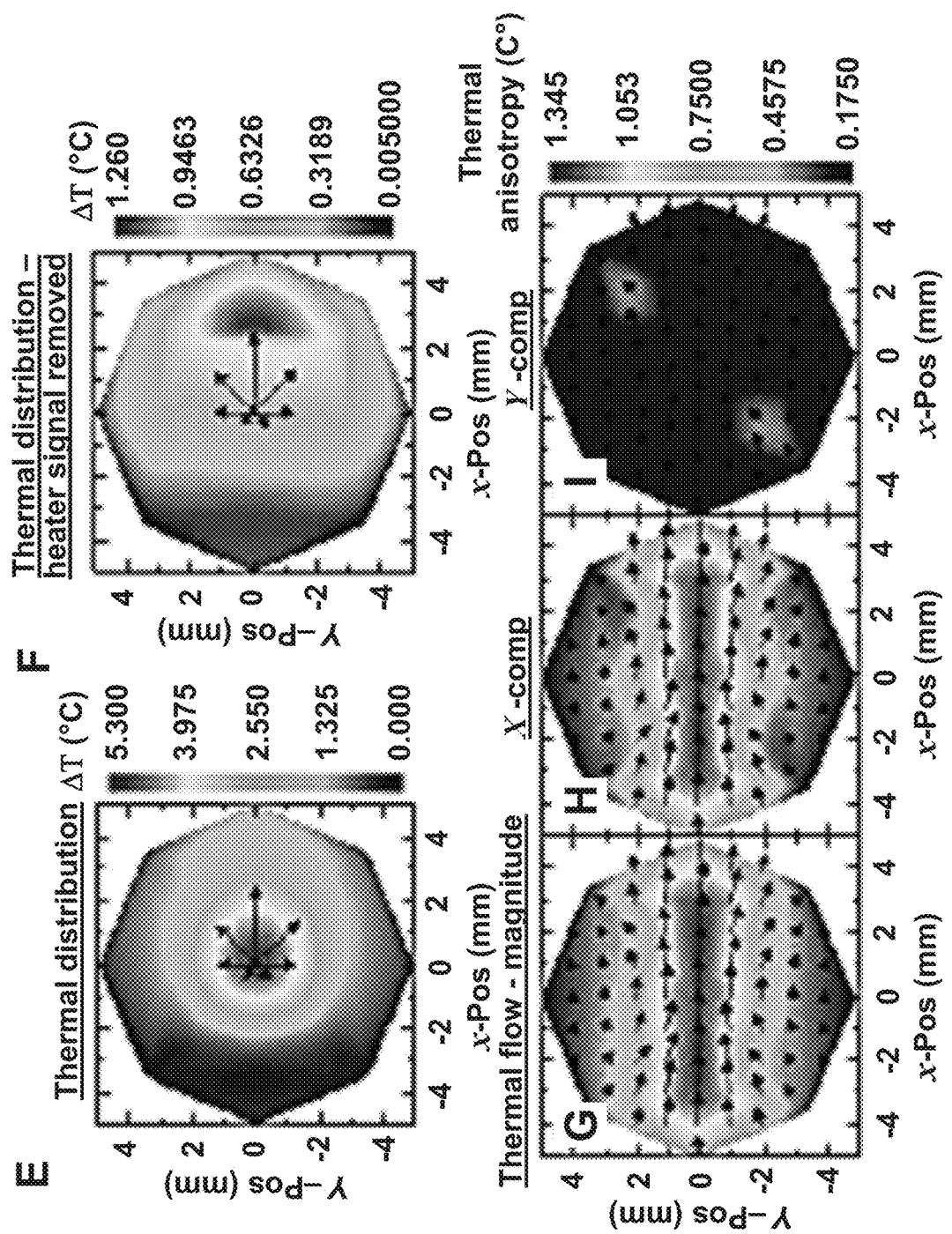

The device incorporates an array of thin (100 nm) metallic thermal actuators and sensors designed for monitoring blood flow beneath a targeted area (~1 cm$^2$ for results presented here) of the skin (FIG. 1a; See Supplemental Information for fabrication details). The array includes a single circular thermal actuator (1.5 mm radius composed of a 15 μm wide filament of 10/100 nm Cr/Au) surrounded by two rings of sensors (0.5 mm radius composed of a 10 μm wide filament of 10/100 nm Cr/Au). The first and second rings lie at a 3 mm and 5 mm center-to-center distance from the central actuator, respectively. Each ring contains 7 sensors, spaced at 45° angular increments around the ring (one 45° location is vacant to allow for interconnect wiring). The construction uses narrow, filamentary serpentine traces and thin, low modulus silicon substrates, using concepts in ultrathin, stretchable electronic sensor design [26-33], to yield a device platform that naturally conforms to the surface of the skin (FIG. 1b) for the type of intimate thermal contact that is critical to the measurements. The sensors rely on temperature dependent values of their resistance according to previously reported results, and offer measurement precision in the range of ~0.01° C. with a 2 Hz sampling rate.

Figure 8:
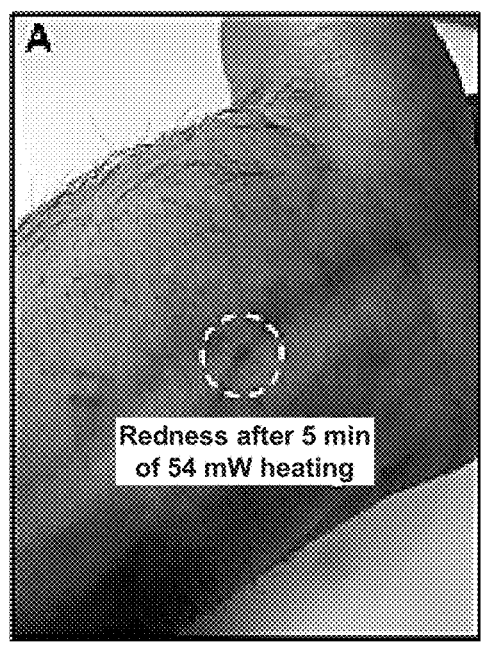
FIG. 8: Analysis of thermal actuator power levels. (A) Photograph of local redness (image levels enhanced for contrast) induced by 5 min of heating at 54 mW power (15.8° C. rise) to the thermal actuator. Power levels are kept below 25 mW in all experiments to avoid this type of issue. (B) Measured temperature differentials, taken over a vein on the wrist, for 4 different power levels. For a constant flow rate, the curves should be independent of power. However, changing flow rate in the vein can be seen by oscillations in the data. Within oscillations, the curves are independent of power until 54 mW, where the signal strength appears slightly amplified, possibly due to the skin changes apparent in (A).
Figure 8:
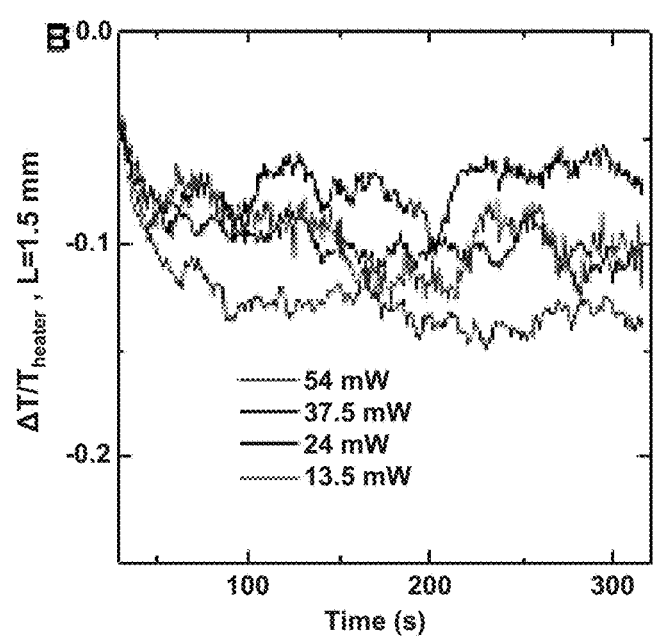
Figure 9:
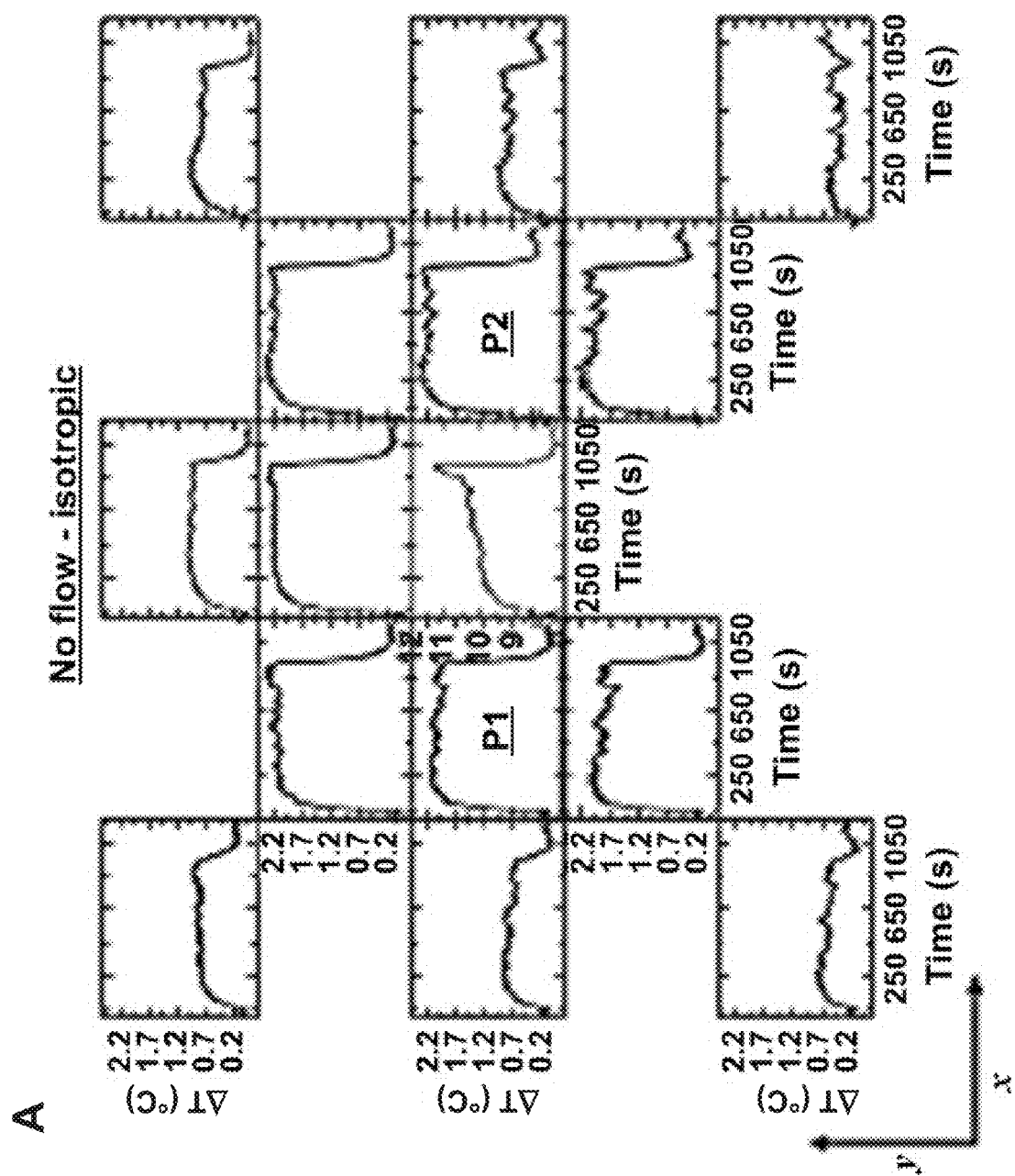
FIG. 9: (A)-(F) Epidermal device data output for skin locations with isotropic thermal transport. Similar datasets as shown in FIG. 1(D-I), except with the device placed on the palm, away from any large blood vessels.
Figure 9:
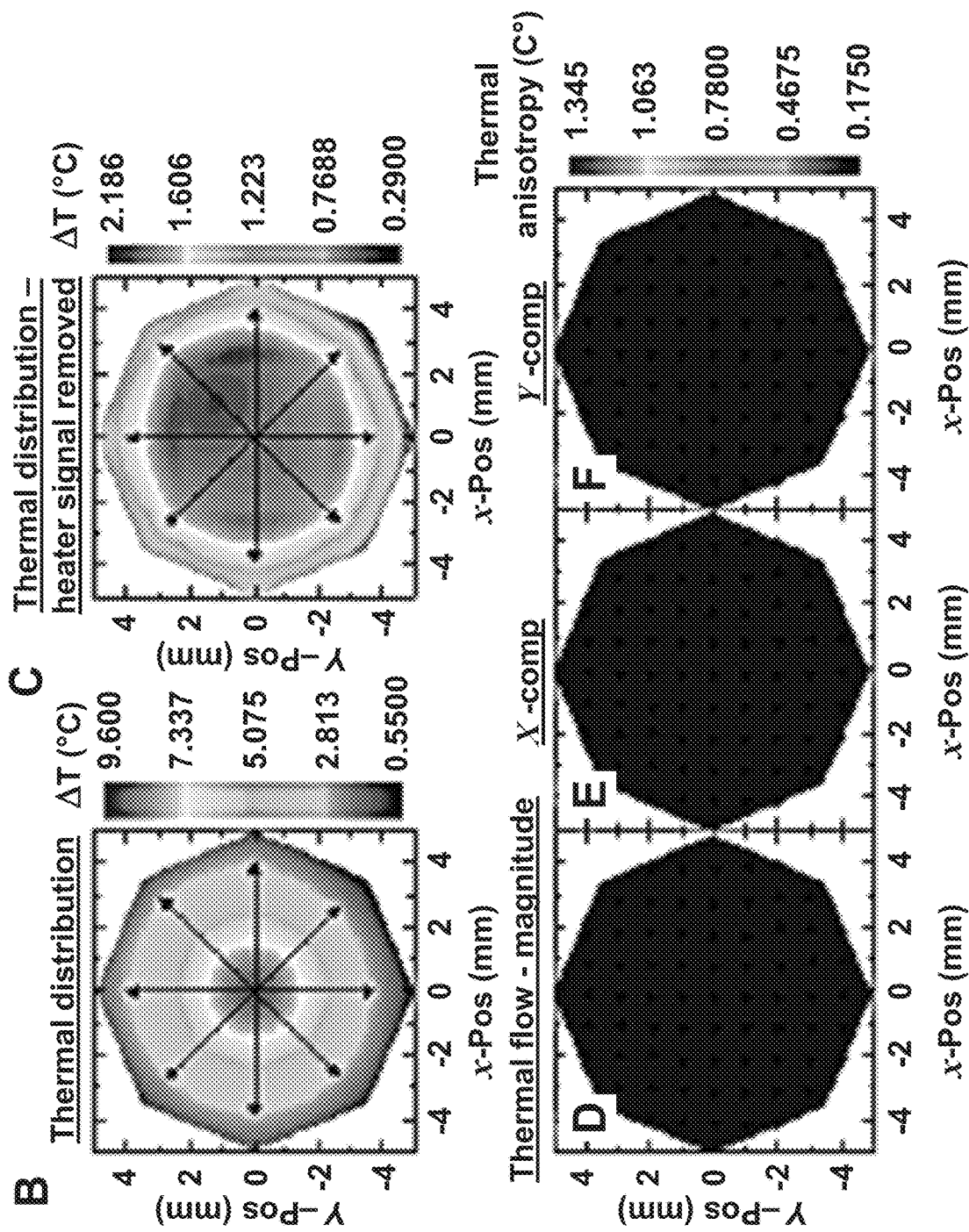

Subsurface blood flow leads to anisotropic thermal transport phenomena that can be accurately quantified using this type of system. The central thermal actuator provides a constant source of thermal power to create a mild, well-controlled increase in temperature at the surface of the skin in the vicinity of a targeted vessel (FIG. 1c). Responses of the sensors determine the spatio-temporal distributions of temperature that result from this heating. The actuator dimensions and operating parameters (typically ~3.5 mW mm$^{-2}$) ensure adequate thermal signals in the surrounding sensors, with peak temperatures (~6° C.) that remain below the threshold for sensation. For all cases reported here, the responses depend linearly on power for peak temperatures below ~10° C. (For effects at higher temperatures, see FIG. 8a, b.) Representative data, in the form of spatially dependent changes in temperature as a function of time, appear in FIG. 1d. FIG. 1e,f summarize color-mapped data interpolations at an instance in time, with and without the actuator signal. The directionality of the local thermal flow can be inferred from differences in the relative increases in temperature at sensors located on opposing sides of the actuator. Such flow field maps indicate relative changes in local flow as well as the directionality components of flow relative to the skin surface (FIGS. 1g-i). Similar data, but with the device placed in a region with no large blood vessels, appear in FIG. 9.

Device Analysis and Modeling

Figure 2:
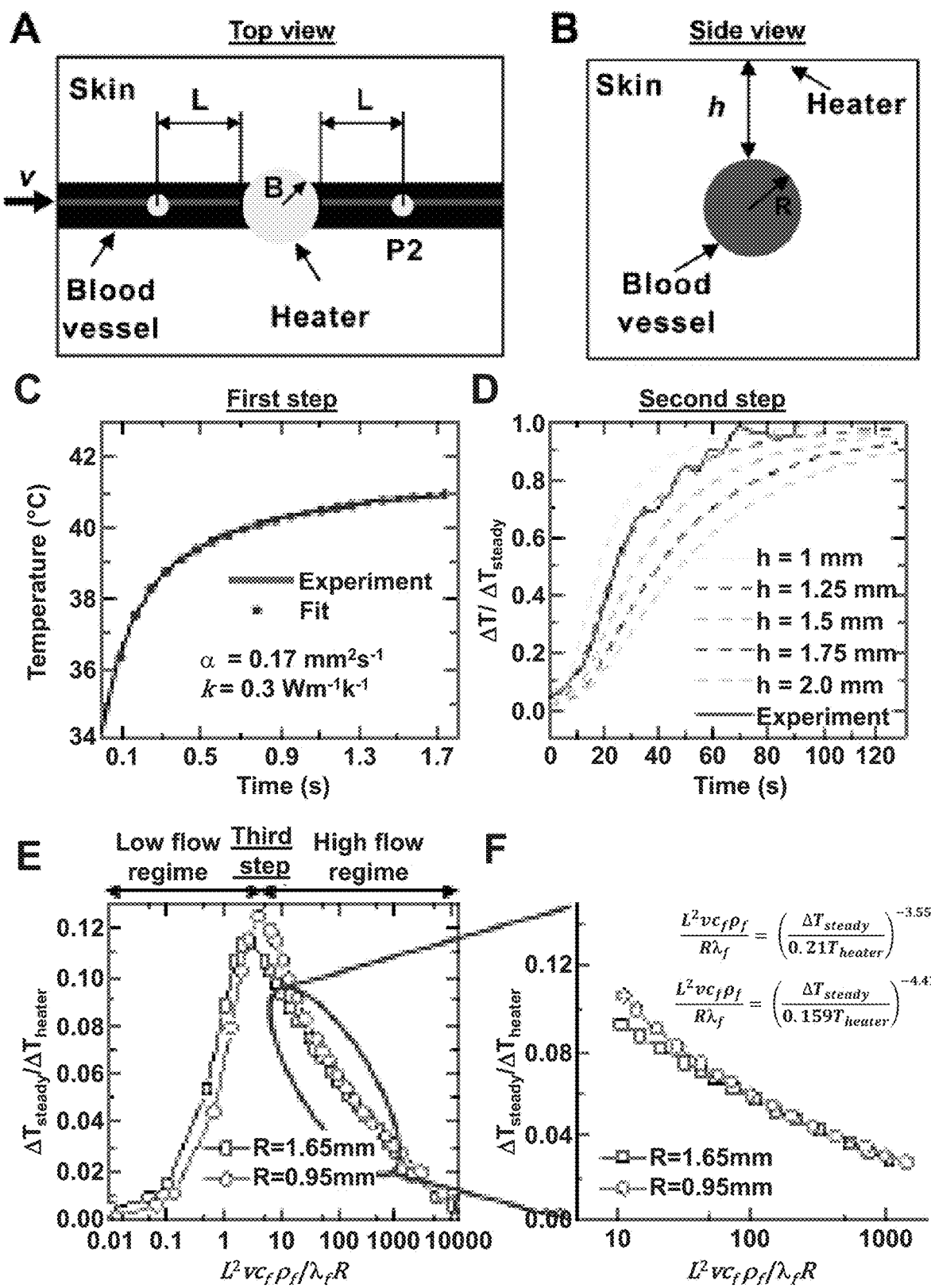
FIG. 2: Process for quantifying blood flow rates from measured thermal signals. Conversion of thermal signals to blood flow rates relies on models that include a linear vessel of radius R, a distance h beneath the surface of the skin, with a central thermal actuator on the skin surface of radius B, and two sensors, one upstream and one downstream along the vessel, at a distance L (from actuator edge to sensor center). a) Top-down and b) cross-sectional views of this model system. c) The first step one determines the thermal transport properties of tissue located at each of the sensors and at the actuator. Here, 2 mA of current is applied to each sensor for 2 s. The local thermal conductivity and thermal diffusivity follow from analysis of the thermal transients associated with heating and cooling. d) The second step approximates the depth of the blood vessel. The experimental initial transient profile of the differential temperature across the thermal actuator is compared to finite element models of the skin to determine the approximate depth of the vessel, using the thermal transport values determined in the first step. e) The third step converts the thermal information to a blood flow velocity, v, using the values determined in the first and second steps. The differential temperature reaches a maximum at low flow velocity. The temperature rise at each sensor determines whether the calculation uses the low or high flow regimes. Most physiologically relevant flow rates are expected to fall in the high flow regime. f) The radius of the underlying blood vessel, R, has a minor impact on the responses in the high flow regime, due to their dependence on R/L. The equations represent the numerical fits at R=0.95 mm and 1.65 mm of the high flow regime.
Figure 13:
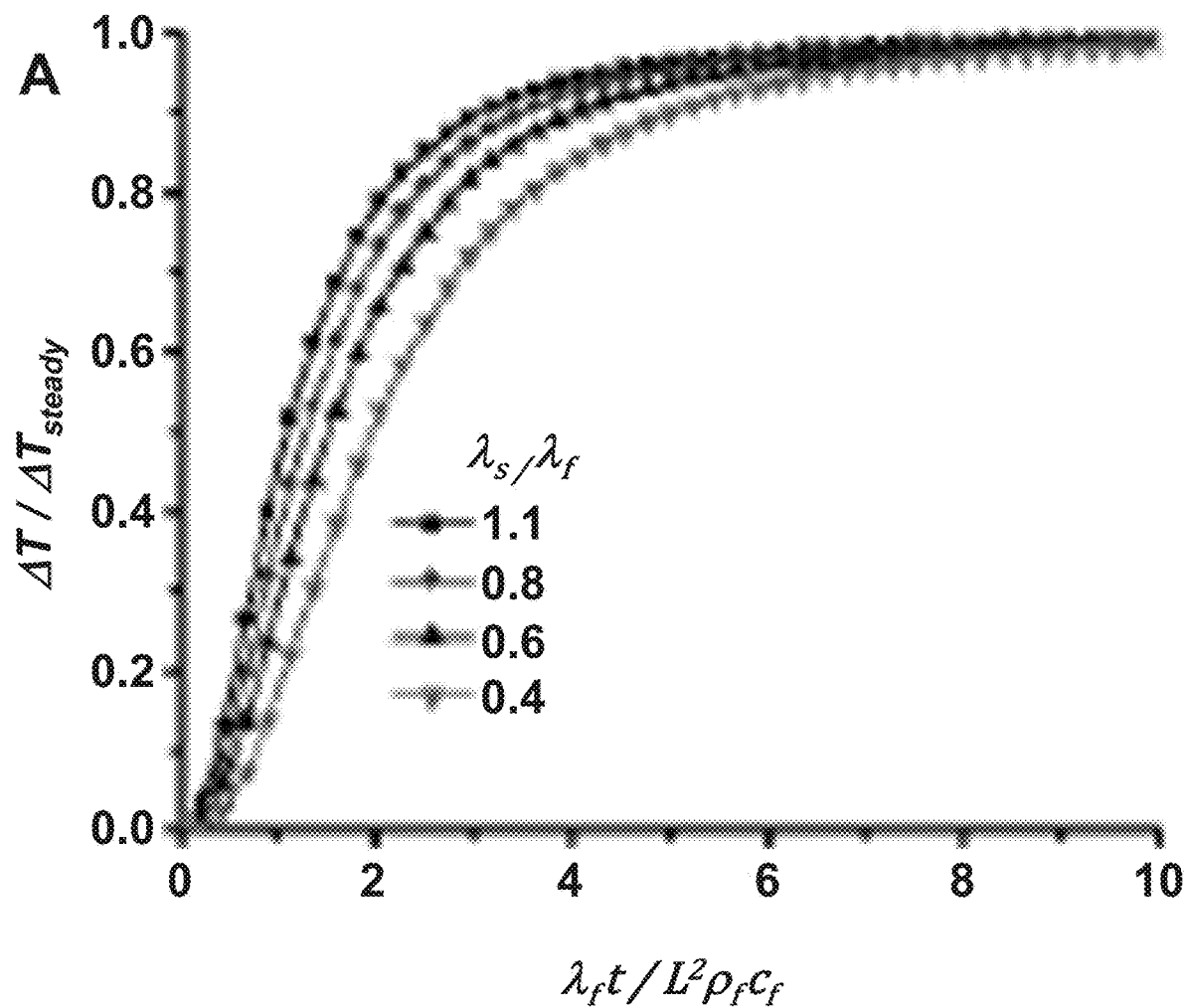
FIG. 13: The influence of variation of $\lambda_s/\lambda_f$, $\rho_f c_f/\rho_s c_s$ and B/L on the transient scaling law. The thermal parameters of the tissues ($\lambda_s$, $\rho_s$ and $c_s$) are highly variable, based on skin location, individual person, etc. A clinical study of 25 people (33) was run in which thermal diffusivities ($\lambda_s/\rho_s c_s$) that varied from 0.11-0.2 mm$_2$ s$_{-1}$, and thermal conductivities ($\lambda_s$) that varied from 0.2-0.55 Wm$_{-1}$k$_{-1}$ were measured. This corresponds to the parameters $\lambda_s/\lambda_f$=0.4-1.1, and $\rho_s c_s/\rho_s c_s$=0.38-0.7. (A, B) The transient scaling law (Equation 1) with different $\lambda_s/\lambda_f$ (0.54-0.72) and different $\rho_s c_s/\rho_s c_s$ (0.38-0.7), illustrates that the transient scaling law depends on the thermal parameters of the issues strongly. (C) The transient scaling law (Equation 1) with B/L=⅓-1, shows the influence of the size of the actuator on the transient scaling law.
Figure 13:
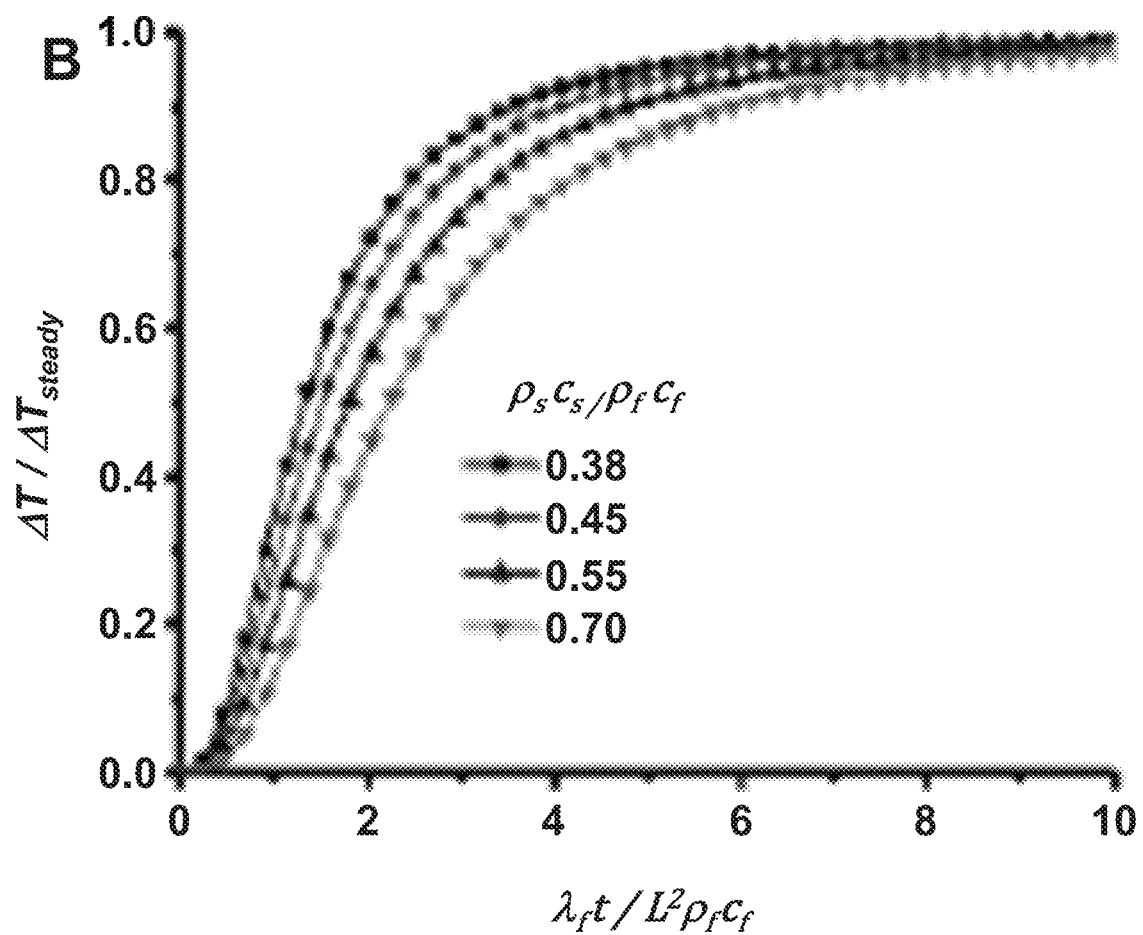
Figure 13:
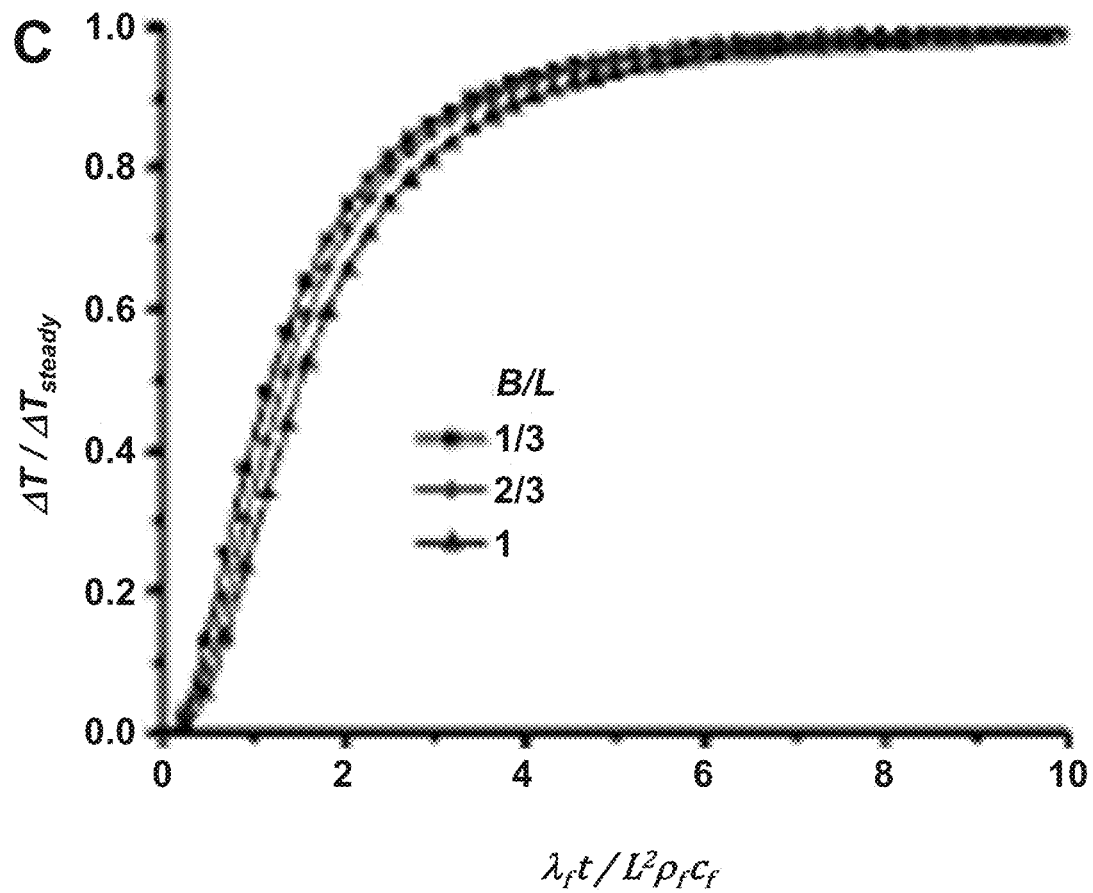
Figure 14:
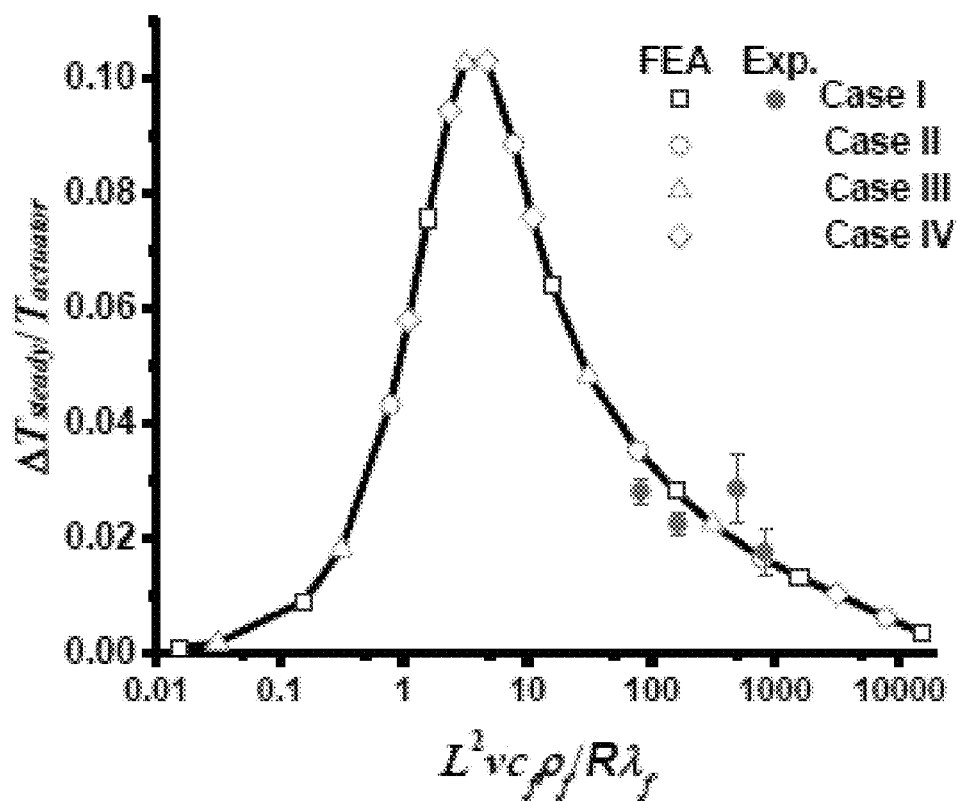
FIG. 14: Verification for the steady-state scaling law by FEA and experiment. Case I is the base line for comparison (water: $\lambda_f$=0.6 W·mm$_{-1}$K$_{-1}$, $\rho_f$=1,000 kg/m$_3$, $c_f$=4184 J·kg$_{-1}$·K$_{-1}$, PDMS: $\lambda_s$=0.18 W·mm$_{-1}$K$_{-1}$, $\rho_s$=970 kg/m$_3$, $c_s$=1380 J·kg$_{-1}$·K$_{-1}$, h=0.55 mm, L=1.5 mm, B=1.5 mm, R=1 mm). Case II (double $\rho_f$) and Case III (double $\lambda_f$ and $\lambda_s$) change the material properties while Case IV varies the geometric parameters (h, L, B, R). All confirm the steady-state scaling law. PDMS experiments agree well with the steady-state scaling law without any parameter fitting.

Conversion of the data into quantitative blood flow rates depends on the heterogeneous and time dynamic properties of the tissue. Variables that influence the signals, in addition to blood flow rate and direction, include thermal conductivity ($\lambda$), heat capacity (c), density ($\rho$) of blood (subscript f) and local tissue (subscript s), blood vessel depth (h in FIG. 2b), blood vessel radius (R in FIG. 2b) and geometrical parameters of the device (L=3.5 mm, B=1.5 mm in FIG. 2a). In general, the thermal properties of blood ($\lambda_f$=0.5 W·mm$^{-1}$K$^{-1}$, $c_f$=3659 J·kg$^{-1}$·K$^{-1}$, $\rho_f$=1069 kg/m$^3$) are well established [34, 35] and assumed to be known a priori. The tissue properties and blood vessel parameters are unknowns, with values that fall within established physiological ranges [34]. Our analysis combines systematic experimental measurement steps, an analytical scaling law and finite element analysis (FEA). FIG. 2 illustrate these steps, along with a representation of the blood vessel under the skin used in modeling (top-down and cross-section view of the model system appear in FIGS. 2a and b, respectively). In the first step, a short (2 s) input of power (7-8 mW mm$^{-2}$) is applied to each sensor in the device sequentially (FIG. 2c), as a means to probe the local tissue properties. Analysis of the time dynamics of the temperature rise at each sensor determines the thermal characteristics of the corresponding regions of the skin (thermal diffusivity $\lambda_s/\rho_s c_s$=0.17 mm$^2$ s$^{-1}$, and thermal conductivity $\lambda_s$=0.3 W m$^{-1}$ k$^{-1}$ for the case in FIG. 2c) following procedures reported elsewhere [36]. The results represent important information for the thermal models. The second step involves activating the central thermal actuator, while simultaneously recording the temperature of this element and those of the surrounding sensors. Analysis establishes the following transient scaling law, as verified by FEA and in vitro experiments (FIGS. 10 and 11, see Materials and Methods for details)

$$\frac{\Delta T}{\Delta T_{stesdy}} = f\left(\frac{\lambda_f t}{h^2 \rho_f c_f}, \frac{\lambda_s}{\lambda_f}, \frac{\rho_s c_s}{\rho_f c_f}, \frac{h}{L}, \frac{B}{L}\right) \quad (1)$$

where ΔT is the difference between the temperatures of a pair of sensors on opposing sides of the actuator and which lie along the direction of the targeted vessel; $\Delta T_{steady}$ is the final steady-state value of ΔT. A venous optical imager (VeinViewer Flex, Christie Medical, USA) is useful, during in vivo experiments, for venous mapping of the human forearm (volar aspect, FIG. 10) to assist in accurate placement of the device on the vein. The temperature ΔT normalized by its steady-state value $\Delta T_{steady}$ is independent of the radius of the blood vessel R and the blood flow velocity v (FIGS. 11 and 12); and its dependence on the normalized material properties $\lambda_s/\lambda_f$ and $\rho_s c_s/\rho_f c_f$ and actuator radius B/L on the transient scaling law appears in FIG. 13. The only unknown parameter is the depth h. As a result, a comparison of experimental results of $\Delta T/\Delta T_{steady}$ versus time, t, to FEA results that employ different vessel depths, using the tissue thermal properties measured in the first step, can yield accurate estimates for h. For the case of FIG. 2d, h=1.25 mm. In the third step, the steady-state temperature difference $\Delta T_{steady}$ between the sensors on opposing sides of the actuator normalized by the temperature at the actuator $\Delta T_{actuator}$ depends on blood flow velocity along the direction defined by the sensors. Here, the following steady-state scaling law applies, as verified by FEA and in vitro experiments (FIG. 14, see Materials and Methods for details)

$$\frac{\Delta T_{steady}}{\Delta T_{actuator}} = f\left(\frac{L^2 v c_f \rho_f}{R\lambda_f}, \frac{\lambda_s}{\lambda_f}, \frac{h}{L}, \frac{B}{L}, \frac{R}{L}\right) \quad (2)$$

Figure 15:
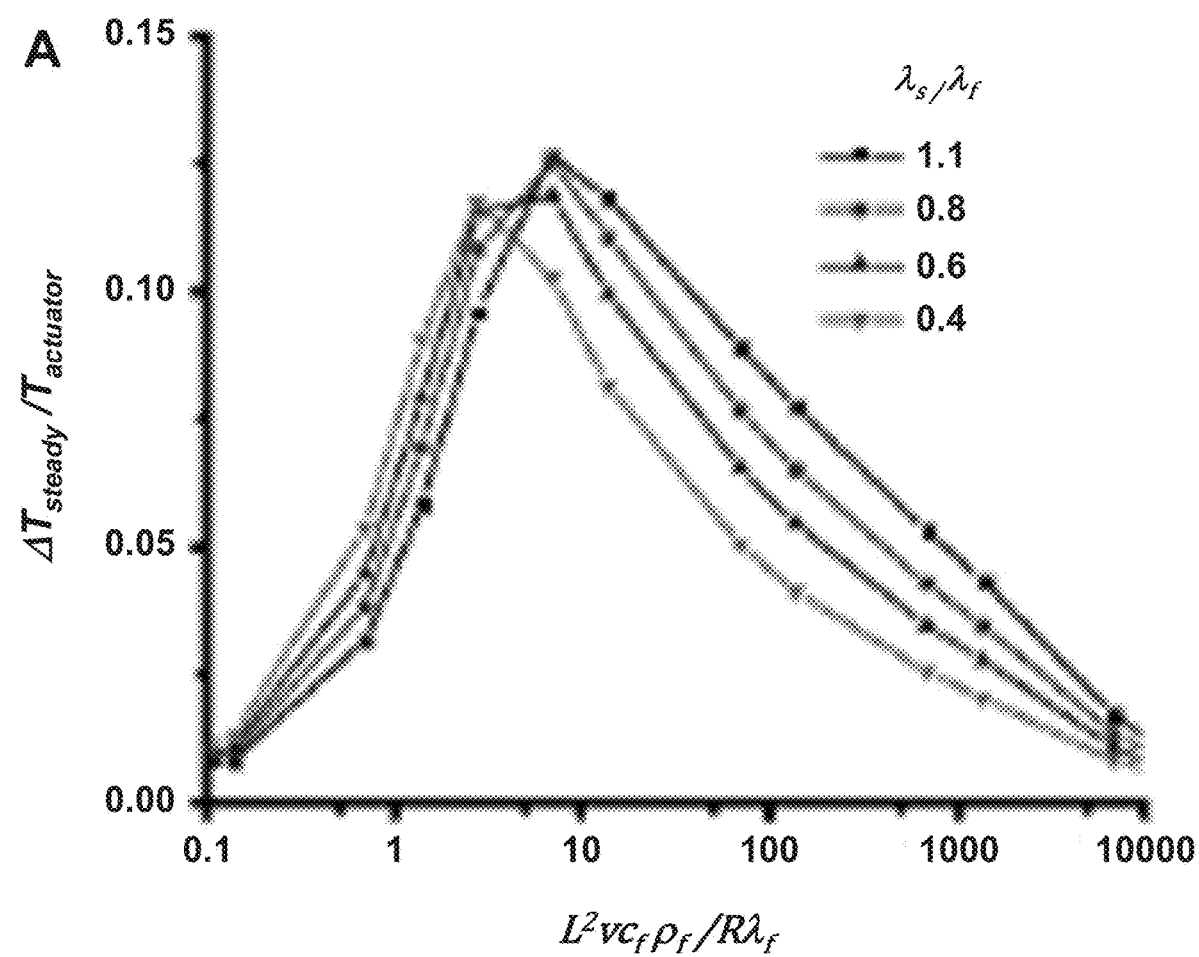
FIG. 15: The influence of variation of $\lambda_s/\lambda_f$, h/L and B/L on the steady-state scaling law. The steady-state scaling law (Equation 2) with (A) different $\lambda_s/\lambda_f$ (0.4-1.1), (B) different h/L (⅔-1) and (C) different h/L (⅓-1), illustrates that these three parameters all play an important role in the steady-state scaling law.
Figure 15:
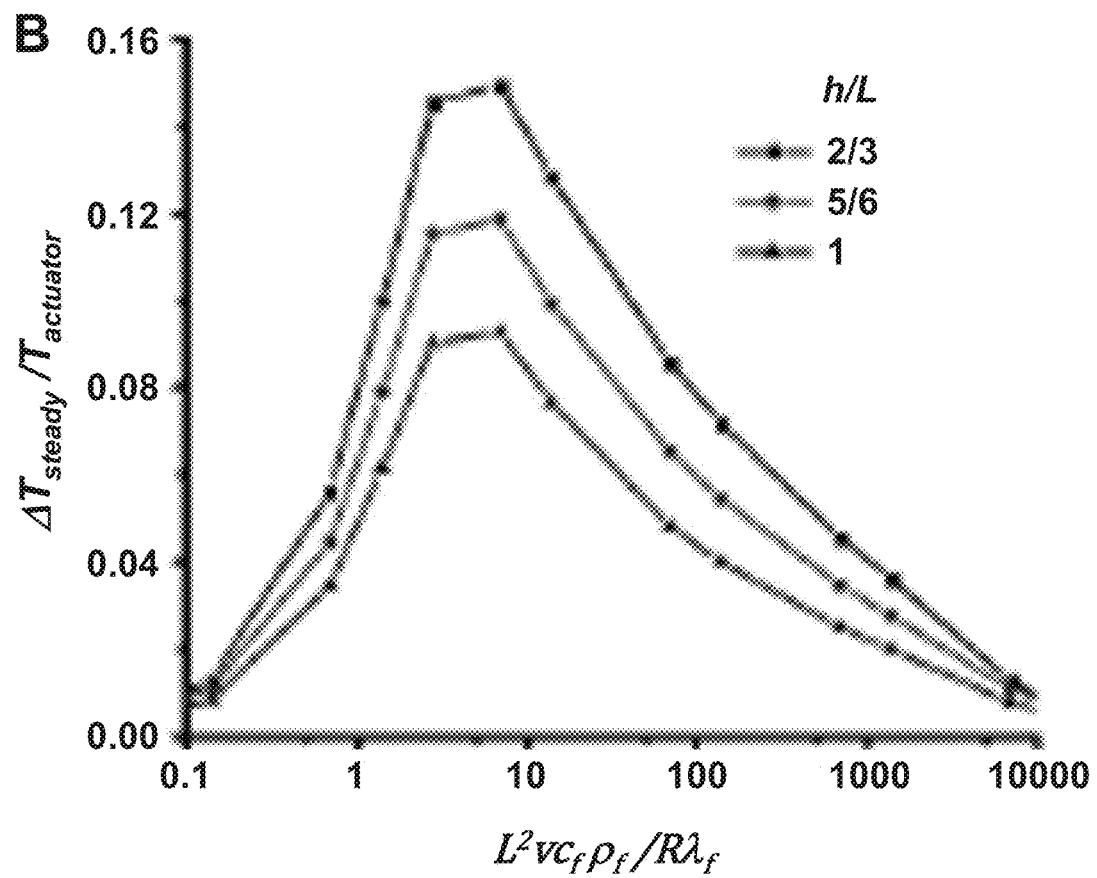
Figure 15:
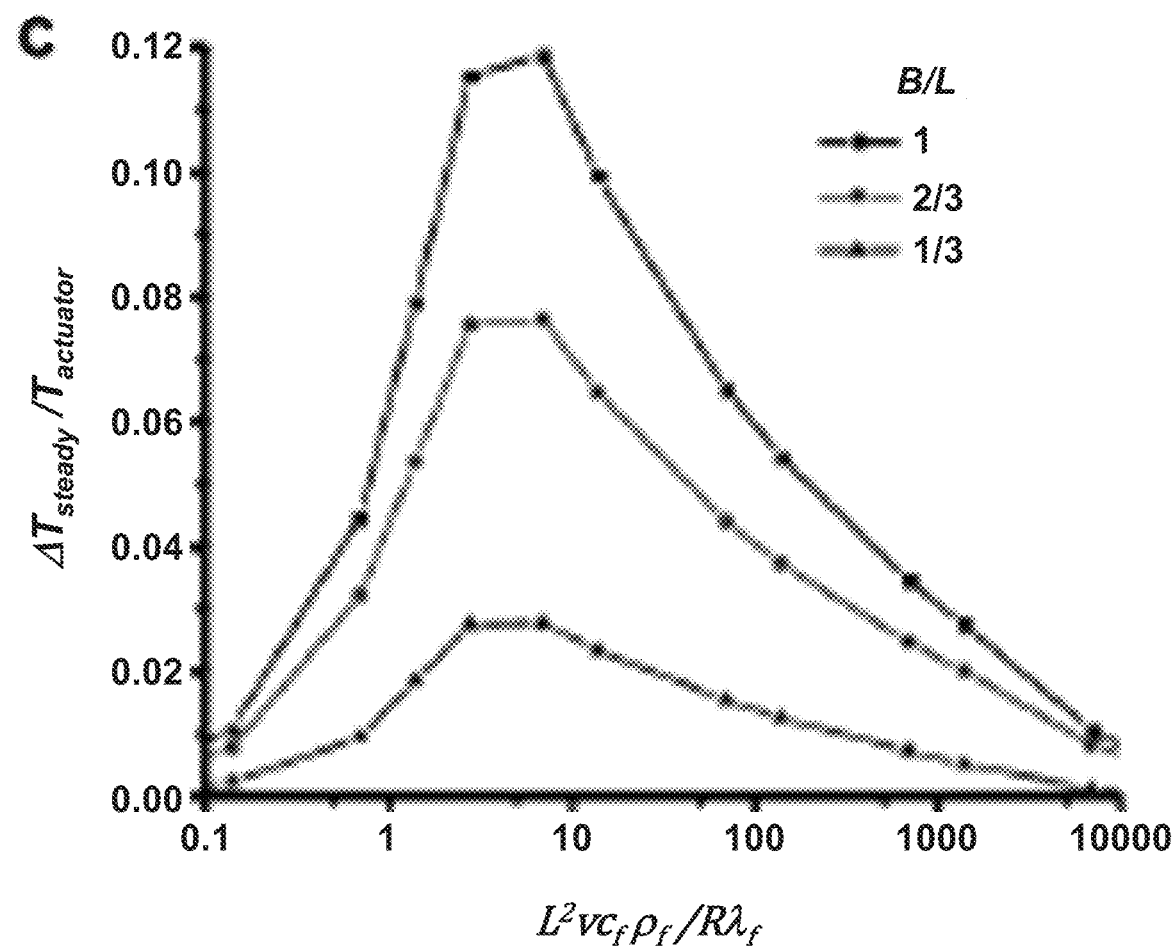

Its dependence on the normalized thermal conductivity $\lambda_s/\lambda_f$, depth of blood vessel h/L, and sensor spacing B/L appears in FIG. 15. The impact of R is relatively small, such that an approximate value based on the vessel location can be used. As an example, the steady-state scaling law for R=0.95 mm and 1.65 mm appear in FIG. 2f. These values of R bound the expected range for the median antebrachial vein segment near the wrist (R=1.3 mm±0.35 mm [37]), which is used in several experiments described subsequently. The two computed curves have similar shapes, but with slightly shifted values. The value of $\Delta T_{steady}$ begins at v=0 by increasing with increasing v ($d\Delta T_{steady}/dv>0$), peaks at a relatively low flow rate, and then begins to decline ($d\Delta T_{steady}/dv<0$) as convective cooling of the downstream sensor begins to dominate. We refer to the two sections of the curve as the 'low flow regime' where $d\Delta T_{steady}/dv>0$ and the 'high flow regime' where $d\Delta T_{steady}/dv<0$ (FIG. 2E). In the high flow regime (corresponding to most physiologically relevant blood flow velocities, FIG. 2f), R/L has a minor impact on the values of the curve, such that the steady-state scaling law is simplified as $$\frac{\Delta T_{steady}}{T_{actuator}} = f_3\left(\frac{L^2 v c_f \rho_f}{R\lambda_f}; \frac{\lambda_s}{\lambda_f}, \frac{h}{L}, \frac{B}{L}\right) \quad (3)$$

The only unknown in Equation 3 is the ratio v/R. As a result, a comparison of $\Delta T_{steady}/T_{actuator}$ from experiment with a numerical fit of the steady-state scaling law obtained by FEA (FIG. 2f shows fits for R=0.95 mm and R=1.65 mm), gives this ratio v/R.

Figure 16:
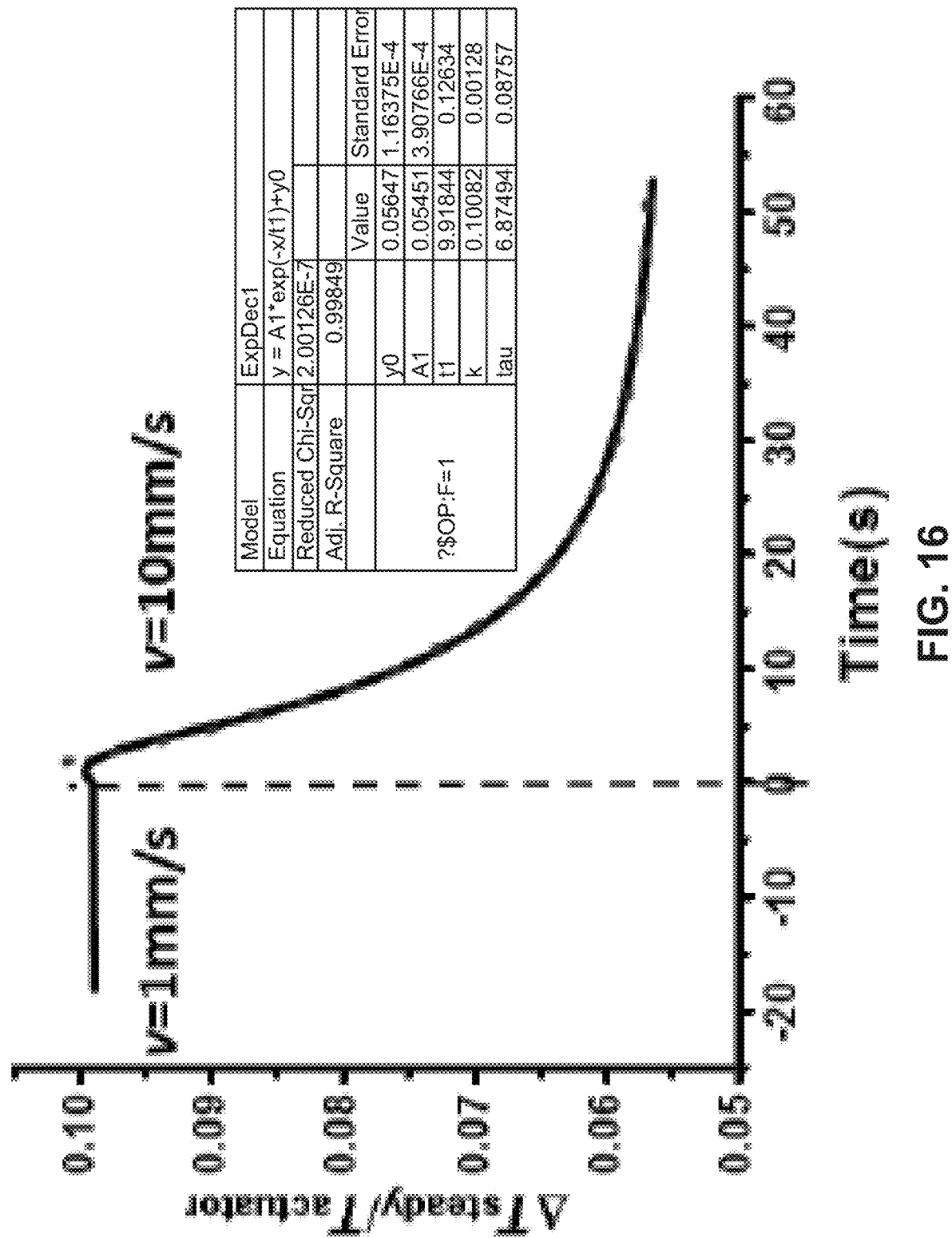
FIG. 16: Transient temperature response caused by flow velocity change. All size and material parameters are the same as the case shown for R=0.95 mm in FIG. 2E. A step-function increase in flow velocity (from 1 mm/s to 10 mm/s) results in a dimensionless temperature response as an exponential decay with a time constant of ~10 s. Conversely, a step-function flow decrease will result in a similar exponential growth function in sensor response.
Figure 17:
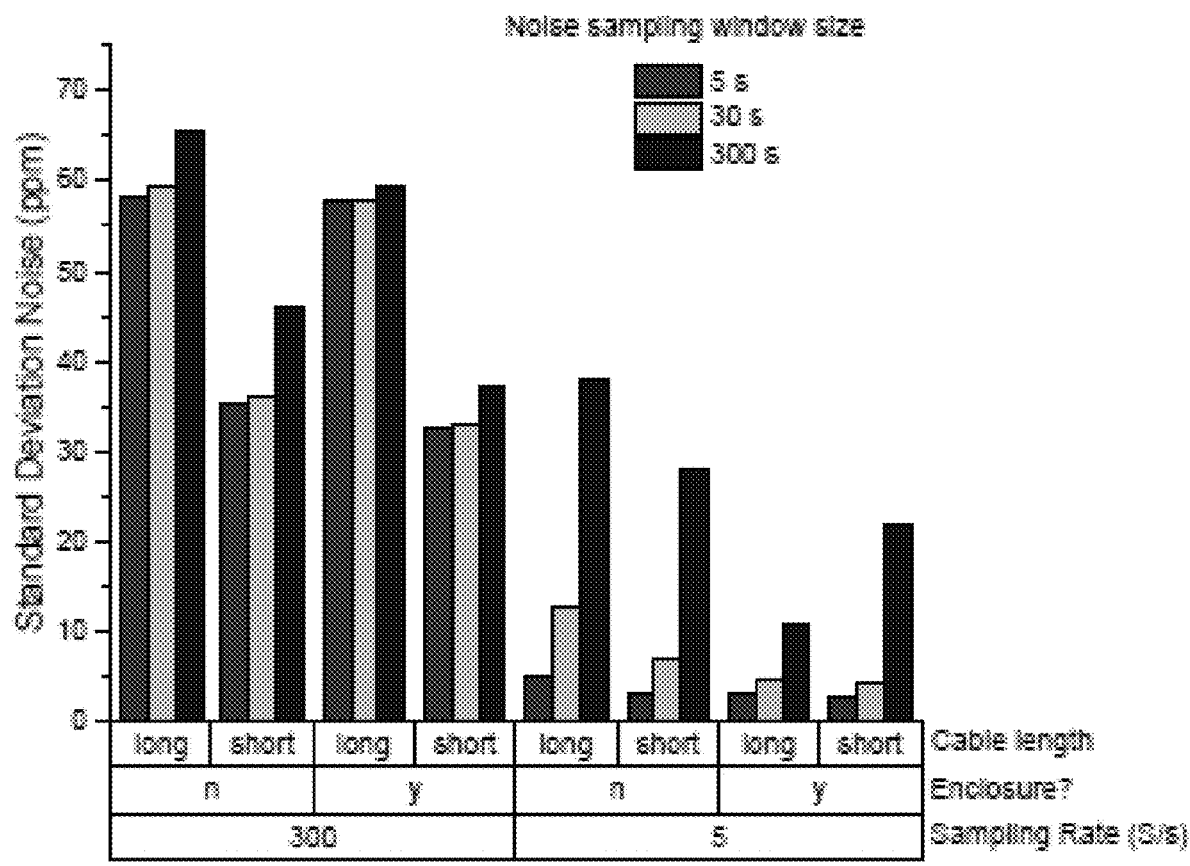
FIG. 17: Noise analysis of epidermal data acquisition system. Results from a series of benchtop experiments analyzing noise levels during different conditions. A change of 1° C. corresponds to a signal of 2500 ppm. At low sampling rates, and short sampling windows, a doubling of the data acquisition cable length results in a noise increase of 5%-30%. Over longer sampling windows, noise increases significantly and is strongly influenced by placing the device in plastic enclosure from the ambient environment, indicating a dominance of environmental induced thermal changes. Over shorter sampling windows (5 s and 30 s), noise scales as (Sampling rate)$^{1/2}$. Over a 300 s sampling window, noise is dominated by environmental changes.
Figure 18:
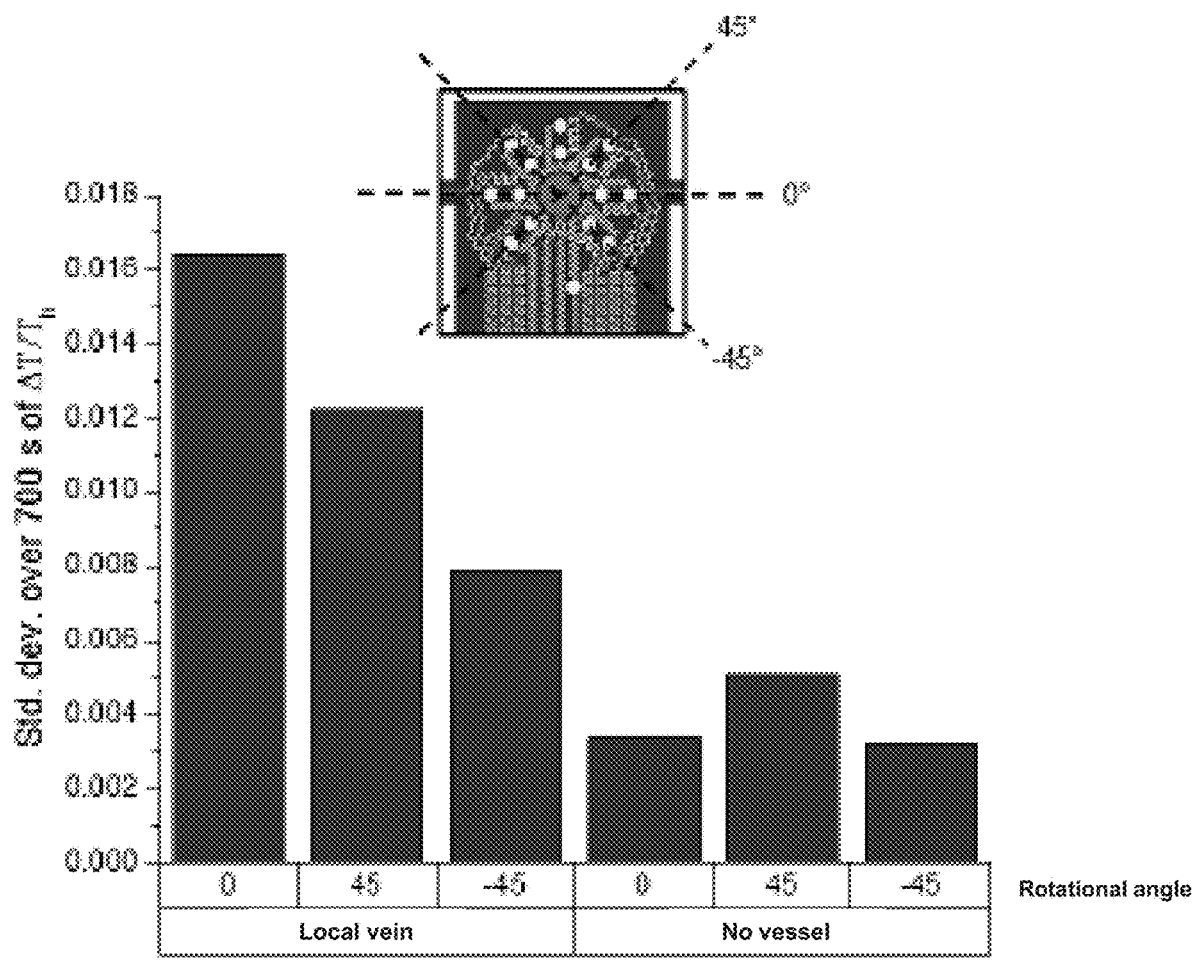
FIG. 18: Noise analysis of epidermal devices on skin. Results from a series of in vivo experiments analyzing noise levels when the device is placed over a vein, compared to a location with no significant visible veins. Results indicate the standard deviation of $\Delta T/\Delta T_h$ over a 700 s sampling window. Analysis of different sensor pairing corresponds to different rotation angles, where the rotation angle is the difference between the measured sensor axis and the vein axis. For the case of no vessel, the rotation angle simply corresponds to different sensor pairings. Signal variations are significantly lower in the case of no local vessel, and are maximized in the local vein case of the sensor pair along the vein axis, which indicates that there is significantly more signal variation due to change in flow through the vein.

The value of $\Delta T_{steady}$ does not, of course, include changes that arise from variations in the blood flow velocity. Experimentally, the sensors respond to an instantaneous change in flow rate with a time constant of ~10 s (FIG. 16), depending on the tissue properties. The result is that changes in flow that have frequencies <0.1 Hz can be readily measured. This includes flow changes related to myogenic activity of vascular smooth muscle (0.1 Hz), neurogenic activity of the vessel wall (0.04 Hz) and vascular endothelium influences (0.01 Hz) [38]. The dimensionless flow parameter alone allows for assessment of relative changes in blood flow. Analyses of potential sources of noise and other potential sources of uncertainty appear in FIGS. 17 and 18. The results confirm that the measured values of $\Delta T_{steady}/T_{actuator}$ used in the analysis are typically >10× stronger than experimentally measured electronic and/or environmental noise, and >5× stronger than signals recorded on skin locations without large vessels. In the following examples, the analysis procedures outlined here provide local values of thermal conductivity and diffusivity, vessel depth, and changes in blood flow.

Measurements of Macrovascular Flow

Figure 12:
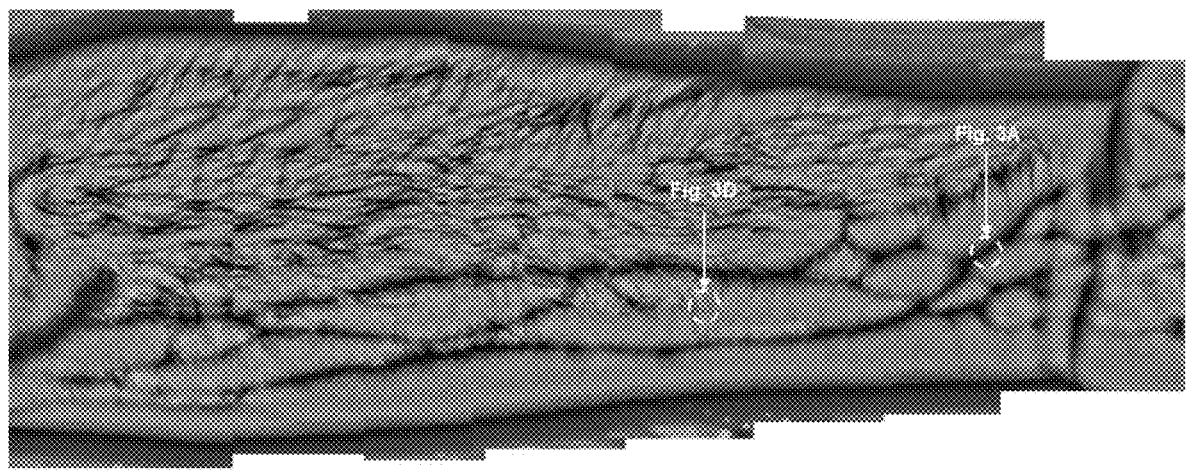
FIG. 12: Optical VeinViewer image used to accurately identify blood vessel locations. Labels indicate actuator placement during data collection for indicated figure.

Various in vivo experiments demonstrate the utility of these approaches. The first example illustrates the capture of time varying thermal flow maps that result from changes in blood flow that follow from local occlusion of a near surface vessel (FIG. 3a-c). Here, the device resides on the volar aspect of the wrist (male, age 27) with the thermal actuator centered above a near surface vessel. Power applied for five minutes to the actuator establishes a baseline level of heating to reach a steady-state response. The experiment involves application of local occlusive pressure, (approximately 25 kPa over a 0.2 cm² area), using a cotton tipped applicator (56810 Solon, USA) with 15 cm wood shaft, to a series of locations around the outside perimeter of the device. Specifically, pressure is applied first along the vein (second panel in FIG. 3a) for sixty seconds, and then released for sixty seconds. Sequential application of the same pressure cycle (sixty seconds pressure, sixty seconds release), at locations shifted 45° relative to the thermal actuator, until returning to the initial position, completes the experiment. Data show that the device records minimal blood flow when pressure is applied directly to the vein, and strong blood flow at all other times. The flow vector fields (vector maps in FIG. 3c) record the flow direction as moving towards the body, as expected for venous flow and confirmed by the VeinViewer (FIG. 12). Control experiments (FIG. 3d-f) conducted on areas of the skin without large vessels indicate negligible effects of applied pressure, as expected. Laser Speckle Contrast Imaging (LSCI) performed under similar conditions yields inconclusive data due to uncontrolled variations associated with distortions of the skin and associated motion artifacts. The device platform reported here does not suffer from such effects.

Figure 3:
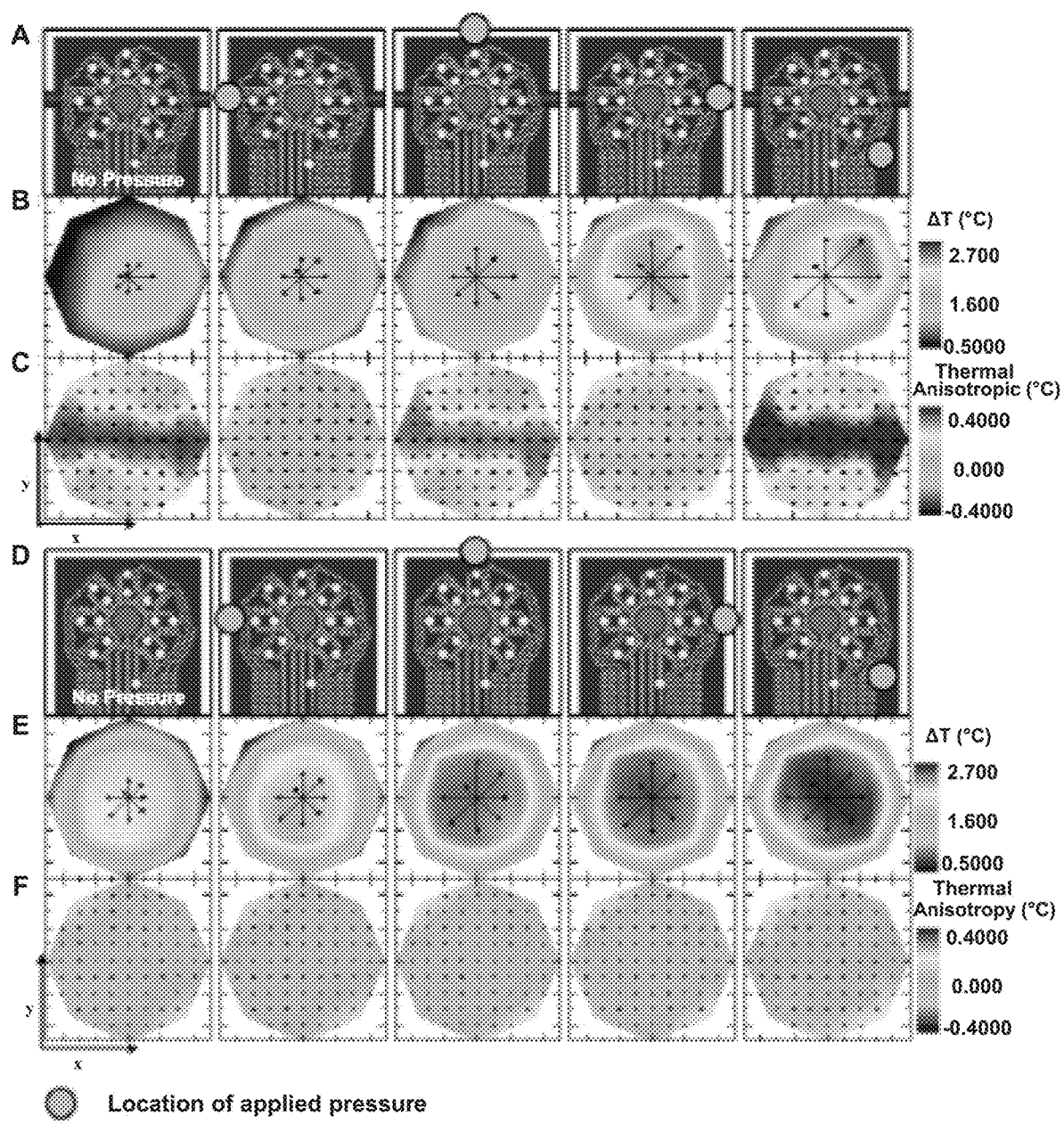
FIG. 3: Measurements of changes in venous blood flow induced by local applied pressure. a) The device resides on the wrist, over a 2 mm diameter vein with orientation shown in the illustration. The location of pressure applied (60 s duration) with a cotton swab is shown by a green circle. b) The local temperature distribution that follows heating for each pressure location. The temperature of the heater has been removed to improve the contrast. c) Measured thermal anisotropy fields corresponding to the applied pressure illustration above. Computed colormaps correspond to the calculated flow components in the x-direction. d-f) Similar analyses to a)-c), except that the device resides over a region of the forearm with no nearby large blood vessels.
Figure 19:
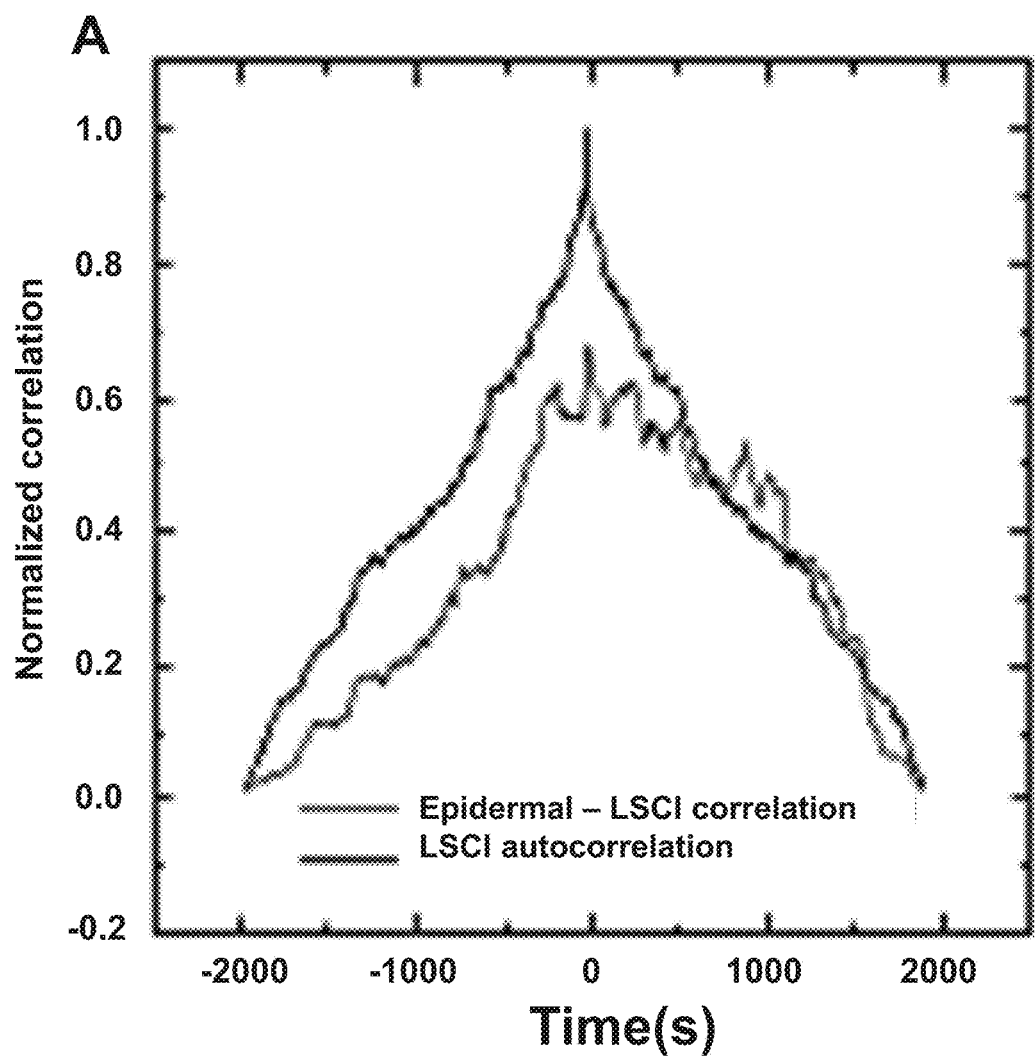
FIG. 19: Statistical correlation between LSCI data and epidermal device data from FIG. 4. LSCI autocorrelation shows the relative integral overlap area of the data when shifting the dataset relative to itself. For the autocorrelation, perfect correlation always occurs at t=0, and the shape of the curve is determined by the time dynamics of the data. The autocorrelation represents a perfect correlation to the LSCI data. Epidermal-LSCI correlation shows the relative signal overlap area between the LSCI data and epidermal device data, which closely matches that of the LSCI autocorrelation. (A) Correlation between raw data sets. (B) Correlation between linearly detrended data sets. (C) Coherence between linearly detrended datasets.
Figure 19:
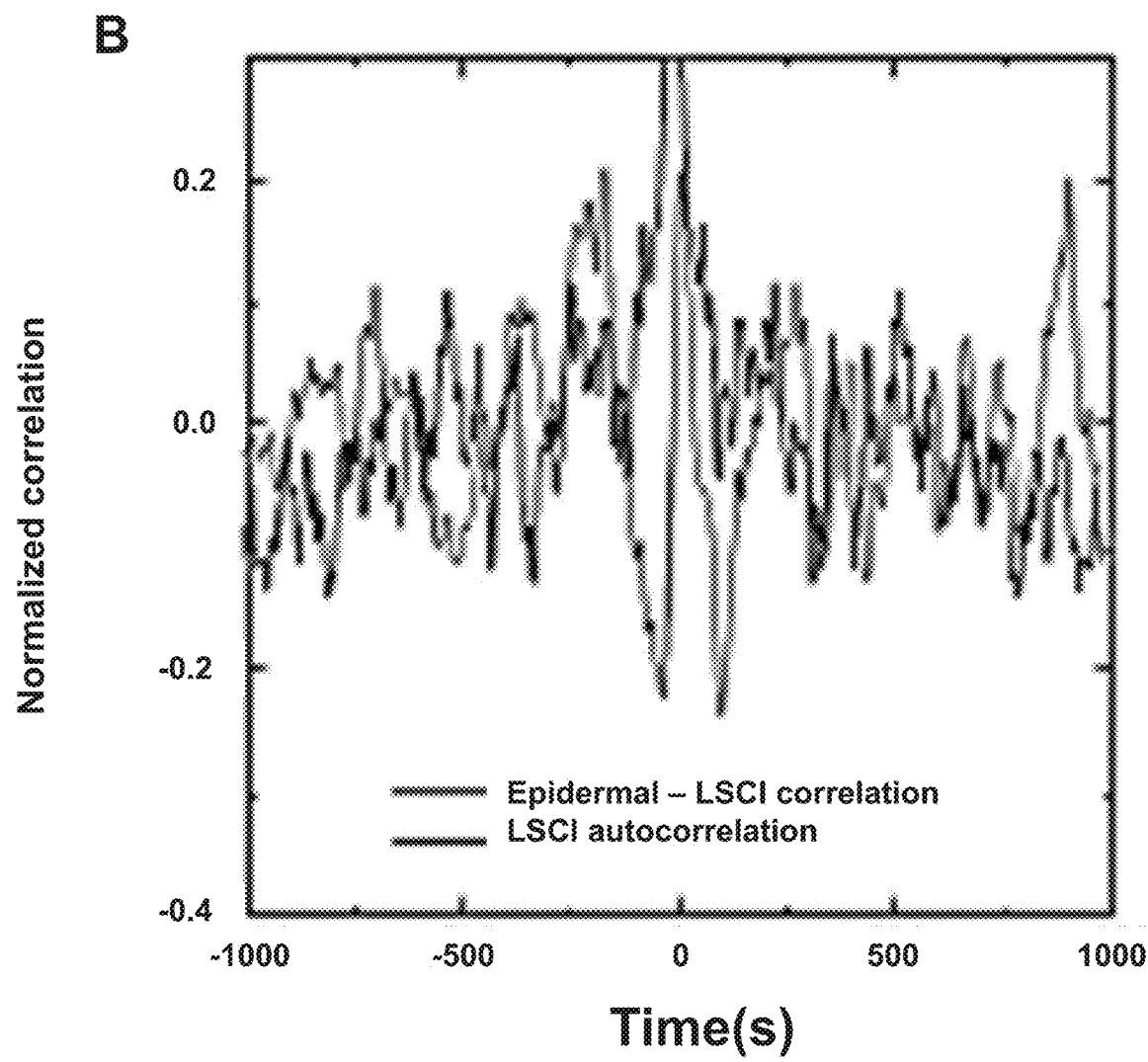
Figure 19:
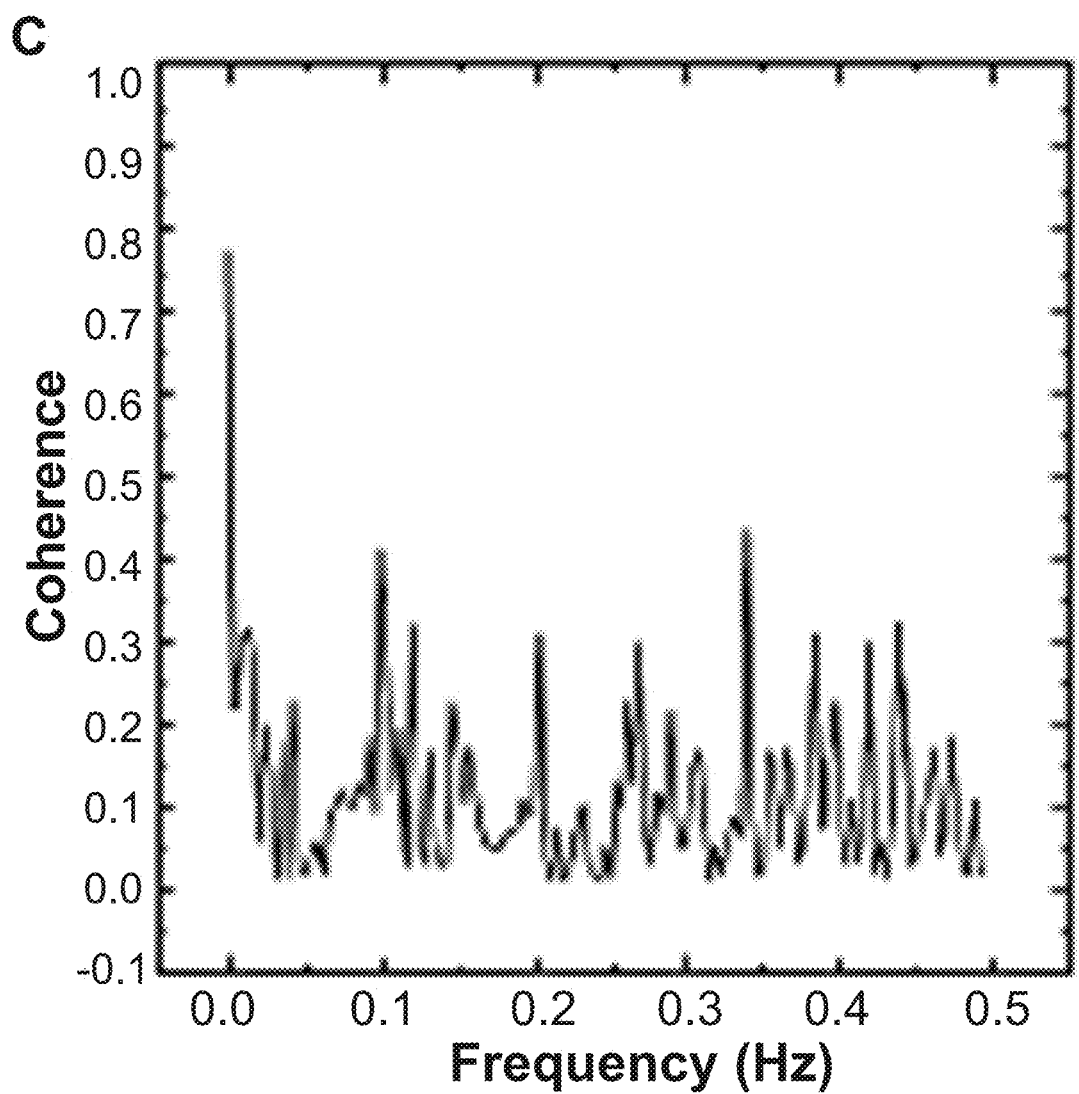
Figure 20:
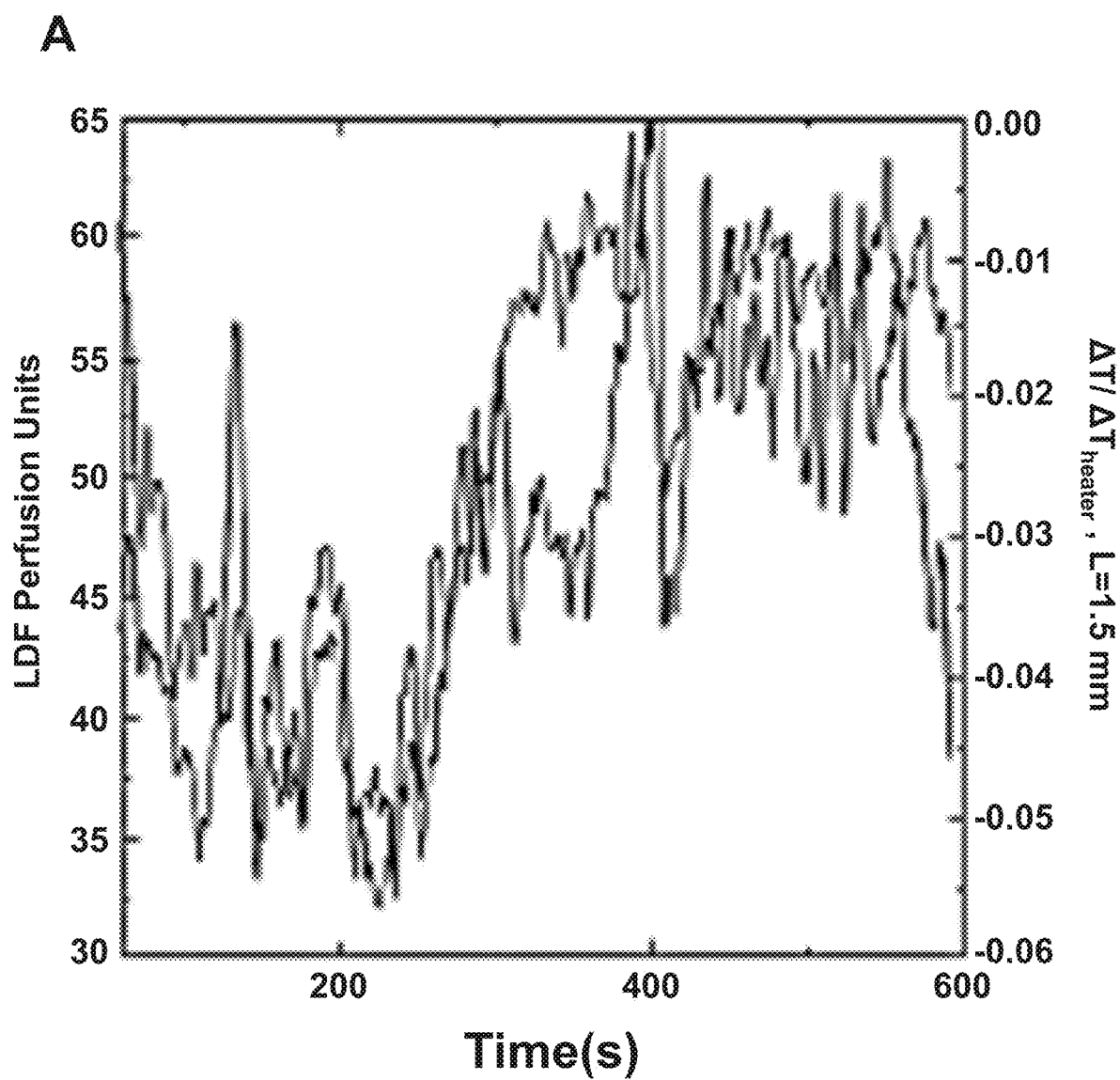
FIG. 20: Comparison between Laser Doppler Flowmetry signal and epidermal device signal during 10 minutes of natural flow on the volar aspect of the wrist of a male, age 33. (A) Laser Doppler and epidermal device signals. (B) Correlation between linearly detrended data sets.
Figure 20:
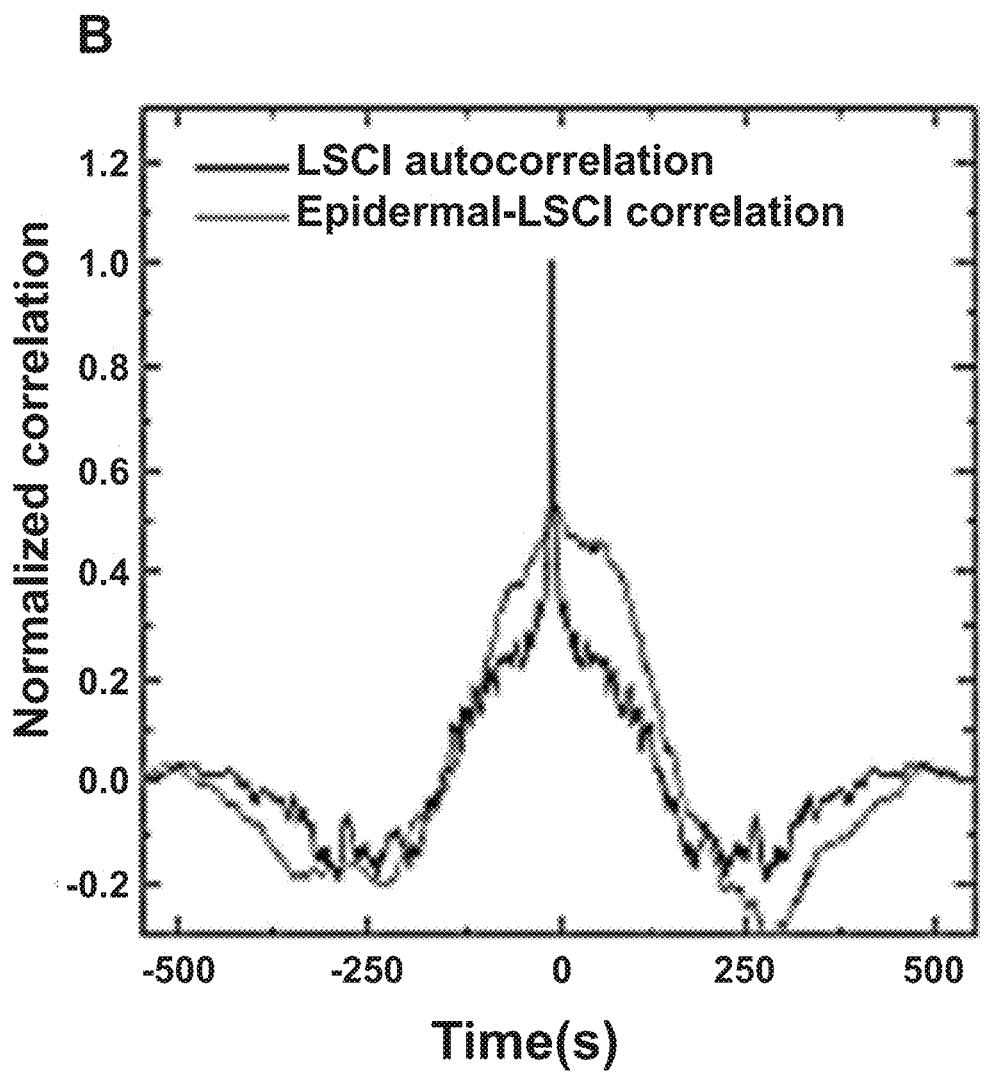
Figure 21:
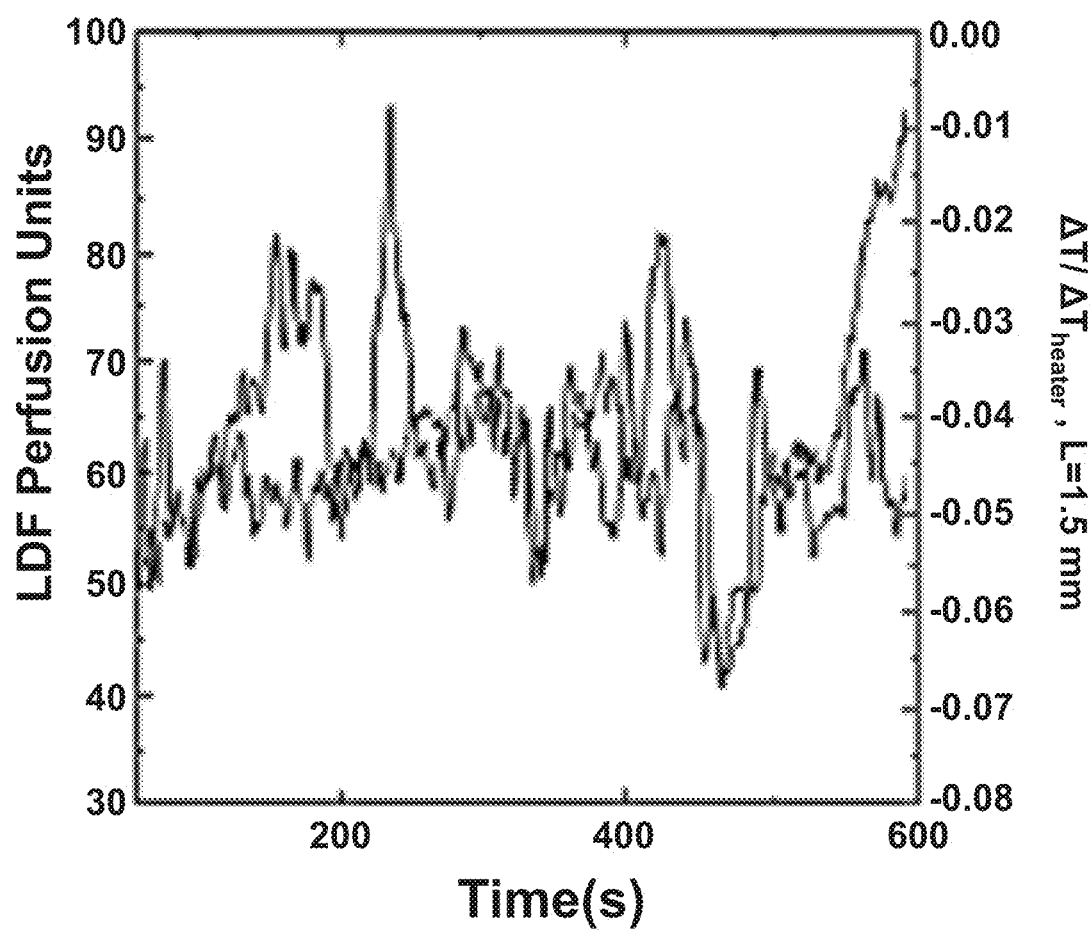
FIG. 21: Comparison between Laser Doppler Flowmetry signal and epidermal device signal during 10 minutes of natural flow on the dorsal aspect of the hand of a male, age 23. (A) Laser Doppler and epidermal device signals. (B) Correlation between linearly detrended data sets.
Figure 21:
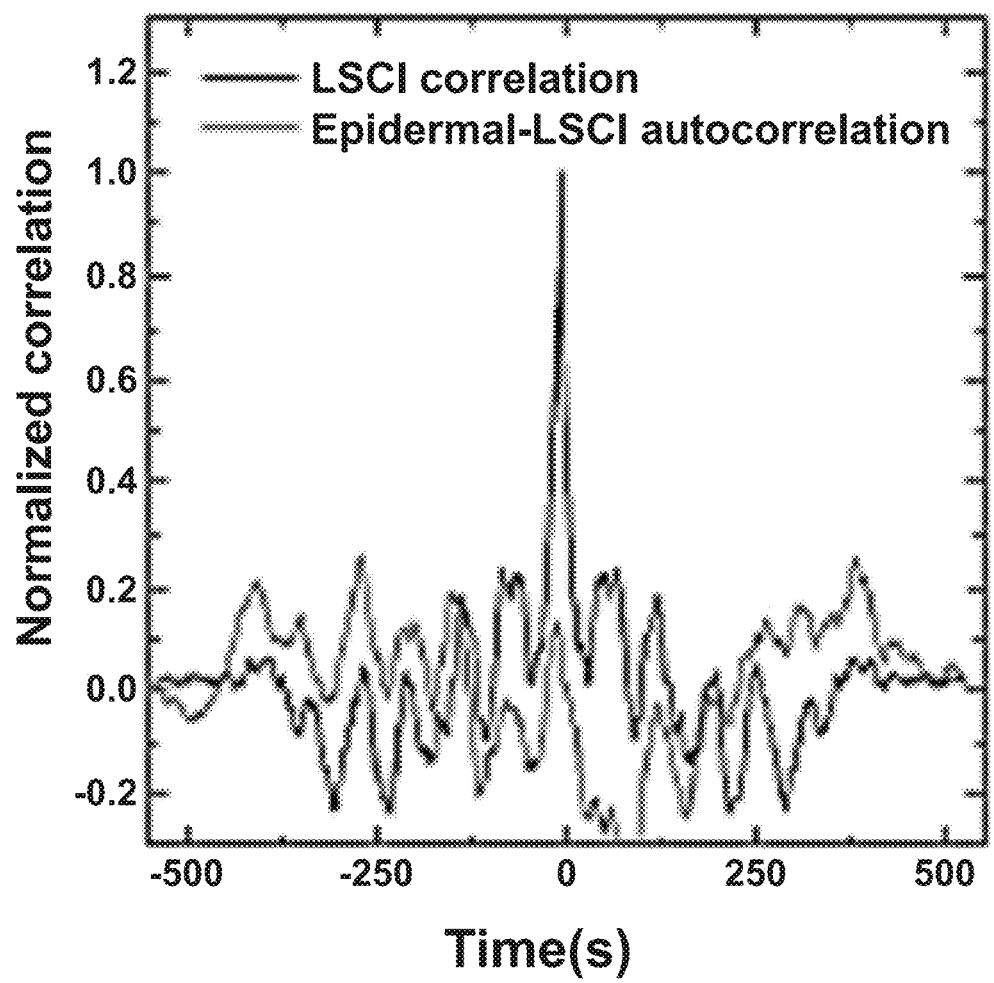
Figure 22:
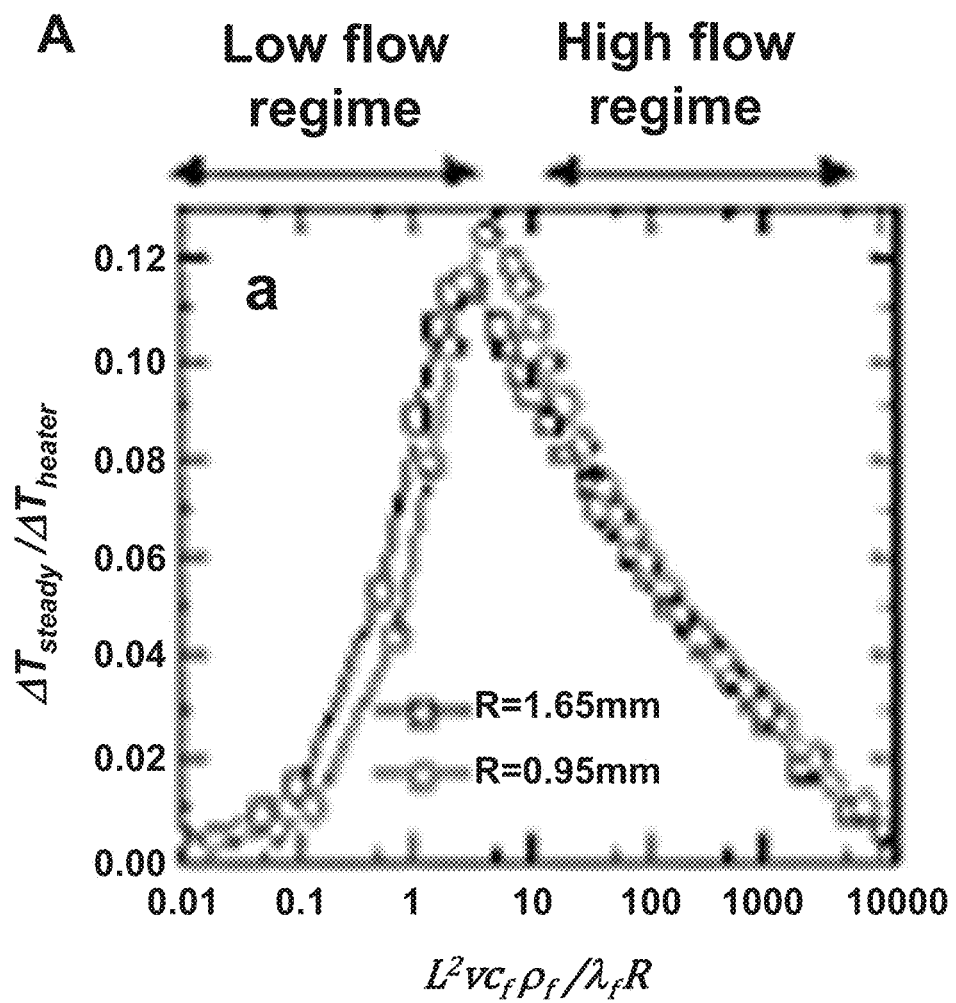
FIG. 22: Quantitative blood flow conversion of FIG. 5(A). (A) Relation between thermal flow signals and blood flow rate, showing low flow and high flow regimes. When transitioning from very low flow to high flow, the relation between the thermal signal and blood flow changes sign, as well as functional form. (B) When the transition from low flow the high flow happens extremely rapidly, in a few seconds as in the experiment in FIG. 5(A), the quantitative relation goes through a rapid transition from the low flow to the high flow regime. This results in a spurious signal depression in the rapid transition region, as indicated.
Figure 22:
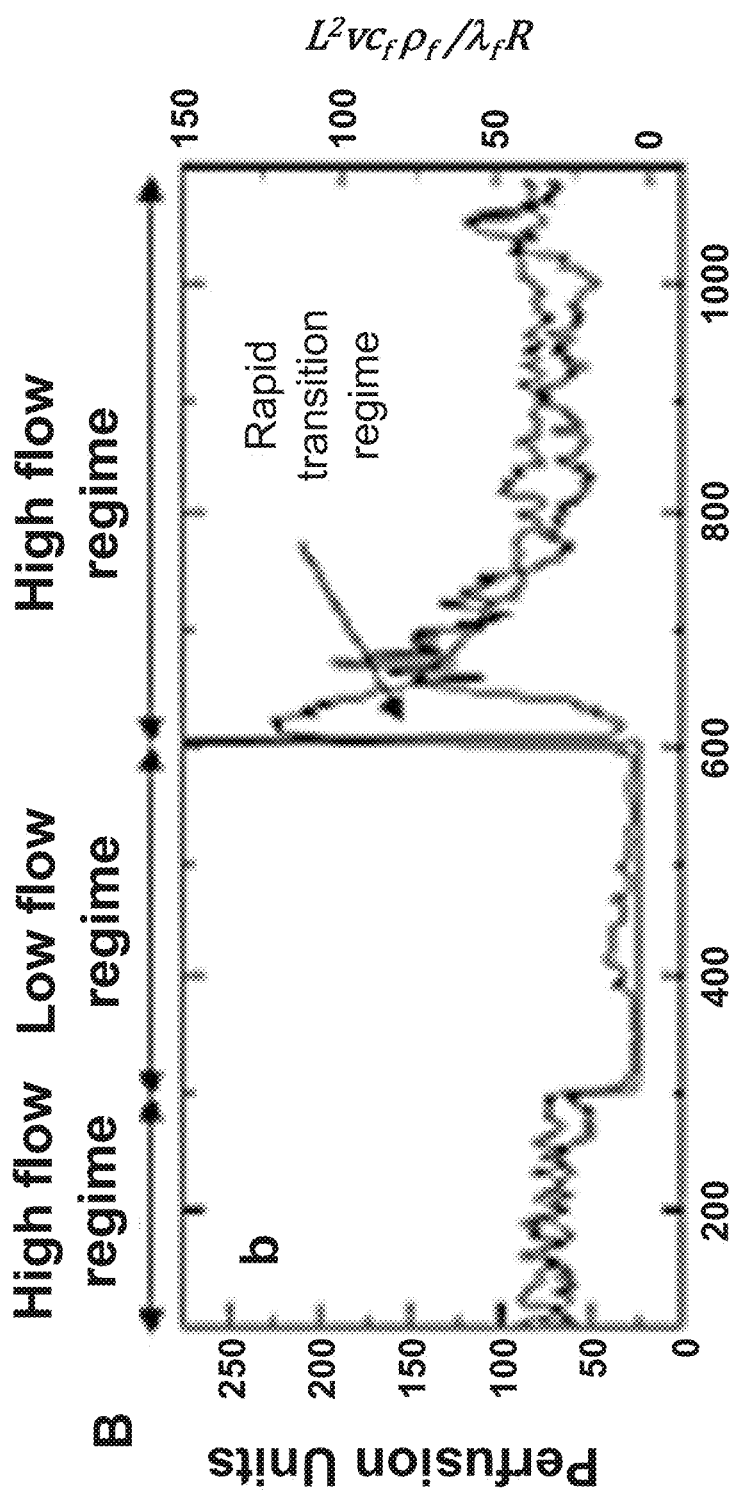
Figure 23:
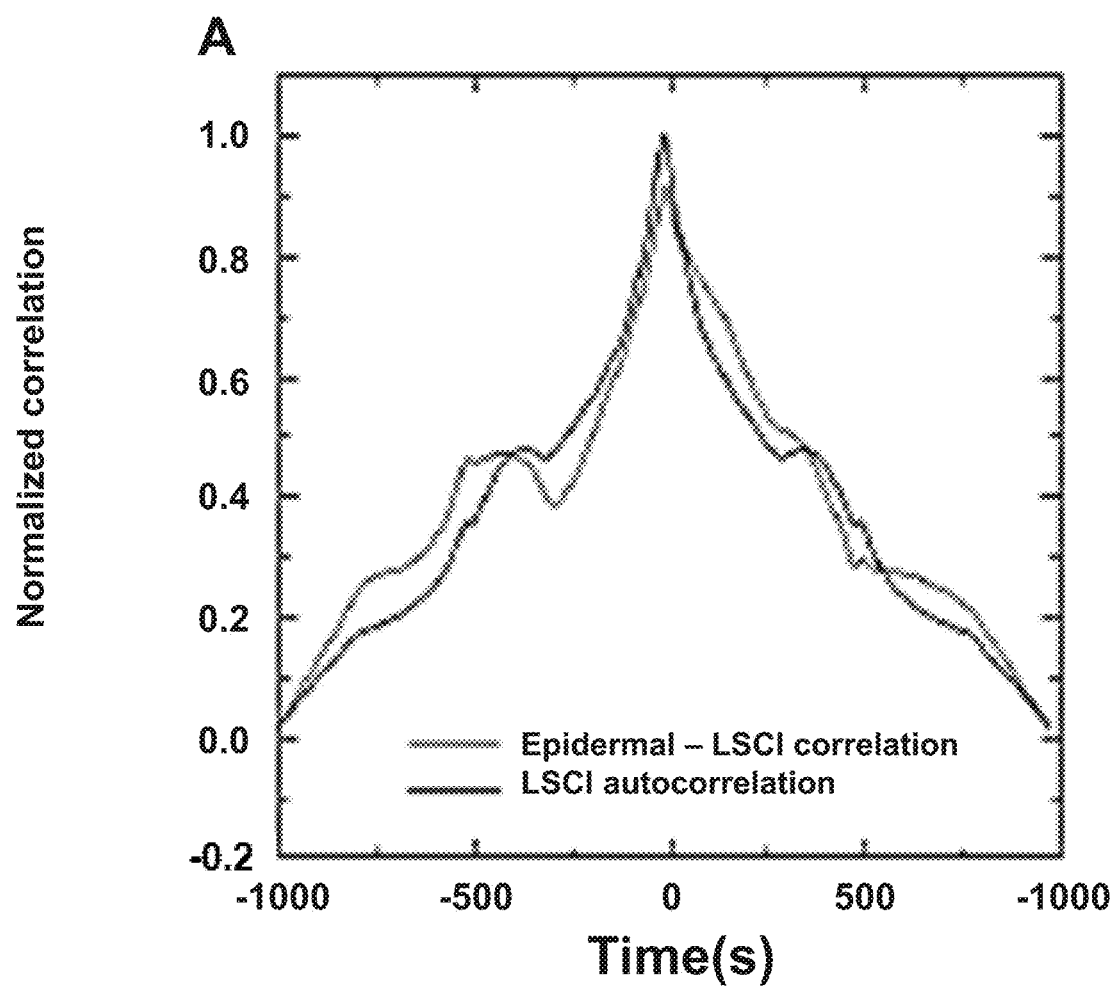
FIG. 23: Statistical correlation between LSCI data and epidermal device data from FIG. 5(A). (A) Same analysis procedure as FIG. 17(A). (B) Coherence between LSCI and epidermal device data.
Figure 23:
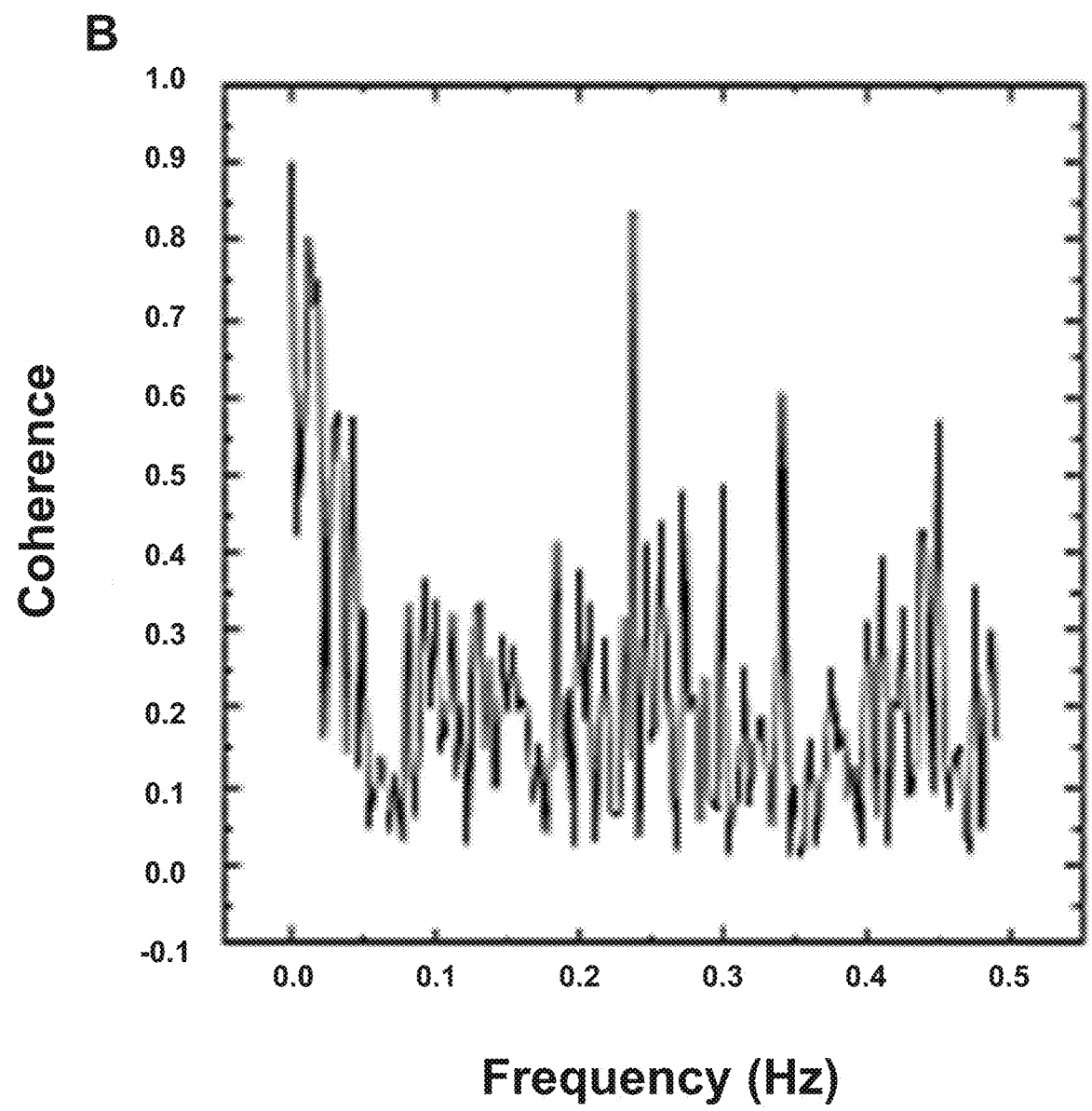

The experiment summarized in FIG. 3 represents one of a range of applications that involve abrupt alteration in blood flow by external forces. Another demonstration illustrates the quantitative analysis routine outlined previously. Here, device function during extended periods, without external stimuli, can reveal natural fluctuations in near-surface blood flow (vasomotion). As before, the device resides on the volar aspect of the wrist (male, age 27), with the thermal actuator centered over a visible vein. Measurements occur continuously as the subject lies still in a dark, quiet room for 45 min. LSCI data is recorded through the transparent regions between the metal traces of the device. Thirty seconds of baseline temperature recording is followed by power application to the thermal actuator at t=30 s. Power is deactivated at t=2430 s to allow another set of baseline temperature recording for the final five minutes. The tissue thermal conductivity and diffusivity are 0.32 W m$^{-1}$ K$^{-1}$ +/− 0.03 W m$^{-1}$ K$^{-1}$ and 0.17 mm² s$^{-1}$ +/−0.02 mm² s$^{-1}$, respectively, according to the method of FIG. 2c. The depth of vessel is 1.3 mm+/−0.2 mm, according to the method of FIG. 2d. Comparison of the LSCI data with the dimensionless flow calculated from the disclosed device shows good agreement, highlighted by the good alignment of peaks and troughs in the flow signal (FIG. 4a,b). Motion artifacts that cannot be completely removed with frame alignment algorithms typically lead to sharp peaks in the LSCI signal. Additionally, we note that neither LSCI nor LDF measurements through the skin provide a direct measurement of blood flow in a subsurface vein, due to the strong influence of signals in the tissue above the vein. However, we find that for near surface veins on the wrist, the agreement is significant (subsequent experiments, discussed in the following paragraph, illustrate an inability of LSCI to capture signals in deeper veins, which are captured by the disclosed device. A comparison of the cross-correlation of the device and LSCI data, compared to the auto-correlation of the LSCI data, as well as the coherence between the two datasets, quantifies the statistical agreement (FIG. 19). Frequency-time spectrograms of the data show similar levels of agreement in terms of the alignment of frequency bands in time (FIG. 4c,d). Related experiments on different subjects and different veins on the wrist and hand yield results that also agree with those of LDF tools (Blood FlowMeter, ADInstruments, USA) (FIGS. 20 and 21).

Another demonstration involving external forces applied to the entire forearm reveals enhanced variations in the signals, without motion, for comparison to optical tools. Here, changes in blood flow are monitored during a reactive hyperemic response induced by occlusion and reperfusion of the forearm. The device again resides on the volar aspect of the left wrist (male, age 27) with the thermal actuator centered over a subcutaneous surface vein. As before, a LSCI tool simultaneously records data through optically semi-transparent regions of the device and around it. The procedure appears in the Materials and Methods, and the results appear in FIG. 5a-i. Measurements of tissue thermal conductivity and diffusivity indicate values of 0.33 W m$^{-1}$ K$^{-1}$+/−0.03 W m$^{-1}$ K$^{-1}$ and 0.17 mm$^2$ s$^{-1}$+/−0.02 mm$^2$ s$^{-1}$, respectively. The depth of vessel is 1.3 mm+/−0.2 mm. These values are consistent with those for the experiments of FIG. 4, as expected. The LSCI data, taken from above the vein and thermal signals recorded from the device, using the thermal signals on opposed sides of the actuator outlined previously, show good agreement throughout the course of the study (FIG. 5a). This experiment does, however, reveal a limitation of the quantitative analysis routine. At the time of reperfusion, the blood flow rapidly transitions from the low flow to the high flow regime (FIG. 20a), which changes and reverses the slope of the relationship between the thermal signal and blood flow (FIG. 20b). As a result, quantitative conversion during this period immediately following reperfusion results in a spurious depression in calculated flow (FIG. 20b). This particular set of circumstances is, however, unlikely to occur without rapid changes in flow due to external perturbation. A comparison of the cross-correlation of our thermal device data with the LSCI data, compared to the auto-correlation of the LSCI data, as well the coherence between datasets, shows excellent statistical consistency (FIG. 21). A comparison of the frequency-time spectrograms of the data in FIG. 5a exhibit similar levels of agreement, including the same step function artifacts (due to the step function in flow data input into the spectrogram) at the time of reperfusion (FIG. 5b,c). Data from the disclosed device, at snapshots in time during peak flow (FIG. 5d-f) and occluded flow (FIG. 5g-i), demonstrate the strength and disappearance of the flow signal corresponds to unoccluded and occluded flow, respectively. An additional experiment, following the same procedure as that described for FIG. 5a, but on a different subject (male, age 23) with apparently deeper veins, appears in FIG. 5j. Here, the disclosed device captures an extraordinary signal from the vein during occlusion (confirmed by infrared) that is almost entirely absent from the LSCI signal. A series of four strong pulses of flow occur during occlusion (possibly due to insufficient occlusion or shunting via collaterals), during the time 400 s<t<600 s, as reflected by four prominent peaks in the signal (FIG. 5j). Close examination of simultaneously recorded infrared signals reveals four strong pulsations of the vein during the occlusion period. Individual frames illustrate pulsation (FIGS. 5k-m).

Measurement of Microvascular Flow

Figure 24:
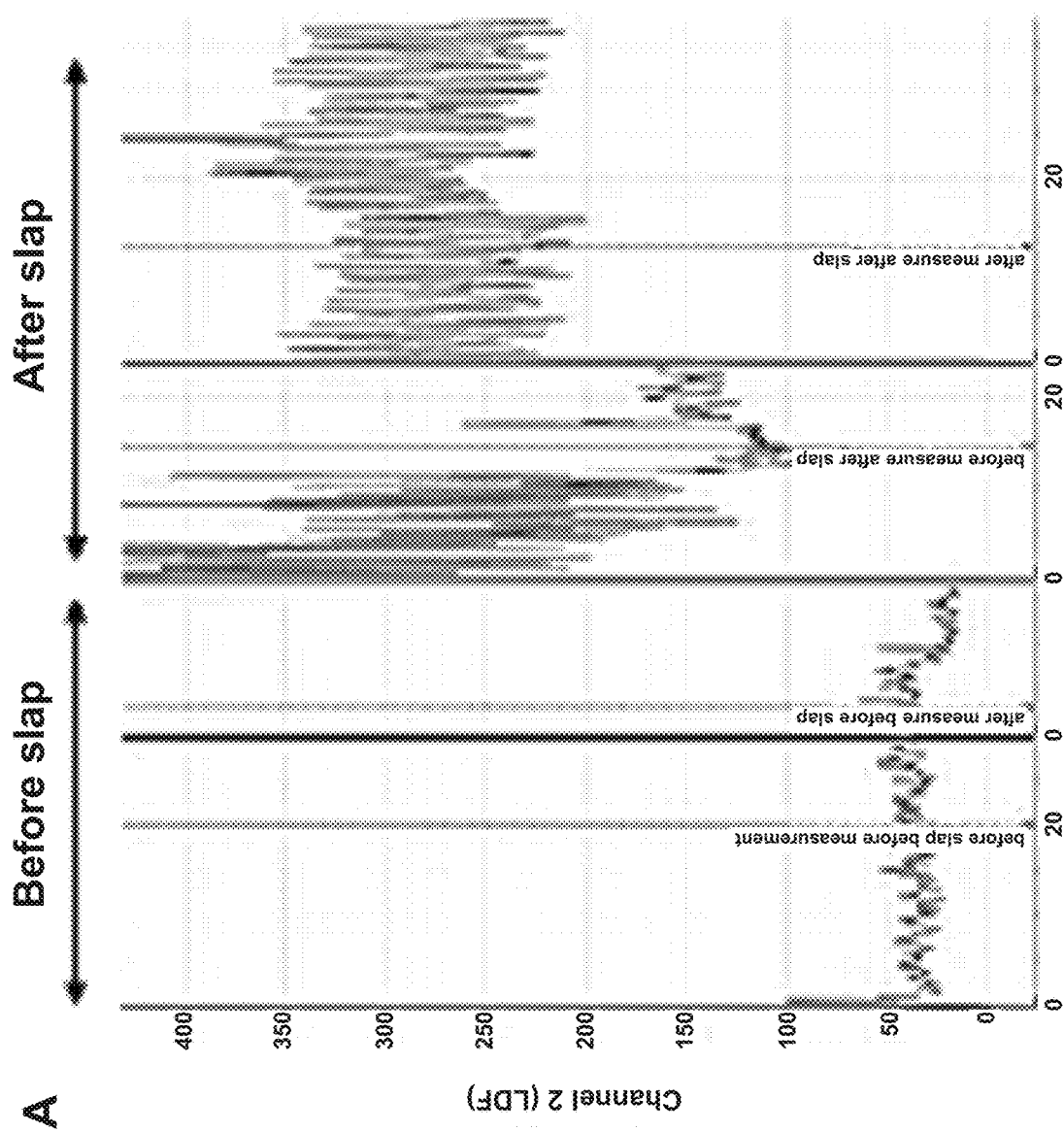
FIG. 24: Laser Doppler flowmetry measurements before and after slap-induced microvascular hyperemia. (A) LDF measurements corresponding to hyperemia shown in FIG. 6(A-D). (B) LDF measurements corresponding to hyperemia shown in FIG. 6(E-H).
Figure 24:
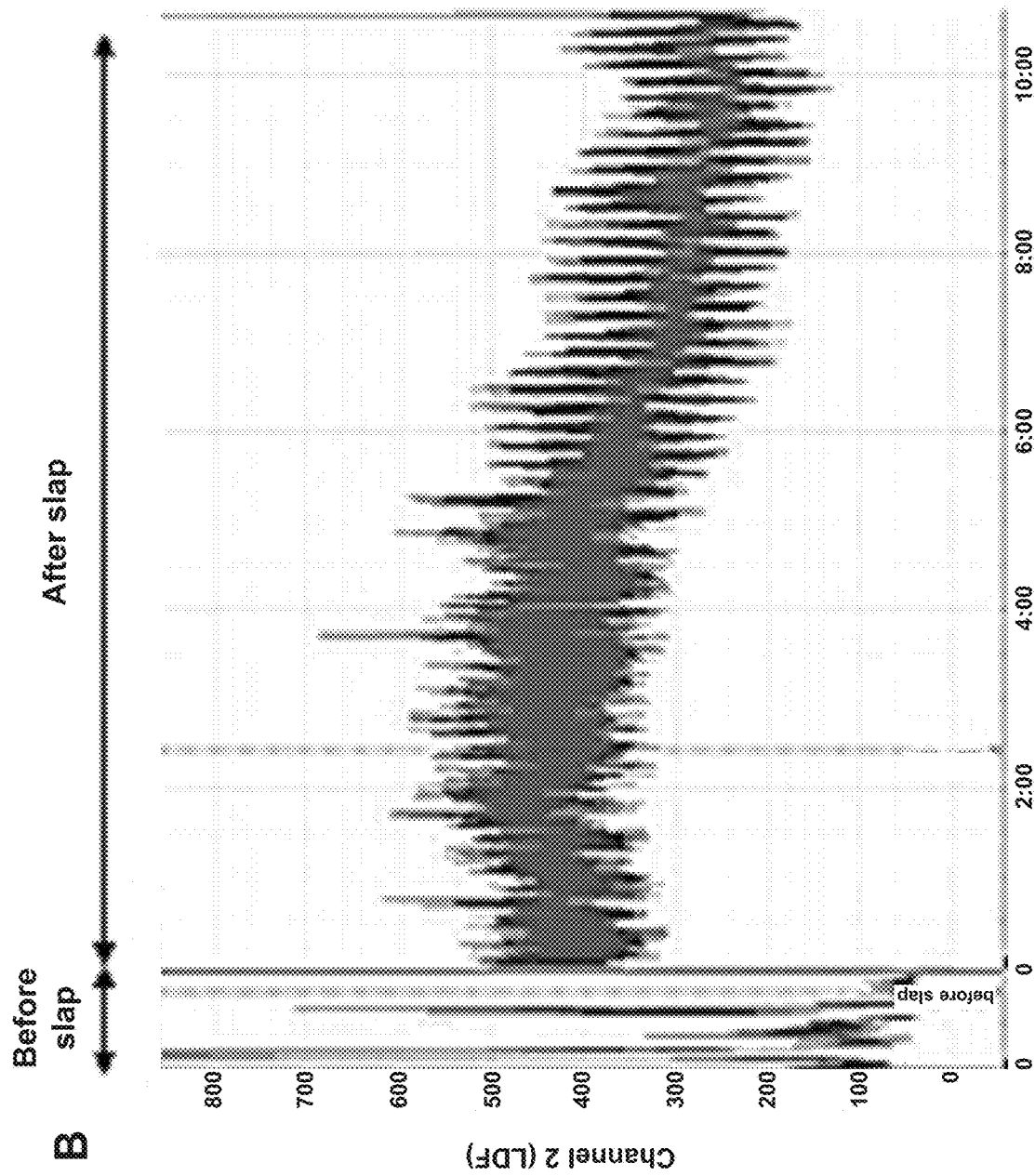

Applications to measurements of changes in microvascular flow, as opposed to the macrovascular applications discussed above, represent related but different areas of interest. For these studies microvascular is defined as those vessels—i.e. arterioles, capillaries and venules, with diameters typically <200 μm [39, 40]. The microvasculature may, or may not, have a significant anisotropic effect on thermal transport in the plane parallel to the skin surface. Experiments using the disclosed device indicate that the net anisotropy in the parallel plane is relatively small in regions that lack local large vessels. A device design with sensor sizes and density modified for arteriole scales, using the same principles as in this report, may potentially monitor more localized individual arteriole anisotropies. More generally, the extent of microvascular anisotropy may be both region- and size-scale dependent, ultimately determined by the net lateral flow across the area of the device. Here, we focus on changes in the millimeter scale isotropic transport between the actuator and surrounding sensors. In one demonstration, local trauma—in the form of a "finger slap"—to the volar surface of the forearm (male, age 59), was utilized to induce dermatographic urticaria, resulting in vasodilation of the local microvasculature and tissue hyperemia (FIGS. 6a, e). A 500%-700% increase in measured LDF perfusion units following the "finger slap" (FIG. 24), measured within the slap area and 2 cm away from the thermal actuator, confirms the hyperemic effect. Local precision temperature measurements of the skin surface, using our device, before and after trauma (FIGS. 6b, f) reveal expected increases in temperature that result from local vasodilation. Isotropic flow will not induce any appreciable differential temperatures. As a result, the previous discussions on blood flow analysis for large vessels do not apply. Instead, changes in microvascular perfusion alter the rate of heat extraction from the actuator into the skin. This effect can be readily observed in the initial time dynamics and saturation temperature of the actuator. Measurements before and after the onset of vasodilation (FIGS. 6c, g) illustrate the effect. Following vasodilation, the actuator reaches a lower differential saturation temperature more rapidly, compared to moments before dilation, quantified as a 130%-250% increase in measured thermal diffusivity and a 6%-19% increase in measured thermal conductivity. The differential saturation temperature of the actuator decreases with vasodilation, even though the base temperature of the skin increases, due to the increase in convective heat transfer extracting thermal energy from the actuator. Isotropic heat distributions both before and after vasodilation illustrate the distinct difference between the macrovascular and microvascular effects (FIGS. 6d, h).

A separate experiment, with the device located on the fingertip (IR image, FIG. 6i; data, FIG. 6j), illustrates continuous measurements of natural changes in microcirculation. Analysis of the temperature difference between the actuator and the inner ring of sensors (averaged) provides a measure of time dynamic changes in the heat transfer coefficient, as a result of changes in blood flow. In this case, several deep breaths can induce variations in peripheral circulation (downward spikes in FIG. 6j consistent with literature), and all variations, whether a result of deep breathing or otherwise, appear to be captured by the device.

Figure 25:
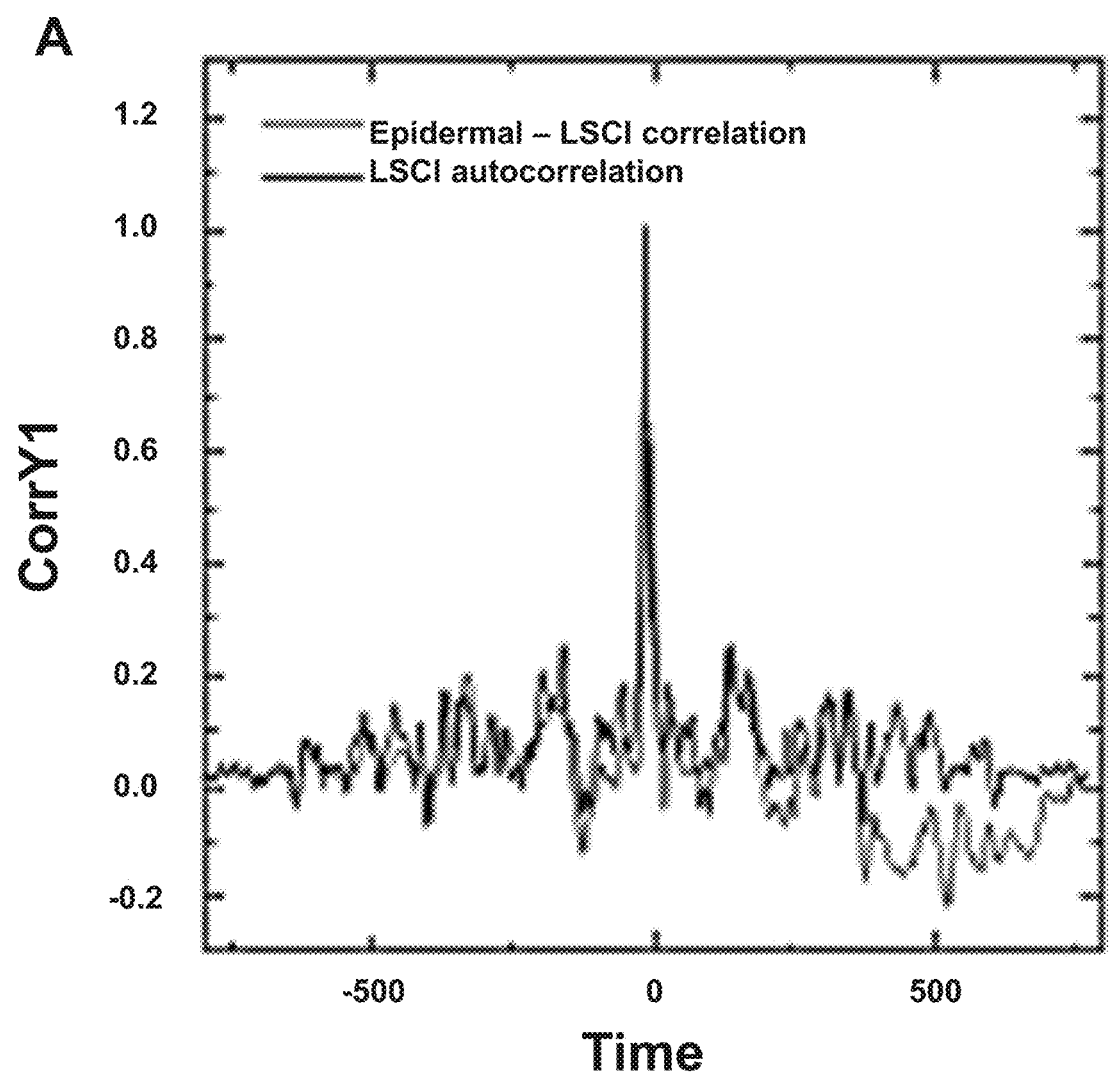
FIG. 25: Statistical correlation between LSCI data and epidermal device data from FIG. 6. (A) Same analysis procedure as FIG. 17B. (B) Coherence between LSCI and epidermal device data.
Figure 25:
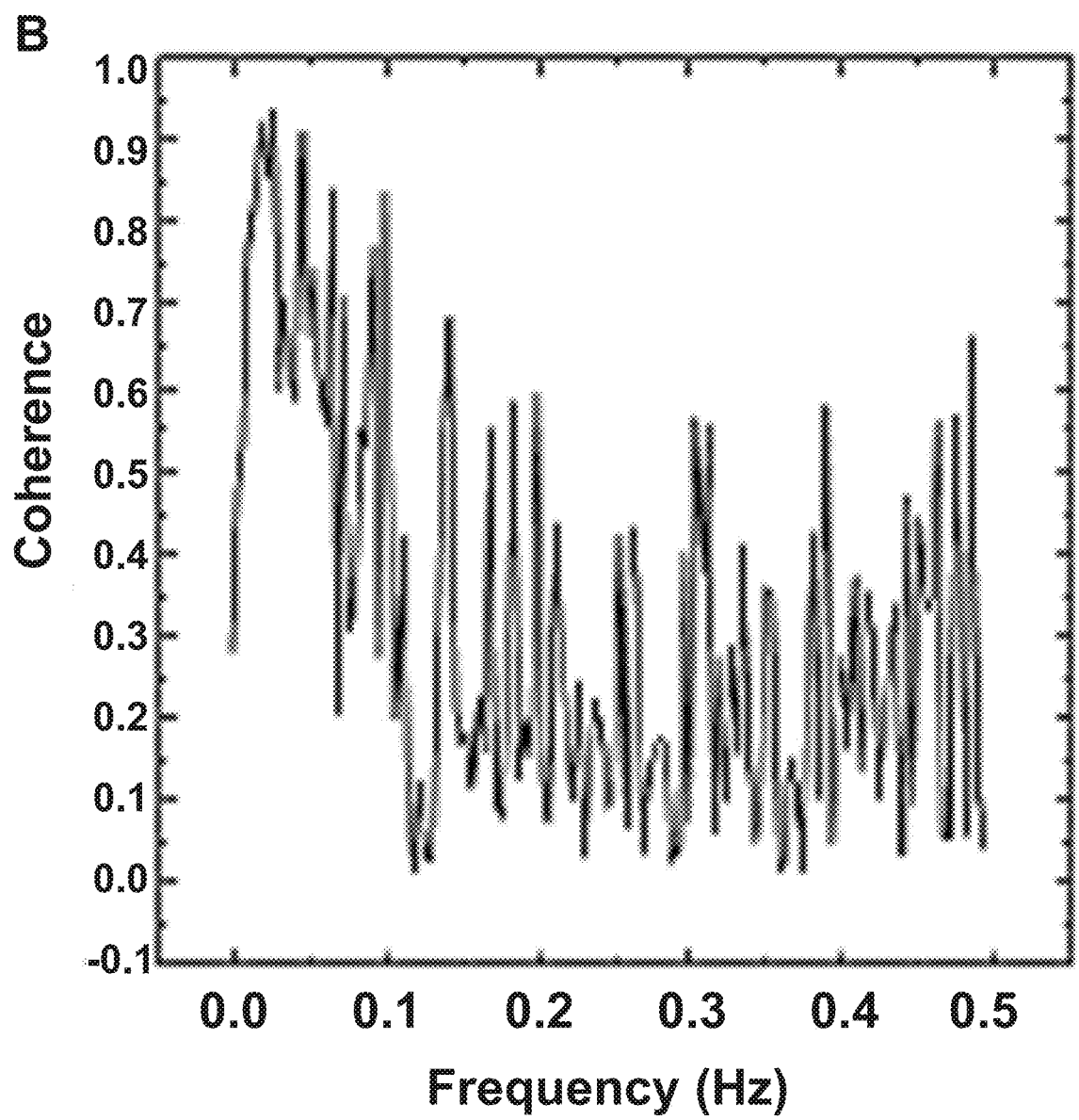

Cross correlation and coherence data show the excellent level of agreement between measurements using LSCI and our device (FIG. 25).

Pulsed Operation Modes

Figure 7:
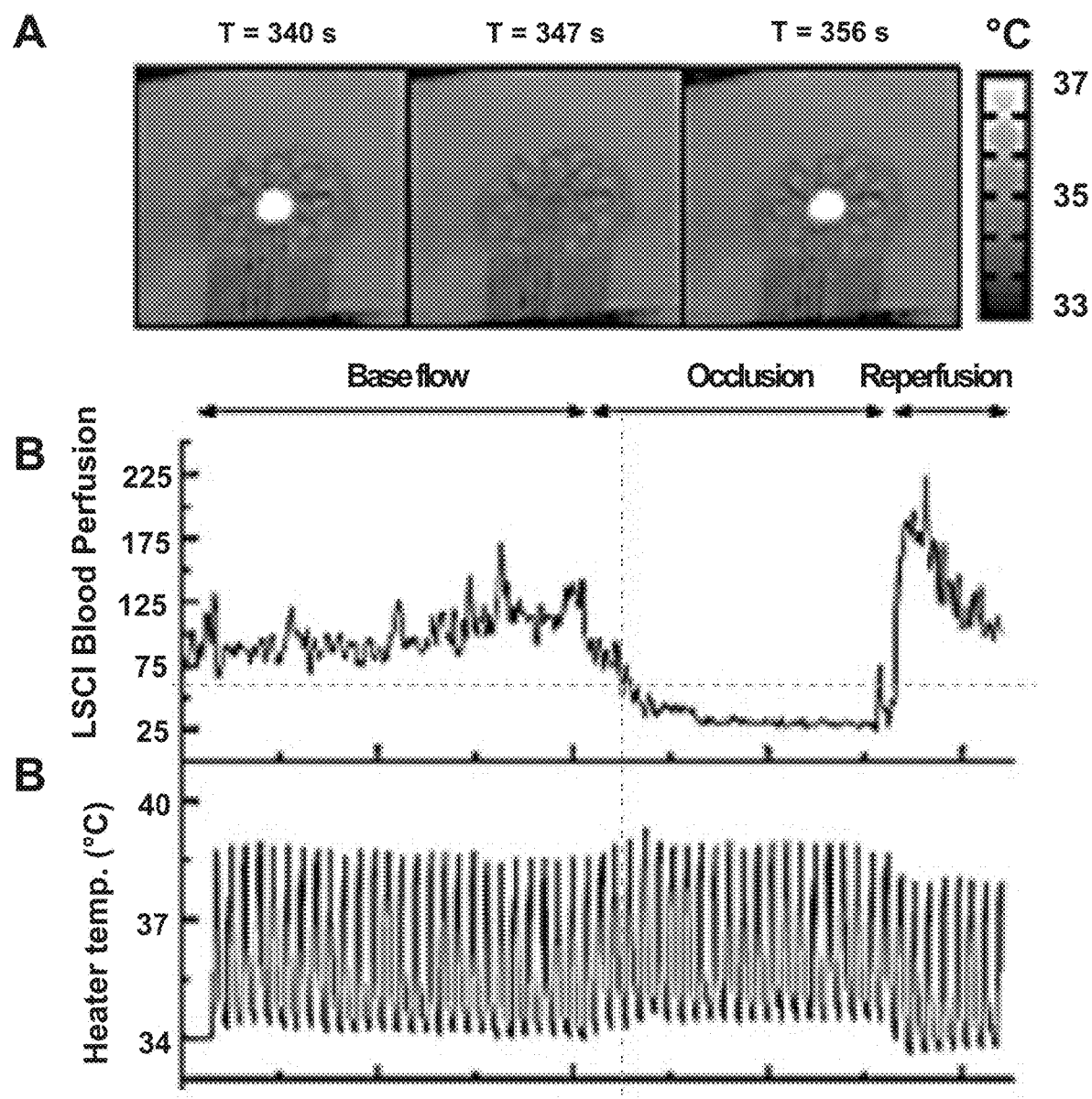
FIG. 7: Pulsed heating as an operation mode that reduces environmental effects and power consumption. The device resides on the volar aspect of the wrist, over a vein, during a reactive hyperemia protocol. Occlusion with a pressure cuff at the bicep, at 200 mmHg, begins at t=400 s and ends at t=700 s. The thermal actuator operates in a pulsed mode, as opposed to the continuous mode shown in prior figures. a) Infrared images of pulsed heating during one cycle. b) LSCI signal measured at a point above the vein, subject to a 0.2 Hz low pass filter. c) Temperature of the thermal actuator, which oscillates continuously throughout the experiment as a square wave with a 33% duty cycle, frequency of 0.067 Hz, 1 mA offset and 2 mA peak-to-peak amplitude. d) The differential temperature measured by sensors on opposing sides of the actuator, along the vein, with L=1.5 mm. e) Fourier transform spectrogram of c). The signal at 0.067 Hz is strong before and after occlusion, and diminishes during occlusion due to loss of anisotropy with loss of venous blood flow. f) Relative amplitude of the signal at 0.067 Hz, extracted from d). Frequency locked analysis allows for removal of drift in exchange for decreased time resolution.
Figure 7:
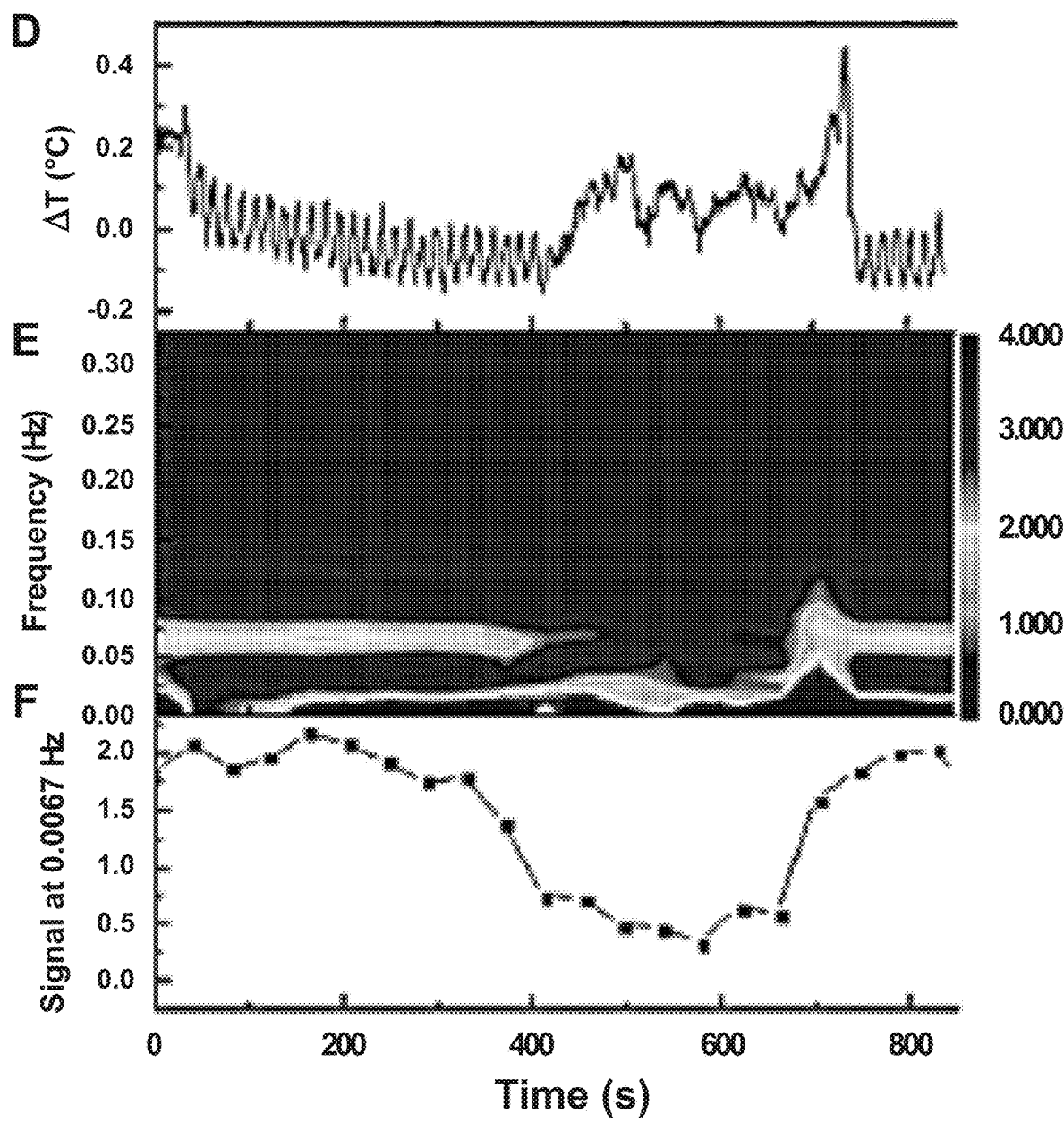
Figure 26:
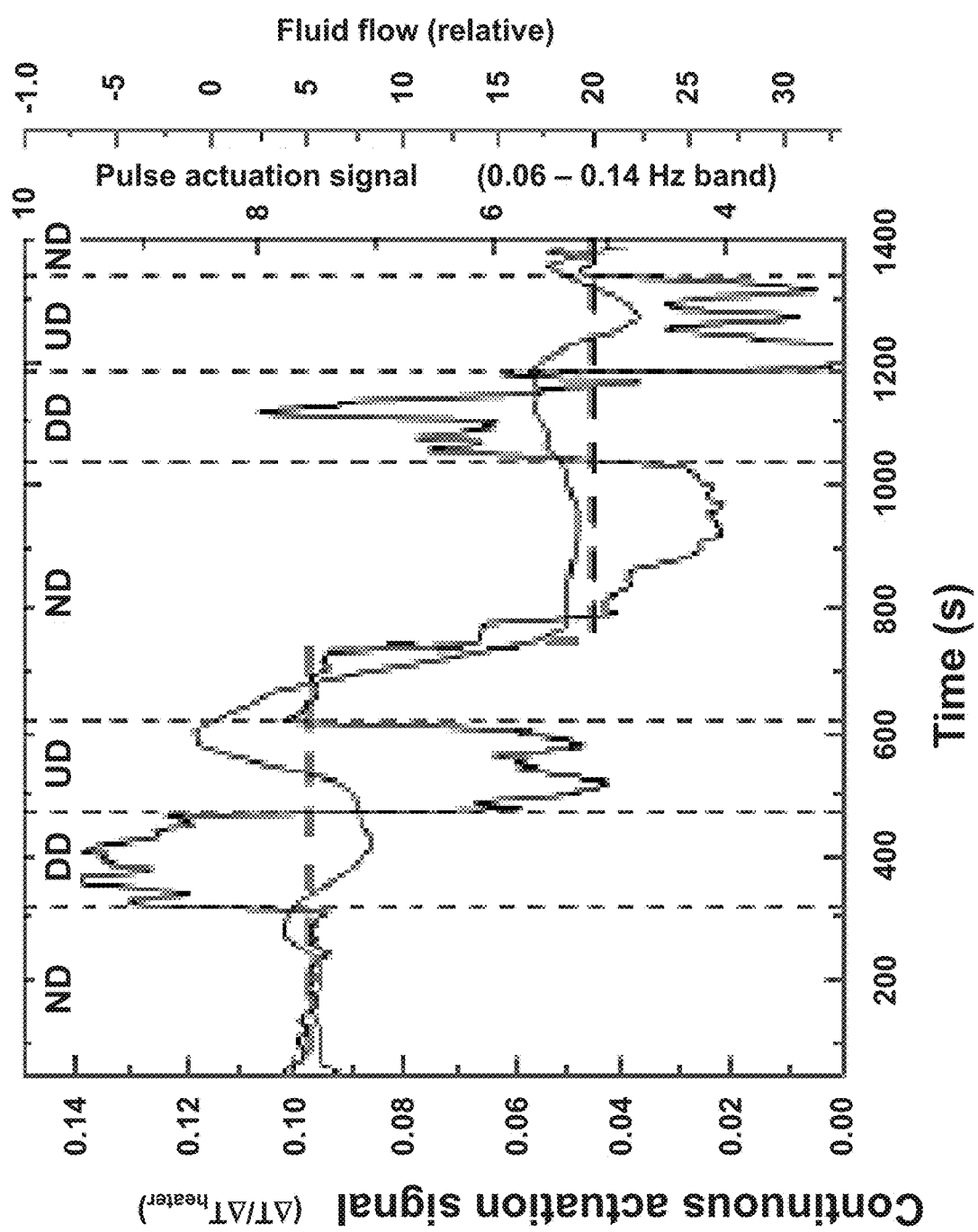
FIG. 26: Comparison of errors induced in the device response for continuous mode and pulsed mode actuation in a control experiment. The device is placed on a molded silicone flow system, designed to mimic a system with blood flow occurring beneath the surface of the skin in a large vessel. Thermal disturbances are applied to various sensors in the device array at various times during flow measurements. Disturbances are induced by bringing a hot solder iron tip, at 65° C., in close proximity to the sensor either downstream (Downstream Disturbance, DD) or upstream (Upstream Disturbance, UD) of the actuator, without physically touching the sensor. The heat from the iron changes the relative temperature differential measured by the two sensors on opposing sides of the actuator, resulting in a measurement error. The experiment is carried out in continuous actuation mode (black; filtered with an adjacent averaging filter, window size=20 points) and pulsed actuation mode (blue, 0.1 Hz actuation at 33% duty cycle; filtered with an adjacent averaging filter, window size=4 points). Fluid flow begins at a baseline value of 5 and increases to 20 (relative values) at t=740 s. The disturbance timing is as follows: 0<t<320 s—No disturbance (ND); 320<t<470 s—DD; 470<t<620 s—UD; 620 s<t<1040 s—ND; 1040 s<t<1190 s—DD; 1190<t<1340 s—UD; 1340 s<t—

Environmentally induced drifts in the device response and inefficiencies in power consumption represent important considerations for long-term continuous monitoring. A pulsed thermal actuation mode represents one simple strategy to address these issues. The ability to operate the actuator at a reduced duty cycle results in a reduction in power consumption. The benefits to long-term drift are more subtle. In a continuous operation mode, information related to blood flow is extracted from the temperature differential of sensors on opposing sides of the actuator. For each sensor, the relevant temperature is not the absolute value, but the change relative to the baseline established after application of power to the actuator. In long-term measurements, local heterogeneous changes in skin temperature may occur for reasons unrelated to the anisotropic convective effects induced by the blood vessel. For example, a local, environmentally induced temperature change at the location of one but not the opposing sensor, will affect the measurement of blood flow. A pulsed actuation mode effectively removes this type of drift error, by continuously adjusting the effective baseline for each temperature differential. FIG. 7 illustrates the use of a pulsed actuation mode in a hyperemic response experiment, similar to the one described for FIG. 5. LSCI data from the experiment, measured through the transparent regions of the device as previously, show the periods of base flow, occlusion and reperfusion (FIG. 7b). The temperature of the thermal actuator (FIG. 7c), pulsing at a frequency of 0.067 Hz with a 33% duty cycle, illustrates the rapid rates of heating enabled by the ultrathin device design and its low thermal mass. The pulsing frequency is not limited by the actuator, but instead by the rate at which heat can transfer through the skin from the actuator to the sensors. The temperature differential of a pair of sensors on opposing sides of the actuator and along the vein (FIG. 7d) reveals a signal at 0.067 Hz that is strong during the periods of flow (due to the anisotropy induced by flow) and weak during occlusion (due to the loss of anisotropy). Note that frequency and power applied to the heater remain fixed, such that changes in the differential signal cannot arise from changes in the heating. The frequency-time spectrogram (FIG. 7e) of the signal in FIG. 7d, and the extracted amplitude at 0.067 Hz (FIG. 7f) illustrates the changes during occlusion. One disadvantage of pulsed actuation is that the time resolution of the extracted blood flow signal is lower than that possible in the continuous operation mode. This limitation follows from the fact that each pulse must be sufficiently long to induce a measurable temperature change in the surrounding sensors, which reduces the effective maximum sampling rate to a value comparable to the pulse rate. Reducing the duration of the pulses leads to decreased signal amplitudes and corresponding reductions in measurement precision but with improved time resolution. In practice, pulse frequencies of 0.05-0.1 Hz generate reasonable signals at thermal actuation levels that remain below the threshold for sensation. A 33% duty cycle provides sufficient time between pulses for the actuator to return to the baseline temperature of the skin. A control experiment, in which application of local heating near individual sensors with a hot iron tip (~10° C. errors are induced in the sensor readings by proximity of the 65° C. iron tip) induces variability, for both the continuous actuation and pulsed actuation modes, results in an average of 5× reduction in error in measured flow for the pulsed mode compared to the continuous mode (FIG. 26).

DISCUSSION

The devices presented here provide a route to wearable, continuous, non-invasive measurements of local blood flow to the macro and microvasculature of the skin. These capabilities follow from materials and designs that eliminate relative motion between the actuator/detectors and blood, minimize effects of thermal loading on the skin, and avoid any external application of pressure during wear and measurement. Comparisons to established commercial optical tools, in immobilized settings, validate the accuracy of the measurement. The flow sensitivity of the device to specific vessels is dependent on numerous parameters, such vessel depth and radius, flow rate regime, and surrounding tissue composition, and can be modified with changes to the device geometry. With these potential variations in mind and based upon experimental and FEA results here, we find general guidelines of macrovascular detection limits to be flow in vessels as deep as 2 mm (sensitivity increases with decreasing depth), flow rates of 0.1 mm/s—100 mm/s ($\Delta T$ at least 3× the standard deviation of sensor noise, keeping in mind that the extent and direction of thermal change per unit flow change depends on the flow rate) and a vessel radius down to 0.25 mm (sensitivity increases with increasing radius). The sensitivity to microvascular flows is highly dependent on skin location, although our results indicate a sensitivity near (~50%) that of the LSCI on the fingertip, and our device does not require the immobilization needed for LSCI. Changes to the device geometry would result in changes in these sensitivity ranges, allowing for device designs tailored to specific anatomy.

This class of devices is amenable to low cost, high volume production using established microfabrication procedures, thereby suggesting a potential for widespread use, both in the clinic and in the home setting. Applications of interest include monitoring of near-surface blood flow as indicators of vascular health, particularly in diseases with vascular-associated pathologies, as either primary or secondary components—i.e. artherosclerosis, sickle cell anemia, diabetes, chronic kidney disease and vasculitides, and more broadly as a tool for clinical research. This technology also has utility to continuous monitoring of local microcirculatory changes due to inflammation induced by trauma, environmental exposure—e.g. sun-burn, chilblains (pernio), and phenomena that involve local blood flow stasis, insufficiency, retrograde flow, and vasodilation or vasoconstriction; and long-term monitoring of chronic conditions that result in alterations of peripheral blood flow and tissue perfusion. Further, the flexible, stretchable format of this type of device also lends itself to straightforward use on internal organs, as an integrated element either with implantable devices, in vivo diagnostics, surgical tools or other therapeutics.

REFERENCES

1. S. D. Shpilfoygel, R. A. Close, D. J. Valentino, G. R. Duckwiler, X-ray videodensitometric methods for blood flow and velocity measurement: a critical review of literature. *Medical physics* 27, 2008-2023 (2000).
2. A. J. Flammer, T. Anderson, D. S. Celermajer, M. A. Creager, J. Deanfield, P. Ganz, N. M. Hamburg, T. F. Luscher, M. Shechter, S. Taddei, J. A. Vita, A. Lerman, The assessment of endothelial function: from research into clinical practice. *Circulation* 126, 753-767 (2012).
3. J. S. Petrofsky, Resting blood flow in the skin: does it exist, and what is the influence of temperature, aging, and diabetes? *Journal of diabetes science and technology* 6, 674-685 (2012).
4. C. I. Wright, C. I. Kroner, R. Draijer, Non-invasive methods and stimuli for evaluating the skin's microcirculation. *Journal of Pharmacological and Toxicological Methods* 54, 1-25 (2006).
5. J. R. Petrie, S. Ueda, A. D. Morris, L. S. Murray, H. L. Elliott, J. M. Connell, How reproducible is bilateral forearm plethysmography? *British journal of clinical pharmacology* 45, 131-139 (1998).
6. I. B. Wilkinson, D. J. Webb, Venous occlusion plethysmography in cardiovascular research: methodology and clinical applications. *British journal of clinical pharmacology* 52, 631-646 (2001).
7. J. Allen, Photoplethysmography and its application in clinical physiological measurement. *Physiol Meas* 28, R1-39 (2007).
8. J. R. Lindner, Microbubbles in medical imaging: Current applications and future directions. *Nature Reviews Drug Discovery* 3, 527-532 (2004).
9. B. A. Schrope, V. L. Newhouse, Second harmonic ultrasonic blood perfusion measurement. *Ultrasound in Medicine and Biology* 19, 567-579 (1993).
10. G. E. Nilsson, T. Tenland, P. A. Oberg, Evaluation of a laser Doppler flowmeter for measurement of tissue blood flow. *IEEE Transactions on Biomedical Engineering* 27, 597-604 (1980).
11. P. A. Oberg, Laser-Doppler flowmetry. *Critical Reviews in Biomedical Engineering* 18, 125-161 (1990).
12. K. Wardell, A. Jakobsson, G. E. Nilsson, Laser Doppler perfusion imaging by dynamic light scattering. *IEEE Transactions on Biomedical Engineering* 40, 309-316 (1993).
13. D. A. Boas, A. K. Dunn, Laser speckle contrast imaging in biomedical optics. *J Biomed Opt* 15, (2010).
14. A. K. Dunn, H. Bolay, M. A. Moskowitz, D. A. Boas, Dynamic imaging of cerebral blood flow using laser speckle. *Journal of Cerebral Blood Flow and Metabolism* 21, 195-201 (2001).
15. M. Draijer, E. Hondebrink, T. Van Leeuwen, W. Steenbergen, Review of laser speckle contrast techniques for visualizing tissue perfusion. *Lasers in Medical Science* 24, 639-651 (2009).
16. H. H. Asada, P. Shaltis, A. Reisner, S. Rhee, R. C. Hutchinson, Mobile monitoring with wearable photoplethysmographic biosensors. *IEEE engineering in medicine and biology magazine: the quarterly magazine of the Engineering in Medicine & Biology Society* 22, 28-40 (2003).
17. T. Fujikawa, O. Tochikubo, N. Kura, T. Kiyokura, J. Shimada, S. Umemura, Measurement of hemodynamics during postural changes using a new wearable cephalic laser blood flowmeter. *Circ J* 73, 1950-1955 (2009).
18. E. Higurashi, R. Sawada, T. Ito, An integrated laser blood flowmeter. *Lightwave Technology, Journal of* 21, 591-595 (2003).
19. P. Zakharov, M. S. Talary, A. Caduff, A wearable diffuse reflectance sensor for continuous monitoring of cutaneous blood content. *Physics in medicine and biology* 54, 5301-5320 (2009).
20. M. Nitzan, S. L. E. Fairs, V. C. Roberts, Simultaneous measurement of skin blood flow by the transient thermal-clearance method and laser Doppler flowmetry. *Medical & Biological Engineering & Computing* 26, 407-410 (1988).
21. M. Nitzan, Y. Mahler, Theoretical-Analysis of the Transient Thermal Clearance Method for Regional Blood-Flow Measurement. *Medical & Biological Engineering & Computing* 24, 597-601 (1986).
22. W. J. B. M. van de Staak, A. J. M. Brakker, H. E. de Rijke-Herweijer, Measurements of Thermal Conductivity of Skin as an Indication of Skin Blood Flow. *J Invest Dermatol* 51, 149-& (1968).
23. S. Thalayasingam, D. T. Delpy, Thermal Clearance Blood-Flow Sensor Sensitivity, Linearity and Flow Depth Discrimination. *Medical & Biological Engineering & Computing* 27, 394-398 (1989).
24. C. Jin, Z. Z. He, S. S. Zhang, M. C. Qi, Z. Q. Sun, D. R. Di, J. Liu, A feasible method for measuring the blood flow velocity in superficial artery based on the laser induced dynamic thermography. *Infrared Physics & Technology* 55, 462-468 (2012).
25. K. I. Jang, S. Y. Han, S. Xu, K. E. Mathewson, Y. Zhang, J. W. Jeong, G. T. Kim, R. C. Webb, J. W. Lee, T. J. Dawidczyk, R. H. Kim, Y. M. Song, W. H. Yeo, S. Kim, H. Cheng, S. I. Rhee, J. Chung, B. Kim, H. U. Chung, D. Lee, Y. Yang, M. Cho, J. G. Gaspar, R. Carbonari, M. Fabiani, G. Gratton, Y. Huang, J. A. Rogers, Rugged and breathable forms of stretchable electronics with adherent composite substrates for transcutaneous monitoring. *Nat Commun* 5, 4779 (2014).
26. D. H. Kim, N. S. Lu, R. Ma, Y. S. Kim, R. H. Kim, S. D. Wang, J. Wu, S. M. Won, H. Tao, A. Islam, K. J. Yu, T. I. Kim, R. Chowdhury, M. Ying, L. Z. Xu, M. Li, H. J. Chung, H. Keum, M. McCormick, P. Liu, Y. W. Zhang, F. G. Omenetto, Y. G. Huang, T. Coleman, J. A. Rogers, Epidermal Electronics. *Science* 333, 838-843 (2011).
27. J. A. Rogers, T. Someya, Y. Huang, Materials and mechanics for stretchable electronics. *Science* 327, 1603-1607 (2010).
28. C. Wang, D. Hwang, Z. Yu, K. Takei, J. Park, T. Chen, B. Ma, A. Javey, User-interactive electronic skin for instantaneous pressure visualization. *Nat Mater* 12, 899-904 (2013).
29. S. D. Wang, M. Li, J. Wu, D. H. Kim, N. S. Lu, Y. W. Su, Z. Kang, Y. G. Huang, J. A. Rogers, Mechanics of Epidermal Electronics. *J Appl Mech-T Asme* 79, (2012).
30. R. C. Webb, A. P. Bonifas, A. Behnaz, Y. H. Zhang, K. J. Yu, H. Y. Cheng, M. X. Shi, Z. G. Bian, Z. J. Liu, Y. S. Kim, W. H. Yeo, J. S. Park, J. Z. Song, Y. H. Li, Y. G. Huang, A. M. Gorbach, J. A. Rogers, Ultrathin conformal devices for precise and continuous thermal characterization of human skin. *Nat Mater* 12, 938-944 (2013).
31. G. Schwartz, B. C. K. Tee, J. Mei, A. L. Appleton, D. H. Kim, H. Wang, Z. Bao, Flexible polymer transistors with high pressure sensitivity for application in electronic skin and health monitoring. *Nature Communications* 4, (2013).
32. M. Kaltenbrunner, T. Sekitani, J. Reeder, T. Yokota, K. Kuribara, T. Tokuhara, M. Drack, R. Schwödiauer, I. Graz, S. Bauer-Gogonea, S. Bauer, T. Someya, An ultralightweight design for imperceptible plastic electronics. *Nature* 499, 458-463 (2013).
33. M. Drack, I. Graz, T. Sekitani, T. Someya, M. Kaltenbrunner, S. Bauer, An imperceptible plastic electronic wrap. *Adv Mater* 27, 34-40 (2015).
34. D. Fiala, K. J. Lomas, M. Stohrer, A computer model of human thermoregulation for a wide range of environmental conditions: The passive system. *Journal of Applied Physiology* 87, 1957-1972 (1999).

35. T. C. Shih, H. S. Kou, W. L. Lin, Effect of effective tissue conductivity on thermal dose distributions of living tissue with directional blood flow during thermal therapy. *International Communications in Heat and Mass Transfer* 29, 115-126 (2002).
36. R. C. Webb, R. M. Pielak, P. Bastien, J. Ayers, J. Niittynen, J. Kurniawan, M. Manco, A. Lin, N. H. Cho, V. Malyrchuk, G. Balooch, J. A. Rogers, Thermal transport characteristics of human skin measured in vivo using ultrathin conformal arrays of thermal sensors and actuators. *PloS one* 10, e0118131 (2015).
37. M. G. ten Berge, T. I. Yo, A. Kerver, A. A. E. A. de Smet, G. J. Kleinrensink, Perforating Veins: An Anatomical Approach to Arteriovenous Fistula Performance in the Forearm. *European Journal of Vascular and Endovascular Surgery* 42, 103-106 (2011).
38. P. Kvandal, S. A. Landsverk, A. Bernjak, A. Stefanovska, H. D. Kvernmo, K. A. Kirkeboen, Low-frequency oscillations of the laser Doppler perfusion signal in human skin. *Microvascular research* 72, 120-127 (2006).
39. M. Intaglietta, W. R. Tompkins, On-line measurement of microvascular dimensions by television microscopy. *J Appl Physiol* 32, 546-551 (1972).
40. J. R. Less, T. C. Skalak, E. M. Sevick, R. K. Jain, Microvascular architecture in a mammary carcinoma: branching patterns and vessel dimensions. *Cancer research* 51, 265-273 (1991).

Materials and Methods

Study Design

This study was designed to test the feasibility of measuring blood flow signals through the skin, in a wearable non-invasive manner, with concepts that build off of recent technology advancements in stretchable, flexible electronics. As such, the experiments were selected to show proof-of-concept with several varied applications. Specific experimental procedures, detailed below, were designed following the development of the technology platform to show the concepts and feasibility of the device. No data points are excluded from device blood flow readings. All subjects were healthy volunteers. Human subjects were enrolled on an NIH research protocol approved by the Institutional Review Board of the National Heart, Lung and Blood Institute (clinicaltrials.gov identifier NCT01441141) and specific university-approved (University of Arizona) protocols for volunteers. Subjects provided written informed consent after the nature and possible consequences of the study were explained.

Statistical Analysis

All graphs that display data over time (for the disclosed device and for LSCI) have been subjected to a 5 s adjacent averaging smoothing filter to improve the display of data. Where specific values of thermal conductivity and diffusivity are reported, they are reported as the mean +/− standard deviation of 12 individual sensor element measurements, where the lowest 2 and highest 2 values (from the array of 16 sensors) have been systematically excluded to account for potential local errors due to body hair. The spatial colormaps of temperature and flow fields are determined by a cubic interpolation of experimental data (MATLAB, MathWorks, USA). Statistical correlation graphs are enabled by a numerical time synchronization between epidermal device and LSCI data (MATLAB).

Fabrication of the Epidermal Device

Detailed fabrication steps appear in the Supplementary Materials. Fabrication begins with a 3" Si wafer coated with a 600 nm layer of poly(methyl methacrylate), followed by 1.5 μm of polyimide. Photolithographic patterning of a bilayer of Cr (6 nm)/Au (100 nm) deposited by electron beam evaporation defines the sensing/heating elements. A second multilayer of Ti (10 nm)/Cu (550 nm)/Ti (20 nm)/Au (25 nm), lithographically patterned, forms the connections to sensing/heating elements and non-oxidizing bonding locations for external electrical connection. A second layer of polyimide (1.5 μm) places the sensing/heating elements in the neutral mechanical plane and provides electrical insulation and mechanical strain isolation. Reactive ion etching of the polyimide defines the mesh layout of the array and exposes the bonding locations. A water-soluble tape (3M, USA) enables removal of the mesh layout from the Si wafer, to expose its back surface for deposition of Ti (3 nm)/$SiO_2$ (30 nm) by electron beam evaporation. Transfer to a thin silicone layer (5 μm; Ecoflex, Smooth-On, USA) spin-cast onto a glass slide, surface treated to reduce adhesion of the silicone, results in the formation of strong bonds due to condensation reactions between exposed hydroxyl groups on the $SiO_2$ and silicone. Immersion in warm water allows removal of the tape. A thin (100 μm), flexible, conductive cable bonded with heat and pressure to contacting pads at the periphery serves as a connection to external electronics. A final layer of silicone (~40 μm) in combination with a frame of medical tape (3M, USA) provides sufficient mechanical support to allow repeated (hundreds of times) use of a single device.

Data Acquisition for the Epidermal Device

Data acquisition occurs via a custom built system of USB-interface control electronics (FIG. 27B) integrated into a suitcase for mobility. The full system consists of one precision DC current source (6220, Keithley Instruments, USA), two 22-bit USB-powered Digital Multimeters (USB-4065, National Instruments, USA), and two voltage isolation mechanical relay switching matrices (U802, Ledgestone Technologies, USA). The wiring diagram appears in FIG. 27A, where S10 is the central thermal actuator and S1-S9, S11-S16 are the surrounding sensors. The surrounding sensor network shares a common ground path, while the thermal actuator (S10) is wired independently. The relays are controlled by a microcontroller that is integrated into the U802 platform. This setup allows for three general modes of operation: 1) To map temperature, the resistance of each sensor element can be sampled sequentially by DMM1, via opening and closing of relevant relays. In this case, DMM1 provides a DC probe current of 0.1 mA and records the resistance. The relays are controlled so that DMM2 takes one resistance recording on one sensor, and then switches to the next sensors for one recording, etc. through the entire array. A DMM aperture time of 0.015 s and a settling time of 0.001 s results in ~2 Hz sampling rate, per sensor, with a resolution of ~0.01 K. 2) To rapidly sample the local thermal conductivity and thermal diffusivity of each sensor, as described in FIG. 2C, each sensor is supplied, sequentially, with 2 mA current from the Keithley 6220, for 2 s each. The voltage from the Keithley 6220 is recorded by DMM2, which allows for calculation of the resistance change over time during actuation. The relay setup allows for isolation from the DMM1 circuit, and sequential actuation of each element. An aperture time of 0.005 s and a settling time of 0.005 s provide an adequate sampling rate (100 Hz) for analysis. 3) To map thermal transport over time, as done for blood flow measurements, the thermal actuator receives a continuous current input (2 mA) from the Keithley 6220. Simultaneously, the sensor resistances are sampled by DMM1, in the same fashion described for mode 1), but this time without sampling S10 (the central actuator). The actuator voltage is read by DMM2. The relay circuit allows isolation of the S10-Keithley-DMM2 circuit from the sensor array-DMM1 circuit.

Mathematical Modeling

The conservation of energy for the model system in FIGS. 2A and B is $$\frac{\partial}{\partial X}\left(\lambda\frac{\partial T}{\partial X}\right) + \frac{\partial}{\partial Y}\left(\lambda\frac{\partial T}{\partial Y}\right) + \frac{\partial}{\partial Z}\left(\lambda\frac{\partial T}{\partial Z}\right) = \rho cv\frac{\partial T}{\partial Z} + \rho c\frac{\partial T}{\partial t}, \quad (4)$$

where $\lambda=\lambda_f$, $\rho=\rho_f$, $c=c_f$ for the fluid (blood), $\lambda=\lambda_s$, $\rho=\rho_s$ and $c=c_s$ for the solid (tissue). This equation is solved numerically by FEA. The dimensional analysis, together with the boundary conditions, give the dependence of normalized temperature on the blood flow velocity v, radius R and depth h of the blood vessel, and other geometric and material parameters, i.e., $$\frac{\Delta T}{T_{actuator}} = g_1\left(\frac{L^2 vc_f\rho_f}{R\lambda_f}, \frac{R}{L}, \frac{h}{L}, \frac{\lambda_f t}{L^2\rho_f c_f}, \frac{\lambda_s}{\lambda_f}, \frac{\rho_s c_s}{\rho_f c_f}, \frac{B}{L}\right). \quad (5)$$

Figure 10:
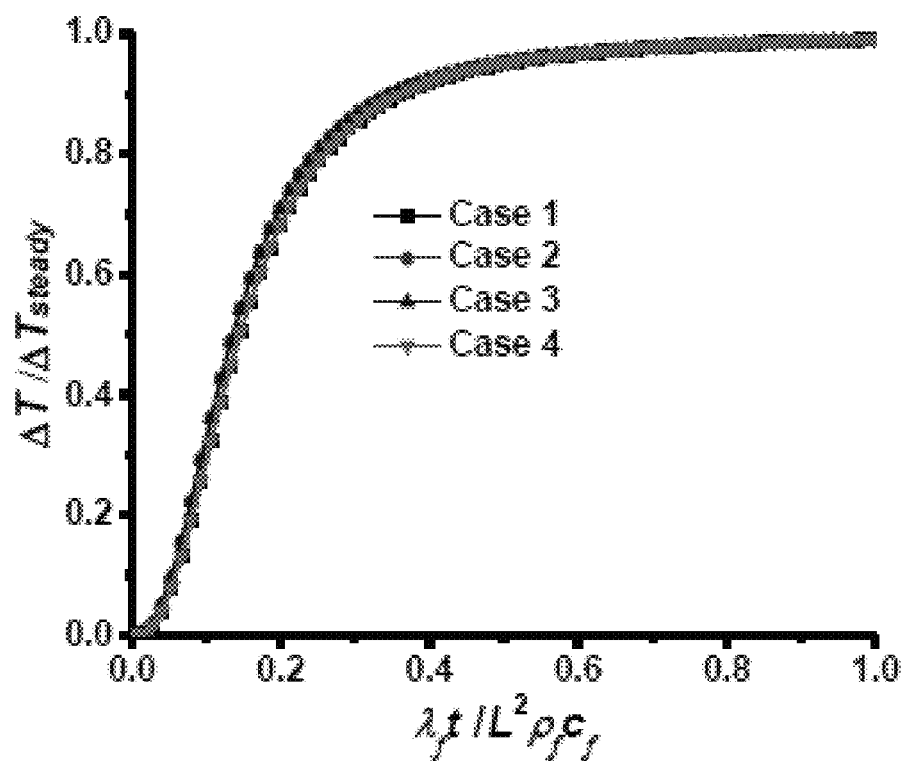
FIG. 10: FEA verification for the transient scaling law. Case 1 is the base line for comparison (water: $\lambda_f=0.6$ W·mm$_{-1}$ K$_{-1}$, $\rho_f=1,000$ kg/m$_3$, $c_f=4184$ J·kg$_{-1}$·K$_{-1}$, PDMS: $\lambda_s=0.18$ W·mm$_{-1}$K$_{-1}$, $\rho_s=970$ kg/m$_3$, $c_s=1380$ J·kg$_{-1}$·K$_{-1}$, h=0.55 mm, L=1.5 mm, B=1.5 mm, R=1 mm, v=5 mm/s). Case 2 gives double the flow velocity. Case 3 changes the material properties (double $\lambda_f$ and $\lambda_s$, quadruple $\rho_f$ and $\rho_s$) while Case 4 varies the geometric parameters (double h, L, B). All confirm the transient scaling law (Equation 1).
Figure 11:
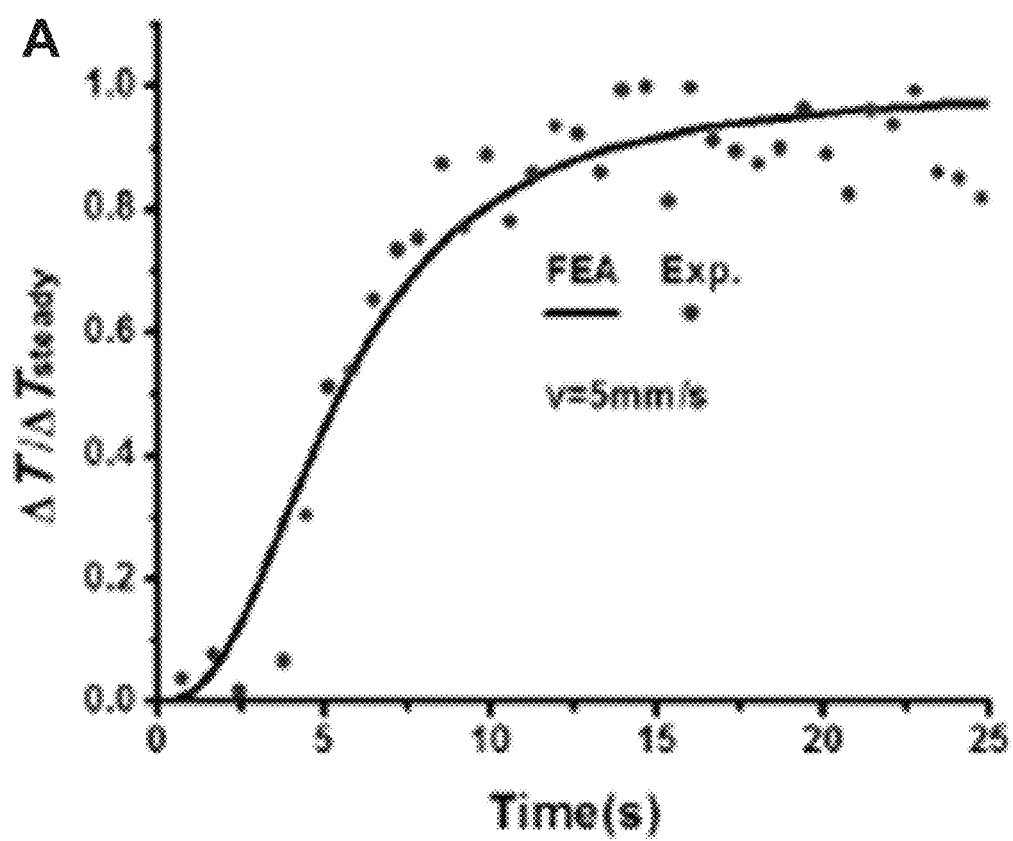
FIG. 11: Comparison between FEA and PDMS experiment. (A) The same conditions as Case 1 in FIG. 10, (B) double the flow velocity. The FEA agrees well with experiment without any parameter fitting. Experiments indeed show that the normalized temperature does not depend on the flow velocity.
Figure 11:
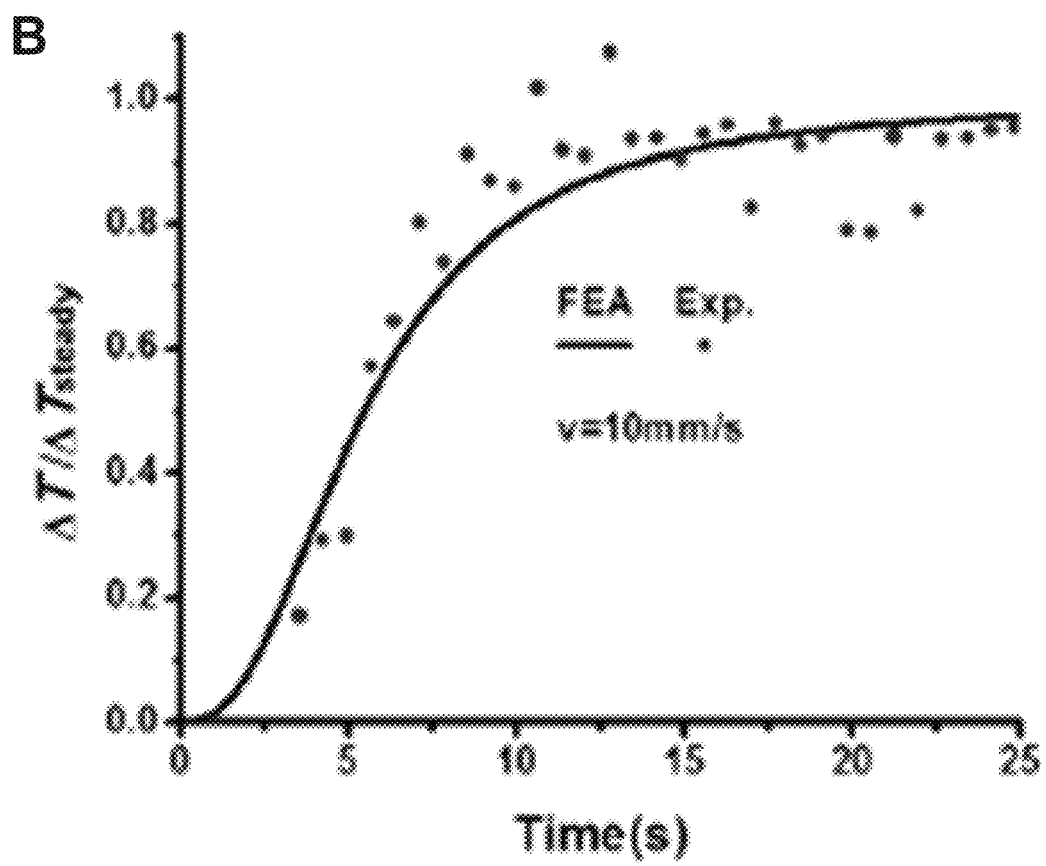

Its steady-state value is the limit of time t approaching infinity, which leads to Equation 2. FIGS. 10 and 11 show that $\Delta T/\Delta T_{steady}$ is approximately independent for vessel radius R and flow velocity v in their physiological ranges, which then lead to Equation 1.

Macrovascular Flow Tests

Local Venous Occlusion with a Cotton Swab (FIG. 3)

FIG. 3(A-C): A volunteer (male, age 27) reclined in a chair with his left forearm placed on an armrest. The epidermal device was placed on the volar aspect of the wrist, with the thermal actuator centered over a near-surface vein, as identified by visual inspection (location indicated in FIG. 12). The infrared camera and laser speckle contrast imager were both positioned 31 cm from the epidermal device. The subject was instructed to relax, and device measurements began at t=0. At t=30 s, continuous application of 2 mA current to the thermal actuator began. At t=330 s, gentle pressure was applied to the skin (above the vein, 1 cm distal to the epidermal thermal actuator; location shown in second panel of FIG. 3A) using a cotton swab held in the hand of an investigator. At t=390 s, pressure was released. At t=450 s, pressure was applied in the same way 1 cm from the actuator, but now at a location rotated 45° clockwise relative to the actuator. Pressure was released at t=510 s. This process of 60 s pressure, 60 s no pressure was repeated a total of 8 times, with each location rotated at 45° clockwise relative to the previous location. One location, at 270° relative to the first location was skipped, and the final location was the same as the first location. Thermal actuation ended at t=1290 s.

FIG. 3(D-F): The control experiment occurred in the same fashion, but with the device placed on an area of the volar forearm with no prominent visible veins (location indicated in FIG. 12).

Figure 4:
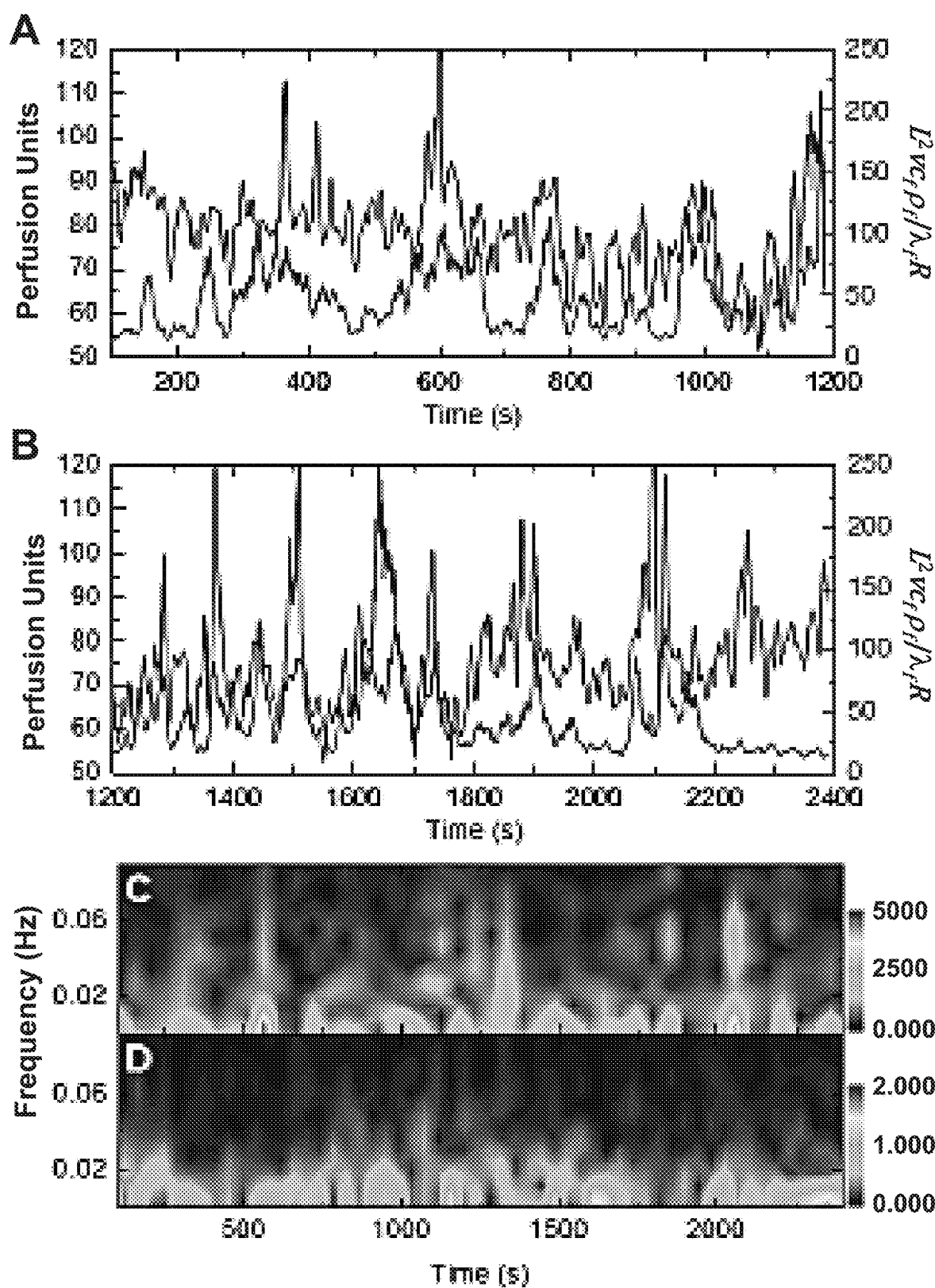
FIG. 4: Measurement of small-scale blood flow oscillations over an extended period. The device resides on the volar aspect of the wrist, over a vein. The subject sits in a reclining chair in a relaxed state with no external stimuli for a 20 min period. a) Changes in blood flow as measured by a Laser Speckle Contrast Imager (LSCI perfusion units, black) and the disclosed device (dimensionless flow, blue) for t=100-1200 s and b) t=1200-2400 s. The peaks in the two measurement techniques align well. c) Fourier transform spectrogram (FFT length=128 s, 5 samples/s; colorbar is amplitude of LSCI spectrogram) for t=100-2400 s determined from LSCI data and d) the disclosed device (FFT length=128 s, 2 samples/s; colorbar is amplitude of thermal anisotropy spectrogram).

Extended Test of Natural Oscillations (FIG. 4)

A volunteer (male, age 27) reclined in a chair with his left forearm placed on an armrest. The epidermal device, infrared camera and laser speckle contrast imager were positioned in the same fashion as for the previous local venous occlusion with a cotton swab. At t=0, room lighting was turned off and the subject was instructed to relax. At t=30 s, continuous application of 2 mA current to the thermal actuator began. Thermal actuation ended at t=2430 s.

Figure 5:
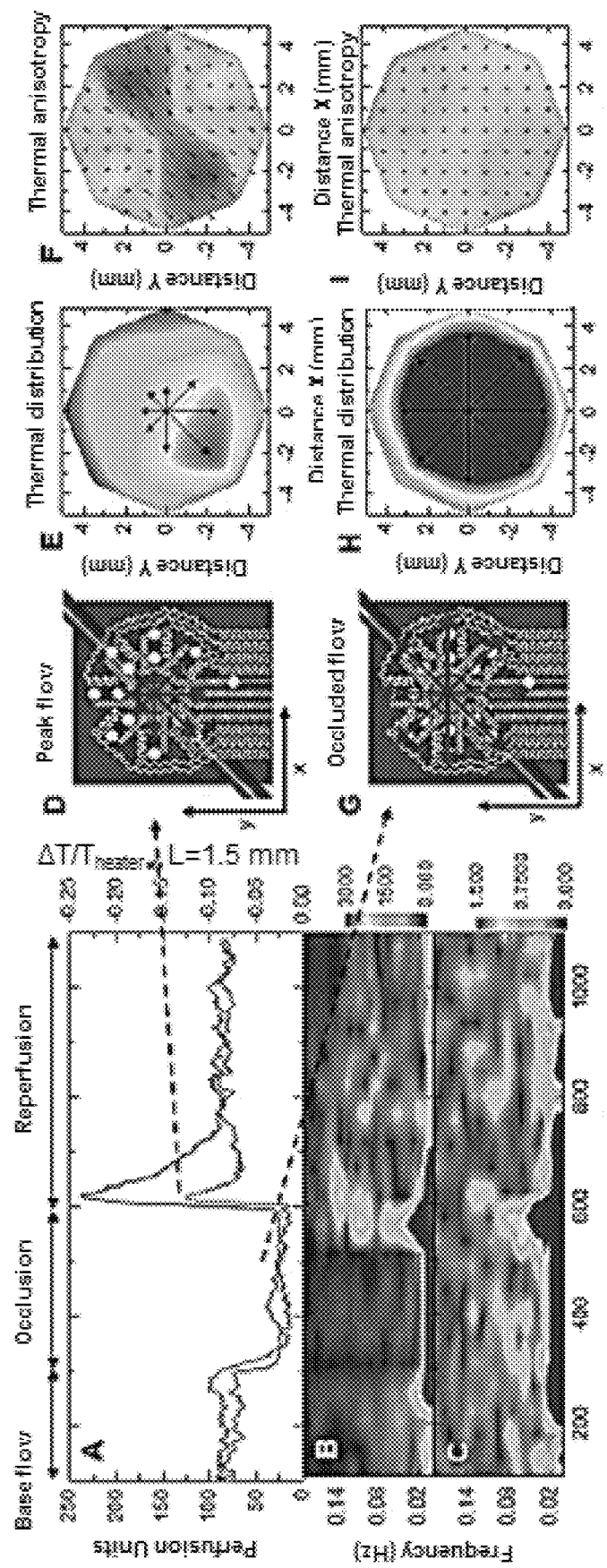
FIG. 5: Measurement of changes in local venous blood flow induced by occlusion and reperfusion of the forearm. The device resides on the volar surface of the wrist, over a vein. Occlusion and reperfusion induce changes in blood flow. Occlusion with a pressure of ~200 mmHg (80 mmHg above systolic pressure) applied to the bicep begins at t=300 s. Pressure is released at t=600 s. a) Changes in blood flow as measured by a Laser Speckle Contrast Imager (LSCI, black) and the disclosed device (blue). b) Fourier transform spectrogram (FFT length=128 s, 5 samples/s; colorbar is amplitude of LSCI spectrogram) determined from LSCI data and c) the disclosed device (FFT length=128 s, 2 samples/s; colorbar is amplitude of thermal anisotropy spectrogram). d) Illustration of the position of the vein relative to the device. The red arrows show the relative magnitudes of the thermal distribution at peak flow. e) Full thermal distribution map and f) flow field map during peak flow as measured by the disclosed device. g-i) Similar analyses as d)-f), except during occluded flow. j) A similar experiment as in a), but on a different subject with apparently deeper veins. Several strong pulsations of flow pulsations appear during occlusion, as measured with the disclosed device, but are entirely absent from the LSCI signal. Infrared images confirm the result from the disclosed device, with examples shown at k) a pulse trough l) a pulse peak (arrow indicates appearance of downstream heating) and m) at reperfusion. (k-m) are uniformly contrast-enhanced to aid visualization. Time points of k-m are indicated in j).
Figure 5:
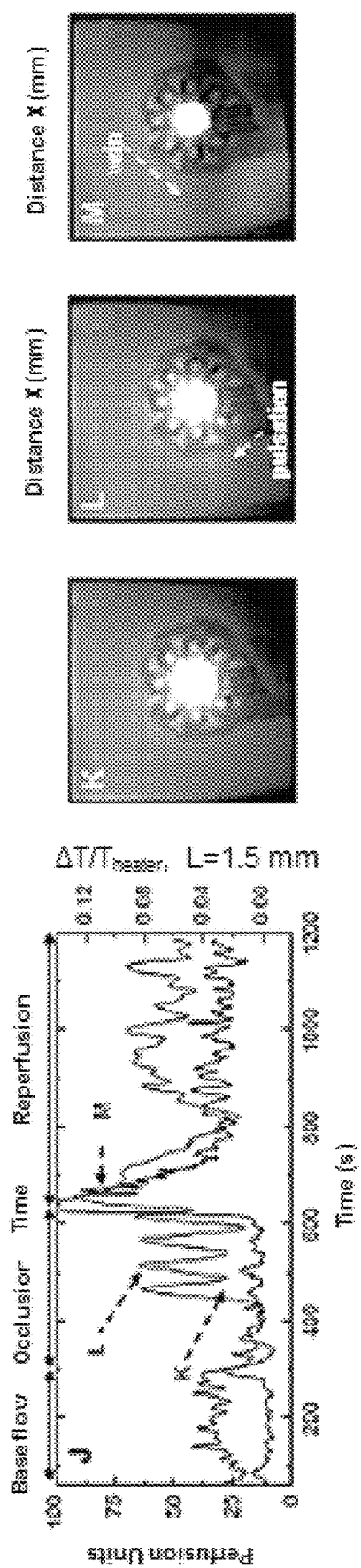

Reactive Hyperemia Test (FIG. 5 and FIG. 7)

FIG. 5(A-I): A volunteer (male, age 27) reclined in a chair with his left forearm placed on an armrest. The epidermal device, infrared camera and laser speckle contrast imager were positioned in the same fashion as for the previous local venous occlusion with a cotton swab. A pressure cuff was applied to the left bicep region. At t=0, room lighting was turned off and the subject was instructed to relax. At t=30 s, continuous application of 2 mA current to the thermal actuator began. At t=330 s, 200 mmHg pressure is applied to the pressure cuff. The pressure is released from the cuff, beginning at t=630 s, at a release rate of 4 mmHg/s. Recordings continued until t=1200 s.

FIG. 5(J-M): Same experiment with a different volunteer (male, age 23). The epidermal device was placed at a skin location identified as being over a vein on the volar forearm by an optical vein imager (VeinViewer Flex, Christie Medical Holdings Inc., USA).

FIG. 7: Same volunteer and procedure as that done for FIG. 5(A-I), except that occlusion begins at t=400 s, occlusion ends at t=700 s, and recordings end at t=900 s. The actuator is pulsed with 2 mA of current at 0.067 Hz with a 33% duty cycle.

Microvascular Flow Tests

Figure 6:
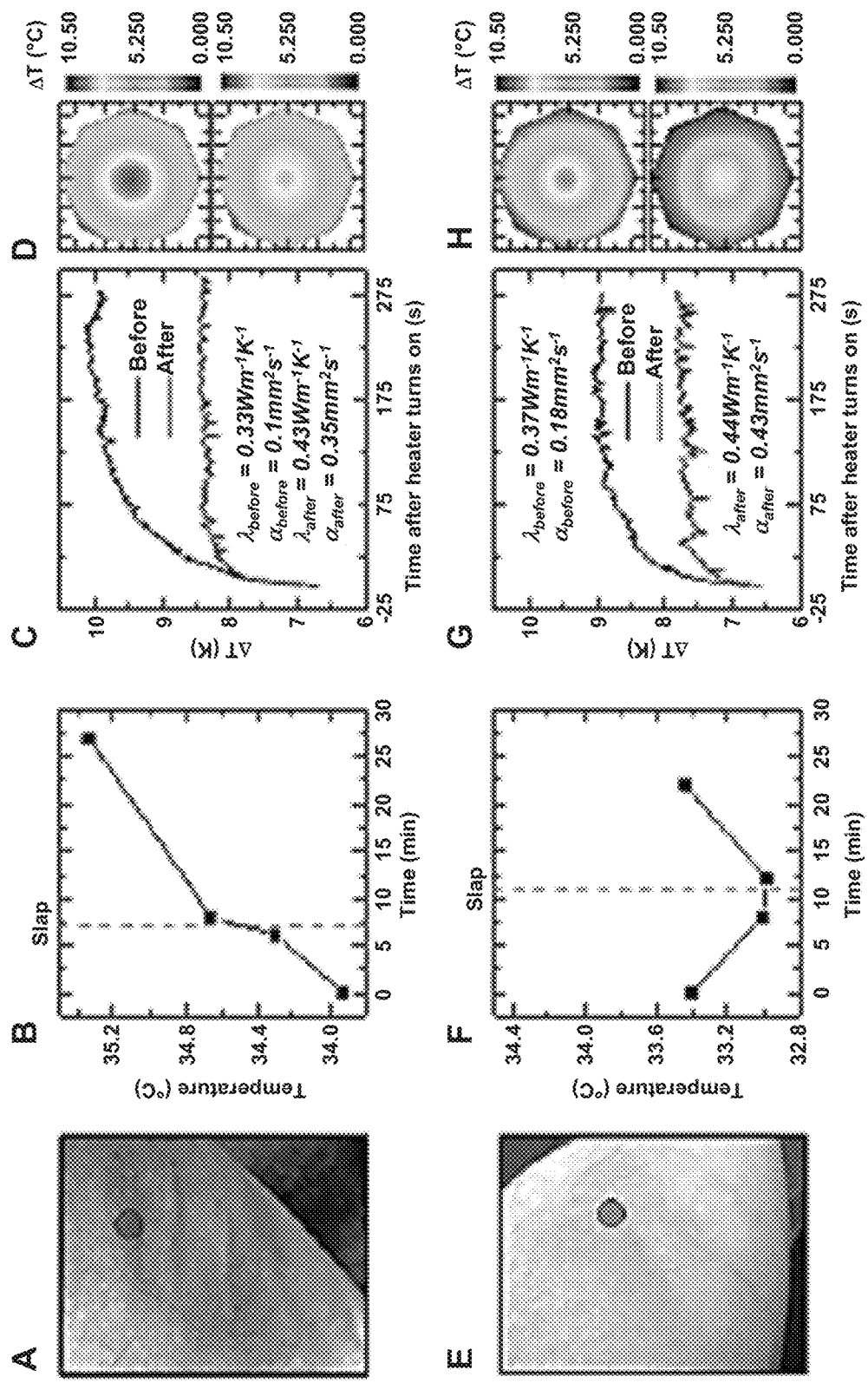
FIG. 6: Analysis of changes in local microcirculation induced by dermatographic urticaria and deep breathing. a) Photograph of slap-induced hyperemia and dermatographic urticarial on the forearm. Location of the thermal actuator during measurement. b) Temperature of the region of interest, measured by the disclosed device, before and after the onset of dermatographic urticaria. The vertical red dashed line indicates the time the slap was administered. c) Temperature profile of the central heating element, with background temperature changes removed, before and after onset of dermatographic urticaria. A change in the time dynamics of heating indicates changes in the local heat transfer coefficient. Analysis of the time dynamics allows for calculation of the local thermal conductivity, $\lambda$, and thermal diffusivity, $\alpha$, before and after the onset of dermatographic urticaria. d) Heat distribution, as measured by the disclosed device 280 s after heating, before (upper) and after (lower) the onset of dermatographic urticaria. Even though the local tissue increases in temperature, the temperature rise of the thermal actuator is lower after trauma due to the increase in local heat transfer. e-h) Similar analyses as shown in a)-d) on a different day and body location. i) Infrared image of the device applied to the fingertip to monitor local changes in microcirculation. j) Results from LSCI (black) and the disclosed device (blue; difference between actuator temperature and the average temperature of the inner ring of sensor). Periodic deep breathing (45 s breath holds) induces rapid dips in blood perfusion, measured by both LSCI and the disclosed device.
Figure 6:
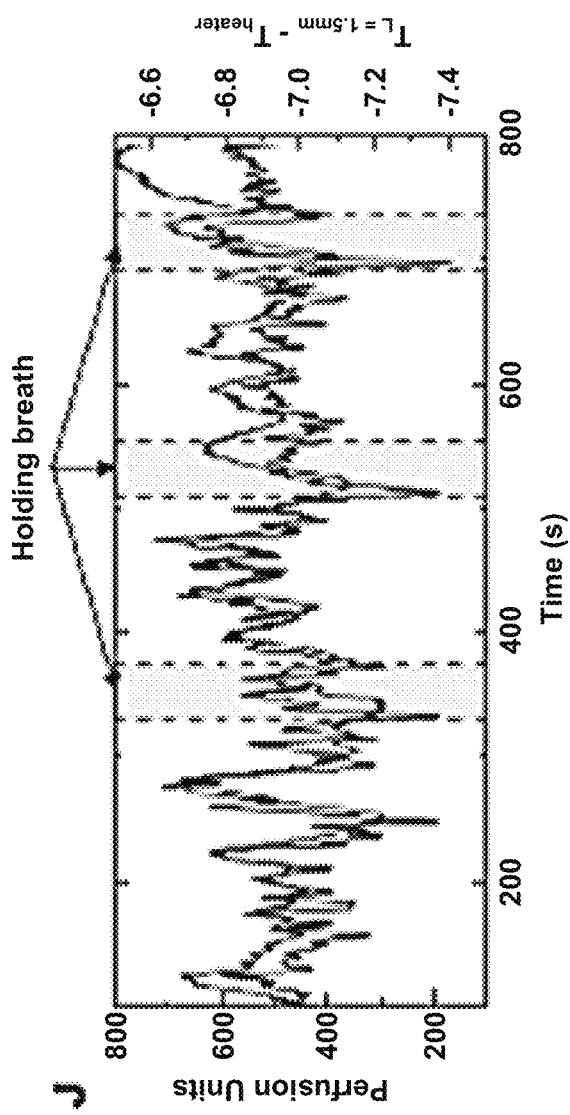
Figure 6:
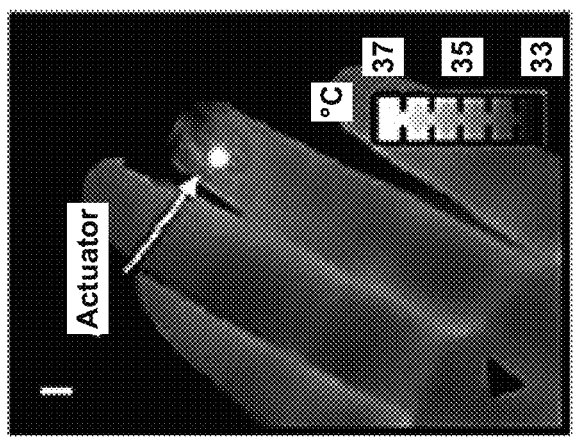

Slap-Induced Dermatographic Urticaria and Associated Hyperemia (FIG. 6, A-H)

A volunteer (male, age 59) sat in a chair with his left forearm resting on a table. The epidermal device was placed on an area of the volar aspect of the forearm without any local, visually prominent veins. At t=0, temperature measurements began with the epidermal device. At t=30 s, continuous application of 2 mA current to the thermal actuator began. Thermal actuation ended at t=330 s. Temperature recordings continued until t=510 s. Following the first set of recordings, the volunteer used his right hand to apply trauma, in the form of a single, rapid finger slap to the measurement location on his left forearm. The device was applied to the same location, approximately 120 s following the slap, and the same epidermal device measurement procedure was conducted again.

Microcirculation on the Fingertip (FIGS. 6, I and J)

A volunteer (male, age 27) reclined in a chair with his left forearm placed in an armrest. The epidermal device was placed on the volar aspect of the most distal digit of the middle finger on the left hand. The infrared camera and laser speckle contrast imager were placed 31 cm from the fingertip. At t=0, room lighting was turned off and the subject was instructed to relax. At t=30 s, continuous application of 2 mA current to the thermal actuator began. At t=330 s, the subject was instructed to inhale deeply. At t=375 s, the subject was instructed to exhale, and then breath normally. At t=510 s, and t=690 s the subject was again instructed to inhale and hold for 45 s. Recordings continued until t=800 s.

Supplementary Materials: Epidermal Devices for Non-Invasive, Precise and Continuous Monitoring of Macrovascular and Microvascular Blood Flow Supplementary Methods: Device Fabrication Prepare Polymer Base Layers 1. Clean a 3" Si wafer (Acetone, IPA→Dry 5 min at 110° C.).
2. Spin coat with PMMA (poly(methyl methacrylate) 495 A6 (Microchem), spun at 3,000 rpm for 30 s.

3. Anneal at 180° C. for 2 min.
4. Spin coat with polyimide (PI, poly(pyromellitic dianhydride-co-4,4'-oxydianiline), amic acid solution, Sigma-Aldrich, spun at 4,000 rpm for 30 s).
5. Anneal at 110° C. for 30 s.
6. Anneal at 150° C. for 5 min.
7. Anneal at 250° C. under vacuum for 1 hr.

Deposit First Metallization

8. Deposit 5/100 nm Cr/Au via electron beam evaporation.
9. Pattern photoresist (PR; Clariant AZ5214, 3000 rpm, 30 s) with 365 nm optical lithography through iron oxide mask (Karl Suss MJB3).

Develop in Aqueous Base Developer (MIF 327).

10. Etch Au with TFA Au etchant (Transene).
11. Etch Cr with CR-7 Cr Mask Etchant (Cyantek).
12. Remove PR with AZ 400-T Stripper.
13. Dry 5 min at 150° C.

Deposit Second Metallization

14. Deposit 10/550/20/25 nm Ti/Cu/Ti/Au via electron beam evaporation.
15. Pattern PR AZ5214.
16. Etch Au with TFA Au etchant.
17. Etch Ti with 6:1 Buffered Oxide Etchant.
18. Etch Cu with CE-100 etchant (Transene).
19. Etch Ti with 6:1 Buffered Oxide Etchant.
20. Remove PR w/Acetone, IPA rinse.
21. Dry 5 min at 150° C.

Isolate Entire Device

22. Spin coat with PI spun at 4,000 rpm for 30 s.
23. Anneal at 110° C. for 30 s.
24. Anneal at 150° C. for 5 min.
25. Anneal at 250° C. under vacuum for 1 hr.
26. Pattern photoresist (PR; Clariant AZ4620, 3000 rpm, 30 s) with 365 nm optical lithography through iron oxide mask (Karl Suss MJB3).

Develop in Aqueous Base Developer (AZ 400K Diluted 1:3, AZ 400K:Water).

27. Reactive ion etch (50 mTorr, 80 sccm $O_2$, 200 W, 30 min).

Release and Transfer

28. Release device by immersing in hot Acetone (60° C.) for 5 min.
29. Remove device with water-soluble tape (Wave Solder Tape, 5414, 3M).
30. Deposit 3/30 nm Ti/$SiO_2$ onto device on water soluble tape, via electron beam evaporation.
31. Expose a ~10 μm silicone sheet (Ecoflex, Smooth-on Co.), coated on silanized glass slide, with broadband UV light for 5 min.
32. Apply water soluble tape with device to exposed silicone sheet.
33. Immerse in warm water to dissolve tape.
34. Immerse quickly in Chrome Mask Etchant to remove any remaining residue.
35. Bond thin, flexible cable (Elform, HST-9805-210) using hot iron with firm pressure.
36. Apply additional silicone (10-100 μm) by doctor blade
37. Apply silicone medical tape frame (Ease Release Tape, 3M) (optional—for robust, repeated applications with a single device).
38. Remove device from glass slide.

Example 2

Epidermal Photonic Devices for Quantitative Imaging of Temperature and Thermal Transport Characteristics of the Skin Precision characterization of temperature and thermal transport properties of the skin can yield important information of relevance to both clinical medicine and basic research in skin physiology. Here, we introduce an ultrathin, compliant skin-like, or 'epidermal', photonic device that combines colorimetric temperature indicators with wireless stretchable electronics for precision thermal measurements when softly laminated on the surface of the skin. The sensors exploit thermochromic liquid crystals (TLC) patterned into large-scale, pixelated arrays on thin elastomeric substrates; the electronics provide means for controlled, local heating by radio frequency (RF) signals. Algorithms for extracting patterns of color recorded from these devices with a digital camera, and computational tools for relating the results to underlying thermal processes near the surface of the skin lend quantitative value to the resulting data. Application examples include non-invasive spatial mapping of skin temperature with milli-Kelvin precision and sub-millimeter spatial resolution. Demonstrations in reactive hyperemia assessments of blood flow and hydration analysis establish relevance to cardiovascular health and skin care, respectively.

Spatio-temporal imaging of skin temperature offers experimental and investigational value for detection of breast cancers and other syndromes, as an adjunctive screening tool to mammography.[1-3] The required milli-Kelvin levels of precision and milli-meter scale resolution are most commonly achieved by use of sophisticated infrared digital imaging cameras. Widespread adoption of such technology is limited, however, by high capital costs, motion artifacts, and inability for use outside of clinical or laboratory settings. Other low cost thermography techniques have been exploited much earlier, for potential screening of deep venous thrombosis[4-7], breast cancer[8-10], spinal root syndromes[11,12], chronic back pain[13] and even pulmonological diagnostics.[14] Recent work[15,16] demonstrates that electronic temperature mapping devices can be constructed in ultra-thin, soft and compliant formats, sometimes referred to as 'epidermal' due to the similarity of their physical characteristics to those of the skin itself. These systems offer impressive capabilities that bypass many limitations of infrared cameras, but provide only modest spatial resolution and imaging fidelity, limited by multiplexing systems needed to address large sensor arrays. Untethered, wireless operation also demands data transmission components and power sources. Other stretchable smart skin devices that can monitor the vital health signals of the wearer with unprecedented function and comfort have been investigated intensively.[17-26] Here, we introduce a simple alternative that combines colorimetric readout and radio frequency (RF) actuation for precision mapping of thermal characteristics of the skin. The sensors exploit thermochromic liquid crystals (TLC) patterned into large-scale, pixelated arrays on thin elastomeric substrates. Co-integration with electronics provides a means for controlled, local heating by RF signals, to enable not only mapping of temperature but also intrinsic thermal constitutive properties. Uniform layers of TLCs in water-impermeable, non-stretchable thick plastic sheaths, and without electronics, have been explored for skin thermography,[27-29] but without the ability to conform sufficiently well to the curved, textured surface of the skin for accurate, reproducible measurements. Such devices also frustrate transepidermal water loss. They thermally load the skin, and cause irritation at the skin interface, thereby preventing reliable, accurate evaluation or use in continuous modes, over long periods of time. Thermochromic textiles are available for cosmetic and fashion purposes,[30-32] but their inability to maintain intimate contact with the skin and the limited capacity to use known thermochromic dyes for precision temperature evaluation prevent their use in the sorts of applications envisioned here. The devices reported here not only avoid these drawbacks, but they also allow precise measurement of thermal conductivity and thermal diffusivity through analysis of spatio-temporal images obtained during operation of integrated RF components. Conventional digital cameras and RF transmission systems enable simultaneous readout of thousands of pixels at resolutions that exceed those needed to image temperature and thermal property variations on the skin. The epidermal format induces minimal perturbations on the natural mechanical and thermal properties of the skin. Results presented in this example establish the foundational aspects in materials, mechanics and thermal physics for both electronically active and passive epidermal TLC (e-TLC) devices, including algorithms for extracting precision, calibrated data from color digital images. Demonstrations in reactive hyperemia assessments of blood flow, as it relates to cardiovascular health, and hydration analysis, as it relates to skin-care, provide two examples of use in clinically meaningful tests.

The e-TLC thermal imagers use a multilayer design that includes (1) a thin (20 μm) black elastomeric membrane as a mechanical support and an opaque background for accurate colorimetric evaluation of the TLC materials, (2) an array of dots of TLC (i.e. pixels, with 25 μm thicknesses, and diameters of either 250 or 500 μm, spaced by 250 or 500 μm), with an optional interspersed array of dots with fixed colors (with 25 μm thicknesses, diameters of 400 μm, spaced by 600 μm) for calibration, both delivered to the surface of the black elastomer by transfer printing, (3) a thin (30 μm) overcoat of a transparent elastomer for encapsulation and (4) optional electronics in thin, stretchable configurations mounted on the back surface for active functionality described subsequently (details appear in FIG. 34 and Supplementary Note 1). The TLC material consists of microencapsulated chiral nematic liquid crystals. With increasing temperature, the phase varies from crystalline solid to smectic, cholesteric and, finally, isotropic liquid, all over a range of a few degrees, dictated by the chemistry.[17,18] In the cholesteric phase, light that reflects from the TLC pixels spans a narrow wavelength range defined by phase coherent interactions with the liquid crystal assemblies. Increases in temperature decrease the pitch, thereby leading to blue-shifts in the peak wavelengths of this reflected light. This behavior provides the basis for colorimetric optical readout. Other phases have no chiral nematic orientation of molecular planes and thus do not yield any strong wavelength dependence to the reflection. The small sizes and large spacings of the TLC and calibration pixels, taken together with the low modulus, elastic properties of the substrate, encapsulation layer and electronics, yield soft, compliant mechanics in the overall e-TLC system. These properties yield devices that are well suited for mounting on the skin.

FIG. 28*a* shows an e-TLC on the skin of the forearm when twisted and gently poked with a mildly heated rod. Low interfacial stresses that follow from the low effective modulus and small thickness of the device enable adequate adhesion through van der Waals interactions alone. The collapse of a free-standing device under its own weight, as in the right frame, provides qualitative evidence of these mechanical characteristics. FIG. 28*b* shows a pair of magnified images of e-TLC devices; those on the bottom include interspersed color calibration pixels consisting of red, green and blue dye in a non-toxic acrylic base (aqueous dispersion of organic pigment and acrylic polymer, Createx). A completed device of this latter type placed on the curved surface of the back of the hand appears in FIG. 28*c*. As previously mentioned, the backside of the black elastomer substrate provides a mounting location for stretchable electronics. The image in FIG. 28*d* shows an example of an e-TLC device with a wireless system integrated in this way, for remote delivery of controlled levels of heat. The folded configuration reveals part of the serpentine antenna structure (inset). An illustration of this system, in the form of three dimensional finite element analysis (3D-FEA), appears in FIG. 28*e*. The antenna captures incident RF energy to power a Joule heating element (inset, FIG. 28*e*). The result provides well-defined, localized increases in temperature, as revealed in the pattern of colors in the TLC pixels of FIG. 28*f* and the infrared images of FIG. 28*g*. As described subsequently, the results from measurements under such conditions allow determination of the thermal conductivity and thermal diffusivity of the skin.

A key design goal is to produce e-TLC systems that induce minimal perturbations to the skin, thereby avoiding irritation, enhancing wearability and ensuring accurate measurement capabilities. The mechanical and thermal properties are particularly important in this context. Experimental and theoretical studies of the former reveal low modulus, elastic characteristics over large ranges of strain. FIG. 29*a* shows the stress/strain responses of an e-TLC device under static uniaxial testing. The results agree well with the predictions of 3D-FEA. In particular, the TLC pixels (~221 MPa) and elastomeric substrate (~131 kPa) yield an effective modulus (~152 kPa and 178 kPa from 3D-FEA and experiment, respectively) that is only slightly larger (by 16-35%) than the intrinsic value associated with the bare elastomer, and is comparable to that of the epidermis itself. The TLC pixels experience ultra-low strain (e.g., <2%) even under extreme stretching (e.g., 200%), as shown in FIG. 29*b*. Negligible deformations of the TLC pixels, as observed in experiment and FEA (FIG. 29*b*), allow approximations for simple, but quantitatively accurate, analytical solutions of the mechanics (see Supplementary Note 2 and FIG. 35*a*). The thicknesses, bending stiffnesses, effective moduli and stretchability of these devices are 50 μm, 3.0 nN·m, 178 kPa and beyond 200%, respectively; these characteristics are superior than those of typical, commercially available TLC sheets with corresponding properties of ~125 μm, 570,000 nN·m, 3.3 GPa and ~5% (Hallcrest). The differences are significant, at a qualitative level of importance for deployment on the skin. In particular, the collective mechanical characteristics allow largely unconstrained natural motions of the skin, including wrinkling and stretching even in challenging regions such as the knees and elbows. Addition of calibration pixels reduces the stretchability and increases the modulus (FIG. 35*b*), but retain elastic strain levels (50%) that exceed those that can be tolerated by the epidermis (linear response to tensile strain up to 15%, nonlinear to 30%, and rupture at >30%[35]). Incorporating a wireless electronic heating system further reduces the accessible strain, but with an elastic stretchability of nearly 20%, which is useful for many applications (see FIG. 36).[36,37] Although the characteristics of the antenna change with mechanical deformation, experiments indicate that uniaxial stretching (up to 50%) does not disrupt the overall function or the efficiency of power harvesting (see FIG. 37); bending decreases the efficiency only slightly.

The thermal characteristics of the systems define the thermal load on the skin, as well as the overall time response. For an active e-TLC device, the thermal mass per unit area is ~7.7 mJ·cm$^{-2}$·K$^{-1}$ (Supplementary Note 3). This value corresponds to an equivalent of skin thickness of ~20 μm, i.e. only 25% of the thickness of the epidermis itself.[22] Water vapor permeability tests on e-TLC and Feverscan™ strip devices (Supplementary Note 4 and FIG. 38) have revealed that e-TLC devices provide a minor moisture barrier for operation on skin. Decreasing the thickness of the device increases the water permeation, as expected (see FIG. 38b). Additional increases can be achieved by microstructuring, i.e. introducing arrays of holes or pores. The small thermal mass and high water permeability minimize changes in skin temperature and hydration level induced by the presence of the device. Temperatures measured with an infrared camera on the forearm adjacent to an e-TLC and directly underneath it (FIG. 39a-c) show minimal differences. The effects of the device on skin hydration (FIG. 39d-e) are also small. A mounted 80 μm thick e-TLC on well hydrated skin (~35) leads to a small percentage increase in hydration (7.5%) after 3 hours. For an otherwise identical set of testing conditions, the Feverscan™ strip led to a ~100% increase in hydration. For monitoring of transient processes, the time response of the system is important. With geometries and materials investigated here, the response time for an e-TLC device is dominated by the thickness and thermal properties of the black elastomer substrate. Transient measurements reveal response times of less than ~30 ms (Supplementary Note 5), consistent with estimates developed using analytical models (FIG. 40). The intrinsic switching times for most TLC materials are ~3-10 ms.[39-42]

Reflection mode spectroscopic characterization (Zeiss Axio Observer D1) of the steady-state response of the TLC material to changes in temperature between 32° C.-39° C. show expected behaviors, as in FIG. 30a. With proper calibration, described next, the temperature extracted from the hue and saturation values determined using a typical digital camera (Canon 5D Mark II) with the e-TLC device held at a nominally constant temperature exhibits a standard deviation of ~30 mK over a measurement time of 760 s. This value is comparable to that observed from temperature readings simultaneously determined with an infrared camera (~50 mK) (FIG. 30b). The measurement precision is, then, at least ±50 mK under these experimental conditions. Equivalent temperatures extracted from analysis of color recorded at the calibration pixels (red, green, blue) show fluctuations with similar magnitudes, as summarized in FIG. 30c. These observations suggest that the process of image capture and color analysis enables levels of precision that are comparable to those of infrared cameras, not limited by the physics of the TLC. Detailed calibration plots and information on temperature extraction appear in FIG. 41.

Analysis of hue/saturation/value data obtained from the digital camera represents the simplest and most straightforward analysis approach. Sophisticated algorithms based on computer vision techniques are advantageous, however, not only for color determination but for full pixelated analysis of complete e-TLC devices. FIG. 30d illustrates an example of a process that exploits computer vision code (OpenCV), in which an image of an e-TLC device that consists of a 7×7 pixel array undergoes a set of color extraction and data transformation steps (details in Supplementary Note 6). A Gaussian filter first reduces noise through smoothing to yield a gray scale rendering for use with an adaptive threshold that compensates for illumination non-uniformities. The output is a binary mask containing value "1" at bright areas and "0" elsewhere. A two-step erode/dilate process eliminates small speckles that arise from defects. A full list of contours can be extracted from this "clean" image, in which each contour bounds a single pixel in the array. An enclosing circle function uses the contours as inputs to define the pixel positions, for extraction of color information from the original, unprocessed image. A typical calibration that relates hue and saturation values extracted in this manner to temperature evaluated with an infrared camera appears in FIG. 30e. The biggest advantage of using hue/saturation/value (HSV) color space instead of red/green/blue (RGB) is that the color information is encoded only in two (hue and saturation), rather than three (red, green and blue) channels. These two values are comparatively resilient to changes in lighting levels since that information is stored separately in the value channel. Any possible hue/saturation combination can be represented by a point in polar coordinates where radial coordinate corresponds to saturation and angular one to hue. The positions of the calibration set are marked with the dots painted with the corresponding hue. These points define the temperature calibration surface by means of two dimensional linear fit. The results allow any hue/saturation combination to be assigned to a temperature value, as indicated in the plot using a color gradient.

Scaled use of this process is summarized in FIG. 30f. Here, a full e-TLC device on a portion of the wrist where near-surface veins are located reveals corresponding variations in temperature of the epidermis. The hue values across the e-TLC yield three dimensional temperature contour plots that reflect the blood vessels with high spatial resolution (FIG. 30g). A direct comparison with temperature distributions measured in the same region with an infrared camera (FIG. 30h) exhibits excellent agreement. Plots of the temperature extracted from these two sets of results at the locations indicated by the dashed red lines in FIG. 30g, h appear in FIG. 30i. These results suggest suitability of e-TLC systems for mapping of vascular distributions in applications such as screening for deep venous thrombosis, without the need for costly infrared camera systems.

In such practical situations, the lighting conditions can strongly affect the precision and accuracy of the temperature determination.[43-46] In particular, the hue and saturation depend on the type of light source used for illumination. The color calibration pixels provide a means to compensate for such effects, since their known colors are influenced by the lighting in the same way as the TLC. As a result, it should be possible to develop algorithms that account for shifts in the apparent colors of these calibration pixels and yield a set of numerical compensations that can restore their actual, known colors. Applying the same compensations to the TLC pixels will serve as the basis for a temperature evaluation process that is independent of illumination conditions, within some reasonable range. Effects of three different lightning conditions appear in FIG. 31. Red, green and blue color calibration pixels, interspersed across the entire device, are present in this active e-TLC sample. FIG. 31a presents an image of the device, with circles that indicate the positions of the TLC pixels. A Joule heating element is present in the center region. Fluorescent, light emitting diode (LED) and halogen (FIGS. 31c-e) light sources provide a range of practical examples. The corresponding temperature calibration data appear in FIG. 31b. The circles correspond to the hue/saturation values of TLC pixels recorded at different temperatures to define calibration fits for specific light sources. The stars delineate the effect of illumination on the colors of the calibration pixels. Red, green and blue calibration pixels are located at ~5°, ~100° and ~240°, respectively. Since these colors are known, data from them allow extraction of compensation factors for any given lighting condition. Applying the results to measurements of TLC pixels dramatically reduces the sensitivity of the temperature detection process to lighting source. FIG. 31f presents computed temperatures evaluated along lines that pass through the central region while the Joule element is activated. The results are comparable for all three lighting sources. To demonstrate the importance of proper calibration, FIG. 31g summarizes data that exploit the fluorescent temperature fit for all lighting conditions explored here. Significant discrepancies occur, as might be expected due to the different color temperatures of the halogen and LED sources. The resulting discrepancies in temperature readings are reflected not only in the temperature maxima, but also the temperature profiles, shapes and noise levels, which again emphasize the importance of proper calibration and potential for compensation approaches.

As suggested by the active e-TLC results in FIG. 31, the local Joule heating element enables additional measurement capabilities. In particular, spatial and temporal variations in temperature at locations near this heater can be used, with thermal models, to extract the thermal conductivity and diffusivity of the skin. Increases in temperature of a few ° C. can be sufficient for accurate evaluation. The thermal conductivity (k) can be determined by comparing measured steady state distributions in temperature to axis-symmetric thermal conduction models (see Supplementary Note 7). Calculations based on this model suggest spatial decays in temperature ($T_{sensor-layer}$) that vary as $1/r$ (except the central sensor), which can be written as $$T_{sensor-layer} \approx T_\infty + \frac{Q}{2\pi k r} \quad (1)$$

where r is the distance from the heat source, Q is the heat generated by the Joule heating element, and T is the temperature of surrounding air. An example appears in FIG. 32a, with details in FIG. 42a,b,e. Calibration can be performed through measurements of materials with known properties (FIG. 32b). FIG. 32c indicates excellent correspondence between thermal conductivity of the skin evaluated with an active e-TLC and hydration levels determined with a moisture meter (Delfin MoistureMeterSC) that relies on electrical impedance. The quantitative values of k fall within a range that is consistent with literature values determined by subcutaneous thermocouples and high speed radiometer etc.[31] By simplifying the heating element as a point heat source turning on at time t=0, the transient temperature variation can be analytically solved as (see Supplementary Note 8)

$$T_{Sensor-layer}(t) \approx T_\infty + \frac{Q}{2\pi k r}\mathrm{erfc}\left(\frac{r}{\sqrt{4\alpha t}}\right) \quad (2)$$

where α is the thermal diffusivity of the skin, and erfc (x) is the complementary error function. Therefore, transient temperature data associated with activation or deactivation of the Joule heating element can be used to determine thermal diffusivity, α, as illustrated in FIG. 32d (see FIG. 42a,b,f). As with conductivity, the device can be calibrated using samples with known diffusivity (FIG. 32e). Here, a wireless active e-TLC system serves as the measurement vehicle. The time dependence of the temperature, rather than the absolute values, is sufficient for extraction of diffusivity. The device operates at frequencies of ~2 GHz with maximum power inputs of ~2.5 W/kg for the subject of the studies described here (i.e. one third of the power limit recommended by the Federal Communications Commission's guidelines). The values also correspond closely to the hydration level, as shown in FIG. 32f. As with k, the values of α are consistent with literature reports based on techniques such as opto-thermal measurement.[48] The values of k and α can be combined to yield the product of the density (ρ) and heat capacity (c) of skin, based on the relation (cρ=k/α). The calculations (See FIG. 42g) show that the heat capacity increases slightly with the increase of hydration level (assuming that ρ is approximately constant), which is consistent with expectation since the heat capacity (~4.2 J/g/K) of water is larger than the human tissue (e.g., ~3.7 J/g/K for dermis, ~2.3 J/g/K for fat).[49]

Spatio-temporal mapping even with passive e-TLC systems yields useful information on blood circulation,[50,51] maximal percentage increase in blood flow rate after occlusion,[52] and duration of reactive hyperaemia.[53] Measurements of temperature fluctuations above the ulnar artery and adjacent veins serve as an important part of a reactive hyperaemia protocol. Here, the flow of blood is temporarily occluded by a pressure cuff on the upper arm, followed by abrupt release. FIGS. 33A and 33B summarize results of measurements performed with an e-TLC device and an infrared camera. FIG. 33C presents representative frames of temperature distributions captured at 20 s intervals throughout the experiment. Occlusion, which begins at t=0 s, causes the temperature of the skin above the ulnar artery and adjacent areas to decrease drastically owing to lack of incoming blood flow and loss of heat to the environment. The minimum temperature is achieved at t=160 s; at this time, the occlusion is released and blood flow resumes. Sharp temperature increases occur in areas above the blood vessels, as shown in FIG. 33C, until the temperature stabilizes. The responses of pixels across the array of the e-TLC vary widely depending on their distance from the blood vessels. The maximum temperature fluctuations are ~1.2° C. and occur immediately above the ulnar artery; the minimum temperature fluctuations are ~0.4° C. and occur at locations away from near-surface blood vessels. Direct comparisons of spatio-temporal variations in temperature obtained from the e-TLC show quantitative agreement with results from an infrared camera (FIG. 43). FIGS. 33D and 33E highlight temperature variations along horizontal and vertical lines illustrated in the right image of FIG. 33A. A thermal model of the human wrist (Supplementary Note 9 and FIG. 44) that accounts for both the time-dynamic effect of occlusion and the thermal diffusion from the ulnar artery can capture the effects revealed in the measurements (FIG. 33F, 33G) and enable extraction of additional physiological information. The temporal variation of blood flow can be described with a piecewise, exponential type function,[54,55] corresponding to the three stages of the process: pre-occlusion, vascular occlusion, and reperfusion. The parameters characterizing this piecewise function can be determined by minimizing the average differences between the temperature-time profiles predicted by the model and those measured by the e-TLC device, during each stage. FIG. 33G shows that the calculated temperature history based on the thermal model agrees with experiment at all six of the pixels near the artery (i.e., distance <6 mm). Due to simplifying assumptions in the models, the FEA does not quantitatively capture the overshoot behavior observed in the two nearest sensors. Discrepancies at the two most distant sensors can be attributed to the neglect of heating associated with a nearby vein (~13 mm from the artery) in the model. For vessel diameters and depths that lie within reported ranges (Supplementary Note 9), the peak blood flow velocity after occlusion is calculated to be 58.8 cm/s, representing a three-fold increase over the baseline of 19.6 cm/s, with reactive hyperemia duration of 144 s. These values match those reported in the literature for a person with low cardiovascular risk.[52,53]

In conclusion, epidermal photonic systems, as embodied by the e-TLC devices introduced here, offer strong potential for characterization of the skin and, by extension, important parameters relevant in determining cardiovascular health and physiological status. These same capabilities can be useful in wound treatment and monitoring during a healing process, cancer screening, core body temperature assessments and others of clinical relevance. In all cases, the ability to wear the devices continuously, over days or weeks, and to perform readout and power delivery via a conventional smartphone, represent uniquely enabling features. Photonic operation in the red and near infrared could enable use in near-surface implantable diagnostics.

Methods

Fabrication of e-TLC Thermal Imaging Devices.

The fabrication (details in FIG. 34) began with spin-coating and curing a thin (20 μm) layer of poly(dimethylsiloxane) (PDMS, Sylgard 184, 40:1 mixing ratio) mixed with Iron Oxide Pigment Black 11 (The Earth Pigments Company, LLC) on a substrate of poly(ethyleneterephthalate) (PET). A PDMS stamp with arrays of square posts (each post, 0.5 mm×0.5 mm over an area of 15 cm$^2$; see Supplementary Note 1a) was contacted against a layer of microencapsulated thermochromic liquid crystals (Hallcrest SSN33R5 W). Removing the stamp and drying it in air resulted in the formation of a solid layer of e-TLC material with an average thickness of 25 μm on the raised regions. A thermal release tape (Nitto Denko REVALPHA 90° C.) facilitated transfer of this material from the stamp to the surface of the black PDMS film. The device was completed by spin-coating and curing a thin (30 μm) layer of transparent PDMS on top of the structure, as an encapsulant. Fabrication of the wireless heater for the active e-TLC devices began with spin-coating of a thin film of polyimide (Sigma Aldrich) on a sacrificial layer of poly(methylmethacrylate) (PMMA; 100 nm, MicroChem) on a silicon wafer. Metal-evaporation (Cr/Au, 5 nm/50 nm), photolithography and wet-etching defined the serpentine structure for the Joule heater. Additional polyimide spin-coating, oxygen reactive ion etching and metal deposition for contacts, interconnects, and antenna circuits completed the wireless system. Dissolving the PMMA and then physically transferring the electronic structure to the back side of the e-TLC device completed the fabrication.

Device Calibration and Test for Noise Level.

An e-TLC device was placed on a metal plate with black matt finish on a hotplate. Two white fluorescent light sources were placed on opposite sides of the device for illumination in a manner that avoided specular reflection. A digital camera (Canon Mark II 5D) and an infrared camera (FLIR ExaminIR) placed side-by-side were focused on the same area of the device at a distance of ~30 cm. The angle between the cameras and each of the light sources was ~90 degrees. The device was heated to 40° C. on the hotplate and then the hotplate was turned off. During the cooling process, high resolution images were collected every 10 seconds with the digital camera; the infrared camera captured frames at a rate of 12.5 s$^{-1}$. The process of cooling from 40° C. to 32° C. lasted about 20 minutes. The color information of the TLC was extracted from 33° C. to 39° C. with steps of 0.5° C. The set of algorithms developed to accomplish this task are based on computer vision OpenCV (opencv.org) library. The main functions are (in alphabetical order) "adaptiveThreshold", "cvtColor", "dilate", "drawContours", "erode", "findContours", "Gaussian Blur", "getStructuring Element", "imread", "inRange", "matchShapes", "minEnclosingCircle", "threshold". In HSV color space, the light intensity information is stored in the "value" channel and is completely separated from the color information which is encoded in the "hue" and the "saturation" channels. Hue and saturation are, therefore, a natural basis for temperature calibration since they are not strongly affected by the change in illumination intensity. Temperature calibration was constructed by means of two dimensional linear fit. The core function used in the process is "lstsq" from linear algebra module of Numerical Python (www.numpy.org). Any combination of hue/saturation values can be assigned to a temperature value. Even for materials that are not temperature sensitive like the calibration color pixels, their hue/saturation can be treated as a specific temperature for consistency of analysis. To test the noise level and precision of the system, the hotplate temperature was set at a fixed value; temporal fluctuations of TLC color, calibration dot color and infrared emission were recorded using the two cameras over a period of 15 minutes. The color changes were converted to temperature fluctuation and compared to infrared fluctuation directly.

Reactive Hyperaemia Test.

A volunteer (female, 27 years old) reclined in a chair with her left forearm secured gently to an arm rest using Velcro strips to reduce movement. A pressure cuff was secured around the subject's left bicep. An e-TLC device was placed on the skin of the left wrist approximately above the ulnar artery. Applying puffs of compressed air ensured full, conformal contact. Infrared and digital cameras placed 30 cm above the subject's left wrist were focused on the location of the device while illuminated with white fluorescent lights. The subject was instructed to relax for 5 minutes. The cuff was inflated to a pressure of 250 mm Hg for 160 seconds. Continuous high resolution color images and infrared temperature measurements were then collected with the two cameras as the occlusion started and was then released. The total duration of the measurement period was 300 seconds.

Thermal Conductivity/Diffusivity and Hydration Measurements.

Thermal conductivity was determined by analyzing the spatial distribution of temperature for a few seconds immediately after activation of a Joule heater in an active e-TLC device. To validate the computational models, an active e-TLC device was floated on the surface of a mixture of ethylene glycol/water preheated to ~33° C. A constant voltage supplied to the e-TLC Joule heating element created a steady state temperature rise of a few degrees at the location of the heater. Images were then collected with a digital and infrared camera set up above the device with only white fluorescent light sources. The spatial decay of temperature in the e-TLC was recorded by analysis of images from the infrared camera and from color images of the device. The same experiment was performed on a volunteer's forearm skin. Here, different hydration levels were achieved by applying various amounts of lotion to the measurement location, prior to application of the active e-TLC device. Immediately after image capture, the e-TLC device was removed and a hydration meter was used to determine the actual moisture level (averaged from 5 readings). Measurements of thermal diffusivity used a wireless, active e-TLC, with a transmission antenna located ~10 cm away and adjusted to achieve a peak change in temperature of a few degrees (RF power below 2.5 W/kg at frequencies between 1.95-2.35 GHz, tuned to match the response of the receiver antenna on the e-TLC). Both digital and infrared cameras were focused on the device with a distance of 30 cm. Videos with 60 second duration recorded the changes in temperature associated with activation and de-activation of the heater. The experiment was validated using the ethylene glycol/water system, and then repeated on skin with different hydration levels, in procedures otherwise similar to those for the thermal conductivity measurements.

REFERENCES

1 Arora, N. et al. Effectiveness of a noninvasive digital infrared thermal imaging system in the detection of breast cancer. *Am. J. Surg.* 196, 523-526, (2008).

2 Kennedy, D. A., Lee, T. & Seely, D. A Comparative Review of Thermography as a Breast Cancer Screening Technique. *Integr. Cancer Ther.* 8, 9-16, (2009).

3 Kerr, J. Review of the effectiveness of infrared thermal imaging (thermography) for population screening and diagnostic testing of breast cancer. *NZHTA Tech Brief Series* 3 (2004).

4 Pochaczevsky, R., Pillari, G. & Feldman, F. Liquid crystal contact thermography of deep venous thrombosis. *Am. J. Roentgenol.* 138, 717-723 (1982).

5 Thomas, E. A., Cobby, M. J. D., Davies, E. R., Jeans, W. D. & Whicher, J. T. Liquid-crystal thermography and c-reactive protein in the detection of deep venous thrombosis. *Bri. Med. J.* 299, 951-952 (1989).

6 Cameron, E. W., Sachdev, D., Gishen, P. & Martin, J. F. Liquid-crystal thermography as a screening-test for deep-vein thrombosis in patients with cerebral infarction. *Eur. J. Clin. Invest.* 21, 548-550 (1991).

7 Kohler, A., Hoffmann, R., Platz, A. & Bino, M. Diagnostic value of duplex ultrasound and liquid crystal contact thermography in preclinical detection of deep vein thrombosis after proximal femur fractures. *Arch. Orthop. Trauma Surg.* 117, 39-42 (1998).

8 Davison, T. W. et al. Detection of breast-cancer by liquid-crystal thermography-preliminary report. *Cancer* 29, 1123 (1972).

9 Pochaczevsky, R. & Meyers, Vacuum contoured, liquid-crystal, dynamic breast thermoangiography as an aid to mammography in the detection of breast-cancer. *Clin. Radiol.* 30, 405-411 (1979).

10 Bakan, J. A. & Schaab, C. K. Liquid-crystal microcapsule medical device used for thermographic examination of the human female breast. *Appl. Biochem. and Biotech.* 10, 289-299 (1984).

11 Pochaczevsky, R. The value of liquid-crystal thermography in the diagnosis of spinal root compression syndromes. *Orthop. Clin. N. Am.* 14, 271-288 (1983).

12 Pochaczevsky, R., Wexler, C. E., Meyers, P. H., Epstein, J. A. & Marc, J. A. Liquid-crystal thermography of the spine and extremities—its value in the diagnosis of spinal root syndromes. *J. Neurosurg.* 56, 386-395 (1982).

13 Newman, R. I., Seres, J. L. & Miller, E. B. Liquid-crystal thermography in the evaluation of chronic back pain—a comparative-study, *Pain* 20, 293-305 (1984).

14 Klosowicz, S. J., Jung, A. & Zuber, J. Liquid-crystal thermography and thermovision in medical applications. Pulmonological diagnostics in *P. Soc Photo-Opt. Ins.* 4535, 24-29 (2001).

15 Kim, D. H. et al. Epidermal Electronics. *Science* 333, 838-843 (2011).

16 Webb, R. C. et al. Ultrathin conformal devices for precise and continuous thermal characterization of human skin. *Nat. Mater.* 12, 938, (2013).

17 Sekitani, T. et al. A rubberlike stretchable active matrix using elastic conductors. *Science* 321, 1468 (2008).

18 Sekitani, T. et al. Organic nonvolatile memory transistors for flexible sensor arrays. *Science* 326, 1516 (2009).

19 Mannsfeld, S. C. B. et al. Highly sensitive flexible pressure sensors with microstructured rubber dielectric layers. *Nat. Mater.* 9, 859-864 (2010).

20 Kim, D. H. et al. Epidermal Electronics. *Science* 333, 838-843 (2011).

21 Tee, B. et al. An electrically and mechanically self-healing composite with pressure- and flexion-sensitive properties for electronic skin applications. *Nat. Nanotechnol.* 7, 825-832 (2012).

22 Kaltenbrunner, M. et al. An ultra-lightweight design for imperceptible plastic electronics. *Nature* 499, 458 (2013).

23 Schwartz, G. et al. Flexible polymer transistors with high pressure sensitivity for application in electronic skin and health monitoring. *Nat. Commun.* 4, 1859 (2013).

24 Wang, C. et al. User-interactive electronic-skin for instantaneous pressure visualization. *Nat. Mater.* 12, 899-904 (2013).

25 Xu, S. et al. Soft Microfluidic Assemblies of Sensors, Circuits, and Radios for the Skin. *Science* 344, 70-74 (2014).

26 Son, D. et al. Multifunctional wearable devices for diagnosis and therapy of movement disorders. *Nat. Nanotechnol.* 9, 397-404 (2014).

27 Brull, S. J. et al. Comparison of crystalline skin temperature to esophageal temperatures during anesthesia. *Anesthesiology*, 73(3A), A472 (1990).

28 Ikeda, T. et al. Influence of thermoregulatory vasomotion and ambient temperature variation on the accuracy of core-temperature estimates by cutaneous liquid crystal thermometers. *Anesthesiology*, 86, 603 (1997).

29 Wisniewski, C. M. A comparison of esophageal temperature readings and liquid crystal temperature readings in the pediatric population. *CRNA Masters Thesis*. (1991).

30 Aitken, D. et al. Textile applications of thermochromic systems. *Rev. Prog. Coloration* 26, 1-8 (1996).

31 Chowdhury, M. A. et al. Application of thermochromic colorants on textiles: temperature dependence of colorimetric properties. *Color. Technol.* 129, 232-237 (2012).

32 Chowdhury, M. A. et al. Photochromic and thermochromic colorants in textile applications. *J. Eng. Fiber. Fabr.* 9, 107-123 (2014)

33 Dolphin, D., Muljiani, Z., Cheng, J. & Meyer, R. B. Low-temperature chiral nematic liquid-crystals derived from beta-methylbutylaniline. *J. Chem. Phys.* 58, 413-419 (1973).

34 Sage, I. Thermochromic liquid crystals. *Liquid Crystals* 38, 1551-1561 (2011).

35 Arumugam, V., Naresh, M. D. & Sanjeevi, R. Effect of strain-rate on the fracture-behavior of skin. Journal of Biosciences. *J. Biosciences* 19, 307-313 (1994).

36 Davis, J. R. *ASM Specialty Handbook: Copper and Copper Alloys*. (ASM International, 2001).

37 William, F. R., Leroy, D. S. & Don, H. M. *Mechanics of Materials*. (Jon Wiley & Sons, 1999).

38 Sandby-Moller, J., Poulsen, T. & Wulf, H. C. Epidermal thickness at different body sites: Relationship to age, gender, pigmentation, blood content, skin type and smoking habits. *Acta. Derm-Venereol.* 83, 410-413 (2003).

39 Kakade, V. U., Lock, G. D., Wilson, M., Owen, J. M. & Mayhew, J. E. Accurate heat transfer measurements using thermochromic liquid crystal. Part 1: Calibration and characteristics of crystals. *Int. J. of Heat. Fluid Fl.* 30, 939-949 (2009).

40 Stasiek, J. A. & Kowalewski, T. A. Thermochromic liquid crystals applied for heat transfer research. *Opto-Electron. Rev.* 10, 1-10 (2002).

41 Rao, Y. & Zang, S. Calibrations and the measurement uncertainty of wide-band liquid crystal thermography. *Meas. Sci. Technol.* 21 (2010).

42 Ireland, P. T. & Jones, T. V. The response-time of a surface thermometer employing encapsulated thermochromic liquid-crystals. *J. Phys. E. Sci. Instrum.* 20, 1195-1199 (1987).

43 Farina, D. J., Hacker, J. M., Moffat, R. J. & Eaton, J. K. Illuminant invariant calibration of thermochromic liquid-crystals. *Exp. Therm. Fluid. Sci.* 9, 1-12 (1994).

44 Anderson, M. R. & Baughn, J. W. Liquid-crystal thermography: Illumination spectral effects. Part 1—Experiments. *J. Heat. Trans-T. Asme* 127, 581-587 (2005).

45 Sabatino, D. R., Praisner, T. J. & Smith, C. R. A high-accuracy calibration technique for thermochromic liquid crystal temperature measurements. *Exp. Fluids.* 28, 497-505 (2000).

46 Kodzwa, P. M., Jr. & Eaton, J. K. Angular effects on thermochromic liquid crystal thermography. *Exp. Fluids.* 43, 929-937 (2007).

47 Cohen, M. L. Measurement of thermal-properties of human-skin-review. *J. Invest Dermatol.* 69, 333-338, (1977).

48 Xiao, P., Cui, Y., Ciortea, L. I., Berg, E. P. & Imhof, R. E. *J. Phys. Conf. Ser.* 214, 012027, (2010).

49 Fiala, D., Lomas, K. J. & Stohrer, M. A computer model of human thermoregulation for a wide range of environmental conditions: the passive system. *J. Appl. Physiol.* 87, 1957-1972 (1999).

50 Holowatz, L. A., Thompson-Torgerson, C. S. & Kenney, W. L. The human cutaneous circulation as a model of generalized microvascular function. *J. App. Physiol.* 105, 370-372 (2008).

51 Gorbach, A. M. et al. Infrared imaging of nitric oxide-mediated blood flow in human sickle cell disease. *Microvasc. Res.* 84, 262-269 (2012).

52 Huang, A. L. et al. Predictive value of reactive hyperemia for cardiovascular events in patients with peripheral arterial disease undergoing vascular surgery. *Arterioscl. Throm. Vasc.* 27, 2113-2119 (2007).

53 Ishibashi, Y. et al. Short duration of reactive hyperemia in the forearm of subjects with multiple cardiovascular risk factors. *Circ. J.* 70, 115-123 (2006).

54 Akhtar, M. W., Kleis, S. J., Metcalfe, R. W. & Naghavi, M. Sensitivity of Digital Thermal Monitoring Parameters to Reactive Hyperemia. *J. Biomech. Eng-T. Asme.* 132 (2010).

55 Deshpande, C. *Thermal analysis of vascular reactivity MS thesis*, Texas A&M University (2007).

Supplementary Information: Epidermal Photonic Devices for Assessing Temperature and Thermal Transport Characteristics of the Skin Supplementary Note 1a: Fabrication Procedure for PDMS Post Stamp Used for Inking Liquid Crystal 1. Clean a 3" Si wafer (Acetone, IPA→Dry 5 min at 110° C.).
2. Spin coat SU8 50 (microchem, 1,000 rpm for 30 s, anneal 65° C. 10 min 95° C. 30 min)
3. Pattern SU8 with 365 nm optical lithography through iron oxide mask (Karl Suss MJB3) develop in SU8 developer
4. post exposure bake at 65° C. 1 min 95° C. 10 min
5. STS ICP RIE silicon etch SF6 20 s at 20 w CF4 10 s at 0 w for 250 cycles to achieve a hole depth of around 400 um
6. Mold the silicon template with PDMS Supplementary Note 1b: Fabrication Procedure for a Single Heater with Wired and Wireless Design Prepare Polymer Base Layers 1. Clean a 3" Si wafer (Acetone, IPA→Dry 5 min at 110° C.).
2. Spin coat with PMMA (poly(methyl methacrylate), spun at 3,000 rpm for 30 s).
3. Anneal at 180° C. for 10 min.
4. Spin coat with polyimide (PI, poly(pyromellitic dianhydride-co-4,4'-oxydianiline), amic acid solution, Sigma-Aldrich, spun at 4,000 rpm for 30 s for wired design and 1,000 rpm for 30 s for wireless design).
5. Anneal at 110° C. for 30 s.
6. Anneal at 150° C. for 5 min.
7. Anneal at 250° C. under vacuum for 1 hr.

Deposit First Metallization

8. E-beam 5/50 nm Cr/Au.
9. Pattern photoresist (PR; Clariant AZ5214, 3000 rpm, 30 s) with 365 nm optical lithography through iron oxide mask (Karl Suss MJB3).

Develop in Aqueous Base Developer (MIF 327)

10. Etch Au with TFA Au etchant (Transene).
11. Etch Cr with CR-7 Cr Mask Etchant (Cyantek).
12. Remove PR w/Acetone, IPA rinse.
13. Dry 5 min at 150° C.

Isolate First Metallization and Pattern Via Holes

14. Spin coat with PI.
15. Anneal at 110° C. for 30 s.
16. Anneal at 150° C. for 5 min.
17. Anneal at 250° C. under vacuum for 1 hr.
18. Pattern photoresist (PR; Clariant AZ4620, 3000 rpm, 30 s) with 365 nm optical lithography through iron oxide mask (Karl Suss MJB3). Develop in aqueous base developer (AZ 400K, diluted 3:1).
19. Reactive ion etch (RIE; March CS-1701, 50 mTorr, 20 sccm $O_2$, 150 W, 35 min).

Deposit Second Metallization

20. E-beam 5/500 nm Cr/Au for wired design or 5/1600 nm Cr/Cu for wireless design.
21. Pattern PR AZ5214.
22. Etch Au with TFA Au etchant or etch Cu with TFA Cu etchant.cs
23. Etch Cr with Cr Mask Etchant.
24. Remove PR w/Acetone, IPA rinse.
25. Dry 5 min at 150° C.

Isolate Entire Device

26. Spin coat with PI.
27. Anneal at 110° C. for 30 s.
28. Anneal at 150° C. for 5 min.
30. Pattern PR AZ4620.

31. RIE (50 mTorr, 20 sccm O$_2$, 150 W, 35 min for wired design and 120 min for wireless design).

Release and Transfer

32. Release w/boiling Acetone.
33. Transfer to water soluble tape.
34. E-beam 3/30 nm Ti/SiO$_2$.
35. Transfer to back of e-TLC device.
36. Bond thin, flexible cable (Elform, HST-9805-210) using hot iron with firm pressure for wired heater Supplementary Note 2: Analytic Solution of Spacing of e-TLC Dots During Uniaxial Stretching The deformation of an e-TLC device under uniaxial stretching (along horizontal direction) is analyzed to determine the change of spacing between pixels associated with the applied strain ($\in$). The e-TLC material (~221 MPa) is much stiffer than the elastomeric substrate (~131 kPa), and therefore undergoes negligible deformation, as evidenced by the experiment images of FEA results in FIG. 29b. The stretching deformation is, as a result, mainly accommodated by the soft substrate material. For pixels (in diameter of $d_{TLC}$) with an initial spacing $\Delta_0$, the horizontal spacing ($\Delta_{horizontal}$) after deformation is given by $$\Delta_{horizontal} = \Delta_0 + (\Delta_0 + d_{TLC})\in. \quad (S1)$$

The vertical spacing ($\Delta_{vertical}$) decreases due to the Poisson effect. For sparsely distributed pixels (e.g., $d_{TLC} < \Delta_0$), the mechanical constrains associated with the e-TLC on the transverse compression can be neglected, such that the vertical spacing ($\Delta_{vertical}$) after deformation can be approximated as $$\Delta_{vertical} = \frac{\Delta_0 + d_{TLC}}{\sqrt{1+\varepsilon}} - d_{TLC}. \quad (S2)$$

Note that the transversely compressive strain of the soft substrate, due to stretching ($\in$), is given by $\in_{compression} = 1-(1+\in)^{-1/2}$, since it is nearly incompressible (i.e., Poisson ratio $v=0.5$). For $\Delta_0=0.3$ mm, $d_{TLC}=0.2$ mm, as adopted in experiments, the analytic results in FIG. 35a, based on Eqs. (S1) and (S2), agree well with the experiment and FEA results.

Supplementary Note 3: Thermal Mass Calculation of e-TLC Device

The thermal mass of the devices are determined for 20 μm silicone and black iron oxide substrate and 30 μm transparent silicone substrate. The devices have an overall aerial coverage of ~15 cm$^2$. The calculated thermal masses that follow are given as thermal mass per unit area of skin. The device construction for the TCR device contains approximately 8.7 ng·cm$^{-2}$ of Au, 56 μg·cm$^{-2}$ of PI, 55.8 μg·cm$^{-2}$ of Cu, 0.64 mg·cm$^{-2}$ of black iron oxide powder, 4.18 mg·cm$^{-2}$ of silicone substrate, ~0.61 mg·cm$^{-2}$ of liquid crystal materials (Hallcrest, density 0.97 g·cm$^{-3}$). The material contributions to aerial thermal mass are: 21.48 μJ·cm$^{-2}$·K$^{-1}$ from Cu, 64.4 μJ·cm$^{-2}$·K$^{-1}$ from PI, 0.42 mJ·cm$^{-2}$·K$^{-1}$ from black iron oxide, ~1.09 mJ·cm$^{-2}$·K$^{-1}$ from liquid crystal (Hallcrest, specific heat 1.8 J·g$^{-1}$·K$^{-1}$), 6.11 mJ·cm$^{-2}$·K$^{-1}$ from the silicone backing (calculate values) and negligible from Au. This results in overall device aerial thermal masses of ~7.7 mJ·cm$^{-2}$·K$^{-1}$. The thermal mass of skin depends on the water content where thermal mass increases with skin hydration and water content[2]. For hydrated skin, the heat capacity is approximately 3.7 J·cm$^{-3}$·K$^{-1}$, and the device aerial thermal mass of 7.7 mJ·cm$^{-2}$·K$^{-1}$ is equivalent to the aerial thermal mass of skin with a thickness of 20.8 μm.

Supplementary Note 4: Water Vapor Permeability Test

Water permeability tests followed the ASTM E96-95 standard, and involved evaluation of e-TLC devices (thicknesses of 80 μm, 50 μm and 30 μm) and a commercial Feverscan™ device (LCR Hallcrest; polyester covering film ~75 μm, liquid crystal layer ~10-50 μm, black backing layer ~10-20 μm and graphic print layer ~10-20 μm). The experiments involved sealing the tops of identical jars, each containing a fixed amount of desiccant (97% anhydrous calcium sulfate and 3% cobalt chloride), with the devices under test. Control samples consist of jars without any seal on top. Diffusion of water vapor through the devices from the surrounding ambient air causes increases in weight, due to uptake by the desiccant. All jars were placed in a room that has consistent temperature (~22° C.) and humidity (~50%). The weight gain of each jar was recorded at the same time of day on a balance that has precision of 0.1 mg. By this test, after a 4-day period, the weight of the jar sealed by the Feverscan™ remains unchanged, consistent with negligible water permeation. By contrast, weight of the jar with the 80 μm e-TLC device increases by an amount that is nearly half (41%) of that compared to the control. The 50 μm and 30 μm e-TLC devices exhibit weight increases that are greater than half of the control, i.e. 60% and 62%, respectively. These results indicate that our formulation of PDMS, at the thicknesses used in our devices, provide only minor barriers to moisture, particularly when compared to conventional analogs.

Supplementary Note 5: Sensor Response Time

The TLC dot array is embedded in between two PDMS layers. The thickness and thermal properties of the black PDMS substrate and the TLC layer will both determine the heat transfer rate from the skin to the top of TLC layer. The effect from the top encapsulation elastomer is neglected to simplify the model.

A warm ethylene glycol bath heats up the entire device from the backside of black PDMS substrate. The in-plane dimensions of the elastomer layer are much larger than its thickness such that the heat flux is mainly along the thickness direction, which can be represented by a one-dimensional heat transfer model described elsewhere.[1]

The sensor response time is defined by the time at which the sensor temperature increase $T_{sensor}$ reaches 90% of $T_0$. For 30 μm black PDMS and 25 μm TLC layer as used in the experiment, the response time is predicted to be ~30 ms. These agree reasonably well with the experimentally measured sensor response time (for $T_{sensor}=0.9T_0$) of 33 ms.

Supplementary Note 6: Color and Temperature Extraction Process

The only parts of TLS sensor that are temperature sensitive are the liquid crystal dots. Finding them in the image and separating from black elastomer background is a necessary first stage in the temperature extraction process. This is a typical computer vision problem (OpenCV, opencv.org). The essential steps of the process are illustrated in FIG. 30a. The first frame shows the original picture of a 7×7 area of the sensor array. Second is the output of a Gaussian filter which reduces noise through image smoothing. Gray scale (third frame) format is a required input for adaptive threshold (fourth frame). Adaptive threshold is the robust algorithm that is aware of the illumination non-uniformity at different parts of the image. The output is the binary mask containing value "1" at bright areas and "0" elsewhere. Small speckles from the defects are visible here as well. They are removed with the two step erode/dilate process. Erode (fifth frame) shrinks the white areas in frame four by removing a few pixels at the border. Due to the small size of the defects they vanish completely. The dilate step (sixth frame) expands the white regions back restoring area of interest by adding the same amount of pixels removed in the previous step. List of contours can be extracted from this "clean" image (seventh frame). Every contour is enclosing a single temperature sensitive dot. The shape of the dot is closely reminiscent of a circle. The obvious choice for dot position detection is the OpenCV's "enclosing circle" function which takes a contour as an input. Last frame is the superposition of the original image and the set of corresponding positions (red dots) and enclosing circles (cyan rings).

Typical output of the digital camera is red-green-blue (RGB) color map. Intensities of all colors are affected by illumination conditions during the experiment. Converting to hue-saturation-value (HSV) color space makes the analysis more resilient to the change in lighting due to the fact that intensity now is encoded in value channel and color is in hue and saturation channels. In order to track the color change only hue and saturation are of interest. FIG. 30b shows the calibration used to convert the colors into temperature. The dots plotted are positioned at corresponding hue/saturation values and painted with their hue value. Background is the temperature evaluated from them with two dimensional linear fit.

Supplementary Note 7: Steady-State Thermal Conduction Model for Prediction of Thermal Conductivity A Cartesian coordinate system is set such that the origin is located at the center of the top surface of PDMS, as shown in FIGS. 41a and 41b, where the schematic illustrations of the device geometry, from both the 3D and cross-sectional views, are presented. FEA indicates that the ultrathin e-TLC dots (~20 μm) have negligible effects on the temperature distributions, and thus are not considered in the analytic model. The skin layer (homogenized from real skin and the underlying tissues, with the thickness >2 mm) are usually much thicker than the PDMS layer (with a thickness of ~60 μm), such that it can be considered as infinitely thick. The steady-state heat conduction equation is $\partial^2 T/\partial x^2 + \partial^2 T/\partial_y^2 + \partial^2 T/\partial_z^2 = 0$ for both the PDMS and skin, where T is the temperature. The square shaped resistor ($a_{Resistor} \times b_{Resistor}$) serves as the heat source, with the heat generation Q that pumps into the PDMS and skin. This can be modeled as a surface heat flux ($q_0 = Q/(a_{Resistor} b_{Resistor})$) for the bilayer system, i.e., $$q_0 = q_{zPDMS}|_{z=-H_{PDMS}} - q_{zSkin}|_{z=-H_{PDMS}}$$

for the region occupied by heat source. The free, top surface of the PDMS has natural convection with the surrounding air ($T_\infty$), i.e., $q_{zPDMS}|_{z=0} = h(T - T_\infty)$, with h denoting the heat transfer coefficient. The continuity conditions include $[T]=0$ and $[q_z]=0$ across the PDMS/skin interface, where $[\ ]=0$ stands for the jump across the interface. By adopting the approach of double Fourier transform, the temperature at the sensor plane ($z = -H_{sensor}$) is obtained as $$T_{Sensor\text{-}layer} = T_\infty + \frac{4q_0}{\pi^2 k_{PDMS}} \cdot \int_0^\infty \cos(\omega x) d\omega \quad \text{(S3)}$$

-continued $$\int_0^\infty \frac{\left(e^{\eta H_{Sensor}} + \frac{k_{PDMS}\eta - h}{k_{PDMS}\eta + h} e^{-\eta H_{Sensor}}\right) \cos(\zeta y) d\zeta}{\omega \zeta \eta \left[\begin{array}{c}\left(1 + \frac{k_{Skin}}{k_{PDMS}}\right) e^{\eta H_{PDMS}} - \\ \frac{k_{PDMS}\eta - h}{k_{PDMS}\eta + h}\left(1 - \frac{k_{Skin}}{k_{PDMS}}\right) e^{-\eta H_{PDMS}}\end{array}\right]} \sin\frac{a_{Resistor}\omega}{2} \sin\frac{b_{Resistor}\zeta}{2},$$

where the subscripts 'PDMS' and 'skin' denote the PDMS and skin, respectively; k is the thermal conductivity. Eq. (S3) corresponds to the temperature solution of the forward thermal conduction problem, given the thermal conductivity of the skin layer. The parameters adopted in experiments include $a_{Resister} = b_{Resister} = 0.5$ mm, $h=5$ W·m$^{-2}$K$^{-1}$, $H_{sensor}=30$ μm, $H_{PDMS}=60$ μm, $k_{PDMS}=0.16$ W·m$^{-1}$K$^{-1}$, and the thermal diffusivity $\alpha_{PDMS}=1.07$ m$^2$·s$^{-1}$. For a representative value of $k_{skin}=0.31$ W·m$^{-1}$K$^{-1}$ and Q=3.8 mW, the distribution of temperature at the sensor plane, as given by Eq. (S3), is shown in FIG. 41c, which agrees reasonably well with FEA results (FIG. 41d). The temperature profile along the x axis (in FIG. 41e) is in quantitative agreement with the FEA results. The relatively large discrepancy at the center region is mainly attributed to the assumption of homogeneous heat generation $q_0$ through the entire heater, adopted for the aim of model simplification. FIG. 41e also shows the temperature gradient is obvious in the region within a distance of ~4 mm from the heater center. For the sensors far from the heater (0.5 by 0.5 mm), the temperature distribution can be approximated by the simple solution of a point heat source, i.e., $$T_{Sensor\text{-}layer} \approx T_\infty + \frac{Q}{2\pi k_{Skin} r}, \quad \text{(S4)}$$

where the ultrathin PDMS layer is neglected, and $r=\sqrt{x^2+y^2}$ is the in-plane distance from the origin. FIG. 41e demonstrates that this approximate solution has very good accuracy for $r \geq a_{Resister}/2$. This simplified solution is adopted to predict the thermal conductivity of skin by fitting the temperature data from the e-TLC device, as shown in FIG. 32a for an example with $T_\infty = 33.9°$ C. and Q=3.83 mW. FIG. 32b demonstrates the prediction of thermal conductivity for the calibration experiment, in which the water/ethylene glycol solutions with different mixing ratios are adopted to mimic real skin in different hydration levels. The thermal conductivities predicted by the current model agree fairly well with those reported in the literature (MEGlobal, Ethylene Glycol Product Guide).

Supplementary Note 8: Transient Thermal Conduction Model for Prediction of Thermal Diffusivity To simplify the analyses for the transient thermal conduction problem, we continue to assume that the heater is a point heat source. Consider that the heater is turned on at time t=0, the induced transient temperature solution is given by $$T_{Sensor\text{-}layer}(t) \approx T_\infty + \frac{Q}{2\pi k_{skin} r} \text{erfc}\left(\frac{r}{\sqrt{4\alpha_{skin} t}}\right), \quad \text{(S5)}$$

where $\alpha_{skin}$ is the thermal diffusivity of the skin, and erfc (x) is the complementary error function. For the representative values of $k_{skin}=0.31$ W·m$^{-1}$K$^{-1}$, $\alpha_{skin}=1.14$ m$^2$·s$^{-1}$, and Q=3.8 mW, the time dynamic temperature given by Eq. (S5) agrees remarkably well with FEA results, as shown in FIG. 41f, for three different points (with a distance of 0.5, 1.0 and 2.0 mm from the origin).

Based on Eq. (S5), we can determine the thermal diffusivity based on the transient temperature data from the e-TLC device, even when the power is unknown (e.g., when the wireless system is adopted to power the heater). FIG. 32d gives an example of temperature profile at the sensor with a distance of 0.5 mm from the heater, where the analytic curve with the thermal diffusivity of $0.43 \times 10^{-7}$ m$^2$/s gives the best match with the experimental data. FIG. 32e demonstrates the predictions of thermal diffusivity for the calibration experiment, which agree reasonably well with those reported in the literature (MEGlobal, Ethylene Glycol Product Guide).

Supplementary Note 9: Mathematical Modeling of Reactive Hyperemia

A two-dimensional (2D), transient, heat transfer model of human wrist was developed, which considers the various tissues surrounding the ulnar artery, and quantitatively characterizes the heat exchange between the blood flow and the surrounding tissues. FIGS. 43a and 43b show the schematic illustration of the tissue geometry, in which a circular cross section is adopted for the wrist to simplify the analyses. The blood at body temperature flows through the circular artery embedded in the fat layer, heating the surrounding tissues. The heat exchange between the blood flow and the fat layer across the artery wall is described with a heat convection model[2], which assumes the exchanged heat flux (q) to be proportional to the blood flow rate, i.e.

$$q = \frac{\rho_b c_{pb} \omega_b(t)}{\pi D_{artery}} (T_{body} - T_s),  \quad (S6)$$

where $\rho_b$, $c_{pb}$, $\omega_b(t)$ are the density, specific heat capacity, and time-dependent flow rate of the blood; $D_{artery}$ is the diameter of the artery; $T_{body}$ and $T_s$ are the body temperature, and the temperature of fat at the artery wall, respectively. Due to the heating of the blood flow, the temperature distributes non-uniformly in these tissues, which is governed by the temporal heat conduction equation of $$\rho_j c_j \frac{\partial T_j}{\partial t} = k_j \left( \frac{\partial^2 T_j}{\partial x^2} + \frac{\partial^2 T_j}{\partial y^2} + \frac{\partial^2 T_j}{\partial z^2} \right) (j = 1 \ldots 4),$$

with the subscript representing different tissues (with skin as j=1, fat as j=2, muscle as j=3, and bone as j=4). The free, outer surface of the skin has natural convection with air, which usually cools down the skin due to a lower room temperature than body temperature. The interior bone layer is assumed to maintain the core-temperature (close to the body temperature $T_{body}$).

The modeling of occlusion involves two steps, starting from the simulation of the steady-state heat conduction in the various tissues due to constant heating of blood flow, corresponding to the stage of pre-occlusion (Stage I). With the steady-state solution as an input, we further simulate the temporal changes in temperature distributions due to the application and release of occlusion, corresponding to the stage of vascular occlusion (Stage II) and reperfusion (Stage III), respectively. Based on previous experimental data, the temporal variation of blood flow during these different stages can be well described by the following piecewise function[2,3]

$$\omega_b^I(t) = \omega_0, \; t \leq t_{occ,st} \quad (S7)$$

$$\omega_b^{II}(t) = (\omega_0 - \omega_s)\exp(-t/\tau_0) + \omega_s, \; t_{occ,st} < t \leq t_{occ,end}$$

$$\omega_b^{III}(t) = \begin{cases} (\omega_{max} - \omega_s)\sin^2\left[\frac{\pi(t - t_{occ,end})}{(2t_{dw})}\right] + \omega_s, & t_{occ,end} < t \leq (t_{occ,end} + t_{dw}) \\ (\omega_{max} - \omega_f)\exp\left[\frac{-(t - t_{occ,end} - t_{dw})}{\tau_h}\right] + \omega_0, & t > (t_{occ,end} + t_{dw}) \end{cases},$$

where $\omega_0$ represents the baseline blood flow; $\omega_s$ is the blood perfusion after the occlusion is applied for a sufficiently long time, 160 s in the case of experiments here; $\omega_{max}$ is the maximum hyperemic blood flow; $\tau_0$ is a time constant depicting the falling speed of blood flow after occlusion is applied; $t_{dw}$ is the time required to reach the maximum hyperemic blood flow after the release of occlusion; $\tau_h$ indicates the rate at which the blood flow returns to the baseline value during the reperfusion; $t_{occ,st}$ and $t_{occ,end}$ denote the starting and ending times of the occlusion, respectively. Except for $t_{occ,st}$ and $t_{occ,end}$, which are known in experiments ($t_{occ,st}=0$ s, $t_{occ,end}=160$ s), there are six parameters in this model of reactive hyperemia which can be varied to simulate the temperature history of blood perfusion. The aim of the thermal analyses is to obtain an optimized set of parameters that can minimize the average difference between the simulations and experiment data of temperature-time profile at those sensors with a distance ≤7 mm from the artery (FIG. 43g). The baseline blood flow $\omega_0$ does not involve the occlusion process, and therefore can be determined using the temperature value measured before the occlusion (Stage I). The blood flow $\omega_s$ and time parameter $\tau_0$ (only related to Stage II) are determined by the measured temperature-time profile during Stage II, and the other three parameters ($\omega_{max}$, $t_{dw}$ and $\tau_h$) are determined by the data during Stage III. In total, there are six parameters in our simulations, i.e., $\omega_0$, $\alpha=\omega_s/\omega_0$, $\beta=\omega_{max}/\omega_0$, $\tau_0$, $t_{dw}$ and $\tau_h$, whose ranges are listed in Table 1, based on reported experiments[2,3].

Finite element analyses (FEA) were adopted to solve the above transient heat transfer equation, and determine the temperature distribution numerically. 4-node linear heat transfer elements were used, and refined meshes were adopted to ensure the accuracy. The boundary conditions include the prescribed temperature (T=$T_{body}$) in the bone layer, the heat convection at the artery wall with blood flow of body temperature (i.e., Eq. (S6)), and the natural convection at the outer surface of skin with air of room temperature (~27.0° C.). The geometric and thermal-physical properties of various tissues are given in Table 2. For the reactive hyperemia model described above, the baseline blood flow rate is determined as $\omega_0=30$ mL/min (19.6 cm/s for a vessel diameter of 1.8 mm), which could minimize the difference between FEA and experiment, i.e., the variance, as shown in FIG. 43c. Based on $\omega_0=30$ mL/min, the calculated temperature decay from the artery at the steady-state indeed agree well with experiment data (FIG. 43d). To minimize the temperature variance during stage II (FIG. 43e), the blood flow $\omega_s$ and time parameter $\tau_0$ are determined as $\omega_s=1.5$ mL/min and $\tau_0=2$ s. Similarly, the other three parameters corresponding to stage III can be obtained as $\omega_{max}$=90 mL/min (58.8 cm/s), $t_{dw}$=15 s and $\tau_h$=35 s. For this set of parameters, the temperature-time profile obtained from FEA agrees reasonably well with the experiment results (FIG. 33g) for all the sensor points close to the artery.

TABLE 1

The parameter range in the model of reactive hyperemia for simulations.

| | $\omega_0$ (mL/min) | $\alpha = \omega_s/\omega_0$ | $\beta = \omega_{max}/\omega_0$ | $T_0$ (s) | $t_{dw}$ (s) | $T_h$ (s) |
|---|---|---|---|---|---|---|
| Range | [10, 45] | [0.05, 0.25] | [3, 10] | [2, 6] | [15, 45] | [35, 75] |

TABLE 2

The geometric and thermal-physical properties of various tissues for the wrist, where t denotes the thickness, D is the diameter of the artery, and d is the depth of the artery.

| Parameter | Skin | Fat | Muscle | Bone | Blood |
|---|---|---|---|---|---|
| $\rho$ (kg/m$^3$) [2, 4] | 1085 | 850 | 1085 | 1357 | 1069 |
| $c_p$ (J/kg/K) [2, 4] | 3680 | 2300 | 3768 | 1700 | 3659 |
| k (W/m/K) [5, 7] | 0.47 | 0.16 | 0.42 | 0.75 | / |
| t (mm) [5-7] | 1.0 | 4.4 | 13.6 | 10.0 | / |
| D (mm) [8] | / | / | / | / | 1.8 |
| d (mm) [9, 10] | / | / | / | / | 2.2 |

REFERENCES

1 Webb, R. C. et al. Ultrathin conformal devices for precise and continuous thermal characterization of human skin. *Nat. Mater.* 12, 938, (2013).

2 Deshpande, C. Thermal analysis of vascular reactivity MS thesis, Texas A&M University, (2007).

3 Akhtar, M. W., Kleis, S. J., Metcalfe, R. W. & Naghavi, M. Sensitivity of digital thermal monitoring parameters to reactive hyperemia. *J. Biomech. Eng-T. Asme.* 132, 051005, (2010)

4 Fiala, D., Lomas, K. J. & Stohrer, M. A computer model of human thermoregulation for a wide range of environmental conditions: The passive system. *J. App. Physiol.* 87, 1957-1972 (1999).

5 Song, W. J., Weinbaum, S., Jiji, L. M. & Lemons, D. A combined macro and microvascular model for whole limb heat transfer. *J. Biomech. Eng-T. Asme.* 110, 259-268 (1988).

6 Sieg, P., Hakim, S. G., Bierwolf, S. & Hermes, D. Subcutaneous fat layer in different donor regions used for harvesting microvascular soft tissue flaps in slender and adipose patients. *Int. J. Oral. Max. Surg.* 32, 544-547 (2003).

7 Shen, H. et al. A genomewide scan for quantitative trait loci underlying areal bone size variation in 451 Caucasian families. *J. Med. Genet.* 43, 873-880 (2006).

8 Shima, H., Ohno, K., Michi, K. I., Egawa, K. & Takiguchi, R. An anatomical study on the forearm vascular system. *J. Cranio. Maxill. Surg.* 24, 293-299 (1996).

9 McCartney, C. J. L., Xu, D., Constantinescu, C., Abbas, S. & Chan, V. W. S. Ultrasound Examination of Peripheral Nerves in the Forearm. *Region. Anesth. Pain. M.* 32, 434-439 (2007).

10 Kathirgamanathan, A., French, J., Foxall, G. L., Hardman, J. G. & Bedforth, N. M. Delineation of distal ulnar nerve anatomy using ultrasound in volunteers to identify an optimum approach for neural blockade. *Eur. J. Anaesth.* 26, 43-46 (2009).

STATEMENTS REGARDING INCORPORATION BY REFERENCE AND VARIATIONS

All references throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods and steps set forth in the present description. As will be obvious to one of skill in the art, methods and devices useful for the present embodiments can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

The following references relate generally to fabrication methods, structures and systems for making electronic devices, and are hereby incorporated by reference to the extent not inconsistent with the disclosure in this application.

| Attorney Docket No. | Application No. | Filing Date | Publication No. | Publication Date | Pat. No. | Issue Date |
|---|---|---|---|---|---|---|
| 145-03 US | 11/001,689 | Dec. 1, 2004 | 2006/0286488 | Dec. 21, 2006 | 7,704,684 | Apr. 27, 2010 |
| 18-04 US | 11/115,954 | Apr. 27, 2005 | 2005/0238967 | Oct. 27, 2005 | 7,195,733 | Mar. 27, 2007 |
| 38-04A US | 11/145,574 | Jun. 2, 2005 | 2009/0294803 | Dec. 3, 2009 | 7,622,367 | Nov. 24, 2009 |
| 38-04B US | 11/145,542 | Jun. 2, 2005 | 2006/0038182 | Feb. 23, 2006 | 7,557,367 | Ju;. 7, 2009 |
| 43-06 US | 11/421,654 | Jun. 1, 2006 | 2007/0032089 | Feb. 8, 2007 | 7,799,699 | Sep. 21, 2010 |
| 38-04C US | 11/423,287 | Jun. 9, 2006 | 2006/0286785 | Dec. 21, 2006 | 7,521,292 | Apr. 21, 2009 |
| 41-06 US | 11/423,192 | Jun. 9, 2006 | 2009/0199960 | Aug. 13, 2009 | 7,943,491 | May 17, 2011 |
| 25-06 US | 11/465,317 | Aug. 17, 2006 | — | — | — | — |
| 137-05 US | 11/675,659 | Feb. 16, 2007 | 2008/0055581 | Mar. 6, 2008 | | |
| 90-06 US | 11/782,799 | Jul. 25, 2007 | 2008/0212102 | Sep. 4, 2008 | 7,705,280 | Apr. 27, 2010 |
| 134-06 US | 11/851,182 | Sep. 6, 2007 | 2008/0157235 | Jul. 3, 2008 | 8,217,381 | Jul. 10, 2012 |
| 151-06 US | 11/585,788 | Sep. 20, 2007 | 2008/0108171 | May 8, 2008 | 7,932,123 | Apr. 26, 2011 |
| 216-06 US | 11/981,380 | Oct. 31, 2007 | 2010/0283069 | Nov. 11, 2010 | 7,972,875 | Jul. 5, 2011 |
| 116-07 US | 12/372,605 | Feb. 17, 2009 | — | — | — | — |
| 213-07 US | 12/398,811 | Mar. 5, 2009 | 2010/0002402 | Jan. 7, 2010 | 8,552,299 | Oct. 8, 2013 |
| 38-04D US | 12/405,475 | Mar. 17, 2009 | 2010/0059863 | Mar. 11, 2010 | 8,198,621 | Jun. 12, 2012 |
| 170-07 US | 12/418,071 | Apr. 3, 2009 | 2010/0052112 | Mar. 4, 2010 | 8,470,701 | Jun. 25, 2013 |
| 216-06A US | 12/522,582 | Jul. 9, 2009 | — | — | — | — |
| 38-04A1 US | 12/564,566 | Sep. 22, 2009 | 2010/0072577 | Mar. 25, 2010 | 7,982,296 | Jul. 19, 2011 |
| 71-07 US | 12/669,287 | Jan. 15, 2010 | 2011/0187798 | Aug. 4, 2011 | — | — |
| 60-09 US | 12/778,588 | May 12, 2010 | 2010/0317132 | Dec. 16, 2010 | — | — |
| 43-06A US | 12/844,492 | Jul. 27, 2010 | 2010/0289124 | Nov. 18, 2010 | 8,039,847 | Oct. 18, 2011 |
| 15-10 US | 12/892,001 | Sep. 28, 2010 | 2011/0230747 | Sep. 22, 2011 | 8,666,471 | Mar. 4, 2014 |
| 19-10 US | 12/916,934 | Nov. 1, 2010 | 2012/0105528 | May. 3, 2012 | 8,562,095 | Oct. 24, 2013 |
| 3-10 US | 12/947,120 | Nov. 16, 2010 | 2011/0170225 | Jul. 14, 2011 | — | — |
| 118-08 US | 12/996,924 | Dec. 8, 2010 | 2011/0147715 | Jun. 23, 2011 | 8,946,683 | Feb. 3, 2015 |
| 126-09 US | 12/968,637 | Dec. 15, 2010 | 2012/0157804 | Jun. 21, 2012 | — | — |
| 50-10 US | 13/046,191 | Mar. 11, 2011 | 2012/0165759 | Jun. 28, 2012 | — | — |
| 151-06A US | 13/071,027 | Mar. 24, 2011 | 2011/0171813 | Jul. 14, 2011 | — | — |
| 137-05A US | 13/095,502 | Apr. 27, 2011 | — | — | — | — |
| 216-06B US | 13/100,774 | May 4, 2011 | 2011/0266561 | Nov. 3, 2011 | 8,722,458 | May 13, 2014 |
| 38-04A2 US | 13/113,504 | May 23, 2011 | 2011/0220890 | Sep. 15, 2011 | 8,440,546 | May 14, 2013 |
| 136-08 US | 13/120,486 | Aug. 4, 2011 | 2011/0277813 | Nov. 17, 2011 | 8,679,888 | Mar. 25, 2014 |
| 151-06B US | 13/228,041 | Sep. 8, 2011 | 2011/0316120 | Dec. 29, 2011 | — | — |
| 43-06B US | 13/270,954 | Oct. 11, 2011 | 2012/0083099 | Apr. 5, 2012 | 8,394,706 | Mar. 12, 2013 |
| 3-11 US | 13/349,336 | Jan. 12, 2012 | 2012/0261551 | Oct. 18, 2012 | — | — |
| 38-04E US | 13/441,618 | Apr. 6, 2012 | 2013/0100618 | Apr. 25, 2013 | 8,754,396 | Jun. 17, 2014 |
| 134-06B US | 13/441,598 | Apr. 6, 2012 | 2012/0327608 | Dec. 27, 2012 | 8,729,524 | May 20, 2014 |
| 28-11 US | 13/472,165 | May 15, 2012 | 2012/0320581 | Dec. 20, 2012 | — | — |
| 7-11 US | 13/486,726 | Jun. 1, 2012 | 2013/0072775 | Mar. 21, 2013 | 8,934,965 | Jan. 13, 2015 |
| 29-11 US | 13/492,636 | Jun. 8, 2012 | 2013/0041235 | Feb. 14, 2013 | — | — |
| 84-11 US | 13/549,291 | Jul. 13, 2012 | 2013/0036928 | Feb. 14, 2013 | — | — |
| 25-06A US | 13/596,343 | Aug. 28, 2012 | 2012/0321785 | Dec. 20, 2012 | 8,367,035 | Feb. 5, 2013 |
| 150-11 US | 13/624,096 | Sep. 21, 2012 | 2013/0140649 | Jun. 6, 2013 | — | — |
| 38-04A3 US | 13/801,868 | Mar. 13, 2013 | 2013/0320503 | Dec. 5, 2013 | 8,664,699 | Mar. 4, 2014 |
| 125-12 US | 13/835,284 | Mar. 15, 2013 | 2014/0220422 | Aug. 7, 2014 | — | — |
| 30-13 US | 13/853,770 | Mar. 29, 2013 | 2013/0333094 | Dec. 19, 2013 | — | — |
| 213-07A US | 13/974,963 | Aug. 23, 2013 | 2014/0140020 | May 22, 2014 | 8,905,772 | Dec. 9, 2014 |
| 19-10A US | 14/033,765 | Sep. 23, 2013 | 2014/0092158 | Apr. 3, 2014 | — | — |
| 15-10A US | 14/140,299 | Dec. 24, 2013 | 2014/0163390 | Jun. 12, 2014 | — | — |
| 38-04A4 US | 14/155,010 | Jan. 14, 2014 | 2014/0191236 | Jul. 10, 2014 | — | — |
| 136-08A US | 14/173,525 | Feb. 5, 2014 | 2014/0216524 | Aug. 7, 2014 | — | — |
| 216-06C US | 14/209,481 | Mar. 13, 2014 | 2014/0373898 | Dec. 25, 2014 | — | — |
| 134-06C US | 14/220,910 | Mar. 20, 2014 | 2014/0374872 | Dec. 25, 2014 | — | — |
| 38-04F US | 14/220,923 | Mar. 20, 2014 | 2015/0001462 | Jan. 1, 2015 | — | — |
| 151-06C US | 14/246,962 | Apr. 7, 2014 | 2014/0361409 | Dec. 11, 2014 | — | — |
| 62-13 US | 14/250,671 | Apr. 11, 2014 | 2014/0305900 | Oct. 16, 2014 | — | — |
| 56-13 US | 14/251,259 | Apr. 11, 2014 | 2014/0323968 | Oct. 30, 2014 | — | — |
| 60-09A US | 12/778,588 | Sep. 5, 2014 | 2015/0132873 | May 14, 2015 | — | — |
| 84-13 US | 14/504,736 | Oct. 2, 2014 | 2015/0141767 | May 21, 2015 | — | — |
| 213-07B US | 14/521,319 | Oct. 22, 2014 | — | — | — | — |
| 7-11A US | 14/532,687 | Nov. 4, 2014 | 2015/0080695 | Mar. 19, 2015 | — | — |
| 2-14 US | 14/599,290 | Jan. 16, 2015 | — | — | — | — |
| 71-07A US | 12/669,287 | Apr. 14, 2015 | — | — | — | — |
| 213-07C US | 12/398,811 | May 7, 2015 | — | — | — | — |
| 15-13 WO | PCT/US2014/015825 | Feb. 19, 2014 | WO2014/126927 | Aug. 21, 2014 | — | — |
| 128-13 WO | PCT/US2014/014932 | Feb. 5, 2014 | WO 2014/124044 | Aug. 14, 2014 | — | — |
| 8-14 WO | PCT/US2014/014944 | Feb. 18, 2014 | WO 2014/124049 | Aug. 14, 2014 | — | — |
| 35-13 WO | PCT/US2014/021371 | Mar. 6, 2014 | WO 2014/138465 | Sep. 12, 2014 | — | — |
| 54-13 WO | PCT/US2014/032848 | Apr. 3, 2014 | WO 2014/165686 | Oct. 9, 2014 | — | — |

Every formulation or combination of components described or exemplified herein can be used to practice the invention, unless otherwise stated.

Whenever a range is given in the specification, for example, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

We claim:

1. A device for interfacing with a tissue in a biological environment, the device comprising:

a flexible or stretchable substrate having a Young's modulus less than or equal to 100 MPa and a bending stiffness less than or equal to 1 mN m to provide a conformable interface that is mechanically matched to a soft tissue surface; and one or more thermal actuators and a plurality of thermal sensors supported by said flexible or stretchable substrate, wherein at least one thermal actuator is a central thermal actuator that provides a source of thermal power to create a mild, well-controlled increase in temperature of less than 10° C. at a tissue surface, and the plurality of thermal sensors determine a spatiotemporal distribution of temperature for characterizing a thermal transport property of said tissue;

wherein said flexible or stretchable substrate, said one or more thermal actuators and said plurality of thermal sensors provide a net bending stiffness such that the device is capable of establishing conformal contact with a skin surface;

wherein the at least one central thermal actuator provides a power input of between 0.1 to 50 mW/mm$^2$ to the skin surface;

wherein two of said thermal sensors form a matched pair on opposing sides of said central thermal actuator for obtaining comparative data as an indication of an anisotropic thermal transport property, wherein said anisotropic thermal transport property indicates a direction of blood flow;

wherein the central thermal actuator has a radius (B) and a distance (L) from the actuator edge to the thermal sensor center, with B/L between ⅓ and 1;

wherein said one or more thermal actuators and plurality of thermal sensors are at least partially encapsulated by a barrier layer; and wherein said thermal sensors provide a spatial resolution greater than or equal to 10 μm and/or a temporal resolution greater than or equal to 1 μs;

wherein each of said plurality of thermal sensors are arranged at distinct angular positions relative to said central thermal actuator so that together the plurality of thermal sensors form a ring of distinct temperature sensors around said thermal actuator;

wherein said thermal sensors are arranged as two concentric rings of sensors relative to said central thermal actuator, with a first ring separated from the actuator by a first separation distance and a second ring separated from the actuator by a second separation distance, and said first separation distance is less than said second separation distance.

2. The device of claim 1, wherein said one or more thermal actuators and said plurality of thermal sensors spatially and/or temporally characterize said thermal transport property of said tissue.

3. The device of claim 1, wherein said thermal sensors are for characterizing the spatio temporal distribution of temperature resulting from heating provided by said one or more thermal actuators.

4. The device of claim 1, wherein said thermal transport property is thermal conductivity, thermal diffusivity or heat capacity.

5. The device of claim 1, wherein said thermal transport property correlates with a tissue property selected from the group consisting of hydration state, inflammation state, occlusion state and any combination of these.

6. The device of claim 1, wherein said thermal transport property correlates with a physiological parameter selected from the group consisting of macrovascular blood flow direction, macrovascular blood flow rate, microvascular blood flow direction, microvascular blood flow rate, presence of an occlusion, macrovascular perfusion, microvascular perfusion, circulation changes due to inflammation, and any combination of these.

7. The device of claim 1, wherein said device does not substantially impact the natural temperature of said tissue upon establishing conformal contact.

8. The device of claim 1, wherein said thermal actuators and thermal sensors comprise stretchable or flexible structures, thin film structures and/or filamentary metal structures.

9. The device of claim 1, wherein at least one of said thermal sensors is a temperature sensor for measuring background temperature to compensate for drift.

10. The device of claim 1, wherein said thermal actuators provide a constant heating of said tissue or a pulsed heating of said tissue.

11. The device of claim 1, wherein said first separation distance is 3 mm and said second separation distance is 5 mm.

12. The device of claim 1, wherein each of the plurality of thermal sensors and the one or more thermal actuators provides an individual pixel independently corresponding to an individual position of a pixelated array, wherein said individual pixels have average lateral dimensions selected from a range of 10 µm to 1 cm.

13. The device of claim 12, wherein said pixelated array comprises 10 to 100,000 pixels and has a footprint selected from the range of 10 mm$^2$ to 2,000 cm$^2$.

14. The device of claim 12, wherein at least a portion of said pixels comprise micro-encapsulated structures or nano-encapsulated structures.

15. The device of claim 1, wherein the device further comprises:
one or more electrodes, transistors, inducers, resistors, light-emitting diodes (LEDs), capacitors, oscillators, photodiodes, diodes or any combinations of these;
one or more amplifiers, strain gauges, temperature sensors, wireless power coils, solar cells, inductive coils, high frequency inductors, high frequency capacitors, high frequency oscillators, high frequency antennae, multiplex circuits, electrocardiography sensors, electromyography sensors, electroencephalography sensors, electrophysiological sensors, thermistors, capacitive sensors, or any combinations of these; and/or
one or more wireless communication antenna structures or near-field communication coils supported by said flexible or stretchable substrate.

16. The device of claim 1, wherein said one or more actuators and/or said plurality of sensors are connected by an electronic circuit, wherein the electronic circuit is flexible or stretchable and comprises one or more electronic devices or device components having a curved, serpentine, bent, wavy or buckled geometry.

17. The device of claim 16, wherein the electronic circuit comprises a plurality of electrodes selected from the group consisting of meander electrodes, interdigitated electrodes, circular electrodes and annular electrodes.

18. The device of claim 1, wherein the flexible or stretchable substrate has an average modulus less than or equal to 100 MPa.

19. The device of claim 1, comprising a multilayer device wherein said sensors and actuators are at least partially encapsulated by said barrier layer.

20. The device of claim 1, wherein the device has an areal mass density less than or equal to 100 mg cm$^{-2}$.

21. A device for interfacing with a tissue in a biological environment, the device comprising:
a flexible or stretchable substrate having a Young's modulus less than or equal to 100 MPa and a bending stiffness less than or equal to 1 mN m to provide a conformable interface that is mechanically matched to a soft tissue surface; and
one or more thermal actuators and a plurality of thermal sensors supported by said flexible or stretchable substrate, wherein at least one thermal actuator is a central thermal actuator that provides a source of thermal power to create a mild, well-controlled increase in temperature of less than 10° C. at a tissue surface, and the plurality of thermal sensors determine a spatiotemporal distribution of temperature for characterizing a thermal transport property of said tissue;
wherein said flexible or stretchable substrate, said one or more thermal actuators and said plurality of thermal sensors provide a net bending stiffness such that the device is capable of establishing conformal contact with a skin surface;
wherein the at least one central thermal actuator provides a power input of between 0.1 to 50 mW/mm$^2$ to the skin surface;
wherein two of said thermal sensors form a matched pair on opposing sides of said central thermal actuator for obtaining comparative data as an indication of an anisotropic thermal transport property, wherein said anisotropic thermal transport property indicates a direction of blood flow;
wherein the central thermal actuator has a radius (B) and a distance (L) from the actuator edge to the thermal sensor center, with B/L between ⅓ and 1;
wherein said one or more thermal actuators and plurality of thermal sensors are at least partially encapsulated by a barrier layer; and
wherein said thermal sensors provide a spatial resolution greater than or equal to 10 µm and/or a temporal resolution greater than or equal to 1 µs;
wherein each of said plurality of thermal sensors are arranged at distinct angular positions relative to said central thermal actuator so that together the plurality of thermal sensors form a ring of distinct temperature sensors around said thermal actuator;
wherein said thermal actuators provide a pulsed heating of said tissue.

22. The device of claim 21, wherein the pulsed heating is at a frequency of between 0.05 Hz and 0.1 Hz.

* * * * *